US011920146B2

(12) United States Patent
Abad et al.

(10) Patent No.: US 11,920,146 B2
(45) Date of Patent: Mar. 5, 2024

(54) INSECTICIDAL POLYPEPTIDES AND USES THEREOF

(71) Applicant: PIONEER HI-BRED INTERNATIONAL, INC., Johnston, IA (US)

(72) Inventors: Andre R Abad, Leander, TX (US); Hua Dong, Johnston, IA (US); Sue B Lo, West Des Moines, IA (US); Brad Poland, Monroe, IA (US); Xiaomei Shi, Johnston, IA (US); Jimei Wang, Johnston, IA (US); Thomas Chad Wolfe, Des Moines, IA (US); Lan Zhou, Ankeny, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 0 days.

(21) Appl. No.: 17/931,210

(22) Filed: Sep. 12, 2022

(65) Prior Publication Data

US 2022/0411815 A1 Dec. 29, 2022

Related U.S. Application Data

(62) Division of application No. 16/771,816, filed as application No. PCT/US2018/060878 on Nov. 14, 2018, now Pat. No. 11,492,639.

(60) Provisional application No. 62/607,372, filed on Dec. 19, 2017.

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01)

(58) Field of Classification Search
None
See application file for complete search history.

(56) References Cited

U.S. PATENT DOCUMENTS

| | | | | |
|---|---|---|---|---|
| 8,575,433 | B2 | 11/2013 | Cerf et al. | |
| 9,567,381 | B2 | 2/2017 | Kennedy et al. | |
| 9,879,277 | B2 | 1/2018 | Abad et al. | |
| 11,492,639 | B2 | 11/2022 | Abad et al. | |
| 2007/0118924 | A1 | 5/2007 | Payne et al. | |
| 2014/0283208 | A1* | 9/2014 | Abad .................. | C07K 14/325 514/4.5 |

FOREIGN PATENT DOCUMENTS

| | | | |
|---|---|---|---|
| WO | 1997/013402 | A1 | 4/1997 |
| WO | 1998/015170 | A1 | 4/1998 |
| WO | 2013/134734 | A3 | 9/2013 |
| WO | 2016/061208 | A1 | 4/2016 |
| WO | 2016/061391 | A2 | 4/2016 |
| WO | 2017/007679 | A1 | 1/2017 |
| WO | 2017/035364 | A1 | 3/2017 |
| WO | 2017/132188 | A1 | 8/2017 |
| WO | 2017/146899 | A1 | 8/2017 |
| WO | 2017/192560 | A1 | 11/2017 |
| WO | 2020/146439 | A1 | 7/2020 |

OTHER PUBLICATIONS

EPO Partial Search of EP Application No. 18892988.9 (International Application No. PCT/US2018/060878), dated Aug. 27, 2021.
Lucena, Wagner A.; et al.: "Molecular Approaches to Improve the Insecticidal Activity of Bacillus thuringiensis Cry Toxins," Toxings, 2014, vol. 6, pp. 2393-2423.
NCBI Reference Sequence: WP_098389584.1. First available online on Oct. 19, 2017 (Year: 2017).
International Search Report and Written Opinion for International Applicat No. PCT/US2018/060878, dated Mar. 8, 2019.
GenBank Sequence: BAC79010.1. Retrieved from https://www.ncbi.nlm.nih.gov/protein/BAC79010.1?report=genbank&log$=prottop&blast_rank=2&RID=HHEP2GDD01R on Sep. 7, 2022.
GenBank Sequence: BAD35170.1. Retrieved from https://www.ncbi.nlm.nih.gov/protein/BAD35170.1?report=genbank&log$=prottop&blast_rank=1&RID=HHEP2GDD01R on Sep. 7, 2022.
Anonymous: "Crystaline Entomocidal Protoxin-Bacillus Thuringiensis Serovar Kim | UniProtKB | UniProt," Oct. 25, 2017, pp. 1-5, XP055982499, [Nov. 17, 2022] Retrieved from URL: https://www.uniprot.org/uniprotkb/A0A242ZSW8/entry.
Extended European Search Report for European Application No. 18892988.9, dated Nov. 29, 2021, 11 Pages.
Extended European Search Report for European Application No. 22180119.4, dated Dec. 5, 2022, 9 Pages.
International Preliminary Report on Patentability for International Application No. PCT/US2018/060878, dated Jul. 2, 2020, 8 Pages.
Response to Extended European Search Report and Request for Examination for EP 22180119.4 filed Jul. 17, 2023, 10 pages.
Zheng J., "Bacillus Thuringiensis Serovar Kim Strain Bgsc 4BP1, Whole Genome Shotgun DE Sequencing Project," Database accession No. NFDH01000000, EMBL, Jun. 9, 2017, XP055982530, Retrieved from URL: https://www.ebi.ac.uk/ena/browser/api/embl/NFDH01000000.1?lineLimit=1000.

* cited by examiner

*Primary Examiner* — Matthew R Keogh

(57) ABSTRACT

The disclosure provides nucleic acids, and variants and fragments thereof, obtained from strains of *Bacillus thuringiensis* encoding polypeptides having pesticidal activity against insect pests, including Lepidopteran and Coleopteran. Particular embodiments of the disclosure provide isolated nucleic acids encoding pesticidal proteins, pesticidal compositions, DNA constructs, and transformed microorganisms and plants comprising a nucleic acid of the embodiments. These compositions find use in methods for controlling pests, especially plant pests.

17 Claims, No Drawings

Specification includes a Sequence Listing.

INSECTICIDAL POLYPEPTIDES AND USES THEREOF

CROSS REFERENCE

This application is a division of U.S. Non-Provisional application Ser. No. 16/771,816 filed Jun. 11, 2020, which claims the benefit of PCT Application No. PCT/US2018/060878 filed Nov. 14, 2018, which claims the benefit of U.S. Provisional Application No. 62/607,372 filed Dec. 19, 2017, the disclosures of each of which are incorporated herein by reference in their entireties.

REFERENCE TO SEQUENCE LISTING SUBMITTED ELECTRONICALLY

An XML formatted sequence listing having the file name "7492-US-PCD_SequenceListing.xml" created on Aug. 30, 2022 and having a size of 579,666 bytes is filed in computer readable form concurrently with the specification. The sequence listing comprised in this XML formatted document is part of the specification and is herein incorporated by reference in its entirety.

FIELD

The present disclosure relates to naturally-occurring and recombinant nucleic acids obtained from novel *Bacillus thuringiensis* genes that encode pesticidal polypeptides characterized by pesticidal activity against insect pests. Compositions and methods of the disclosure utilize the disclosed nucleic acids, and their encoded pesticidal polypeptides, to control plant pests.

BACKGROUND

Insect pests are a major factor in the loss of the world's agricultural crops. For example, armyworm feeding, black cutworm damage, or European corn borer damage can be economically devastating to agricultural producers. Insect pest-related crop loss from European corn borer attacks on field and sweet corn alone has reached about one billion dollars a year in damage and control expenses.

Traditionally, the primary method for impacting insect pest populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including *Lepidoptera, Diptera, Coleoptera, Hemiptera*, and others. *Bacillus thuringiensis* (Bt) and *Bacillus papilliae* are among the most successful biocontrol agents discovered to date. Insect pathogenicity has also been attributed to strains of *B. larvae, B. lentimorbus, B. sphaericus* (Harwook, ed., ((1989) *Bacillus* (Plenum Press), 306) and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants have been genetically engineered to produce pesticidal proteins isolated from strains of Bt (see, e.g., Aronson (2002) *Cell Mol. Life Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. In addition, potatoes genetically engineered to contain pesticidal Cry toxins have been sold to the American farmer. While they have proven to be very successful commercially, these genetically engineered, insect-resistant crop plants provide resistance to only a narrow range of the economically important insect pests.

Accordingly, there remains a need for new Bt toxins with a broader range of insecticidal activity against insect pests, e.g., toxins which are active against a greater variety of insects. In addition, there remains a need for biopesticides having activity against a variety of insect pests and for biopesticides which have improved insecticidal activity.

SUMMARY

Compositions and methods are provided for impacting insect pests. More specifically, the embodiments of the present disclosure relate to methods of impacting insects utilizing nucleotide sequences encoding insecticidal peptides to produce transformed microorganisms and plants that express an insecticidal polypeptide of the embodiments. In some embodiments, the nucleotide sequences encode polypeptides that are pesticidal for at least one insect belonging to the order Lepidoptera.

In some aspects, nucleic acid molecules and fragments and variants thereof are provided, which encode polypeptides that possess pesticidal activity against insect pests. The embodiments further provide fragments and variants of the disclosed nucleotide sequence that encode biologically active (e.g., insecticidal) polypeptides.

In some aspects, isolated pesticidal (e.g., insecticidal) polypeptides are provided, encoded by either a naturally occurring or a modified (e.g., mutagenized or manipulated) nucleic acid of the embodiments. In particular aspects, pesticidal proteins of the embodiments include fragments of full-length proteins and polypeptides that are produced from mutagenized nucleic acids designed to introduce particular amino acid sequences into the polypeptides of the embodiments. In particular aspects, the polypeptides have enhanced pesticidal activity relative to the activity of the naturally occurring polypeptide from which they are derived.

In some aspects, the nucleic acids of the embodiments can also be used to produce transgenic (e.g., transformed) monocot or dicot plants that are characterized by genomes that comprise at least one stably incorporated nucleotide construct comprising a coding sequence of the embodiments operably linked to a promoter that drives expression of the encoded pesticidal polypeptide. Accordingly, transformed plant cells, plant tissues, plants, and seeds thereof are also provided.

In a particular aspects, a transformed plant can be produced using a nucleic acid that has been optimized for increased expression in a host plant. For example, one of the pesticidal polypeptides of the embodiments can be back-translated to produce a nucleic acid comprising codons optimized for expression in a particular host, for example a crop plant such as a corn (Zea mays) plant. Expression of a coding sequence by such a transformed plant (e.g., dicot or monocot) will result in the production of a pesticidal polypeptide and confer increased insect resistance to the plant. In some aspects, transgenic plants expressing pesticidal polypeptides are provide that find use in methods for impacting various insect pests.

In some aspects pesticidal or insecticidal compositions are provided containing the insecticidal polypeptides of the embodiments, and can optionally comprise further insecticidal peptides. The embodiments encompass the application of such compositions to the environment of insect pests in order to impact the insect pests.

DETAILED DESCRIPTION

The disclosure is drawn to compositions and methods for impacting insect pests, particularly plant pests. More specifically, the isolated nucleic acid of the embodiments, and fragments and variants thereof, comprise nucleotide sequences that encode pesticidal polypeptides (e.g., proteins). The disclosed pesticidal proteins are biologically active (e.g., pesticidal) against insect pests such as, but not limited to, insect pests of the order Lepidoptera.

The compositions of the embodiments comprise isolated nucleic acids, and fragments and variants thereof, which encode pesticidal polypeptides, expression cassettes comprising nucleotide sequences of the embodiments, isolated pesticidal proteins, and pesticidal compositions. Some embodiments provide modified pesticidal polypeptides having improved insecticidal activity against Lepidopterans relative to the pesticidal activity of the corresponding wild-type protein. The embodiments further provide plants and microorganisms transformed with these novel nucleic acids, and methods involving the use of such nucleic acids, pesticidal compositions, transformed organisms, and products thereof in impacting insect pests.

The nucleic acids and nucleotide sequences of the embodiments may be used to transform any organism to produce the encoded pesticidal proteins. Methods are provided that involve the use of such transformed organisms to impact or control plant pests. The nucleic acids and nucleotide sequences of the embodiments may also be used to transform organelles such as chloroplasts (McBride et al. (1995) *Biotechnology* 13: 362-365; and Kota et al. (1999) *Proc. Natl. Acad. Sci. USA* 96: 1840-1845).

The embodiments further relate to the identification of fragments and variants of the naturally-occurring coding sequence that encode biologically active pesticidal proteins. The nucleotide sequences of the embodiments find direct use in methods for impacting pests, particularly insect pests such as pests of the order Lepidoptera. Accordingly, the embodiments provide new approaches for impacting insect pests that do not depend on the use of traditional, synthetic chemical insecticides. The embodiments involve the discovery of naturally-occurring, biodegradable pesticides and the genes that encode them.

The embodiments further provide fragments and variants of the naturally occurring coding sequence that also encode biologically active (e.g., pesticidal) polypeptides. The nucleic acids of the embodiments encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The embodiments further provide mutations which confer improved or altered properties on the polypeptides of the embodiments. See, e.g. U.S. Pat. No. 7,462,760.

In the description that follows, a number of terms are used extensively. The following definitions are provided to facilitate understanding of the embodiments.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is generally free of sequences (such as, for example, protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the embodiments means that the isolated protein is substantially free of cellular material and includes preparations of protein having less than about 30%, 20%, 10%, or 5% (by dry weight) of contaminating protein. When the protein of the embodiments or biologically active portion thereof is recombinantly produced, culture medium represents less than about 30%, 20%, 10%, or 5% (by dry weight) of chemical precursors or non-protein-of-interest chemicals.

A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes.

As used herein a "non-genomic nucleic acid sequence" or "non-genomic nucleic acid molecule" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a cDNA. In some embodiments, the non-genomic nucleic acid molecule is a synthetic nucleic acid sequence.

Throughout the specification, the word "comprising," or variations such as "comprises" or "comprising," will be understood to imply the inclusion of a stated element, integer or step, or group of elements, integers or steps, but not the exclusion of any other element, integer or step, or group of elements, integers or steps.

As used herein, the term "impacting insect pests" refers to effecting changes in insect feeding, growth, and/or behavior at any stage of development, including but not limited to: killing the insect; retarding growth; preventing reproductive capability; antifeedant activity; and the like.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins.

As used herein, the term "pesticidally effective amount" means a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

As used herein, the term "recombinantly engineered" or "engineered" means the utilization of recombinant DNA technology to introduce (e.g., engineer) a change in the protein structure based on an understanding of the protein's mechanism of action and a consideration of the amino acids being introduced, deleted, or substituted.

As used herein, the term "mutant nucleotide sequence" or "mutation" or "mutagenized nucleotide sequence" means a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a mutant insecticidal toxin showing improved or decreased insecticidal activity, or an amino acid sequence which confers improved or decreased insecticidal activity on a polypeptide containing it. As used herein, the term "mutant" or "mutation" in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A mutant polypeptide shows improved or decreased insecticidal activity, or represents an amino acid sequence which confers improved insecticidal activity on a polypeptide containing it. Thus, the term "mutant" or "mutation" refers to either or both of the mutant nucleotide sequence and the encoded amino acids. Mutants may be used alone or in any compatible combination with other mutants of the embodiments or with other mutants. A "mutant polypeptide" may conversely show a decrease in insecticidal activity. Where more than one mutation is added to a particular nucleic acid or protein, the mutations may be added at the same time or sequentially; if sequentially, mutations may be added in any suitable order.

As used herein, the term "improved insecticidal activity" or "improved pesticidal activity" refers to an insecticidal polypeptide of the embodiments that has enhanced insecticidal activity relative to the activity of its corresponding wild-type protein, and/or an insecticidal polypeptide that is effective against a broader range of insects, and/or an insecticidal polypeptide having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type insecticidal polypeptide determined against the same insect.

For example, an improved pesticidal or insecticidal activity is provided where a wider or narrower range of insects is impacted by the polypeptide relative to the range of insects that is affected by a wild-type Bt toxin. A wider range of impact may be desirable where versatility is desired, while a narrower range of impact may be desirable where, for example, beneficial insects might otherwise be impacted by use or presence of the toxin. While the embodiments are not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

The term "toxin" as used herein refers to a polypeptide showing pesticidal activity or insecticidal activity or improved pesticidal activity or improved insecticidal activity. "Bt" or "*Bacillus thuringiensis*" toxin is intended to include the broader class of Cry toxins found in various strains of Bt, which includes such toxins as, for example, Cry1s, Cry2s, or Cry3s.

The terms "proteolytic site" or "cleavage site" refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

Research has shown that the insect gut proteases of Lepidopterans include trypsins, chymotrypsins, and elastases. See, e.g., Lenz et al. (1991) *Arch. Insect Biochem. Physiol.* 16: 201-212; and Hedegus et al. (2003) *Arch. Insect Biochem. Physiol.* 53: 30-47. For example, about 18 different trypsins have been found in the midgut of *Helicoverpa armigera* larvae (see Gatehouse et al. (1997) *Insect Biochem. Mol. Biol.* 27: 929-944). The preferred proteolytic substrate sites of these proteases have been investigated. See, e.g., Peterson et al. (1995) *Insect Biochem. Mol. Biol.* 25: 765-774.

Efforts have been made to understand the mechanism of action of Bt toxins and to engineer toxins with improved properties. It has been shown that insect gut proteases can affect the impact of Bt Cry proteins on the insect. Some proteases activate the Cry proteins by processing them from a "protoxin" form into a toxic form, or "toxin." See, Oppert (1999) *Arch. Insect Biochem. Phys.* 42: 1-12; and Carroll et al. (1997) *J. Invertebrate Pathology* 70: 41-49. This activation of the toxin can include the removal of the N- and C-terminal peptides from the protein and can also include internal cleavage of the protein. Other proteases can degrade the Cry proteins. See Oppert, ibid.

A comparison of the amino acid sequences of Cry toxins of different specificities reveals five highly-conserved sequence blocks. Structurally, the toxins comprise three distinct domains which are, from the N- to C-terminus: a cluster of seven alpha-helices implicated in pore formation (referred to as "domain 1"), three anti-parallel beta sheets implicated in cell binding (referred to as "domain 2"), and a beta sandwich (referred to as "domain 3"). The location and properties of these domains are known to those of skill in the art. See, for example, Li et al. (1991) *Nature*, 305:815-821 and Morse et al. (2001) *Structure*, 9:409-417. When reference is made to a particular domain, such as domain 1, it is understood that the exact endpoints of the domain with regard to a particular sequence are not critical so long as the sequence or portion thereof includes sequence that provides at least some function attributed to the particular domain. Thus, for example, when referring to "domain 1," it is intended that a particular sequence includes a cluster of seven alpha-helices, but the exact endpoints of the sequence used or referred to with regard to that cluster are not critical. One of skill in the art is familiar with the determination of such endpoints and the evaluation of such functions.

In an effort to better characterize and improve Bt toxins, strains of the bacterium Bt were studied. Crystal preparations prepared from cultures of the Bt strains were discovered to have pesticidal activity against numerous Lepidopteran pests (see, e.g., Experimental Example 1). An effort was undertaken to identify the nucleotide sequences encoding the crystal proteins from the selected strains, and the wild-type (i.e., naturally occurring) nucleic acids of the embodiments were isolated from these bacterial strains, cloned into an expression vector, and transformed into E coli. Depending upon the characteristics of a given preparation, it was recognized that the demonstration of pesticidal activity sometimes required trypsin pretreatment to activate the pesticidal proteins. Thus, it is understood that some pesticidal proteins require protease digestion (e.g., by trypsin, chymotrypsin, and the like) for activation, while other proteins are biologically active (e.g., pesticidal) in the absence of activation.

Such molecules may be altered by means described, for example, U.S. Pat. No. 7,462,760. In addition, nucleic acid sequences may be engineered to encode polypeptides that contain additional mutations that confer improved or altered pesticidal activity relative to the pesticidal activity of the naturally occurring polypeptide. The nucleotide sequences of such engineered nucleic acids comprise mutations not found in the wild type sequences.

The mutant polypeptides of the embodiments are generally prepared by a process that involves the steps of: obtaining a nucleic acid sequence encoding a Cry family polypeptide; analyzing the structure of the polypeptide to identify particular "target" sites for mutagenesis of the underlying gene sequence based on a consideration of the proposed function of the target domain in the mode of action of the toxin; introducing one or more mutations into the nucleic acid sequence to produce a desired change in one or more amino acid residues of the encoded polypeptide sequence; and assaying the polypeptide produced for pesticidal activity.

Many of the Bt insecticidal toxins are related to various degrees by similarities in their amino acid sequences and tertiary structure and means for obtaining the crystal structures of Bt toxins are well known. Exemplary high-resolution crystal structure solution of both the Cry3A and Cry3B polypeptides are available in the literature. The solved structure of the Cry3A gene (Li et al. (1991) *Nature* 353: 815-821) provides insight into the relationship between structure and function of the toxin. A combined consideration of the published structural analyses of Bt toxins and the reported function associated with particular structures, motifs, and the like indicates that specific regions of the toxin are correlated with particular functions and discrete steps of the mode of action of the protein. For example, many toxins isolated from Bt are generally described as comprising three domains: a seven-helix bundle that is involved in pore formation, a three-sheet domain that has been implicated in receptor binding, and a beta-sandwich motif (Li et al. (1991) *Nature* 305: 815-821).

As reported in U.S. Pat. Nos. 7,105,332, and 7,462,760, the toxicity of Cry proteins can be improved by targeting the region located between alpha helices 3 and 4 of domain 1 of the toxin. This theory was premised on a body of knowledge concerning insecticidal toxins, including: 1) that alpha helices 4 and 5 of domain 1 of Cry3A toxins had been reported to insert into the lipid bilayer of cells lining the midgut of susceptible insects (Gazit et al. (1998) *Proc. Natl. Acad. Sci. USA* 95: 12289-12294); 2) the inventors' knowledge of the location of trypsin and chymotrypsin cleavage sites within the amino acid sequence of the wild-type protein; 3) the observation that the wild-type protein was more active against certain insects following in vitro activation by trypsin or chymotrypsin treatment; and 4) reports that digestion of toxins from the 3' end resulted in decreased toxicity to insects.

A series of mutations may be created and placed in a variety of background sequences to create novel polypeptides having enhanced or altered pesticidal activity. See, e.g., U.S. Pat. No. 7,462,760. These mutants include, but are not limited to: the addition of at least one more protease-sensitive site (e.g., trypsin cleavage site) in the region located between helices 3 and 4 of domain 1; the replacement of an original protease-sensitive site in the wild-type sequence with a different protease-sensitive site; the addition of multiple protease-sensitive sites in a particular location; the addition of amino acid residues near protease-sensitive site(s) to alter folding of the polypeptide and thus enhance digestion of the polypeptide at the protease-sensitive site(s); and adding mutations to protect the polypeptide from degradative digestion that reduces toxicity (e.g., making a series of mutations wherein the wild-type amino acid is replaced by valine to protect the polypeptide from digestion). Mutations may be used singly or in any combination to provide polypeptides of the embodiments.

Homologous sequences were identified by similarity search on the non-redundant database (nr) of National Center for Bioinformatics Information (NCBI) using BLAST and PSI-BLAST. The homologous proteins were made up of Cry toxins primarily from *Bacillus thuringiensis*.

A mutation which is an additional or alternative protease-sensitive site may be sensitive to several classes of proteases such as serine proteases, which include trypsin and chymotrypsin, or enzymes such as elastase. Thus, a mutation which is an additional or alternative protease-sensitive site may be designed so that the site is readily recognized and/or cleaved by a category of proteases, such as mammalian proteases or insect proteases. A protease-sensitive site may also be designed to be cleaved by a particular class of enzymes or a particular enzyme known to be produced in an organism, such as, for example, a chymotrypsin produced by the corn earworm *Heliothis zea* (Lenz et al. (1991) *Arch. Insect Biochem. Physiol.* 16: 201-212). Mutations may also confer resistance to proteolytic digestion, for example, to digestion by chymotrypsin at the C-terminus of the peptide.

The presence of an additional and/or alternative protease-sensitive site in the amino acid sequence of the encoded polypeptide can improve the pesticidal activity and/or specificity of the polypeptide encoded by the nucleic acids of the embodiments. Accordingly, the nucleotide sequences of the embodiments can be recombinantly engineered or manipulated to produce polypeptides having improved or altered insecticidal activity and/or specificity compared to that of an unmodified wild-type toxin. In addition, the mutations disclosed herein may be placed in or used in conjunction with other nucleotide sequences to provide improved properties. For example, a protease-sensitive site that is readily cleaved by insect chymotrypsin, e.g., a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be placed in a Cry background sequence to provide improved toxicity to that sequence. In this manner, the embodiments provide toxic polypeptides with improved properties.

For example, a mutagenized Cry nucleotide sequence can comprise additional mutants that comprise additional codons that introduce a second trypsin-sensitive amino acid sequence (in addition to the naturally occurring trypsin site) into the encoded polypeptide. An alternative addition mutant of the embodiments comprises additional codons designed to introduce at least one additional different protease-sensitive site into the polypeptide, for example, a chymotrypsin-sensitive site located immediately 5' or 3' of the naturally occurring trypsin site. Alternatively, substitution mutants may be created in which at least one codon of the nucleic acid that encodes the naturally occurring protease-sensitive site is destroyed and alternative codons are introduced into the nucleic acid sequence in order to provide a different (e.g., substitute) protease-sensitive site. A replacement mutant may also be added to a Cry sequence in which the naturally-occurring trypsin cleavage site present in the encoded polypeptide is destroyed and a chymotrypsin or elastase cleavage site is introduced in its place.

It is recognized that any nucleotide sequence encoding the amino acid sequences that are proteolytic sites or putative proteolytic sites (for example, sequences such as RR, or LKM) can be used and that the exact identity of the codons used to introduce any of these cleavage sites into a variant polypeptide may vary depending on the use, i.e., expression in a particular plant species. It is also recognized that any of the disclosed mutations can be introduced into any polynucleotide sequence of the embodiments that comprises the codons for amino acid residues that provide the native trypsin cleavage site that is targeted for modification. Accordingly, variants of either full-length toxins or fragments thereof can be modified to contain additional or alternative cleavage sites, and these embodiments are intended to be encompassed by the scope of the embodiments disclosed herein.

It will be appreciated by those of skill in the art that any useful mutation may be added to the sequences of the embodiments so long as the encoded polypeptides retain pesticidal activity. Thus, sequences may also be mutated so that the encoded polypeptides are resistant to proteolytic digestion by chymotrypsin. More than one recognition site can be added in a particular location in any combination, and multiple recognition sites can be added to or removed from the toxin. Thus, additional mutations can comprise three, four, or more recognition sites. It is to be recognized that multiple mutations can be engineered in any suitable polynucleotide sequence; accordingly, either full-length sequences or fragments thereof can be modified to contain additional or alternative cleavage sites as well as to be resistant to proteolytic digestion. In this manner, the embodiments provide Cry toxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with wild-type toxins or by comparing mutant toxins which differ in their amino acid sequence. Putative proteolytic sites and proteolytic sites include, but are not limited to, the following sequences: RR, a trypsin cleavage site; LKM, a chymotrypsin site; and a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Compositions of the embodiments include nucleic acids, and fragments and variants thereof that encode pesticidal polypeptides. In particular, the embodiments provide for isolated nucleic acid molecules comprising nucleotide sequences encoding the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 264, SEQ ID NO: 266, SEQ ID NO: 268, SEQ ID NO: 270, SEQ ID NO: 272, SEQ ID NO: 274, SEQ ID NO: 276, SEQ ID NO: 278, SEQ ID NO: 280, SEQ ID NO: 282, and SEQ ID NO: 284, and the nucleotide sequences encoding said amino acid sequence, for example the nucleotide sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 265, SEQ ID NO: 267, and SEQ ID NO: 269, and fragments and variants thereof.

In particular, the embodiments provide for isolated nucleic acid molecules encoding the amino acid sequence shown in SEQ ID NO: 64, SEQ ID NO: 152, SEQ ID NO: 170 or SEQ ID NO: 184 or the nucleotide sequences encoding said amino acid sequence, for example the nucleotide sequence set forth in SEQ ID NO: 63, SEQ ID NO: 151, SEQ ID NO: 169 or SEQ ID NO: 183, and fragments and variants thereof.

Also of interest are optimized nucleotide sequences encoding the pesticidal proteins of the embodiments. As used herein, the phrase "optimized nucleotide sequences" refers to nucleic acids that are optimized for expression in a particular organism, for example a plant. Optimized nucleotide sequences may be prepared for any organism of interest using methods known in the art. See, for example, U.S. Pat. No. 7,462,760, which describes an optimized nucleotide sequence encoding a disclosed pesticidal protein. In this example, the nucleotide sequence was prepared by reverse-translating the amino acid sequence of the protein and changing the nucleotide sequence so as to comprise maize-preferred codons while still encoding the same amino acid sequence. This procedure is described in more detail by Murray et al. (1989) *Nucleic Acids Res.* 17:477-498. Optimized nucleotide sequences find use in increasing expression of a pesticidal protein in a plant, for example monocot plants of the Gramineae (Poaceae) family such as, for example, a maize or corn plant.

In particular embodiments, pesticidal proteins of the embodiments provide full-length insecticidal polypeptides, fragments of full-length insecticidal polypeptides, and variant polypeptides that are produced from mutagenized nucleic acids designed to introduce particular amino acid sequences into polypeptides of the embodiments. In particular embodiments, the amino acid sequences that are introduced into the polypeptides comprise a sequence that provides a cleavage site for an enzyme such as a protease.

It is known in the art that the pesticidal activity of Bt toxins is typically activated by cleavage of the peptide in the insect gut by various proteases. Because peptides may not always be cleaved with complete efficiency in the insect gut, fragments of a full-length toxin may have enhanced pesticidal activity in comparison to the full-length toxin itself. Thus, some of the polypeptides of the embodiments include fragments of a full-length insecticidal polypeptide, and some of the polypeptide fragments, variants, and mutations will have enhanced pesticidal activity relative to the activity of the naturally occurring insecticidal polypeptide from which they are derived, particularly if the naturally occurring insecticidal polypeptide is not activated in vitro with a protease prior to screening for activity. Thus, the present application encompasses truncated versions or fragments of the sequences.

Mutations may be placed into any background sequence, including such truncated polypeptides, so long as the polypeptide retains pesticidal activity. One of skill in the art can readily compare two or more proteins with regard to pesticidal activity using assays known in the art or described elsewhere herein. It is to be understood that the polypeptides of the embodiments can be produced either by expression of a nucleic acid disclosed herein, or by the use of standard molecular biology techniques.

It is recognized that the pesticidal proteins may be oligomeric and will vary in molecular weight, number of residues, component peptides, activity against particular pests, and other characteristics. However, by the methods set forth herein, proteins active against a variety of pests may be isolated and characterized. The pesticidal proteins of the embodiments can be used in combination with other Bt toxins or other insecticidal proteins to increase insect target range. Furthermore, the use of the pesticidal proteins of the embodiments in combination with other Bt toxins or other insecticidal principles of a distinct nature has particular utility for the prevention and/or management of insect resistance. Other insecticidal agents include protease inhibitors (both serine and cysteine types), α-amylase, and peroxidase.

Fragments and variants of the nucleotide and amino acid sequences and the polypeptides encoded thereby are also encompassed by the embodiments. As used herein the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. Thus, it is acknowledged that some of the polynucleotide and amino acid sequences of the embodiments can correctly be referred to as both fragments and mutants.

It is to be understood that the term "fragment," as it is used to refer to nucleic acid sequences of the embodiments, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a nucleotide sequence of the embodiments that encodes a biologically active portion of a pesticidal protein of the embodiments will encode at least 15, 25, 30, 50, 100, 200, 250 or 300 contiguous amino acids, or up to the total number of amino acids present in a pesticidal polypeptide of the embodiments. Fragments of a nucleotide sequence of the embodiments that are useful as hybridization probes or PCR primers generally need not encode a biologically active portion of a pesticidal protein. Thus, a fragment of a nucleic acid of the embodiments may encode a biologically active portion of a pesticidal protein, or it may be a fragment that can be used as a hybridization probe or PCR primer using methods disclosed herein. A biologically active portion of a pesticidal protein can be prepared by isolating a portion of one of the nucleotide sequences of the embodiments, expressing the encoded portion of the pesticidal protein (e.g., by recombinant expression in vitro), and assessing the activity of the encoded portion of the pesticidal protein.

Nucleic acids that are fragments of a nucleotide sequence of the embodiments comprise at least 16, 20, 50, 75, 100, 150, 200, 250, 300, 350, 400, 450, 500, 600, 700, 800, 850, 900 or 950 nucleotides, or up to the number of nucleotides present in a nucleotide sequence disclosed herein. Particular embodiments envision fragments derived from (e.g., produced from) a first nucleic acid of the embodiments, wherein the fragment encodes a truncated toxin having pesticidal activity. Truncated polypeptides encoded by the polynucleotide fragments of the embodiments are having pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' end of the native or corresponding full-length coding sequence.

The term "variants" is used herein to refer to substantially similar sequences. For nucleotide sequences, conservative variants include those sequences that, because of the degeneracy of the genetic code, encode the amino acid sequence of one of the pesticidal polypeptides of the embodiments. Those having ordinary skill in the art will readily appreciate that due to the degeneracy of the genetic code, a multitude of nucleotide sequences encoding of the present disclosure exist.

In some embodiments, the nucleic acid molecule encoding the polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a cDNA. In some embodiments, the non-genomic nucleic acid molecule is a synthetic nucleic acid sequence.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, and Liu H et al. *Mol Bio Rep* 37:677-684, 2010, herein incorporated by reference. A Zea maize codon usage table can be also found at kazusa.or.jp/codon/cgi-bin/showcodon.cgi?species=4577, which can be accessed using the www prefix.

A *Glycine max* codon usage table is shown in Table 3 and can also be found at kazusa.or.jp/codon/cgi-bin/showcodon.cgi?species=3847&aa=1&style=N, which can be accessed using the www prefix.

The skilled artisan will further appreciate that changes can be introduced by mutation of the nucleic acid sequences thereby leading to changes in the amino acid sequence of the encoded polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Naturally occurring allelic variants such as these can be identified with the use of well-known molecular biology techniques, such as, for example, polymerase chain reaction (PCR) and hybridization techniques as outlined herein.

In some embodiments the polynucleotide encoding the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 264, SEQ ID NO: 266, SEQ ID NO: 268 or SEQ ID NO: 270, is a non-genomic nucleic acid sequence.

Variant nucleotide sequences also include synthetically derived nucleotide sequences, such as those generated, for example, by using site-directed mutagenesis but which still encode a pesticidal protein of the embodiments, such as a mutant toxin. Generally, variants of a particular nucleotide sequence of the embodiments will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the embodiments may differ from that sequence by as few as 1-15 nucleotides, as few as 1-10, such as 6-10, as few as 5, as few as 4, 3, 2, or even 1 nucleotide.

Variants of a particular nucleotide sequence of the embodiments (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptides SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 264, SEQ ID NO: 266, SEQ ID NO: 268 or SEQ ID NO: 270 are disclosed. Percent sequence identity between any two polypeptides can be calculated using sequence alignment programs described elsewhere herein using default parameters. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

As used herein, the term "variant protein" encompasses polypeptides that are derived from a native protein by: deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term "variant protein" encompasses biologically active fragments of a native protein that comprise a sufficient number of contiguous amino acid residues to retain the biological activity of the native protein, i.e., to have pesticidal activity. Such pesticidal activity may be different or improved relative to the native protein or it may be unchanged, so long as pesticidal activity is retained.

Variant proteins encompassed by the embodiments are biologically active, that is they continue to possess the desired biological activity of the native protein, that is, pesticidal activity as described herein. Such variants may result from, for example, genetic polymorphism or from human manipulation. Biologically active variants of a native pesticidal protein of the embodiments will have at least about 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the embodiments may differ from that protein by as few as 1-15 amino acid residues, as few as 1-10, such as 6-10, as few as 5, as few as 4, 3, 2, or even 1 amino acid residue.

In some embodiments, the insecticidal polypeptide has at least 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 264, SEQ ID NO: 266, SEQ ID NO: 268 or SEQ ID NO: 270.

In some embodiments, the polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments, the polypeptide has increased digestibility of proteolytic fragments in an insect gut. In some embodiments, the polypeptide has increased stability in an insect gut. Models for digestion by simulated simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

The embodiments further encompass a microorganism that is transformed with at least one nucleic acid of the embodiments, with an expression cassette comprising the nucleic acid, or with a vector comprising the expression cassette. In some embodiments, the microorganism is one that multiplies on plants. An embodiment of the disclosure relates to an encapsulated pesticidal protein which comprises a transformed microorganism capable of expressing at least one pesticidal protein of the embodiments.

The embodiments provide pesticidal compositions comprising a transformed microorganism of the embodiments. In such embodiments, the transformed microorganism is generally present in the pesticidal composition in a pesticidally effective amount, together with a suitable carrier. The embodiments also encompass pesticidal compositions comprising an isolated protein of the embodiments, alone or in combination with a transformed organism of the embodiments and/or an encapsulated pesticidal protein of the embodiments, in an insecticidally effective amount, together with a suitable carrier.

The embodiments further provide a method of increasing insect target range by using a pesticidal protein of the embodiments in combination with at least one other or "second" pesticidal protein. Any pesticidal protein known in the art can be employed in the methods of the embodiments. Such pesticidal proteins include, but are not limited to, Bt toxins, protease inhibitors, α-amylases, and peroxidases.

The embodiments also encompass transformed or transgenic plants comprising at least one nucleotide sequence of the embodiments. In some embodiments, the plant is stably transformed with a nucleotide construct comprising at least one nucleotide sequence of the embodiments operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes whole plants, plant organs (e.g., leaves, stems, roots, etc.), seeds, plant cells, and progeny of same. Parts of transgenic plants are within the scope of the embodiments and comprise, for example, plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, originating in transgenic plants or their progeny previously transformed with a DNA molecule of the embodiments and therefore consisting at least in part of transgenic cells. The class of plants that can be used in the methods of the embodiments is generally as broad as the class of higher plants amenable to transformation techniques, including both monocotyledonous and dicotyledonous plants.

While the embodiments do not depend on a particular biological mechanism for increasing the resistance of a plant to a plant pest, expression of the nucleotide sequences of the embodiments in a plant can result in the production of the pesticidal proteins of the embodiments and in an increase in the resistance of the plant to a plant pest. The plants of the embodiments find use in agriculture in methods for impacting insect pests. Certain embodiments provide transformed crop plants, such as, for example, maize plants, which find use in methods for impacting insect pests of the plant, such as, for example, Lepidopteran pests.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences of proteins of agricultural interest.

Thus, the proteins of the embodiments may be altered in various ways including amino acid substitutions, deletions, truncations, and insertions. Methods for such manipulations are generally known in the art. For example, amino acid sequence variants of the pesticidal proteins can be prepared by introducing mutations into a synthetic nucleic acid (e.g., DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein.

The mutagenized nucleotide sequences of the embodiments may be modified so as to change about 1, 2, 3, 4, 5, 6, 8, 10, 12 or more of the amino acids present in the primary sequence of the encoded polypeptide. Alternatively, even more changes from the native sequence may be introduced such that the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more of the codons altered, or otherwise modified compared to the corresponding wild-type protein. In the same manner, the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more additional codons compared to the corresponding wild-type protein. It should be understood that the mutagenized nucleotide sequences of the embodiments are intended to encompass biologically functional, equivalent peptides which have pesticidal activity, such as an improved pesticidal activity as determined by antifeedant properties against European corn borer larvae. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary amino acid substitution groups that take various of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the embodiments include both the naturally occurring sequences and mutant forms. Likewise, the proteins of the embodiments encompass both naturally occurring proteins and variations (e.g., truncated polypeptides) and modified (e.g., mutant) forms thereof. Such variants will continue to possess the desired pesticidal activity. Obviously, the mutations that will be made in the nucleotide sequence encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al. (1985) *J. Econ. Entomol.* 78: 290-293 and Czapla and Lang (1990) *J. Econ. Entomol.* 83: 2480-2485, herein incorporated by reference.

Variant nucleotide sequences and proteins also encompass sequences and proteins derived from a mutagenic and recombinogenic procedure such as DNA shuffling. With such a procedure, one or more different coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence of the embodiments may be shuffled between the nucleotide sequences of the embodiments and corresponding portions of other known Cry nucleotide sequences to obtain a new gene coding for a protein with an improved property of interest.

Properties of interest include, but are not limited to, pesticidal activity per unit of pesticidal protein, protein stability, and toxicity to non-target species particularly humans, livestock, and plants and microbes that express the pesticidal polypeptides of the embodiments. The embodiments are not bound by a particular shuffling strategy, only that at least one nucleotide sequence of the embodiments, or part thereof, is involved in such a shuffling strategy. Shuffling may involve only nucleotide sequences disclosed herein or may additionally involve shuffling of other nucleotide sequences known in the art. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York), hereinafter "Sambrook". See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cry sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1× SSC at 60 to 65° C. for at least about 20 minutes. Optionally, wash buffers may comprise about 0.1% to about 1% SDS. The duration of hybridization is generally less than about 24 hours, usually about 4 to about 12 hours.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, California, USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Center for Biotechnology Information website on the world wide web at ncbi.hlm.nih.gov. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% 80% 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures, and the like.

A further embodiment relates to a transformed organism such as an organism selected from the group consisting of plant and insect cells, bacteria, yeast, baculoviruses, protozoa, nematodes, and algae. The transformed organism comprises: a DNA molecule of the embodiments, an expression cassette comprising the said DNA molecule, or a vector comprising the said expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions, contiguous and in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the Cry toxin sequence to be under the transcriptional regulation of the regulatory regions. The DNA construct may additionally contain selectable marker genes.

The DNA construct will include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481; and U.S. Pat. Nos. 7,709,702; and 7,462,481); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology, Vol.* 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the embodiments.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6: 923-926); and LecI transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature (London)* 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the Cry toxin protein or variants and fragments thereof directly into the plant or the introduction of the Cry toxin transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cry toxin polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants, including, but not limited to: corn, alfalfa, sunflower, *Brassica* spp., soybean, cotton, safflower, peanut, sorghum, wheat, millet, tobacco, sugarcane, etc.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, Brassica, maize, alfalfa, palm, coconut, flax, castor, olive etc. Leguminous plants include beans and peas. Beans include guar, locust bean, fenugreek, soybean, garden beans, cowpea, mung bean, lima bean, fava bean, lentils, chickpea, etc.

In certain embodiments, the nucleic acid sequences of the embodiments can be stacked with any combination of polynucleotide sequences of interest in order to create plants with a desired phenotype. For example, the polynucleotides of the embodiments may be stacked with any other polynucleotides encoding polypeptides having pesticidal and/or insecticidal activity, such as other Bt toxic proteins (described in U.S. Pat. Nos. 5,366,892; 5,747,450; 5,736,514; 5,723,756; 5,593,881; and Geiser et al. (1986) *Gene* 48:109), pentin (described in U.S. Pat. No. 5,981,722) and the like. The combinations generated can also include multiple copies of any one of the polynucleotides of interest. The polynucleotides of the embodiments can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,049); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12: 123)); increased digestibility (e.g., modified storage proteins (U.S. Pat. No. 6,858,778); and thioredoxins (U.S. Pat. No. 7,009,087), the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262: 1432; and Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene as disclosed in U.S. Pat. Nos. 7,709,702; and 7,462,481; and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170: 5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

In some embodiment the stacked trait may be a trait or event that has received regulatory approval which are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications isaaa.org/gmapprovaldatabase/default.asp, which can be accessed using the www prefix).

These stacked combinations can be created by any method including but not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

In some embodiments, the disclosed polynucleotide compositions can be introduced into the genome of a plant using genome editing technologies, or previously introduced polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed polynucleotide has previously been introduced into a genome, genome editing technologies may be used to alter or modify the introduced polynucleotide sequence. Site specific modifications that can be introduced into the disclosed polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a nucleotide sequence encoding a pesticidal protein of the embodiments may be treated with a seed protectant coating comprising a seed treatment compound, such as, for example, captan, carboxin, thiram, methalaxyl, pirimiphos-methyl, and others that are commonly used in seed treatment. In one embodiment, a seed protectant coating comprising a pesticidal composition of the embodiments is used alone or in combination with one of the seed protectant coatings customarily used in seed treatment.

It is recognized that the genes encoding the pesticidal proteins can be used to transform insect pathogenic organisms. Such organisms include baculoviruses, fungi, protozoa, bacteria, and nematodes.

A gene encoding a pesticidal protein of the embodiments may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook; Maniatis et al. (Cold Spring Harbor Laboratory Press, Cold Spring Harbor, New York); Davis et al., eds. (1980) *Advanced Bacterial Genetics* (Cold Spring Harbor Laboratory Press, Cold Spring Harbor, New York) and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*, Azotobacteraceae and Nitrobacteraceae. Among eukaryotes are fungi, such as *Phycomycetes* and *Ascomycetes*, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa, P. fluorescens*), *Erwinia* spp., and *Flavobacterium* spp., and other such organisms, including Bt, *E. coli, Bacillus subtilis*, and the like.

Genes encoding the pesticidal proteins of the embodiments can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the embodiments can be introduced into a root-colonizing *Bacillus cereus* by standard methods known in the art.

Genes encoding pesticidal proteins can be introduced, for example, into the root-colonizing *Bacillus* by means of electrotransformation. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria, such as *E. coli*, for example. Advantages of having pesticidal proteins secreted are: (1) avoidance of potential cytotoxic effects of the pesticidal protein expressed; and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Pesticidal proteins of the embodiments can be fermented in a bacterial host and the resulting bacteria processed and used as a microbial spray in the same manner that Bt strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express Bt toxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EP0192319, and the references cited therein.

In the embodiments, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal composition(s) that is, for example, a suspension, a solution, an emulsion, a dusting powder, a dispersible granule or pellet, a wettable powder, and an emulsifiable concentrate, an aerosol or spray, an impregnated granule, an adjuvant, a coatable paste, a colloid, and also encapsulations in, for example, polymer substances. Such formulated compositions may be prepared by such conventional means as desiccation, lyophilization, homogenization, extraction, filtration, centrifugation, sedimentation, or concentration of a culture of cells comprising the polypeptide.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the pesticidal proteins produced by the bacterial strains of the embodiments include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the embodiments can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins of the embodiments, can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In other embodiments, it may be advantageous to treat the Cry toxin polypeptides with a protease, for example trypsin, to activate the protein prior to application of a pesticidal protein composition of the embodiments to the environment of the target pest. Methods for the activation of protoxin by a serine protease are well known in the art. See, for example, Cooksey (1968) *Biochem. J.* 6:445-454 and Carroll and Ellar (1989) *Biochem. J.* 261:99-105, the teachings of which are herein incorporated by reference. For example, a suitable activation protocol includes, but is not limited to, combining a polypeptide to be activated, for example a purified novel Cry polypeptide (e.g., having the amino acid sequence set forth in SEQ ID NO: 4 or SEQ ID NO: 8, and trypsin at a 1/100 weight ratio of protein/trypsin in 20 nM $NaHCO_3$, pH 8 and digesting the sample at 36° C. for 3 hours.

The compositions (including the transformed microorganisms and pesticidal proteins of the embodiments) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the pesticidal protein and/or transformed microorganisms of the embodiments may be mixed with grain to protect the grain during storage. It is generally important to obtain good control of pests in the early stages of plant growth, as this is the time when the plant can be most severely damaged. The compositions of the embodiments can conveniently contain another insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, an herbicide, an insecticide, a fertilizer, an inert carrier, and dead cells of a *Bacillus* strain or transformed microorganism of the embodiments.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae: *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (*Xylomyges*) *curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Mamestra configurata* Walker (bertha armyworm); *M. brassicae* Linnaeus (cabbage moth); *Melanchra picta* Harris (zebra caterpillar); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth); *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape colaspis); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); Blostomatidae spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); Cimicidae spp.; Coreidae spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); Pyrrhocoridae spp.; *Quadraspidiotus perniciosus* Comstock (San Jose scale); Reduviidae spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); Tinidae spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Willer (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cylindrotermes nordenskioeldi* Holmgren and *Pseudacanthotermes militaris* Hagen (sugarcane termite). Insects of the order Thysanoptera are also of interest, including but not limited to thrips, such as *Stenchaetothrips minutus* van Deventer (sugarcane thrips).

Insect pests may be tested for pesticidal activity of compositions of the embodiments in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83(6): 2480-2485. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXPERIMENTALS

Example 1—Gene Identification and *E. coli* Expression

Polynucleotides encoding insecticidal proteins were obtained from a screen of *Bacillus thuringiensis* isolates from an internal DuPont proprietary collection of *Bacillus thuringiensis* isolates. Table 1 shows the insecticidal protein identifier, the sequence identifier number for the polynucleotides encoding the insecticidal proteins, the sequence identifier number for the insecticidal proteins, and the internal strain designations.

TABLE 1

| Identifier | polynucleotide | polypeptide | Strain ID |
| --- | --- | --- | --- |
| MP032 | SEQ ID NO: 1 | SEQ ID NO: 2 | DP606 |
| MP049 | SEQ ID NO: 3 | SEQ ID NO: 4 | DP606 |
| MP051 | SEQ ID NO: 5 | SEQ ID NO: 6 | BD2101 |
| MP066 | SEQ ID NO: 7 | SEQ ID NO: 8 | DP606 |
| MP068 | SEQ ID NO: 9 | SEQ ID NO: 10 | DP606 |
| MP070 | SEQ ID NO: 11 | SEQ ID NO: 12 | DP606 |
| MP091S | SEQ ID NO: 13 | SEQ ID NO: 14 | DP2561 |
| MP109S | SEQ ID NO: 15 | SEQ ID NO: 16 | DP1644 |
| MP114 | SEQ ID NO: 17 | SEQ ID NO: 18 | BD574 |
| MP121 | SEQ ID NO: 19 | SEQ ID NO: 20 | DP432 |
| MP134S | SEQ ID NO: 21 | SEQ ID NO: 22 | BD574 |
| MP183S | SEQ ID NO: 23 | SEQ ID NO: 24 | DP1247 |
| MP185S | SEQ ID NO: 25 | SEQ ID NO: 26 | DP1247 |
| MP186S | SEQ ID NO: 27 | SEQ ID NO: 28 | DP1247 |
| MP195S | SEQ ID NO: 29 | SEQ ID NO: 30 | DP1247 |
| MP197S | SEQ ID NO: 31 | SEQ ID NO: 32 | DP1247 |
| MP208S | SEQ ID NO: 33 | SEQ ID NO: 34 | DP3219 |
| MP209S | SEQ ID NO: 35 | SEQ ID NO: 36 | DP3219 |
| MP212S | SEQ ID NO: 37 | SEQ ID NO: 38 | DP511 |
| MP214S | SEQ ID NO: 39 | SEQ ID NO: 40 | DP41 |
| MP217S | SEQ ID NO: 41 | SEQ ID NO: 42 | DP3219 |
| MP222S | SEQ ID NO: 43 | SEQ ID NO: 44 | DP3219 |
| MP234S | SEQ ID NO: 45 | SEQ ID NO: 46 | DP3219 |
| MP235S | SEQ ID NO: 47 | SEQ ID NO: 48 | DP3219 |
| MP237S | SEQ ID NO: 49 | SEQ ID NO: 50 | DP3219 |
| MP242S | SEQ ID NO: 51 | SEQ ID NO: 52 | DP1415 |
| MP243 | SEQ ID NO: 53 | SEQ ID NO: 54 | DP1415 |
| MP248 | SEQ ID NO: 55 | SEQ ID NO: 56 | DP227 |
| MP249S | SEQ ID NO: 57 | SEQ ID NO: 58 | DP371 |
| MP251M | SEQ ID NO: 59 | SEQ ID NO: 60 | DP616 |
| MP252S | SEQ ID NO: 61 | SEQ ID NO: 62 | DP552 |
| MP253 | SEQ ID NO: 63 | SEQ ID NO: 64 | DP264 |
| MP259S | SEQ ID NO: 65 | SEQ ID NO: 66 | DP552 |
| MP287S | SEQ ID NO: 67 | SEQ ID NO: 68 | MG5517 |
| MP288S | SEQ ID NO: 69 | SEQ ID NO: 70 | DP1415 |
| MP295S | SEQ ID NO: 71 | SEQ ID NO: 72 | DP940 |
| MP296S | SEQ ID NO: 73 | SEQ ID NO: 74 | DP760 |
| MP297S | SEQ ID NO: 75 | SEQ ID NO: 76 | DP760 |
| MP300S | SEQ ID NO: 77 | SEQ ID NO: 78 | DP1180 |
| MP304S | SEQ ID NO: 79 | SEQ ID NO: 80 | DP2087 |
| MP306S | SEQ ID NO: 81 | SEQ ID NO: 82 | DP59 |
| MP310S | SEQ ID NO: 83 | SEQ ID NO: 84 | BD380 |
| MP312S | SEQ ID NO: 85 | SEQ ID NO: 86 | DP996 |
| MP314S | SEQ ID NO: 87 | SEQ ID NO: 88 | DP736 |
| MP319S | SEQ ID NO: 89 | SEQ ID NO: 90 | DP760 |
| MP325S | SEQ ID NO: 91 | SEQ ID NO: 92 | DP2079 |
| MP326S | SEQ ID NO: 93 | SEQ ID NO: 94 | DP2079 |
| MP327S | SEQ ID NO: 95 | SEQ ID NO: 96 | DP2073 |
| MP334S | SEQ ID NO: 97 | SEQ ID NO: 98 | DP2079 |
| MP337S | SEQ ID NO: 99 | SEQ ID NO: 100 | DP2079 |
| MP342S | SEQ ID NO: 101 | SEQ ID NO: 102 | DP932 |
| MP356S | SEQ ID NO: 103 | SEQ ID NO: 104 | DP2093 |
| MP359S | SEQ ID NO: 105 | SEQ ID NO: 106 | DP1134 |
| MP360S | SEQ ID NO: 107 | SEQ ID NO: 108 | AM858 |
| MP437S | SEQ ID NO: 109 | SEQ ID NO: 110 | AM2753 |
| MP451S | SEQ ID NO: 111 | SEQ ID NO: 112 | AM1080 |
| MP452S | SEQ ID NO: 113 | SEQ ID NO: 114 | AM1096-2 |
| MP466S | SEQ ID NO: 115 | SEQ ID NO: 116 | DP2611 |
| MP468S | SEQ ID NO: 117 | SEQ ID NO: 118 | DP1659 |
| MP476S | SEQ ID NO: 119 | SEQ ID NO: 120 | AM2549 |
| MP482S | SEQ ID NO: 121 | SEQ ID NO: 122 | AM1118 |
| MP522S | SEQ ID NO: 123 | SEQ ID NO: 124 | JAPH0545 |
| MP529S | SEQ ID NO: 125 | SEQ ID NO: 126 | BD1553 |
| MP548S | SEQ ID NO: 127 | SEQ ID NO: 128 | AM16230 |
| MP552S | SEQ ID NO: 129 | SEQ ID NO: 130 | JAPH0797 |
| MP562S | SEQ ID NO: 131 | SEQ ID NO: 132 | PO423 |
| MP564S | SEQ ID NO: 133 | SEQ ID NO: 134 | JAPH0790 |
| MP566S | SEQ ID NO: 135 | SEQ ID NO: 136 | JAPH0842 |
| MP567S | SEQ ID NO: 137 | SEQ ID NO: 138 | PO450 |
| MP569S | SEQ ID NO: 139 | SEQ ID NO: 140 | PO219 |
| MP573S | SEQ ID NO: 141 | SEQ ID NO: 142 | AM15623 |
| MP574S | SEQ ID NO: 143 | SEQ ID NO: 144 | AM16083 |
| MP575S | SEQ ID NO: 145 | SEQ ID NO: 146 | AM15623 |
| MP581S | SEQ ID NO: 147 | SEQ ID NO: 148 | PO230 |
| MP599S | SEQ ID NO: 149 | SEQ ID NO: 150 | DP1021 |
| MP600S | SEQ ID NO: 151 | SEQ ID NO: 152 | DP1019 |
| MP601S | SEQ ID NO: 153 | SEQ ID NO: 154 | DP1289 |
| MP602S | SEQ ID NO: 155 | SEQ ID NO: 156 | DP333 |
| MP604S | SEQ ID NO: 157 | SEQ ID NO: 158 | DP1289 |
| MP626S | SEQ ID NO: 159 | SEQ ID NO: 160 | DP1246 |
| MP629S | SEQ ID NO: 161 | SEQ ID NO: 162 | DP1319 |
| MP630S | SEQ ID NO: 163 | SEQ ID NO: 164 | DP1246 |
| MP631S | SEQ ID NO: 165 | SEQ ID NO: 166 | DP1289 |
| MP632S | SEQ ID NO: 167 | SEQ ID NO: 168 | DP1289 |
| MP633S | SEQ ID NO: 169 | SEQ ID NO: 170 | DP1168 |
| MP634S | SEQ ID NO: 171 | SEQ ID NO: 172 | DP1168 |
| MP635S | SEQ ID NO: 173 | SEQ ID NO: 174 | DP1168 |
| MP639S | SEQ ID NO: 175 | SEQ ID NO: 176 | DP333 |
| MP640S | SEQ ID NO: 177 | SEQ ID NO: 178 | DP879 |
| MP644S | SEQ ID NO: 179 | SEQ ID NO: 180 | DP1019 |
| MP649S | SEQ ID NO: 181 | SEQ ID NO: 182 | DP1144 |
| MP651S | SEQ ID NO: 183 | SEQ ID NO: 184 | DP2398 |
| MP652S | SEQ ID NO: 185 | SEQ ID NO: 186 | DP2009 |
| MP653S | SEQ ID NO: 187 | SEQ ID NO: 188 | DP2059 |
| MP661S | SEQ ID NO: 189 | SEQ ID NO: 190 | DP1083B |
| MP666S | SEQ ID NO: 191 | SEQ ID NO: 192 | DP2083 |
| MP672S | SEQ ID NO: 193 | SEQ ID NO: 194 | DP2009 |
| MP696S | SEQ ID NO: 195 | SEQ ID NO: 196 | DP1798 |
| MP704S | SEQ ID NO: 197 | SEQ ID NO: 198 | DP1954 |
| MP724S | SEQ ID NO: 199 | SEQ ID NO: 200 | DP1940M |
| MP729S | SEQ ID NO: 201 | SEQ ID NO: 202 | PO573 |
| MP739S | SEQ ID NO: 203 | SEQ ID NO: 204 | DP2160M |
| MP755S | SEQ ID NO: 205 | SEQ ID NO: 206 | DP529M |
| MP773S | SEQ ID NO: 207 | SEQ ID NO: 208 | DP744 |
| MP799S | SEQ ID NO: 209 | SEQ ID NO: 210 | JAPH01606 |
| MP800S | SEQ ID NO: 211 | SEQ ID NO: 212 | JAPH01969 |
| MP801S | SEQ ID NO: 213 | SEQ ID NO: 214 | AM16543 |
| MP802S | SEQ ID NO: 215 | SEQ ID NO: 216 | AM16543 |
| MP805S | SEQ ID NO: 217 | SEQ ID NO: 218 | AM16543 |
| MP809S | SEQ ID NO: 219 | SEQ ID NO: 220 | JAPH01306 |
| MP815S | SEQ ID NO: 221 | SEQ ID NO: 222 | DP2581M |
| MP828S | SEQ ID NO: 223 | SEQ ID NO: 224 | DP3557M |

TABLE 1-continued

| Identifier | polynucleotide | polypeptide | Strain ID |
|---|---|---|---|
| MP831S | SEQ ID NO: 225 | SEQ ID NO: 226 | DP3073M |
| MP844S | SEQ ID NO: 227 | SEQ ID NO: 228 | DP3073M |
| MP852 | SEQ ID NO: 229 | SEQ ID NO: 230 | DP3632M |
| MP865S | SEQ ID NO: 231 | SEQ ID NO: 232 | DP638 |
| MP879S | SEQ ID NO: 233 | SEQ ID NO: 234 | JAPH01218 |
| MP887S | SEQ ID NO: 235 | SEQ ID NO: 236 | DP372 |
| MP891S | SEQ ID NO: 237 | SEQ ID NO: 238 | DP2290M |
| MP896S | SEQ ID NO: 239 | SEQ ID NO: 240 | DP2327M |
| MP898S | SEQ ID NO: 241 | SEQ ID NO: 242 | DP563M |
| MP935S | SEQ ID NO: 243 | SEQ ID NO: 244 | BD2894 |
| MP968 | SEQ ID NO: 245 | SEQ ID NO: 246 | JAPH2628M |
| MP989 | SEQ ID NO: 247 | SEQ ID NO: 248 | JAPH2732M |
| MP993 | SEQ ID NO: 249 | SEQ ID NO: 250 | JAPH2732M |
| MP997 | SEQ ID NO: 251 | SEQ ID NO: 252 | JAPH2754M |
| MP1049 | SEQ ID NO: 253 | SEQ ID NO: 254 | DP3227M |
| MP1066 | SEQ ID NO: 255 | SEQ ID NO: 256 | JAPH2416M |
| MP1067 | SEQ ID NO: 257 | SEQ ID NO: 258 | DP3104M |
| MP1080 | SEQ ID NO: 259 | SEQ ID NO: 260 | RGB0275B |
| MP1081 | SEQ ID NO: 261 | SEQ ID NO: 262 | BD2855 |
| MP1200 | SEQ ID NO: 263 | SEQ ID NO: 264 | BD2357 |
| MP1206 | SEQ ID NO: 265 | SEQ ID NO: 266 | BD3063 |
| MP1233 | SEQ ID NO: 267 | SEQ ID NO: 268 | BD2614 |
| MP1311 | SEQ ID NO: 269 | SEQ ID NO: 270 | 104429.0 |

The polynucleotides encoding the insecticidal polypeptides of Table 1 were cloned into a pET28a vector (Novagen®) and transformed into *E. coli* BL21 cells (Invitrogen). Large scale 1.0 L cultures were grown until O.D.600 nm~0.8 and then the cultures were induced with isopropyl β-D-1-thiogalactopyranoside (IPTG) 1 mM and allowed to grow for 16 hours at 16° C. The cell pellets were lysed with 50 mL of 500 mM NaCl/20 mM Tris/5 mM Imidazole/pH 7.9 with 0.02% lysozyme (w/v) and 0.1% Tween-20 and 1 tablet of Complete Protease Inhibitor (Roche) added. After lysis, the solutions were sonicated and the lysate centrifuged at 25,000 rpm for 30 minutes. The supernatant containing the soluble protein fraction were filtered through a 0.45 u vacuum filter and then 1 ml of Talon (Clontech) slurry is added and then incubated for binding on rotator at 100 rpm for 1 hour. The lysate is then added to a column and the bound protein is isolated and washed with 20 ml of 50 mmM NaCl/20 mM Tris/5 mM Imidazole/pH 7.9 and then eluted with 1.5 ml of 50 mmM NaCl/20 mM Tris/500 mM Imidazole/pH 7.9. The purified protein is then dialyzed into 50 mM sodium carbonate buffer pH10. The purified protein was submitted for insecticidal activity in panel of Lepidoptera and Coleoptera in vitro feeding assays.

Example 2—Insect Assays with Partially Purified Proteins

Insecticidal activity bioassay screens were conducted to evaluate the effects of the insecticidal proteins on a variety of Lepidoptera species: European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*) and the Coleoptera species western corn rootworm (*Diabrotica virgifera virgifera*).

Lepidoptera feeding assays were conducted on an artificial diet containing the purified protein in a 96 well plate set up. The purified protein (25 ul) is then added to the artificial diet. Two to five neonate larvas were placed in each well to feed ad libitum for 5 days. Results were expressed as positive for larvae reactions such as stunting and or mortality. Results were expressed as negative if the larvae were similar to the negative control that is feeding diet to which the above buffer only has been applied. A primary bioassay screen was performed for each purified protein at a single concentration on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*). The insect assays were scored as follows: 1=insecticidal activity; 0=no activity at the highest concentration tested.

The primary insecticidal assay results for the insecticidal polypeptides are shown in Table 2.

TABLE 2

| Identifier | polypeptide | WCRW | FAW | CEW | ECB | SBL | BCW | VBC |
|---|---|---|---|---|---|---|---|---|
| MP032 | SEQ ID NO: 2 | 0 | 0 | 0 | 0 | 0 | 0 | 1 |
| MP049 | SEQ ID NO: 4 | 0 | 0 | 0 | 0 | 0 | 0 | 1 |
| MP051 | SEQ ID NO: 6 | 0 | 0 | 0 | 0 | 1 | 0 | 1 |
| MP066 | SEQ ID NO: 8 | 0 | 0 | 0 | 0 | 0 | 0 | 1 |
| MP068 | SEQ ID NO: 10 | 0 | 0 | 0 | 0 | 0 | 0 | 1 |
| MP070 | SEQ ID NO: 12 | 0 | 0 | 0 | 0 | 0 | 0 | 1 |
| MP091S | SEQ ID NO: 14 | 1 | 0 | 0 | 0 | 0 | 0 | 0 |
| MP109S | SEQ ID NO: 16 | 0 | 0 | 0 | 0 | 0 | 0 | 1 |
| MP114 | SEQ ID NO: 18 | 0 | 0 | 0 | 0 | 1 | 0 | 1 |
| MP121 | SEQ ID NO: 20 | 0 | 0 | 0 | 0 | 1 | 0 | 1 |
| MP134S | SEQ ID NO: 22 | 0 | 0 | 0 | 0 | 1 | 0 | 1 |
| MP183S | SEQ ID NO: 24 | 0 | 0 | 0 | 0 | 0 | 0 | 1 |
| MP185S | SEQ ID NO: 26 | 0 | 0 | 0 | 0 | 1 | 0 | 1 |
| MP186S | SEQ ID NO: 28 | 0 | 0 | 0 | 0 | 1 | 0 | 1 |
| MP195S | SEQ ID NO: 30 | 0 | 0 | 0 | 0 | 0 | 0 | 1 |
| MP197S | SEQ ID NO: 32 | 1 | 0 | 0 | 0 | 0 | 0 | 0 |
| MP208S | SEQ ID NO: 34 | 0 | 0 | 0 | 0 | 1 | 0 | 1 |
| MP209S | SEQ ID NO: 36 | 0 | 0 | 0 | 0 | 1 | 0 | 1 |
| MP212S | SEQ ID NO: 38 | 0 | 0 | 0 | 0 | 0 | 0 | 1 |
| MP214S | SEQ ID NO: 40 | 1 | 0 | 0 | 0 | 0 | 0 | 0 |
| MP217S | SEQ ID NO: 42 | 1 | 0 | 0 | 0 | 0 | 0 | 0 |
| MP222S | SEQ ID NO: 44 | 0 | 0 | 0 | 1 | 1 | 0 | 1 |
| MP234S | SEQ ID NO: 46 | 0 | 0 | 0 | 0 | 1 | 0 | 1 |
| MP235S | SEQ ID NO: 48 | 0 | 0 | 0 | 0 | 1 | 0 | 0 |
| MP237S | SEQ ID NO: 50 | 0 | 0 | 1 | 1 | 1 | 0 | 0 |
| MP242S | SEQ ID NO: 52 | 0 | 1 | 0 | 1 | 1 | 0 | 0 |
| MP243 | SEQ ID NO: 54 | 0 | 0 | 0 | 1 | 1 | 0 | 1 |
| MP248 | SEQ ID NO: 56 | 0 | 0 | 0 | 0 | 1 | 0 | 0 |
| MP249S | SEQ ID NO: 58 | 0 | 0 | 0 | 0 | 0 | 0 | 1 |

TABLE 2-continued

| Identifier | polypeptide | WCRW | FAW | CEW | ECB | SBL | BCW | VBC |
|---|---|---|---|---|---|---|---|---|
| MP251M | SEQ ID NO: 60 | 0 | 1 | 1 | 0 | 1 | 0 | 1 |
| MP252S | SEQ ID NO: 62 | 0 | 0 | 0 | 1 | 0 | 0 | 1 |
| MP253 | SEQ ID NO: 64 | 0 | 1 | 1 | 1 | 1 | 0 | 1 |
| MP259S | SEQ ID NO: 66 | 0 | 0 | 1 | 1 | 1 | 0 | 0 |
| MP287S | SEQ ID NO: 68 | 0 | 0 | 0 | 1 | 0 | 0 | 0 |
| MP288S | SEQ ID NO: 70 | 0 | 0 | 1 | 1 | 1 | 0 | 0 |
| MP295S | SEQ ID NO: 72 | 0 | 0 | 1 | 1 | 1 | 0 | 0 |
| MP296S | SEQ ID NO: 74 | 1 | 0 | 0 | 0 | 0 | 0 | 0 |
| MP297S | SEQ ID NO: 76 | 0 | 1 | 1 | 1 | 1 | 0 | 1 |
| MP300S | SEQ ID NO: 78 | 0 | 1 | 1 | 1 | 1 | 0 | 1 |
| MP304S | SEQ ID NO: 80 | 0 | 0 | 0 | 0 | 1 | 0 | 1 |
| MP306S | SEQ ID NO: 82 | 0 | 0 | 0 | 0 | 1 | 0 | 1 |
| MP310S | SEQ ID NO: 84 | 0 | 0 | 0 | 0 | 1 | 0 | 0 |
| MP312S | SEQ ID NO: 86 | 0 | 1 | 0 | 1 | 1 | 0 | 1 |
| MP314S | SEQ ID NO: 88 | 0 | 0 | 0 | 0 | 1 | 0 | 0 |
| MP319S | SEQ ID NO: 90 | 0 | 0 | 0 | 1 | 0 | 0 | 1 |
| MP325S | SEQ ID NO: 92 | 0 | 0 | 0 | 1 | 1 | 0 | 0 |
| MP326S | SEQ ID NO: 94 | 0 | 0 | 0 | 0 | 1 | 0 | 0 |
| MP327S | SEQ ID NO: 96 | 0 | 0 | 0 | 1 | 1 | 0 | 1 |
| MP334S | SEQ ID NO: 98 | 0 | 0 | 0 | 0 | 1 | 0 | 1 |
| MP337S | SEQ ID NO: 100 | 0 | 0 | 0 | 0 | 0 | 0 | 1 |
| MP342S | SEQ ID NO: 102 | 0 | 0 | 0 | 1 | 0 | 0 | 0 |
| MP356S | SEQ ID NO: 104 | 0 | 1 | 0 | 1 | 1 | 0 | 1 |
| MP359S | SEQ ID NO: 106 | 0 | 0 | 0 | 1 | 0 | 0 | 0 |
| MP360S | SEQ ID NO: 108 | 0 | 0 | 0 | 0 | 0 | 0 | 1 |
| MP437S | SEQ ID NO: 110 | 0 | 0 | 0 | 0 | 1 | 0 | 1 |
| MP451S | SEQ ID NO: 112 | 0 | 0 | 0 | 1 | 1 | 0 | 1 |
| MP452S | SEQ ID NO: 114 | 0 | 0 | 0 | 1 | 1 | 0 | 1 |
| MP466S | SEQ ID NO: 116 | 1 | 0 | 0 | 0 | 0 | 0 | 0 |
| MP468S | SEQ ID NO: 118 | 1 | 0 | 0 | 0 | 0 | 0 | 0 |
| MP476S | SEQ ID NO: 120 | 0 | 0 | 0 | 1 | 1 | 0 | 1 |
| MP482S | SEQ ID NO: 122 | 0 | 1 | 1 | 1 | 1 | 1 | 1 |
| MP522S | SEQ ID NO: 124 | 0 | 0 | 0 | 1 | 0 | 0 | 0 |
| MP529S | SEQ ID NO: 126 | 0 | 0 | 0 | 1 | 1 | 0 | 0 |
| MP548S | SEQ ID NO: 128 | 0 | 0 | 0 | 1 | 1 | 0 | 0 |
| MP552S | SEQ ID NO: 130 | 0 | 0 | 0 | 0 | 1 | 0 | 0 |
| MP562S | SEQ ID NO: 132 | 0 | 0 | 0 | 1 | 1 | 0 | 0 |
| MP564S | SEQ ID NO: 134 | 0 | 1 | 1 | 1 | 1 | 0 | 1 |
| MP566S | SEQ ID NO: 136 | 0 | 0 | 0 | 0 | 1 | 0 | 0 |
| MP567S | SEQ ID NO: 138 | 0 | 0 | 0 | 0 | 1 | 0 | 0 |
| MP569S | SEQ ID NO: 140 | 0 | 0 | 0 | 0 | 1 | 0 | 1 |
| MP573S | SEQ ID NO: 142 | 0 | 0 | 1 | 0 | 1 | 0 | 0 |
| MP574S | SEQ ID NO: 144 | 0 | 0 | 1 | 0 | 1 | 0 | 0 |
| MP575S | SEQ ID NO: 146 | 0 | 0 | 0 | 0 | 1 | 0 | 0 |
| MP581S | SEQ ID NO: 148 | 0 | 0 | 0 | 0 | 1 | 0 | 0 |
| MP599S | SEQ ID NO: 150 | 0 | 1 | 0 | 0 | 0 | 1 | 0 |
| MP600S | SEQ ID NO: 152 | 0 | 1 | 1 | 1 | 1 | 1 | 1 |
| MP601S | SEQ ID NO: 154 | 0 | 0 | 0 | 1 | 1 | 0 | 1 |
| MP602S | SEQ ID NO: 156 | 0 | 0 | 0 | 1 | 1 | 0 | 1 |
| MP604S | SEQ ID NO: 158 | 0 | 0 | 1 | 0 | 1 | 0 | 0 |
| MP626S | SEQ ID NO: 160 | 0 | 0 | 0 | 1 | 1 | 0 | 1 |
| MP629S | SEQ ID NO: 162 | 0 | 1 | 1 | 1 | 1 | 1 | 0 |
| MP630S | SEQ ID NO: 164 | 0 | 0 | 1 | 0 | 1 | 0 | 1 |
| MP631S | SEQ ID NO: 166 | 0 | 0 | 1 | 1 | 1 | 1 | 1 |
| MP632S | SEQ ID NO: 168 | 0 | 0 | 1 | 1 | 1 | 1 | 1 |
| MP633S | SEQ ID NO: 170 | 0 | 0 | 0 | 0 | 1 | 0 | 1 |
| MP634S | SEQ ID NO: 172 | 0 | 0 | 0 | 0 | 1 | 0 | 1 |
| MP635S | SEQ ID NO: 174 | 0 | 0 | 0 | 1 | 1 | 0 | 1 |
| MP639S | SEQ ID NO: 176 | 0 | 0 | 0 | 0 | 1 | 0 | 1 |
| MP640S | SEQ ID NO: 178 | 0 | 0 | 0 | 1 | 0 | 0 | 0 |
| MP644S | SEQ ID NO: 180 | 0 | 0 | 0 | 1 | 0 | 0 | 0 |
| MP649S | SEQ ID NO: 182 | 0 | 0 | 0 | 1 | 1 | 0 | 1 |
| MP651S | SEQ ID NO: 184 | 0 | 0 | 0 | 1 | 1 | 0 | 1 |
| MP652S | SEQ ID NO: 186 | 0 | 0 | 0 | 1 | 1 | 0 | 0 |
| MP653S | SEQ ID NO: 188 | 0 | 0 | 0 | 1 | 1 | 0 | 0 |
| MP661S | SEQ ID NO: 190 | 0 | 0 | 0 | 1 | 1 | 0 | 1 |
| MP666S | SEQ ID NO: 192 | 0 | 0 | 0 | 1 | 1 | 0 | 1 |
| MP672S | SEQ ID NO: 194 | 0 | 0 | 0 | 0 | 0 | 0 | 1 |
| MP696S | SEQ ID NO: 196 | 0 | 0 | 0 | 1 | 1 | 0 | 1 |
| MP704S | SEQ ID NO: 198 | 0 | 0 | 0 | 1 | 1 | 0 | 1 |
| MP724S | SEQ ID NO: 200 | 0 | 0 | 0 | 1 | 1 | 1 | 1 |
| MP729S | SEQ ID NO: 202 | 0 | 0 | 0 | 0 | 0 | 0 | 1 |
| MP739S | SEQ ID NO: 204 | 0 | 0 | 0 | 0 | 0 | 0 | 1 |
| MP755S | SEQ ID NO: 206 | 0 | 0 | 0 | 0 | 0 | 0 | 1 |
| MP773S | SEQ ID NO: 208 | 0 | 0 | 0 | 0 | 1 | 0 | 1 |
| MP799S | SEQ ID NO: 210 | 0 | 0 | 0 | 1 | 0 | 0 | 0 |
| MP800S | SEQ ID NO: 212 | 0 | 0 | 0 | 0 | 1 | 0 | 0 |
| MP801S | SEQ ID NO: 214 | 0 | 0 | 0 | 1 | 0 | 0 | 0 |

TABLE 2-continued

| Identifier | polypeptide | WCRW | FAW | CEW | ECB | SBL | BCW | VBC |
|---|---|---|---|---|---|---|---|---|
| MP802S | SEQ ID NO: 216 | 0 | 0 | 1 | 1 | 1 | 1 | 1 |
| MP805S | SEQ ID NO: 218 | 0 | 0 | 0 | 0 | 1 | 0 | 0 |
| MP809S | SEQ ID NO: 220 | 0 | 0 | 0 | 1 | 0 | 0 | 0 |
| MP815S | SEQ ID NO: 222 | 0 | 0 | 1 | 1 | 1 | 0 | 1 |
| MP828S | SEQ ID NO: 224 | 0 | 0 | 0 | 1 | 1 | 0 | 0 |
| MP831S | SEQ ID NO: 226 | 0 | 0 | 0 | 1 | 1 | 0 | 1 |
| MP844S | SEQ ID NO: 228 | 0 | 0 | 0 | 1 | 1 | 0 | 1 |
| MP852 | SEQ ID NO: 230 | 0 | 0 | 0 | 1 | 1 | 0 | 0 |
| MP865S | SEQ ID NO: 232 | 0 | 0 | 0 | 0 | 0 | 0 | 1 |
| MP879S | SEQ ID NO: 234 | 1 | 0 | 0 | 0 | 0 | 0 | 0 |
| MP887S | SEQ ID NO: 236 | 0 | 1 | 0 | 1 | 0 | 0 | 0 |
| MP891S | SEQ ID NO: 238 | 0 | 0 | 1 | 1 | 1 | 0 | 1 |
| MP896S | SEQ ID NO: 240 | 0 | 0 | 0 | 0 | 1 | 0 | 0 |
| MP898S | SEQ ID NO: 242 | 0 | 0 | 0 | 1 | 1 | 0 | 0 |
| MP935S | SEQ ID NO: 244 | 0 | 0 | 0 | 0 | 1 | 0 | 1 |
| MP968 | SEQ ID NO: 246 | 0 | 0 | 0 | 1 | 0 | 0 | 0 |
| MP989 | SEQ ID NO: 248 | 0 | 0 | 0 | 0 | 1 | 0 | 1 |
| MP993 | SEQ ID NO: 250 | 1 | 0 | 0 | 0 | 0 | 0 | 1 |
| MP997 | SEQ ID NO: 252 | 0 | 0 | 0 | 0 | 1 | 0 | 1 |
| MP1049 | SEQ ID NO: 254 | 1 | 0 | 0 | 1 | 0 | 0 | 0 |
| MP1066 | SEQ ID NO: 256 | 0 | 0 | 0 | 0 | 0 | 0 | 1 |
| MP1067 | SEQ ID NO: 258 | 0 | 0 | 0 | 0 | 0 | 0 | 1 |
| MP1080 | SEQ ID NO: 260 | 0 | 0 | 0 | 0 | 0 | 0 | 1 |
| MP1081 | SEQ ID NO: 262 | 0 | 0 | 0 | 0 | 0 | 0 | 1 |
| MP1200 | SEQ ID NO: 264 | 0 | 0 | 0 | 0 | 0 | 0 | 1 |
| MP1206 | SEQ ID NO: 266 | 1 | 0 | 0 | 0 | 0 | 0 | 0 |
| MP1233 | SEQ ID NO: 268 | 0 | 1 | 1 | 1 | 1 | 1 | 1 |
| MP1311 | SEQ ID NO: 270 | 1 | 1 | 1 | 1 | 1 | 1 | 1 |

Example 3—Transient Expression in Soybean Leaves and Insect Bioassay

For soybean expression optimized coding sequences are designed. To confirm activity of the insecticidal polypeptides of the disclosure a transient expression system under control of the AtUBQ10 promoter (Day, et. al., (1999) *Plant Mol. Biol.* 40:771-782; Norris S R et al (1993) *Plant Mol Biol.* 21(5):895-906) can be utilized. The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, excised leaf disks of soybean (*Glycine max*), are agro-infiltrated with normalized bacterial cell cultures of test and control strains. After 4 days leaf disks are infested with 2 neonates of Soybean Looper (SBL) (*Chrysodeixis includens*), Corn Earworm, (CEW) (*Helicoverpa zea*), Velvetbean Caterpillar (VBC) (*Anticarsia gemmatalis*), or Fall Armyworm (*Spodoptera frugiperda*) alone. Control leaf discs are generated with *Agrobacterium* containing only a DsRed2 fluorescence marker (Clontech™, 1290 Terra Bella Ave. Mountain View, California 94043) expression vector. Leaf discs from noninfiltrated plants are included as a second control. The consumption of green leaf tissue is scored three days after infestation and given scores of 0 to 9.

Example 4—Transient Expression and Insect Bioassay on Transient Maize Leaf Tissues Polynucleotides of the disclosure are cloned into a transient expression vector under control of the maize ubiquitin promoter (Christensen and Quail, (1996) *Transgenic Research* 5:213-218) and a duplicated version of the promoter from the mirabilis mosaic virus (DMMV PRO; Dey and Maiti, (1999) *Plant Mol. Biol.,* 40:771-82). The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, young plantlets of maize are agro-infiltrated with normalized bacterial cell cultures of test and control strains. Leaf discs are generated from each plantlet and infested WCRW (*Diabrotica virgifera*) along with appropriate controls. The degree of consumption of green leaf tissues is scored after 2 days of infestation.

Example 5—*Agrobacterium*-Mediated Transformation of Maize and Regeneration of Transgenic Plants For *Agrobacterium*-mediated transformation of maize with a polynucleotide of the disclosure the method of Zhao can be used (U.S. Pat. No. 5,981,840 and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the polynucleotide to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 6—Transformation of Soybean Embryos

Soybean embryos are bombarded with a plasmid containing a polynucleotide of the disclosure operably linked to a suitable promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures are maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures are then transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation includes, but is not limited to: the 35S promoter from Cauliflower Mosaic Virus (Odell, et al., (1985) Nature 313:810-812), the hygromycin phosphotransferase gene from plasmid pJR225 (from *E. coli*; Gritz, et al., (1983) Gene 25:179-188), and the 3' region of the nopaline synthase gene from the T DNA of the Ti plasmid of *Agrobacterium tumefaciens*. The expression cassette comprising a polynucleotide of the disclosure operably linked to a suitable promoter can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1M), and 50 µL CaCl2 (2.5M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension is sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue is divided in half and placed back into liquid and cultured as described above.

Five to seven days post bombardment the liquid media is exchanged with fresh media, and eleven to twelve days post-bombardment with fresh media containing 50 mg/mL hygromycin. This selective media is refreshed weekly. Seven to eight weeks post-bombardment, green, transformed tissue is observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos or regenerated into whole plants by maturation and germination of individual somatic embryos.

Example 7—Regeneration of Soybean Somatic Embryos into Plants

In order to obtain whole plants from embryogenic suspension cultures, the tissue must be regenerated.

Embryo Maturation

Embryos are cultured for 4-6 weeks at 26 □C in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/m$^2$s. After this time embryo clusters are removed to a solid agar media, SB166, for 1-2 weeks. Clusters are then subcultured to medium SB103 for 3 weeks. During this period, individual embryos are removed from the clusters and screened for ABA accumulation. It should be noted that any detectable phenotype, resulting from the expression of the genes of interest, could be screened at this stage.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then planted in Redi-Earth™ in 24-cell pack tray, covered with clear plastic dome. After 2 weeks the dome is removed and plants hardened off for a further week. If plantlets looked hardy they are transplanted to 10" pot of Redi-Earth™ with up to 3 plantlets per pot.

Analysis of Leaf Tissues from Transgenic Soybean Events

Leaf tissue is harvested at approximately V3/V4 and fed to Lepidopteran species of interest. leaf disks are infested with 2 neonates of Soybean Looper (SBL) (*Chrysodeixis includens*), Corn Earworm, (CEW) (*Helicoverpa zea*), Velvetbean Caterpillar (VBC) (*Anticarsia gemmatalis*), or Fall Armyworm (*Spodoptera frugiperda*) alone. Leaf discs from wild type plants are included as a control. The consumption of green leaf tissue is scored five days after infestation and given scores of 0 to 9. Protein expression of can be confirmed by western blot using antibodies raised to the polypeptide.

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed:

1. A recombinant polynucleotide encoding an insecticidal polypeptide comprising an amino acid sequence having at least 90% sequence identity to SEQ ID NO: 268, wherein the polynucleotide is operably linked to a heterologous regulatory element.

2. The recombinant polynucleotide of claim 1, wherein the polynucleotide is SEQ ID NO: 267.

3. The recombinant polynucleotide of claim 1, wherein the polynucleotide is codon optimized for expression in an agricultural crop.

4. A DNA construct comprising the recombinant polynucleotide of claim 1.

5. A host cell comprising the recombinant polynucleotide of claim 1.

6. A host cell comprising the DNA construct of claim 4.

7. A transgenic plant comprising the polynucleotide of claim 1.

8. A transgenic plant comprising the DNA construct of claim 4.

9. A method of inhibiting growth or killing an insect pest or pest population, comprising contacting the insect pest with the insecticidal polypeptide of claim 1.

10. A method of inhibiting growth or killing an insect pest or pest population comprising expressing in a plant the polynucleotide of claim 1.

11. A method for controlling a pest infestation comprising providing in the diet of the pest the transgenic plant of claim 7 or a part thereof.

12. A method for improving the yield of a crop comprising growing the transgenic plant of claim 7, wherein the yield of the crop is increased in the presence of an insect pest relative to the crop not comprising said transgenic plant.

13. The method of claim 9, wherein the insect pest or pest population is resistant to at least one Cry insecticidal protein.

14. The host cell of claim 5, wherein the host cell is a bacterial cell or a plant cell.

15. The host cell of claim 14, wherein the plant cell is a monocot or a dicot plant cell.

16. The transgenic plant of claim 7, wherein the plant is selected from maize, soybean, wheat, rice, sorghum, sunflower, barley, sugarcane, potatoes, tomatoes, cotton, *Brassica* spp., peanut, or alfalfa.

17. The transgenic plant of claim 7, further comprising an additional polynucleotide of interest selected from a polynucleotide encoding a polypeptide having pesticidal activity, insecticidal activity, herbicide resistance, or disease resistance.

\* \* \* \* \*

SEQUENCE LISTING

```
Sequence total quantity: 270
SEQ ID NO: 1            moltype = DNA  length = 2370
FEATURE                 Location/Qualifiers
source                  1..2370
                        mol_type = other DNA
                        organism = Bacillus thuringiensis
SEQUENCE: 1
atgtccgagg gctatgatag agaatatttt gcaaatcctg aagtgtttgc tgtaccatcg  60
ggagttacaa cggggattaa tatagttact aaattactgg gatggttagg ggttccattg  120
gttggagaag cagcgacagc tcttaatctc attctaggtc aattatggcc ggcatcagga  180
aacccgtggg ctgaattaat gataatggta gaagaactca taaatcaaaa aatagaagag  240
gctgtaagaa acaaagcact tgcagatttg gccaattcag gtagagcgct ccaatcctat  300
ttaaacgcat ttgaagattg gcaaaaaaac cctaataatt ttcggagtaa agagctagta  360
agagaaagat tttcaaacgc ggaacattca ttgcgcaccg aaatgagttc ttttgccata  420
agaggatttg aaataccact tttggcaaca tatgcgcaag ctgctaattt acatttattt  480
ctaattaaag atgttcaaat ttatgggaaa gaatggggat attctcaagg tgatattgat  540
ttattttata gagaacaagt agagtttacg aaagaataca ccgaacactg tatcaatatt  600
tataatgatg gtctaaataa attaaaaggt tcgagtgcta agcaatggat tacatttaat  660
cgcttccgta gagaaatgac tttgacggta ctagatgtgg tttcattatt cccgaactat  720
gatgtacgta tgtacccttt aaaaacaaat acagagctaa cgagaacaat ttatactgat  780
ccgcttggtt acacgaaaac ggattctagt aatacaccac catggtataa ttatgggtct  840
agtttctcat atatagaaag tatagcgatt ccatccccta cagcggttaa gtggttacag  900
tcagttagaa tttattcaaa attcacaagg gctacaccac aaagtgcgga ttattgggca  960
ggacatacta taacatatcg atttactggc gatagttata atgtattggc taattatgga  1020
gatatatcga atcctgtagc tgtagataat tattattttg acacgactga aatttataga  1080
gtttcatcat ctgttgcttc aagcacaaat gctggtgtta agttattaac tactaaggct  1140
atatttaatg ggataaatac acaaaatgga ttagagagtt atgagtatgt aaaatcatcg  1200
aactttttta atgaactaaa agacacaatt acagagctac ctgttcagtt atccaatcct  1260
cctacctacg gggatcctga acagtacagc cataggctat cctatatttc taatgctcca  1320
acagagtaca gttggggagg atatagaatt gagggactaa tcccagtact tggttggaca  1380
catactagtt taactcgaca acaccagata aattctgaaa caattactca aattccaatg  1440
gtaaaacaaa atttcggatt acctatcata gctggacctg gatttacagg gggagatata  1500
ctaaatttaa ctattcaggc aattaaagag aaatcattga cgctaagagt taagtacgat  1560
ggttctccat cgcaaaaatt ccgtattaga atcaagtatg catctatcag agcaggaaac  1620
tttaaaatat cttctaaatc tgttgagaac ccttcaatag atgagacttc atttgcattt  1680
aaaaaatcga tggatagcac tactgattta acatacgaaa attttgtata tgcagaatcc  1740
tcacctatag cattgggaaa tccaggtatc tcgcgtaatt tcgatataac gctaacaaaa  1800
caagcggctt ctggcgccaa tgtttctact atggatacta tatatattga tagaattgaa  1860
ttcatcccag taaaggcaac atacgaggcg gagacagatt tagaaacagc gaagaaagca  1920
gtgaatgcct tgtttacaaa tacaaaagat ggcttacgaa caggcgtaac ggattatgaa  1980
gtgaatcaag cggcaaactt agtggaatgc ctatcggatg atttgtatcc aaatgaaaaa  2040
cgcttgttat ttgatgcagt cagagaggca aaacgactca gcgaggcacg taatttacta  2100
caagatccag atttccaaga gataaatgga gaaaatggat ggacggcaag tacgggagtc  2160
gagattatag aaggagatgc tgtatttaaa ggacgttatc tacgcctacc aggtgcacga  2220
gaaatggata cggaaacgta tcctacgtat ctatatcaaa aagtagagga aggtgtatta  2280
aaaccataca caagatatag attgagaggg tttgtcggaa gtagtcaagg cttggaaatt  2340
ttcacaattc gtcatcagac gaatcgaatt                                  2370

SEQ ID NO: 2            moltype = AA  length = 790
FEATURE                 Location/Qualifiers
source                  1..790
                        mol_type = protein
                        organism = Bacillus thuringiensis
SEQUENCE: 2
MSEGYDREYF ANPEVFAVPS GVTTGINIVT KLLGWLGVPL VGEAATALNL ILGQLWPASG  60
NPWAELMIMV EELINQKIEE AVRNKALADL ANSGRALQSY LNAFEDWQKN PNNFRSKELV  120
RERFSNAEHS LRTEMSSFAI RGFEIPLLAT YAQAANLHLF LIKDVQIYGK EWGYSQGDID  180
LFYREQVEFT KEYTEHCINI YNDGLNKLKG SSAKQWITFN RFRREMTLTV LDVVSLFPNY  240
DVRMYPLKTN TELTRTIYTD PLGYTKTDSS NTPPWYNYGS SFSYIESIAI PSPTAVKWLQ  300
SVRIYSKFTR ATPQSADYWA GHTITYRFTG DSYNVLANYG DISNPVAVDN YYFDTTEIYR  360
```

```
VSSSVASSTN AGVKLLTTKA IFNGINTQNG LESYEYVKSS NFFNELKDTI TELPVQLSNP  420
PTYGDPEQYS HRLSYISNAP TEYSWGGYRI EGLIPVLGWT HTSLTRQHQI NSETITQIPM  480
VKQNFGLPII AGPGFTGGDI LNLTIQAIKE KSLTLRVKYD GSPSQKFRIR IKYASIRAGN  540
FKISSKSVEN PSIDETSFAF KKSMDSTTDL TYENFVYAES SPIALGNPGI SRNFDITLTK  600
QAASGANVST MDTIYIDRIE FIPVKATYEA ETDLETAKKA VNALFTNTKD GLRTGVTDYE  660
VNQAANLVEC LSDDLYPNEK RLLFDAVREA KRLSEARNLL QDPDFQEING ENGWTASTGV  720
EIIEGDAVFK GRYLRLPGAR EMDTETYPTY LYQKVEEGVL KPYTRYRLRG FVGSSQGLEI  780
FTIRHQTNRI                                                         790

SEQ ID NO: 3              moltype = DNA  length = 2583
FEATURE                   Location/Qualifiers
source                    1..2583
                          mol_type = other DNA
                          organism = Bacillus thuringiensis
SEQUENCE: 3
atgttttga atgggtatgt aaatactgtg tacgcagaca gtaagacaaa tcagatttct    60
acaacgcagg aaaaccaaca gaaagagatg gatcgaaaag gattacttgg gtattatttc   120
aaaggaaaag attttagtaa tcttattatg ttttcaccaa cacgtgataa taccctatt   180
tatgaccaac aaacagcgaa tacattacta gataaaaaac aacaagaata tcagtctatt   240
cgctggattg gtttgatcca gagtaaagaa acgggtgatt tcacatttaa cttatcagat   300
gatgaacatg cgattataga aatagatgga aaagttattt ctcataaagg taagaaaag    360
caagttgttc atttggaaaa agggaagttg gttccaataa aagttgagta tcaatcagat   420
gaaacattaa atatggatag tcaaaccttt aaaaatctta agctattcaa agtcgatagt   480
caaaatcaat cccatcaagt ccaactagat gaattaagaa accctgcgtt taataaaaaa   540
gaaacacaag aattcatagc gaaagcatca aaaacaaatc ttttactca aaaaactaag    600
agagacattg atgaagtcat ggatacagat ggagactcat ttccagattt ttgggaggaa   660
aatggataca cgattcaaaa taaaattgct gtcaaatggg atgattcgct agcaagtaaa   720
gggtatacaa aatttgtttc gaatccacta gatagccaca cagttggcga tcctatacc    780
gattatgaaa aagcagcgag agatttagat ctagcaaatg caaagaaac atttaaccca    840
ttagtagctg cttttccaag cgtgaatgtt aatatgaaa aagtaatatt atcccaat      900
gaaaatttat ctaacagcgc agagtctcac tcatctacaa attggtccta tacaaataca   960
gaaggagcat ctgttgaagc agggattgga ccaacaggtc tttcttttgg agtgagtgta  1020
aactatcaac attctgaaac agttgcacag gaatggggga catctacagg aaatacttcg  1080
caattcaata cagcttcagc agggtatttg aatgcgaata ttcgtataa taatgtaggg  1140
actggtgcca tctatgaggt gaaacctaca acaagttttg tgctggataa aaataccatc  1200
gcaacgatta cggcaaaatc gaattcaaca gctttaaaata tatctcctgg agaaagttat  1260
ccgaaaaaag gcaaaatgg aatcgctata acatcaatgg atgattttaa ttcccatcca   1320
attacattaa ataaacaaca agtagatcaa ttgttaaata ataaacctat gatgttggaa   1380
acaaaccaaa cagatggcgt ttataaaata aagatacag gtggtaatct tgtgaccagt   1440
ggcgaatgga atggtgtgac acaacaagtt gaagccaaaa ctgcttctat tatcgtggat   1500
gatgaaaac gtgtggcaga gaaacgtgtg gccgcaaaag attataatta tccggaagat   1560
aaaacaccat cgttaacctt aaaagatgcg ctgaagcttt cataccctga ccagataaaa   1620
gaagtcgatg gattgttgta ttttgatgaa caacccatct atgaagcgtc tgtaatgact   1680
tacctagatg aaaatacagc aaaagaagtg aagaaacaaa tcaatgatac aaccggaaaa   1740
ttcaaggatg tcaataagtt atatgatgta aaactgacac aaagatgaa ttttacgctt    1800
aaaatggcta cattgtatga tgacgcggag caggggaaa acattgaacc tttaggacc    1860
tggtattaca cttataatgt tgttggggaa aataccggaa aagacagta tcgatcagct   1920
catcctagtg catctgtagc tctatcctca gaaatgaaaa agaaactaaa taaaaatacg   1980
aattattatc taagcatgta tatgaaggcc gattctaata cagagcctac aatagaagta   2040
actggtgaga atccgcaat aacgagtaaa aaagtaaaat taataatca gggttatcaa    2100
agagttgata ttttaataaa aaattttgaa agaaatccaa tagataaaat atatataaga   2160
ggaaatgata cgacaaatgt atattgggat gatatcgcta tttcagaggt atcagctata   2220
agtccagcta gtctatcaga tcaagaaatt aaggaaatat ataaagatta caccgaacaa   2280
attgttgatt ggtcaaatgg gaagtattta gacaatgtta ctttcaagaa tatcaaaccc   2340
ttacaaaatt atgtaaaaaa atacagagtt gaatatctca gattcggaca tcctgaggat   2400
acaattaatc aggttagaga cagccgtgaa gttaatgcta atggaagtgt gcaagttaat   2460
atgttggatt ataataaagg acatggaatt aatgtaggtt tttggggagg aggatacgct   2520
gtaactattt ttgctgtaac agatgacgga agagaaatac cggtttatga cataggtagc   2580
aaa                                                                 2583

SEQ ID NO: 4              moltype = AA  length = 861
FEATURE                   Location/Qualifiers
source                    1..861
                          mol_type = protein
                          organism = Bacillus thuringiensis
SEQUENCE: 4
MFLNGYVNTV YADSKTNQIS TTQENQQKEM DRKGLLGYYF KGKDFSNLIM FSPTRDNTLI    60
YDQQTANTLL DKKQQEYQSI RWIGLIQSKE TGDPFTFNLSD DEHAIIEIDG KVISHKGEK   120
QVVHLEKGKL VPIKVEYQSD ETLNMDSQTF KNLKLFKVDS QNQSHQVQLD ELRNPAFNKK   180
ETQEFIAKAS KTNLFTQKTK RDIDEVMDTD GDSIPDFWEE NGYTIQNKIA VKWDDSLASK   240
GYTKFVSNPL DSHTVGDPYT DYEKAARDLD LANAKETFNP LVAAFPSVNV NMEKVILSPN   300
ENLSNSAESH SSTNWSYTNT EGASVEAGIG PTGLSFGVSV NYQHSETVAQ EWGTSTGNTS   360
QFNTASAGYL NANVRYNNVG TGAIYEVKPT TSFVLDKNTI ATITAKSNST ALNISPGESY   420
PKKGQNGIAI TSMDDFNSHP ITLNKQQVDQ LLNNKPMMLE TNQTDGVYKI KDTGGNLVTG   480
GEWNGVTQQV EAKTASIIVD DGKRVAEKRV AAKDYNYPED KTPSLTLKDA LKLSYPDQIK   540
EVDGLLYFDE QPIYEASVMT YLDENTAKEV KKQINDTTGK FKDVNKLYDV KLTPKMNFTL   600
KMATLYDDAE QGENIEPLGH WYYTYNVVGG NTGKQYRSA HPSASVALSS EMKKKLNKNT   660
NYYLSMYMKA DSNTEPTIEV TGEKSAITSK KVKLNNQGYQ RVDILIKNFE RNPIDKIYIR   720
GNDTTNVYWD DIAISEVSAI SPASLSDQEI KEIYKDYTEQ IVDWSNGKYL DNVTFKNIKP   780
```

LQNYVKKYRV EYTRFGHPED TINQVRDSRE VNANGSVQVN MLDYNKGHGI NVGFWGGGYA 840
VTIFAVTDDG REIPVYDIGS K 861

```
SEQ ID NO: 5            moltype = DNA  length = 3084
FEATURE                 Location/Qualifiers
source                  1..3084
                        mol_type = other DNA
                        organism = Bacillus thuringiensis
SEQUENCE: 5
atgattagaa ataaaataga agaacgtatt gatatagaat cttcacaaat aagaacatgg   60
ataaattcag gtaaattctc agaagaaatg ttctctaatc gtttgaaaga acttaattta  120
acccttaata attttgtaag cattttaat gcaaaagaat tttatttaga taatagtgca  180
atgcactgga ttaatacttt attaaatgta ttaaaagaac aaaccacttc tgcagaatat  240
ggggagttta gtaaagcact tccttttaat agctttgtaa taccccttct agcttatgga  300
gataaactat tattaaaaga agttaatatt atcaattccg aattaatcga atggttttca  360
atacgtaaat ctatactttc agcactagcg cgtgaactaa gtgagctatc attaaaggtt  420
ttaatcaaag aaatacatat atcaaaaaaa ttaggagagc ttaaggggga agataagtat  480
tctcgttata agtatttcaa cgaaataatg cttaaggata atgattttgt tatcgacata  540
ttactagcat atccggtttt aacaaggtta ttaatcgaaa aaactgaaaa tttagttgct  600
tcatatattg aggcgctatc ccgttatata aatgattttc cttctataaa gattgatttt  660
catattgatg gttaattt gaaaaatata gaaggtaata atggagattc tcataaaat   720
ggcagaagtg ttatgctatt tgagtagag aatggtgaga agttggtata taaccacgt   780
tctatgagtg ttgatgagca ttttaatgat ttacttgaat ggataaattt taaagagaca  840
acatttgaat ttaaagggcc aaaaacaaaa aattataata catatggttg gcaagaattt   900
attaaacata accttgtga aacgtgaaa gaagtggagc aattttacta cgacaaggt    960
ggatatttag cactcttata tttattacga tcaaaagatt ttcattatga aaatttaatt 1020
gcaaatggag cacacccgat cttaatagac ttagaaactt tatttgataa tgtgattaat 1080
ttccaaaaca ttgatactaa atttggcgat ggtgtttcgg actatacgga atcaattta  1140
ggttctgcta tgttaccatt taattttgtc aaacgtaaag gtatggattt agattttagt 1200
gcattaggag ttcagaaga aggtgaacta gctgagtttt ctaaaatta tacaattgct  1260
aatgaaaata ctgatgaaat tcggttaaag gaaatacctg tgaaggctga aaaaaaagaa 1320
aatctccctg ttttatctaa tatatcagtt ggttcatatg agtatattga tgttatagaa 1380
gagggtttc aaacgttata cactttttc cttcgtaata agaagaatt agcttctaaa 1440
caaggtccta tttataaatt tgaaaatgat gaaattcgcc atgtgtttag aaatacaaat 1500
ctatatgtaa atttcctagt ttgtggaaag catccgaat acttacaaga tggcctaat  1560
aggaataaat tgttgatat ttatgggga gatgttaaaa atgaaagtaa atatattaaa  1620
tttgttaata gtgaatgtaa tgaccttttg aatcaagatg ttccatactt cactttaaa  1680
tttaatagca aggatttaat aaaatagtaaa gggaatatta ttaaagactt tatgataa  1740
agtagtttag aattagtatt agaacgttgt atgaagctta gtttaaatga ttgtcgacga 1800
caaagcagat atacgaat gtctttatct acattaaata aggatagagg agaagcggtt 1860
attaaaccta atcagaaaaa aatagctggt gttaaatctc aagatttctt agaagagtct 1920
ttaaacatag gtgaagaaat ttcaaatcat ttaagaccat tatcatccga aagagaaata 1980
aatcgtttg cttcatctat ggggaaaaat attgagggaa atggtattac tttgggccta 2040
ttagatgagg ggatttatga tggatttct gggttagcag tatttttgg ccagttagct 2100
tcagaaacaa atgataagtc tttaaaaata ttgtctgaag atattttga ttcgcttat  2160
aaaacagcta aatttaatca aagagatta aaaaatccct ctgcatttac tggaattggt 2220
tcgatactat acactgccgc ttattttcat ttgttatggg atggtcctaa atattgat   2280
gtagtagtag agaatttgaa tcttctagag aactaaatc aaacaaataa agtcacatgac 2340
tatcttactg gagaggcagg agtaattcta gtatgtctac gtatatacga aaaattctct 2400
aacgaacaag cactttcaat tgctattaaa ttaggagaat atatagtga agagtatctt 2460
gttccaggag aaatagacaa gttattaact ggttttttcgc gtggtgctta agggtatgca 2520
tggcccttaa tgtcattagg acatataaca aaagacgaga attttataaa attagctaat 2580
aaattaataa gatatgaaaa taattttattc gataagcaat atcaaaattg gcttgatttg 2640
aggcctcaag tgaaaataa aactggatct tattattggt gtcatgggc accaggtata  2700
gcattagcac gtcataatat cttgcagttg aatatgaacc ctcaagaaca aagggaacaa 2760
ttaactgaag atcttagaat tgcagttaaa gctactttaa agaatggatt aagtttaat  2820
cattgtttat gtcatggaga tttaggaaat atagatattt tgttaacaat agctaaagaa 2880
caaaataata tacaattatt aactgaagtc ttaagtatag gatttggcgt tttagaacaa 2940
ggtaaaaaat taaagtggat gaatggtatt gataaaaat ctgaaatgta tgggtttatg 3000
ctaggattat caggcatagg atttgaacta ttaagacttt ggaataatga tattccttca 3060
atactaaatt tagaattacc ttca                                        3084

SEQ ID NO: 6            moltype = AA  length = 1028
FEATURE                 Location/Qualifiers
source                  1..1028
                        mol_type = protein
                        organism = Bacillus thuringiensis
SEQUENCE: 6
MIRNKIEERI DIESSQIRTW INSGKFSEEM FSNRLKELNL TLNNFVSIFN AKEFYLDNSA   60
MHWINTLLNV LKEQTTSAEY GEFSKALPFN SFVIPLLAYG DKLLLKEVNI INSELIEWFS  120
IRKSILSALA RELSELSLKV LIKEIHISKK LGELKGEDKY SRYKYFNEIM LKDNDFVIDI  180
LLAYPVLTRL LIEKTENLVA SYIEALSRYI NDFPSIKIDF HIDGLILKNI EGNNGDSHKN  240
GRSVMLFEYE NGEKLVYKPR SMSVDEHFND LLEWINFKET TFEFKGPKTK NYNTYGWQEF  300
IKHKPCENVK EVEQFYYRQG GYLALLYLLR SKDFHYENLI ANGAHPILID LETLFDNVIN  360
FQNIDTKFGD GVSDYTESIL GSAMLPFNFV KRKGMDLDFS ALGVLEEGEL AEFSKNYTIA  420
NENTDEIRLK EIPVKAEKKE NLPVLSNISV GSYEYIDVIE EGFQTLYTFF LRNKEELASK  480
QGPIYKFEND EIRHVFRNTN LYVNFLVCGK HPEYLQDGLN RNKLFDILWG DVKNESKYIK  540
FVNSECNDLL NQDVPYFTFK FNSKDLINSK GNIIKDFYDK SSLELVLERC MKLSLNDCRR  600
QSRYIRMSLS TLNKDRGEAV IKPNPEKIAG VKSQDFLEES LNIGEEISNH LRPLSSEREI  660
```

```
NRFASSMGKN IEGNGITLGP LDEGIYDGFS GLAVFFGQLA SETNDKSLKI LSEDIFDYAY    720
KTAKFNHKRL KNPSAFTGIG SILYTAAYFH LLWDGPKYYD VVVENLNLLE ELNQTNKVHD    780
YLTGEAGVIL VCLRIYEKFS NEQALSIAIK LGEYIVEELS VPGEIDKLLT GFSHGASGYA    840
WPLMSLGHIT KDEKFIKLAN KLIRYENNLF DKQYQNWLDL RPQVKNKTGS YYWCHGAPGI    900
ALARHNILQL NMNPQEQREQ LTEDLRIAVK ATLKNGFKFN HCLCHGDLGN IDILLTIAKE    960
QNNIQLLTEV LSIGFGVLEQ GKKLKWMNGI DKKSEMYGFM LGLSGIGFEL LRLWNNDIPS   1020
ILNLELPS                                                           1028

SEQ ID NO: 7            moltype = DNA  length = 1668
FEATURE                 Location/Qualifiers
source                  1..1668
                        mol_type = other DNA
                        organism = Bacillus thuringiensis
SEQUENCE: 7
atgcaacatt tagttcaatt tgtatgggca tataaattag cgaaacaagg aaaggaagga     60
tttgctagtc catatgtata tgtaagagaa tttcaagatg agatccttga tttcatctct    120
acaaaccccac ctaaattcgg ggtgaattgg acatgtacta tggacgttgc gattcgggcg   180
gctaattggc ttttagttta tgatttattt aaagtacaag gagtcgaatt tgataaggaa    240
tttgaaaaaa tatttgtact ttctatgcat gatcatggta atttttatttt taataattta   300
gagcgtaata aggatataag gaataatcat tatttatcta atattgtggg gctattcttt    360
atagctacat accttcctgc cacagaagtg gtatcacagt ggttaaattt ttcattccaa    420
gaattaattc aagagatgag tttcaatttt atgaagaagg gctcaaactt tgaaaattca    480
actacttatc atcgcttatc tagcgaactc atgctttatg caacaacagt agcgctagca    540
ttacctgaag agaaaataaa ggtattgcat agttatagat tgcaaaatca tattgaaatt    600
tgtaaaaaac taggatttga aattgattcg gataaatttt gggatttcca taatgggaaa    660
attttcccaa attggtatat agagagatta gaaaaaacgg ctgagtttac agctgatatt    720
actaagccta atggagaggt tgcacagttt ggtgataatg atagtggaag attctttaag    780
atacagccgt cttataattt attaacagtt caggaagcta agcaaagata cttaaattta    840
agtacttata atgaattaag tgataaagaa aattactggg atgaggactt tttagaacat    900
cgcttttctag tagcgggaat taatgcttta tttaaaaggg agaaatttt tagctttgta    960
aataaacctt ctatagaata tgtattaatt aaaaatatgg tgaaggatca tatgcgaaaca  1020
tatgaagaat ctattttacc gttttaaaa tataatgttt tagaaatctc tataaataaa    1080
aaggaaaaaa atgaaataaa taattagag caacaagaaa attttgttca atatgttttt    1140
tattctaaat ctaatttagt tgagggtata aaaaagtaca catatcctga ctttggtatg   1200
tatattttta aatctcaaga ttttttattta gctattagat gtgggaagct aggtagtaat   1260
ggaaaaggaa gtcatgatca taatgatcaa cttagtatcg aattagtaat agatggtaaa   1320
aatgttataa aagatcctgg aacatatcta tacaccccaa taccagaaa aagaaattta    1380
tttagatcaa caaaagcaca ttttacaatc caatcaggtg atatagaaca aaataatttt   1440
tatgctggat tgaatggttt gttagttta gaacataaa caaatagccca gtgtttggaa    1500
tttaaaaata atagttttgt agggtgccca agtggttatg gtcagaaagt atataggaa    1560
atagaaatat gtgacaaaca agtagtgata ccgattttg gaacagtat tgttaatcca    1620
gaattcaatt actattcaaa tggttacgga cgaattata ggaataaa                  1668

SEQ ID NO: 8            moltype = AA  length = 556
FEATURE                 Location/Qualifiers
source                  1..556
                        mol_type = protein
                        organism = Bacillus thuringiensis
SEQUENCE: 8
MQHLVQFVWA YKLAKQGKEG FASPYVYVRE FQDEILDFIS TNPPKFGVNW TCTMDVAIRA     60
ANWLLVYDLF KVQGVEFDKE FEKIFVLSMH DHGNFIFNNL ERNKDIRNNH YLSNIVGLFF    120
IATYLPATEV VSQWLNFSFQ ELIQEMSFQF YEEGSNFENS TTYHRLSSEL MLYATTVALA    180
LPEEKIKVLH SYRLQNHIEI CKKLGFEIDS DKFWDFHNGK IFPNWYIERL EKTAEFTADI    240
TKPNGEVAQF GDNDSGRFFK IQPSYNLLTV QEAKQRYLNL STYNELSDKE NYWDEDFLEH    300
RPLVAGINAL FKRKKFFSFV NKPSIEYVLI KNMVKDHMET YEESILPFLK YNVLEISINK    360
KEKNEINKLE QQENFVQYVF YSKSNLVEGI KKIAYPDFGM YIFKSQDFYL AIRCGKLGSN    420
GKGSHDHNDQ LSIELVIDGK NVIKDPGTYL YTPIPEKRNL FRSTKAHFTI QSGDIEQNNF    480
YAGLNGLFSL EHTNSQCLE FKNNSFVGCH SGYGQKVYRE IEICDKQVVI TDFGTSIVNP    540
EFNYYSNGYG RIIRNK                                                   556

SEQ ID NO: 9            moltype = DNA  length = 2106
FEATURE                 Location/Qualifiers
source                  1..2106
                        mol_type = other DNA
                        organism = Bacillus thuringiensis
SEQUENCE: 9
atggatttca aagatttagg tattagctat caatatagat ctggtgatga agaacaaaat     60
attgtaaatg atttttatgt acctacgtta tctcagacaa agatatataa gcgcgcagta    120
ggctattta cgagtcgcttc cttagctatt gtaggaaaag ggttaaatga gatgattagt    180
aataacggaa aaatgtactt gattgcttca ccatatcttg aaaaagcaga tattgaagcg    240
atcgaatctg gatataaagc acgtaatgaa gtgatagagg aatccttatt aagagcttta    300
aatcagccag tagatttagt tgttaaagaa cgactaaatt atttagcatg gttaatagca    360
aatggaaggt tagagataaa aattgctact ctatcaaata gcgctaccta tggttttatat   420
catgagaaaa tcggttgtat ggaggatgga gaaggaaata gcgctaccta tggttttatat   480
gctaatgaaa cagagggtgg tctatataa aattttgaat ctattgatgt attttgctcg    540
tggaacaaaa acgagtgat aagagtagag agaaagata gagattcga tttgttatgg    600
cagaatgaaa caaatagt tcaggttatc gattttcctc aagctgctaa ggaaaaatta    660
ttaagctta aagaatatac aatcaagaag gttgatccag aaatccagtc taatattgtt    720
attaaggaag ataatcaacg ttgctacttt cccgatattc ctaaagagta acaataaga    780
```

-continued

```
aattatcaaa aggaagctat aaagagttgg tttgaaaacg aatgtaaagg tctactcgag    840
atggcaacgg gcacagggaa aactattacg gcattgtcag cggtatcatt cttatggaaa    900
gcgttatcaa ggaggttagc ggtgattata gtttgtccgt atacacattt agtagatcaa    960
tgggtaaaag acattaaaaa atttaatatg aacccattgg tagcgaaaca atctcgaaat   1020
ttatgggaag aagatttgag gttcaatatt agtgcgttta aaaatggtat tattaatcat   1080
ttttgtttaa taaccacaaa taaaactttt tcaagcaaga cgatgcaaga tttattatct   1140
caattaaaag gagaagttgt atttgtagcg gatgaagccc atcatctagg tgctattaat   1200
aatagaatga atcttatgga gcatttcccg tatcgtttag ctttatctgc aacacctaat   1260
cgttggtatg atgaggaagg aagtgaagcg ttgctaaaat attttggagg aaaagtagtt   1320
tttgagtttg gtttaaaaaa agctatagga gaattttaa cagaatatta ttattatcct    1380
catgtggttt atctaggtat agatgaaaat gaaaaatact atgaaattac aaggaaacta   1440
tcgaaatttt atagtcctaa tggagaatta gacttaaagg acaatgaggg attacaaaaa   1500
ttattgattg aaagagcgag gattttaaat agtgcaagaa ataaacttat taaattaaaa   1560
gaattgatag ggggaaataa agaatctaaa tataatatta tatactgtgg agatagctca   1620
atagataacg aaaaacaggt tagtgcagtt gtgaaattgt tgggtaatga attaaatatg   1680
agagctcata catttacatc taatgaaagt agtttacaga gacaagagtc attaaaaaga   1740
tttgaactag gagagctcca agcactggta gctataaaat gtttagatga aggtgtagat   1800
gtaccagcta cccagaatgc ttatattctt gctagtagta ctaatccaag agagtttatt   1860
caaaggagag aagggtatt aagaaaaacac cctaataagc ggtattcata tattcatgat   1920
tttattgtta ttccaagaga gattgatgag attgaatatt tggagcctag tgtttttaat   1980
atagaacgaa aaatggtgaa acgtgaatta ataaggtttg tagaatttgc taatttggca   2040
cgaaatggtc cagtagcaca tgagcaacta gaagaaataa aaaagcctta atctcatta   2100
gatatg                                                              2106

SEQ ID NO: 10           moltype = AA   length = 702
FEATURE                 Location/Qualifiers
source                  1..702
                        mol_type = protein
                        organism = Bacillus thuringiensis
SEQUENCE: 10
MDFKDLGISY QYRSGDEEQN IVNDFYVPTL SQTKIYKRAV GYFTSASLAI VGKGLNEMIS    60
NNGKMYLIAS PYLEKADIEA IESGYKARNE VIEESLLRAL NQPVDLVVKE RLNYLAWLIA   120
NGRLEIKIAT LSNSATYGLY HEKIGIMEDG EGNKIAFSGS ANETEGGLYN NFESIDVFCS   180
WNKNELIRVE RKDRDFDLLW QNKTNKVQVI DFPQAAKEKL LSPFKEYTIKK VDPEIQSNIV   240
IKEDNQRCYF PDIPKEYTIR NYQKEAIKSW FENECKGLLE MATGTGKTIT ALSAVSFLWK   300
ALSRRLAVII VCPYTHLVDQ WVKDIKKFNM NPLVAKQSRN LWEEDLRFNI SAFKNGIIINH   360
FCLITTNKTF SSKTMQDLLS QLKGEVVFVA DEAHHLGAIN NRMNLMEHFP YRLALSATPN   420
RWYDEEGSEA LLKYFGGKVV FEFGLKKAIG EFLTEYYYP HVVYLGIDEN EKYYEITRKL    480
SKFYSPNGEL DLKDNEGLQK LLIERARILN SARNKLIKLK ELIGGNKESK YNIIYCGDSS   540
IDNEKQVSAV VKLLGNELNM RAHTFTSNES SLQRQESLKR FELGELQALV AIKCLDEGVD   600
VPATQNAYIL ASSTNPREFI QRRGRVLRKH PNKRYSIHD FIVIPREIDE IEYLEPSVFN    660
IERKMVKREL IRFVEFANLA RNGPVAHEQL EEIKKPYNLL DM                      702

SEQ ID NO: 11           moltype = DNA   length = 2016
FEATURE                 Location/Qualifiers
source                  1..2016
                        mol_type = other DNA
                        organism = Bacillus thuringiensis
SEQUENCE: 11
atgattttag aatctattat tttaaggaac ttcaggcagt actatagctc gcaaattatt     60
gaattttctc aatcaaacac tcgaaatgta acagttatcc atgggaaaa tggtgcagta    120
aagacagcac ttcttaatgc atttagttgg tgcctatatg gagagcttaa tttgcccaat    180
gctagtaata tcataaatga acatgctgtg aatgaaatag aagatggaga ggaagttgag    240
gcacttgtca ctattcaatt taggagaaa gttaaggtt cagtggcaca tgaaaagcat     300
tattcgctta ctagaagtat caaggcaaga aaaattactg aggaacagat aaattactcc    360
gaaccagaag tgagattaga atacagagaa gatggtcaat cgaaattaga agttgctaac    420
attggaatag atataaatcg gattttaccg gagcaacttt catcttattt tttctttgat    480
ggagagagaa tagataattt atcgaaagaa tctggaactg aagaagtaaa agaagctatt    540
aaaacaatga tgggactaga aattttgagt cgttctattt tacatacgga aggcgcgaga    600
aaaagatttt taacagtagt aaaacaatat ggtgacgtgg aaacaagaaa tttagtagaa    660
gaaattgaaa atttacataa gcaaaaagaa gagttggaat cagaagaaaa agaatttaaa    720
cagtatcata agtcaataga aagcagata aagaaaaag aagaacgatt aagacaaatt     780
gaagattcaa agcgtctaca agaacagaga gatgtaaaga caaagagct aatacttct    840
gaagaagaac ttgttagtac tcggaaaaga ttagctgatt tgatgagtaa acaaggttat    900
ttagcattta gtttcctggc tatagataaa gctcaagatt tactcgcgaa taaaaattta    960
aacaataata cctatacagg gattaatgct tcgtttcttg atcaattgat tattcaagaa   1020
gaatgtatat gtggaaccca tttaataaca ggttcagcag agtataataa agttatagat   1080
actaaaaaatt atttggctcc cataagtctt gaacatgcta ttgcagaatt tcaaagtgac   1140
gtaaaaaata caaaagatag aaaacagaag ttatttgaag gtatgggaca attaaggtta   1200
caggagtcta atttaagca aaagatacga ttgctaaatg aagcaattga ggaaataggc   1260
aaaaaaaattt cggataagga ttctgaggag attgtaactc ttgaaaatgt aagagaacaa   1320
ttaattacaa agaagagtca aatagatcaa agaatttggggg ttattcaaca tcaactaat   1380
gaaataagtg agaaactaga taaaaaaat aatgagcgag aaaaacttaa tcaaaaagtg   1440
gaaaaagcag ctgttacaga aagaaagaatt taggcttgg aagaattaat tgaggtaagt   1500
aagaaatct acaagttacg cgaaaagatc gtaaaagagc aactcaaga gcgtgttgcc    1560
aaagtataca ctaagttttt aagaaaagat tataaaatta gattatctaa tgactatgaa   1620
ctagatgtta ttaatggtaa cggaaataaa gtgggtatgt ctcaaggaga acgccaaatt   1680
acaagttttgt ctttatatagg ggcgattgtg gatattgcaa gagagcaatt taatgaaaag   1740
aatataaaata gatttgaaga ggaggcatt tatccaattg taatgattc accctttgga    1800
```

```
gctttagatt cagatcatcg tgaaagaata gcaaaaggaa ttcctgaact ttcagaccaa  1860
gtcattgtta ttgttttctac ttctcaatgg aaaggagaag tagaggagaa aatgcgtgat  1920
aaaaattgaa aagagtacgg actaaattat aatgatccac gtattaataa agagaaaaac  1980
tatgaattta cagaaattac cgaggtcgta acaaaa                             2016

SEQ ID NO: 12          moltype = AA   length = 672
FEATURE                Location/Qualifiers
source                 1..672
                       mol_type = protein
                       organism = Bacillus thuringiensis
SEQUENCE: 12
MILESIILRN FRQYYSSQII EFSQSNTRNV TVIHGENGAG KTALLNAFSW CLYGELNLPN   60
ASNIINEHAV NEIEDGEEVE ALVTIQFKEK VKGSVAHEKH YSLTRSIKAR KISEEQINYS  120
EPEVRLEYRE DGQSKLEVAN IGIEINRILP EQLSSYFFFD GERIDNLSKE SGTEEVKEAI  180
KTMMGLEILE RSILHTEGAR KRFLTELKQY GDVETRNLVE EIENLHKQKE ELESEEKEFK  240
QYHKSIEKQI KEKEERLRQI EDSKRLQEQR DVKTKELNTS EEELVSTRKR LADLMSKQGY  300
LAFSFLAIDK AQDVLANKNL NNNTYTGINA SFLDQLIIQE ECICGTHLIT GSAEYNKVID  360
TKNYLAPISL EHAIAEFQSD VKITKDRKQK LFEGMGQLRL QESNFKQKIR LLNEAIEEIG  420
KKISDKDSEE IVTLENVREQ LITKKSQIDQ RIGVIQHQLN EISEKLDKKN NEREKLNQKV  480
EKAAVTEKRI KACEELIEVM KEIYKLREKI VKEQLQERVA KVYTKFLRKD YKIRLSNDYE  540
LDVINGNGNK VGMSQGERQI TSLSFIGAIV DIAREQFNEK NINRFEEGGI YPIVMDSPFG  600
ALDSDHRERI AKGIPELSDQ VIVIVSTSQW KGEVEEKMRD KIGKEYGLNY NDPRINKEKN  660
YEFTEITEVV TK                                                     672

SEQ ID NO: 13          moltype = DNA   length = 1332
FEATURE                Location/Qualifiers
source                 1..1332
                       mol_type = other DNA
                       organism = Bacillus thuringiensis
SEQUENCE: 13
atgaaggtaa atttgttaaa aaaaactctt atttgtatgt ctttattaac aatccctatg   60
tcttacaata cagtattcgc tcatagcagc aacgaaataa atctataggt atattcaaat  120
agaggattag aagataaatt aatagatttt aagaagaaca agaaaaagc gaaagaatgg  180
ggaaagaaa aagcgaaaga gtggaaacta aatgctgctg aaaaaacaca aattaataaa  240
tttctagatg atatggatgg attaaaaaca aaatataaag aaattaattt ttctaaaaac  300
ttcgactacg aaaaagagct taagagttta gaaaagatta tgaaggact gaatagagcc  360
aatctaacaa attcaattgt cacttacaaa aatgtggatc cagcaatgat tggatttaat  420
aaatcccttaa ctaatggaga gcagattagt tctgaaactt tacaaaagtt taaagtacaa  480
tttttaggga aggatattaa atttgatagt tatttggata cacaattaaa tgagcaaaat  540
attcttggta agaaaagagt tattttaaaa gttaccgtac caagtggtaa aagctcttct  600
ccaacaaag caggcgttat tttaaataat ggcgaataca aaatgctaat tgaaaatgga  660
tatttacttc atgtagaaaa gatatcaaaa actgtaaaga aaggacatga gtatttgcaa  720
gttgaaggat ctttaaaaaa gagtctggac tttaaaaatg atagcgatgg taagggagat  780
tcttggggaa agaaaaatta taggagtgg tccgattttt taacagcaga acaaagagca  840
gacttaaatt attatggtca agagggtat actgagataa ataaatttt gcgtgacgaa  900
agtactggga atactaattt agaagaaaaa ataaaaaata tttctgaagc gctgaaaaaa  960
aagccgatat ctgaaaatat tactgtttat agatattgta gatgatgga atttggctac 1020
caaattagtg acccttttacc ttctgtaaaa gattttgaag aaaagtttt aaatataatt 1080
aaagaagaaa aaggatatat gagtacaagt atatctagtg atgcaacgcc ttttggaact 1140
agaagaatta taatgagact gcaagtacca aaaggaagtg caggagcgta tgtaaatggt 1200
ttagatggtt ttaagacatc tgaaaaagag atgctccttg ataaggggag taaatatcac 1260
attgataaag ttacagaagt aattgtcaaa ggccaagaa aacttgtagt agatgcaaca 1320
ttattaacaa aa                                                    1332

SEQ ID NO: 14          moltype = AA   length = 444
FEATURE                Location/Qualifiers
source                 1..444
                       mol_type = protein
                       organism = Bacillus thuringiensis
SEQUENCE: 14
MKVNLLKKTL ICMSLLTIPM SYNTVFAHSS NEIKSIGYSN RGLEDKLIDF KEDKEKAKEW   60
GKEKAKEWKL NAAEKTQINK FLDDMDGLKT KYKEINFSKN FDYEKELKEL EKINEGLNRA  120
NLTNSIVTYK NVDPAMIGFN KSLTNGEQIS SETLQKFKVQ FLGKDIKFDS YLDTQLNEQN  180
ILGKERVILK VTVPSGKSSS PTKAGVILNN GEYKMLIENG YLLHVEKISK TVKKGHEYLQ  240
VEGSLKKSLD FKNDSDGKGD SWGKKNYKEW SDFLTAEQRA DLNYYGQRGY TEINKYLRDE  300
STGNTNLEEK IKNISEALKK KPISENITVY RYCGMMEFGY QISDPLPSVK DFEEKFLNII  360
KEEKGYMSTS ISSDATPFGT RRIIMRLQVP KGSAGAYVNG LDGFKTSEKE MLLDKGSKYH  420
IDKVTEVIVK GQRKLVVDAT LLTK                                        444

SEQ ID NO: 15          moltype = DNA   length = 1041
FEATURE                Location/Qualifiers
source                 1..1041
                       mol_type = other DNA
                       organism = Bacillus thuringiensis
SEQUENCE: 15
atgagggatt ttttttaaga taattacaat aatattgagt ttaataaaaa tttaataaac   60
ttaataagtg aaataagtga atataagggg aaattaaccg cctatcaaga acaagtgccc  120
catatatttta aagatttgaa ggaaaacatt ccctttcaat atgtaaaaaa tttcaatgct  180
atttatgggg agaagaaagt tactaataaa agattaaagg aactgttatt ttataatgca  240
```

```
gtacctcaaa ctgtcattga agattcagtt ttttgctatc atcaaacttt tccttata      300
aataagaatt attgcactt gtcgattagt ccagaaaata tactagaatt gcattcaa        360
ttaattaatt atattacctc ggatactgca aatggcgtg agaaaccaat ttctatcctt      420
gggacaccgg aaaaggaat tcctactat tgttatcgct ctcttccaca tacgcttata      480
ccacaaacta tggagcaatt atgtaatcaa taattatt taagtagtag taagaaatta      540
cactcactat tattgatagc atatttatg ttaaattatt actgcatagt accttttaac     600
caaggaagtg aaaaactagc atttatgata atgaaattat tattaataaa aagtggacat    660
acatttgtac aatatattg tttagataaa tatattgaga agaatgaatt agaatattat     720
gactccctt ataaatcatc cgttaattgg tactataga agcataatac tagctttg         780
ctacaaacac tattaattat tgttttagag gcttatcaag atttgtatga tacaatagtt    840
gatttcatat gtaaacaaac taaatttgaa cgtattcaag attttgttct taaacaaaaa    900
caaacttta caaagatta tattcgtgac atgtatccag atatagctga gagtacaatt      960
aataaagcat tagctactct tcacgattta gggcaaataa agttagtctc taaggaaga    1020
acagcccatt ggataaaagt c                                              1041

SEQ ID NO: 16          moltype = AA   length = 347
FEATURE                Location/Qualifiers
source                 1..347
                       mol_type = protein
                       organism = Bacillus thuringiensis
SEQUENCE: 16
MRDFFKDNYN NIEFNKNLIN LISEISEYKG KLTAYQEQVP HIFKDLKENI PFQYVKNFNA    60
IYGEKKVTNK RLKELLFYNA VPQTVIEDSV FCYHQTFSFI NKNYCTLSIS PENILELHFQ   120
LINYITSDTA KWREKPISIL GTPEKGIPTI CYRSLPHTLI PQTMEQLCNQ YNYLSSSKKL   180
HSLLLIAYFM LNYYCIVPFN QGSEKLAFMI MKLLLIKSGH TFVQYICLDK YIEKNELEYY   240
DSLYKSSVNW YYNEHNTSFW LQTLLIIVLE AYQDLYDTIV DFICKQTKFE RIQDFVLKQK   300
QTFTKDYIRD MYPDIAESTI NKALATLHDL GQIKLVSKGR TAHWIKV                 347

SEQ ID NO: 17          moltype = DNA   length = 3291
FEATURE                Location/Qualifiers
source                 1..3291
                       mol_type = other DNA
                       organism = Bacillus thuringiensis
SEQUENCE: 17
atggaatatt ggaaaagggg gcgaaatgaa aagaggcaa gtatacctaa gagaaaagat      60
ttgaagggg aaacttgcag cattttacag aaagaacagg gggaaataat ttgaaaaat     120
atttacaagt gtttaacagt cacagcatta ctaacacaac ttgcaacttt ccaacagca    180
tctttagcag aaaatgaaac acggcccgaa agtagaagca acaaaagtga acaaaatagt    240
gttaatggtc taatgggaca atattttaca gatgatgcat tttctcaatt ggcatatatt    300
caagtaggtg agcatagtga actaatgaag aaaaacaaaa tgcatgaaga tgaaaaaagg    360
attcaatctg taaggtggtt agggaaacta aaaccttctc aatcgggaga atatcaaatt    420
tctacatcga atgatcaaaa tgtaatattg caattaatg gtgagacaat cgtaaatcaa    480
aagagccgg atcaatctat taagttagaa aaagatcaag agtatgaaat taaaataagag   540
ttccaaaata aagataataa agagttgcaa ttgttctgga ctatgaatca atctgaaaaa   600
ataaaaattc ctggtaaaaa tatcatgtca cctgattttt ctgcaaaggt aaatgtacct    660
gataaccaaa aagatcagaa attaatacca gaaagtaacc tattcgataa aaaaggacaa    720
gctcgacaag cacctatgtt ggtagatacg gataaggatg ataccgcatg cgttttggag    780
gaaaatggtt acacgtttaa agataatcaa attgttccat ggaatgaatc ctttgcaacc    840
gtaggatata aaagtatat atcgaatccg agaagtgcaa gaacagcggc tgatccatat    900
acagattttg aaaagtaac aggacatatg ccagcggcaa aaagatgaa agcaaaagat    960
ccacttgtag ctgcatatcc tgctgtaggg gtaggatg ggt agaaatttca ttttttcgcca   1020
aatgaaaatg tatcagaagg aacttcaggt acgaaaacaa aaagtgtaac agatacaagt   1080
acaacatcaa atagtgtgga tcttggtggg aaaatcggat tacaggagg agaaaaatca   1140
gcgtttagtt ttgaatttc tccaaagtat acgcattcct ggagcaatag tacttcaatt    1200
caaatacag agagtgaaac ttggtcaaa cagattgccg ttaatcccgc agaaagggca    1260
ttttaaaatg cgaatattcg atactataa gcaggaaaccg ctccaatcta tgatgtcaaa    1320
ccaacatcaa attttgtact tcaacattcg ggagcatcaa tcgcgacgat acatccaggt    1380
ccaaatcaaa tcggcaatag tttagcacca ggggatacat atccgaaacg tggacaggcg   1440
cctatatctt tgaatacagc aaatgaagca ggaacagtta aaattccaat taacggagag    1500
caattggata aaatacaatc cggtgatgag atattaaatc ttgagactac gcaaaataaa    1560
ggcaatatg caacagtaga ttcaactgga atccaacaa cagatccatc aaggcagtgg    1620
gatccaattc gcacaaacat cgatgctgta tcggggcat aacattgaa ctttggaaca     1680
ggaaaagata gtttagaacg aagagtggct gcaaaaatc caataatcc agaggataaa    1740
acaccgaaa ttacaattaa agaagcaatt aaaaaggatt ttggtgcaaa agagaaagat    1800
ggtagattgt atgttatgga tcgaaatgga aaaatatttt ggattgatga atctgcagtt    1860
aacttaatcg gcgatgcgaa aaccccaaaaa gaaattgaaa atcagttaaa aaatatgccg   1920
gataaaaaag tgtataatgc aaagtggaag cgtgggtatga aatcacatt acatattcca    1980
actgcctatc acgattttga agccaatagt gcaggatggt attatacgta taaggacaat   2040
ggaggatata caggacaaaa acgtggtaga ataggtaga atggaaacgg atacacagtg    2100
agagacttgg ctttaaaacc gtatacaagt tatactgcga gagcttatgt aagaacagga    2160
gtaagtactg gaagtaatga tgttacattt tatgtagata taaaaattgg ttcaggaaaa    2220
ggagcgaaaa cgtctggtaa agtaacagga acaaatggg atggtggaa gttttctttc    2280
aatactggag ggaatccaga gttctttctc aaaatcggtt ttcaaaataa agggaatgcg    2340
caattacatt ttgatgatgt gtctgtaaca gagtgggcac aaagtgaaga tttgcaaaaa    2400
gggcacagag tagaaacgtg gcaaacctca tcatccaatc gtattgacgg tgtgacactt    2460
tcgaaatcc catcgcaaa gttaaggtat caattggaga ttgaagggac attcacagag    2520
attggtcag atgcagtaac agatacgaat ggaagagat tttaaactt taataaattt    2580
aataataatc aagggattga taattataaa aaattgcag tgtatgcagt agatgagaag    2640
aatgatcatc taaagatgaa attgcaggaa atgaaccac agcaccaatt taagaattgg    2700
```

```
aatatcgtga atcatgtgaa taaaaaatat gtgaatggtg ttacattccg aaaaatccca  2760
actgaagcgg tgaattatca attgaaagtg aatggtagtt ggacggcaat taaaccagga  2820
aacactgttc aacctgatgg ttccaaatat cttaatttcc ttgaatttaa tggtgggtat  2880
ggatatgcag aaagtacttc tattgaagtg tgggctgtaa ataaatccaa taatacgaag  2940
aaaacaaaaa tagctcatta taataataaa gagacattag tggcaacagt ttcatctaat  3000
tcttcgccat cgccagggca aaaaaatagg tcaagtcaaa actttactat tagtaattta  3060
ccggctggaa cgaaagggtt gaaatgggta gtagaaccaa caacgccaga ttcggtatca  3120
aatattcgat ttaaacttat gcgtgatgta agtggaggta cagacccagt tatttggaat  3180
gatttgttta atcaaaaaac aacagatatt caaacgagtt ctaaatttta tatttcaaac  3240
ccacagggag cgtctaaaaa ctttactgta aaggtatatg cgatttcgaa t            3291

SEQ ID NO: 18          moltype = AA  length = 1097
FEATURE                Location/Qualifiers
source                 1..1097
                       mol_type = protein
                       organism = Bacillus thuringiensis
SEQUENCE: 18
MEYWKRGRNE KEASIPKRKD LKGETCSILQ KEQGEIILKN IYKCLTVTAL LTQLATFPTA    60
SLAENETRPE SRSNKSEQNS VNGLMGQYFT DDAFSQLAYI QVGEHSELMK KNKMHEDEKR   120
IQSVRWLGKL KPSQSGEYQI STSNDQNVIL QINGETIVNQ KSADQSIKLE KDQEYEIKIE   180
FQNKDNKELQ LFWTMNQSEK IKIPGKNIMS PDFSAKVNVP DNQKDQKLIP ESNLFDKKGQ   240
ARQAPMLVDT DKDGIPDVLE ENGYTFKDNQ IVPWNESFAT VGYKKYISNP RSARTAADPY   300
TDFEKVTGHM PAATKDEAKD PLVAAYPAVG VGMEKFHFSP NENVSEGTSG TKTKSVTDTS   360
TTSNSVDLGG KIGFTGGEKS AFSFEFSPKY THSWSNSTSI QNTESETWSK QIGVNPAERA   420
FLNANIRYYN AGTAPIYDVK PTSNFVLQHS GASIATITSG PNQIGNSLAP GDTYPKRGQA   480
PISLNTANEA GTVKIPINGE QLDKIQSGDE ILNLETTQNK GQYATVDSTG NPTTDPSRQW   540
DPIRTNIDAV SGALTLNFGT GKDSLERRVA AKNPNNPEDK TPEITIKEAI KKAFGAKEKD   600
GRLYVMDRNG KNIWIDESAV NLIGDAKTQK EIENQLKNMP DKKVYNAKWK RGMKITLHIP   660
TAYHDFEANS AGWYYTYKDN GGYTGQKRGR IGENGNGYTV RDLALKPYTS YTARAYVRTG   720
VSTGSNDVTF YVDNKIGSGK GAKTSGKVTG NKWEMVEFSF NTGGNPEFFS KIGFQNKGNA   780
QLHFDDVSVT EWAQSEDLQK GHRVETWQTS SSNRIDGVTF SKFPSAKLRY QLEIEGTFTE   840
IRSDAVTDTN GKRYLNFNKF NNNQGIDNYK KIAVYAVDEK NDHLKMKLQE NEPQHQPKNW   900
NIVNHVNKKY VNGVTFRKIP TEAVNYQLKV NGSWTAIKPG NTVQPDGSKY LNFLEFNGGY   960
GYAESTSIEV WAVNKSNNTK KTKIAHYNNK ETLVATVSSN SSPSPGQKNR SSQNFTISNL  1020
PAGTKGLKWV VEPTTPDSVS NIRFKLMRDV SGGTDPVIWN DLFNQKTTDI QTSSKFYISN  1080
PQGASKNFTV KVYAISN                                                 1097

SEQ ID NO: 19          moltype = DNA  length = 774
FEATURE                Location/Qualifiers
source                 1..774
                       mol_type = other DNA
                       organism = Bacillus thuringiensis
SEQUENCE: 19
atgatctata gaagaggaga attaaaattg aaaccaacta gagaaagta cgtaattaat     60
ggggagtaca aatagaacg taagctttta cataatgaaa tcattaaatt atttctaaat   120
gatcaaccgc agcaagagca agaacctgag gctatattac ttggtggtgg ttctgctgct   180
ggaaaaagcc caattggaga gttagtaagt aagggatata aacatcagaa acaaaacatg   240
gtttggatag atcctgataa gatcaaagaa aaataccag aatatcaaga gttaatagaa   300
tccggaaaca ttgagttaat aaaacaagca gctttttttag ttcatgatga agtagtgat   360
attaccatga aactttaaa aatctgcatg aaaagaaaaa taaactgtat gtatgatggt   420
acaatgaaaa atgaagtaaa atacaaaaag ttaattcaac aattaagact agcaggtttt   480
agtattaaag caattattgt agatgttcca atcaaggttg ccttagagcg atccaatttg   540
cgttttaaag taacaggaag attggtaccc caaagtataa ttgaagaaag ccatatgaaa   600
gtagcgacta ctttttctaa aattaaagat ttaatagatt gctatacttt atatgataat   660
acagggaagg aaccagaagt ttttgctttt aagaatcaa aacgagtaaa agaaattatt   720
gttgatgaat gtagaaataa tcaatttatc gagaaatcag ctcttgtttt caag         774

SEQ ID NO: 20          moltype = AA  length = 258
FEATURE                Location/Qualifiers
source                 1..258
                       mol_type = protein
                       organism = Bacillus thuringiensis
SEQUENCE: 20
MIYRRGELKL KPTREKYVIN GEYTIERKLL HNEIIKLFLN DQPQQEQEPE AILLGGGSAA    60
GKSPIGELVS KGYKHQKQNM VWIDPDKIKE KIPEYQELIE SGNIELIKQA AFLVHDESSD   120
ITMKLLKICM KRKINCMYDG TMKNEVKYKK LIQQLRLAGF SIKAIIVDVP IKVALERSNL   180
RFKVTGRLVP QSIIEESHMK VATTFSKIKD LIDCYTLYDN TGKEPEVFAF KESKRVKEII   240
VDECRNNQFI EKSALVFK                                                 258

SEQ ID NO: 21          moltype = DNA  length = 2967
FEATURE                Location/Qualifiers
source                 1..2967
                       mol_type = other DNA
                       organism = Bacillus thuringiensis
SEQUENCE: 21
atgaagaaaa acaaaatgca tgaagatgaa aaaaggattc aatctgtaag gtggttaggg    60
aaactaaaac cttctcaatc gggagaatat caaatttcta catcgaatga tcaaaatgta   120
atattgcaaa ttaatggtga gacaatcgta aatcaaaaga gcgcagatca atctattaag   180
ttagaaaaag atcaagagta tgaaattaaa atagagttcc aaaataaaga taataaagag   240
```

```
ttgcaattgt tctggactat gaatcaatct gaaaaaataa aaattcctgg taaaatatc    300
atgtcacctg attttctgc aaaggtaaat gtacctgata accaaaaaga tcagaaatta    360
ataccagaaa gtaacctatt cgataaaaaa ggacaagctc gacaagcacc tatgttggta    420
gatacggata aggatggtat accggatgtt ttggaggaaa atggttacac gtttaaagat    480
aatcaaattg ttccatggaa tgaatccttt gcaaccgtag gatataaaaa gtatatatcg    540
aatccgagaa gtgcaagaac agcggctgat ccatatacag attttgaaaa agtaacaggg    600
catatgccag cggcaacaaa agatgaagca aaagatccac ttgtagctgc atatcctgct    660
gtaggggtag ggatggagaa atttcatttt tcgccaaatg aaaatgtatc agaaggaact    720
tcaggtacga aaacaaaaag tgtaacagat acaagtacaa catcaaatag tgtggatctt    780
ggtgggaaaa tcggatttac aggaggagaa aaatcagcgt ttagttttga attttctcca    840
aagtatacgc attcctggag caatagtact tcaattcaaa atacagagag tgaaacttgg    900
tctaaacaga ttggtgttaa tcccgcagaa agggcatttt taaatgcgaa tattcgatac    960
tataatgcag gaaccgctcc aatctatgat gtcaaaccaa catcaaattt tgtacttcaa   1020
cattcgggag catcaatcgc gacgattaca tcaggtccaa atcaaatcgg caatagttta   1080
gcaccagggg atacatatcc gaaacgtgga caggcgccta tatctttgaa tacagcaaat   1140
gaagcaggaa cagttaaaat tccaattaac ggagagcaat tggataaaat acaatccggt   1200
gatgagatat aaatcttgaa gactacgcaa aataaagggc aatatgcaac agtagattca   1260
actggaaatc caacaacaga tccatcaaag cagtgggatc caattcgcac aaacatcgat   1320
gctgtatcgg gggcattaac attgaacttt ggaacaggaa aagatagttt agaacgaaga   1380
gtggctgcaa aaaatccaaa taatccagag gataaaacac ccgaaattac aattaaagaa   1440
gcaattaaaa aggcttttgg tgcaaaagag aaagatggta gattgtatgt tatggatcga   1500
aatggaaaaa atatttggat tgatgaatct gcagttaact taatcggcga tgcgaaaacc   1560
caaaaagaaa ttgaaaatca gttaaaaaat atgccggata aaaaagtgta taatgcaaag   1620
tggaagcgtg gtatgaaaat cacattacat attccaactg cctatcacga ttttgaagcc   1680
aatagtgcag gatggtatta tacgtataag gacaatggag gatatacagg acaaaaacgt   1740
ggtagaatag gtgaaaatgg aaacggatac acagtgaggac acttggcttt aaaaccgtat   1800
acaagttata ctgcgagagc ttatgtaaga acaggagtaa gtactggaag taatgatgtt   1860
acattttatg tagataataa aattggttca ggaaaaggag cgaaaacgtc tggtaaagta   1920
acaggaaaca aatgggagat ggtggagttt ctttcaata ctggagggaa tccagagttc   1980
ttttctaaaa tcggttttca aaataaaggg aatgcgcaat tacattttga tgatgtgtct   2040
gtaacagagt gggcacaaag tgaagatttg caaaagggc acagagtaga aacgtggcaa   2100
acctcatcat ccaatcgtat tgacggtgtg acatttcga aattcccatc ggcaaagtta   2160
aggtatcaat tggagattga agggacattc acagagatta ggtcagatgc agtaacagat   2220
acgaatggaa agagatattt aaactttaat aaatttaata ataatcaagg gattgataat   2280
tataaaaaaa ttgcagtgta tgcagtagat gagaagaatg atcatctaaa gatgaaattg   2340
caggaaaatg aaccacagca ccaatttaag aattggaata tcgtgaatca tgtgaataaa   2400
aaatatgtga atggtgttac attccgaaaa atcccaactg aagcggtgaa ttatcaattg   2460
aaagtgaatg gtagttggac ggcaattaaa ccaggaaaca ctgtccaacc tgatggttcc   2520
aaatatctta atttccttga atttaatggt gggtatgaat atgcagaaag tactctatt   2580
gaagtgtggg ctgtaaataa atccaataat acgaagaaaa caaaaatagc tcattataat   2640
aataaagaga cattagtggc aacagtttca tctaattctt cgccatcgcc agggcaaaaa   2700
aataggtcaa gtcaaaactt tactattagt aatttaccgg ctggaacgaa agggttgaaa   2760
tgggtagtag aaccaacaac gccagattcg gtatcaaata ttcgatttaa acttatgcgt   2820
gatgtaagtg gaggtacaga tccagttatt tggagtgatt tgtttaatca aaaaacaaca   2880
gatattcaaa cgagttctaa attttatatt tcaaatccac agggagcgtc taaaaacttt   2940
actgtaaagg tatatgcgat ttcgaat                                       2967

SEQ ID NO: 22           moltype = AA  length = 989
FEATURE                 Location/Qualifiers
source                  1..989
                        mol_type = protein
                        organism = Bacillus thuringiensis
SEQUENCE: 22
MKKNKMHEDE KRIQSVRWLG KLKPSQSGEY QISTSNDQNV ILQINGETIV NQKSADQSIK    60
LEKDQEYEIK IEFQNKDNKE LQLFWTMNQS EKIKIPGKNI MSPDFSAKVN VPDNQKDQKL   120
IPESNLFDKK GQARQAPMLV DTDKDGIPDV LEENGYTFKD NQIVPWNESF ATVGYKKYIS   180
NPRSARTAAD PYTDFEKVTG HMPAATKDEA KDPLVAAYPA VGVGMEKPHF SPNENVSEGT   240
SGTKTKSVTD TSTTSNSVDL GGKIGFTGGE KSAFSFEFSP KYTHSWSNST SIQNTESETW   300
SKQIGVNPAE RAFLNANIRY YNAGTAPIYD VKPTSNFVLQ HSGASIATIT SGPNQIGNSL   360
APGDTYPKRG QAPISLNTAN EAGTVKIPIN GEQLDKIQSG DEILNLETTQ NKGQYATVDS   420
TGNPTTDPSK QWDPIRTNID AVSGALTLNF GTGKDSLERR VAAKNPNNPE DKTPEITIKE   480
AIKKAFGAKE KDGRLYVMDR NGKNIWIDES AVNLIGDAKT QKEIENQLKN MPDKKVYNAK   540
WKRGMKITLH IPTAYHDFEA NSAGWYYTYK DNGGYTGQKR GRIGENGNGY TVRDLALKPY   600
TSYTARAYVR TGVSTGSNDV TFYVDNKIGS GKGAKTSGKV TGNKWEMVEF SFNTGGNPEF   660
FSKIGFQNKG NAQLHFDDVS VTEWAQSEDL QKGHRVETWQ TSSSNRIDGV TFSKFPSAKL   720
RYQLEIEGTF TEIRSDAVTD TNGKRYLNFN KFNNQGIDN YKKIAVYAVD EKNDHLKMKL    780
QENEPQHQFK NWNIVNHVNK KYVNGVTFRK IPTEAVNYQL KVNGSWTAIK PGNTVQPDGS   840
KYLNFLEFNG GYGYAESTSI EVWAVNKSNN TKKTKIAHYN NKETLVATVS SNSSPSPGQK   900
NRSSQNFTIS NLPAGTKGLK WVVEPTTPDS VSNIRFKLMR DVSGGTDPVI WSDLFNQKTT   960
DIQTSSKFYI SNPQGASKNF TVKVYAISN                                    989

SEQ ID NO: 23           moltype = DNA  length = 990
FEATURE                 Location/Qualifiers
source                  1..990
                        mol_type = other DNA
                        organism = Bacillus thuringiensis
SEQUENCE: 23
atgtcaataa ttgacttttc aaaaaaagca tatgaattta tagattggca tgcaaatacc    60
caaaatcctc acaaacctaa gaatcacgac acattatat atccgtatgc ctacgatgca   120
```

```
tactcagagg tacaacaaaa aacttttcat ataggaaatc ccaccccagt tgctggagct  180
tttagggtaa ttgaaaataa tagtgatgta caacaaaagc aaactgttaa attttctgaa  240
aaaacagtca atacagtcac acataccact gtgaacggtt ataaagtagg aggtggaatc  300
aaaagcacca caaaagcatc tctagaatgt tcatttatag cagcaggtaa actagagcaa  360
tctgttgaag tctctgtaac tggtgaatat aatcatagtt ccacagatac taatacaaat  420
accgttgaaa aagtatggga attaactgag gaagtacagg cccctcctaa gtcacgtata  480
gttgcaaggc ttgtaattat gagagcaaaa atacaagtac ctgtaaaatt gacgacttat  540
ctgtatggta caactagaaa agaagaatat aactttccgg cacttgtagg ttatgattat  600
gattatgatg catctagaaa ttactaccct acctggtggg attttgccgg ttattcgcta  660
ggagcagcaa attggcctgg taaacctgaa agtttttctt acaaagaggg ggatccttcg  720
cttattatta ctggggaggg gataacaact gttgatttag ggctgtatgt tactactaga  780
tacgatcaat tcccaatatc ttctcctaat tattatgaag tatcatctga tagtaattta  840
gatcctttat ttagtcatac tgggtcctat gattgtattc ctactgaagc cgctaatggc  900
tcttctgatt gctcaggaaa tacagatgca actacatggt attctaaaaa catattacta  960
gcagatggaa gaataataaa agttcgtaaa                                   990
```

```
SEQ ID NO: 24          moltype = AA  length = 330
FEATURE                Location/Qualifiers
source                 1..330
                       mol_type = protein
                       organism = Bacillus thuringiensis
SEQUENCE: 24
MSIIDFSKKA YEFIDWHANT QNPHKPKNHD HIIYPYAYDA YSEVQQKTFH IGNPTPVAGA  60
FRVIENNSDV QQKQTVKFSE KTVNTVTHTT VNGYKVGGGI KSTTKASLEC SFIAAGKLEQ  120
SVEVSVTGEY NHSSTDTNTN TVEKVWELTE EVQAPPKSRI VARLVIMRAK IQVPVKLTTY  180
LYGTTRKEEY NFPALVGYDY DYDASRNYYP TWWDFAGYSL GAANWPGKPE SFSYKEGDPS  240
LIITGEGITT VDLGLYVTTR YDQFPISSPN YYEVSSDSNL DPLFSHTGSY DCIPTEAANG  300
SSDCSGNTDA TTWYSKNILL ADGRIIKVRK                                   330
```

```
SEQ ID NO: 25          moltype = DNA  length = 5175
FEATURE                Location/Qualifiers
source                 1..5175
                       mol_type = other DNA
                       organism = Bacillus thuringiensis
SEQUENCE: 25
atggtcaaaa tattccgaaa aaaaaggtgt atgtccctga tttcgaaaca gggacaggca  60
ttaccaatct ttcagctcat ttatttgacg gaggcgaaat tcatggcgaa tagagttaat  120
tgtaaaaaat tccctaatca tccaggctgt aagaaaacac ctacaacacc tacaacacct  180
ggaacaccta caacacctgg aacacctaca acacctaaaa aggacccatt caaggaatat  240
cccaagctaa accaagacat acaaaaacta ttagaaatcg atagcgatgg ggatggaatc  300
cctgatgccc tagaaaagaa tggttataca atttctgaag tatttgacca ggaacatggc  360
tattttaatg tcatgccttg gtccgaaaca tacgatcata atcctgattt ttataatcat  420
caccccaaat atatttcgaa cccctttgac aagaatacgg taggggaccc ttacacagat  480
ttagaaaaag caggccgaag catctatata gaggggagca tattaccgga agcctatcat  540
ccattagtag ctgcttgtcc aagtgttgca acatttatgg aggggtttat tttaaaagat  600
gtgcaagaca aagaaaatac cagcacaact ggtcattctt atcatacaag ttatggattt  660
gaagatacga gaacggttgg aagcggaaca gatttagcca atgcaggaaa gctcgagttc  720
ggcggaaaag gcgtaaaaaa tggaaaaagt ggagaacagg gaggcgaaac atcaaacatt  780
tcaggttccg tgcacctttc taggaactta aaacaccata cgaatgaaca acaaggggtg  840
acaacaatct cctccttgca agaagctcat caacaaacta ccgaatcatc aacaaccatt  900
cattcggcaa gtgctgccat cttacaagga attgttcgtt atcagaatat gggaaccgct  960
aagattagta atatgcgtcc gacactaaat tttcaagtgg aagaccgacc gttgttcacg  1020
tataaagtac ctgacggagt agaaaaatta agtccgggag acagctaccc atctttagat  1080
gcaacaggag caatcgttac accgggcgat tcatttcaag gacatccgtc taccatcgat  1140
acaggagcga aaaagaagct ggcagaagga aaaccattga aagtcgtgac aactcaaatt  1200
gacggaacat tcaaggccac agctggttcg ggaaagtatg ccccaggaag agaggtagag  1260
tggtcccaag ttacagatac aatgatgcag cgcacagcac gtatactctt agaaacacca  1320
aatgaaacgc tagatagaag agtcgcggct ccttccacag atgaggttgt tggaacaccc  1380
gacaaaatga aacagaatc gggtataccg cgaattacag tggaacaagc catccaattt  1440
gcctttggag ccaaaaaaga taatcgcggg aacctcgtca tgacaacaca acaagggctg  1500
acgtataaaa tcgatcgttc ccatgtagct ttgcatatga atcaaaaaac agatgcatta  1560
atctcgaaac agctgcaggc ttttaaggac aaaggcgacg acacgaaaag tgtatacgat  1620
gtgactctca cgaaagagat ggttatttta attaaaccta ttttagaagt gaatgctttt  1680
ttaaataata actatttata tatagaaaat tacttcgacc agagcttgtc gtatagtgta  1740
tggaaaaaca cgggaacaag cagcgagcta ctgaaacaag gaattgtacc gtctgcttcc  1800
acgataggaa ccgggtacct atgtgataat ccggctgaag agttacacat ttcggtgtca  1860
aaacacgtat cacaagttat ttttaagggg aaagtttcaa gtttacgagg gtttaatcgg  1920
aaagaagaaa aagaagaaaa actattaccg atacaacaat gttttggaaa atgtaaaggt  1980
tttacaaagg aggaattaaa atcctccacc cccccctgtga tgtattggct tacggattac  2040
ggtgatgata catggtggag attggattat aaaaccagaa gaaatcgtaa cctcacaatt  2100
ttatacagaa gaaaattaga agatgagacg aagcaatcta gagaagctga attgggaact  2160
gatagagagg tgcttctgtt taagaaaaca gaaggattag atcctgatga taaactttct  2220
gtccaaatag acggaggtaa aaaatatggt ttaaactcac attttgattt taaccattgg  2280
ctagaagtac ctcccgggaa tgaaaggata tttgatctaa acctatctat aagatatcta  2340
aaatatgatt ataataaaat agtagaggat agagtagaaa acttaggacc tatcaaggtt  2400
cctaacagga aattttatac acaagaacat agactttcta aaactcaagt gaaaatttca  2460
gaaaaaaaga aggttctatt atatcaaaca agtgattctg gtgaaatatg tttgcttaat  2520
aaacaactgg aaaccgtctc ttattgcata caaacgcctt atcaagaatg gatatggaag  2580
ggggagttgc gtccattcga gatattaaaa ttcactaaag gcaatccgat tattccaaaa  2640
```

```
cgctataaat ttggtacctt ccaaccatta atgtctgatg aaataattat taccattgat  2700
gatataccaa ttttttatgg aatcccagaa cgagatttg tgtataagga aaaaatagat  2760
accttgcaga aagtttgttt agattattgg cattttaatg aaaataatgg tcatcagact  2820
tatgattatg taagttttaa accactaaat ggtgaactta ttaacactgt gagggatttt  2880
gaactcatag ttgagcacaa tagtattgga aaacattcca cacgtccttt agaattaaac  2940
ggaaaattga ttgttaattt ctttgattac acaggtgata caaatcagca tccaagaaaa  3000
ggacagcagg tagatattat tgctcatgat atatttggaa atacacatac tgtatttagt  3060
ggaaaagctg aattaacaga tgctttatgg aaagcacaat ataaggtaag tgagtggcat  3120
aaaaaaggtg aacagtttga tgccttatac ctttctccta taccaactgg ccttacagag  3180
gatgtaaagt catatgatat acagattaat caggatatat acaagtctgt ttcatttgaa  3240
cgtcaagata atggtggata tgttcgagat caacgattga aattagattt ttctaatagt  3300
aaattctctc aggaaaaact tccaagatta ggagattcta ttaaattaac tattcataca  3360
atggatgata agcgtgttga aattgattta ggaaaagtag aggaatgtac taatccagac  3420
agtattaata ttttggaaag ggtacatgag attacagaat ggactaaaaa aggtaatcat  3480
tatacatgtg tacattttaa agaaggaaat aaagaagagg aaaaggcaca gatagatcat  3540
agtaaaagct atgtatcaag ctatttgttt aaagtgaata atcgttatta tggagaaatt  3600
tctataagta acgaaacaca aaaattggat ttaacggaat gtaataacaa tatgaagata  3660
caaaaaggcg actatgttga aatctatgcg tataaaaaag atggagaagg agtactcatt  3720
caaagtcgat atgctggcac cacaggcctt ctaggagagt atccgataga agatagtatg  3780
aataatgcat gtgttataac aagttggtct aaaacaaaca attcatatac ttcatttaca  3840
atagatcaat tgtcagaccc agttgatagt tatattaaaa agtatgaggg acatattaac  3900
aataaagtag tgaatttgac tcagaaagat aaaacatttg catttgatgc acaacaagcc  3960
ccgcgtcatg gagatatcgt tcaaatcaac gcatatacgt atacagggaa agtgattaaa  4020
ttagcgggac ggcttgcggg agctactggt ccggtagatg ataaggacgt ttgctctatt  4080
cataaaataa aaggttggga aaatgagaat aagacgattg ttttcgatac aagtgaattg  4140
aaagattcca tacaagcgca tatacaatca tatacaattg aagtttggaa aggtgctaat  4200
accccatggg aatcttttgg taatccaatt tatataaatg aaaagggaga attgcattta  4260
caagattgta atgcaaataa accatttcct cagcatccta acgtagtaaa agttattgct  4320
aatttgtttg aatctaaaag aaaagtaagc gtcatggtaa gaaaagtagg cgtaacaaac  4380
ccacctccga ctgaacagga cattcttaca gcacacaaaa atttcaactg ggactttgag  4440
agggagaagt taaagtcgat tacattccct caagtagata gtgagttggc aagttatatt  4500
tcttcttatc aaataaagaa atggtcaaat ttgataacag agaaaactgc attcaaagtc  4560
aaagaaaaca aaggactaac tgtaaccttt gagaatgcga ttgatgtgac tagcctgcag  4620
aaaattgctg tagggaatgg gaaaacggaa gaaagaaagg tacaagatga gatttccgct  4680
tatgcccatt gtattaacat aggagaaaaa acagaactca aaccaatttt agttatagga  4740
acgtatgaag gagcaaaaaa tgtaagagga gtcaagcctg aacgccctat atcaaaagaa  4800
gatattgtaa aagcacatca aatagagaac tgggtttacg attggaatgg aactcatgtt  4860
actgtatttt acttcaataa acagttgcaa ccatatttaa cggatataca atactatagt  4920
atccaaatta atggtacgga acatcttcct ccagattacg ttaaaagtca agatttatct  4980
ttggaaacag aggaaggcaa ggacgggaaa gcaaacggac cacaaggcct tccaattaga  5040
tttaatacgt ttaatctgac tggtggagtt ggaaaagaac tgccaagtcc aggggataca  5100
ttagatgtaa ctgcgcattt aaaagataac tcctcattga aagtaattaa aaattacaca  5160
attccatcta acaag                                                   5175

SEQ ID NO: 26          moltype = AA  length = 1725
FEATURE                Location/Qualifiers
source                 1..1725
                       mol_type = protein
                       organism = Bacillus thuringiensis
SEQUENCE: 26
MVKIFRKKRC MSLISKQGQA LPIFQLIYLT EAKFMANRVN CKKFPNHPGC KKTPTTPTTP  60
GTPTTPGTPT TPKKDPFKEY PKLNQDIQKL LEIDSDGDGI PDALEKNGYT ISEVFDQEHG  120
YFNVMPWSET YDHNPDFYNH HPKYISNPFD KNTVGDPYTD LEKAGRSIYI EGSILPEAYH  180
PLVAACPSVA TFMEGFILKD VQDKENTSTT GHSYHTSYGF EDTRTVGSGT DLANAGKLEF  240
GGKGVKNGKS GEQGGETSNI SGSVHLSRNL KHHTNEQQGV TTISSLQEAH QQTTESSTTI  300
HSASAAILQG IVRYQNMGTA KISNMRPTLN FQVEDRPLFT YKVPDGVEKL SPGDSYPSLD  360
ATGAIVTPGD SFQGHPSTID TGAKKKLAEG KPLKVVTTQI DGTFKATAGS GKYAPGREVE  420
WSQVTDTMMQ RTARILLETP NETLDRRVAA PSTDEVVGTP DKMKTESGIP RITVEQAIQF  480
AFGAKKDNRG NLVMTTQQGL TYKIDRSHVA LHMNQKTDAL ISKQLQAFKD KGDDTKSVYD  540
VTLTKEMVIL IKPILEVNAF LNNNYLYIEN YFDQSLSYSV WKNTGTSSEL LKQGIVPSAS  600
TIGTGYLCDN PAEELHISVS KHVSQVIFKG KVSSLRGFNR KEEKEEKLLP IQQCFGKCKG  660
FTKEELKSST PPVMYWLTDY GDDTWWRLDY KTRRNRNLTI LYRRKLEDET KQSREAELGT  720
DREVLLFKKT EGLDPDDKLS VQIDGGKKYG LNSHFDFNHW LEVPPGNERI FDLNLSIRYL  780
KYDYNKIVED RVENLGPIKV PNRKFYTQEH RLSKTQVKIS EKKKVLLYQT SDSGEICLLN  840
KQLETVSYCI QTPYQEWIWK GELRPFEILK FTKGNPIIPK RYKFGTFQPL MSDEIIITID  900
DIPIFYGIPE RDFVYKEKID TLQKVCLDYW HFNENNGHQT YDYVSFKPLN GELINTVRDF  960
ELIVEHNSIG KHSTRPLELN GKLIVNFFDY TGDTNQHPRK GQQVDIIAHD IFGNTHTVFS  1020
GKAELTDALW KAQYKVSEWH KKGEQFDALY LSPIPTGLTE DVKSYDIQIN QDIYKSVSFE  1080
RQDNGGYVRD QRLKLDFSNS KFSQEKLPRL GDSIKLTIHT MDDKRVEIDL GKVEECTNPD  1140
SINILERVHE ITEWTKKGNH YTCVHFKEGN KEEEKAQIDH SKSYVSSYLF KVNNRYYGEI  1200
SISNETQKLD LTECNNNMKI QKGDYVEIYA YKKDGEGVLI QSRYAGTTGL LGEYPIEDSM  1260
NNACVITSWS KTNNSYTSFT IDQLSDPVDS YIKKYEGHIN NKVVNLTQKD KTFAFDAQQA  1320
PRHGDIVQIN AYTYTGKVIK LAGRLAGATG PVDDKDVCSI HKIKGWENEN KTIVFDTSEL  1380
KDSIQAHIQS YTIEVWKGAN TPWESFGNPI YINEKGELHL QDCNANKPFP QHPNVVKVIA  1440
NLFESKRKVS VMVRKVGVTN PPPTEQDILT AHKNFNWDFE REKLKSITFP QVDSELASYI  1500
SSYQIKKWSN LITEKTAFKV KENKGLTVTF ENAIDVTSLQ KIAVGNGKTE ERKVQDEISA  1560
YAHCINIGEK TELKPILVIG TYEGAKNVRG VKPERPISKE DIVKAHQIEN WVYDWNGTHV  1620
TVFYFNKQLQ PYLTDIQYYS IQINGTEHLP PDYVKSQDLS LETEEGKDGK ANGPQGLPIR  1680
FNTFNLTGGV GKELPSPGDT LDVTAHLKDN SSLKVIKNYT IPSNK                  1725
```

```
SEQ ID NO: 27          moltype = DNA  length = 4764
FEATURE                Location/Qualifiers
source                 1..4764
                       mol_type = other DNA
                       organism = Bacillus thuringiensis
SEQUENCE: 27
atggcaacaa ccaattctgt ttcacaaaat tctttcgatt tagcgcccct agggttatat  60
ggaatttttt acaaaaaagc tctttttcag gacatgatac taggggttca aggagaaaat  120
gatggaggga tttttcattt tatgagccct caaaagtatc aatcagattt gcatctcact  180
tcttttgaat cagcgagatg ggttggaaga ctgaaaatct ctgaagcggg tgattatctt  240
ttttcttcat ccgataaatg gcgttcttgt atgaaaattt ggaagcaagt tacatttcaa  300
gtttccccaa aggtactgaa acaaatgaaa tgcacagaag ataaggacga caaaatatat  360
acgattccgg aaaaaacaga tcctaatgcg aagaatgcct ttcgtgtaac atgtaagcaa  420
ggcgtgtatc aggtgttaaa agaagacaat gaggatgaca attggaatgt ggagatacgt  480
gtacctaaga catcgaatgg agaaacgtat agcggaacaa tttcatacct gatgcaacaa  540
ggagatctga ctggtcatct agaggaaggc atctataaaa ttcgagttga atatatgcca  600
cttataccaa tagtagcgaa tgaaaacatc tttacattat attggcaaac tcctacaatt  660
ctaaagaaat caggaggaga tcctgctaag aatacggtaa tccctacgga aaatttaaga  720
ggacccgatt gtttagattc agattatttc cctacacata ttaccgataa tttatttaat  780
agtaagcaat atatgattct tgattcagag gaaatacagt ctttggtatc tagtaatcag  840
catcctgaaa cacaaaccat tgtctcatat aaccgtatat cagcagatac cgagttgaca  900
gatgaatcta acacagatga gtccaaagga gcggataggg ccatcaacat aacattagat  960
caactgaaag ctatgacgct tatacaaaat cgtatcaagc agattgggaa cgatcaaaat  1020
gtgatggaag agcaaatgaa gcgttgggcg aaagcgcgca aggatgaaaa tatagctttc  1080
aatatggaaa cgatgataca aatgctctgg aaagagaaag cacctaagtt cattcagcag  1140
ttaaagaatt ctctttcgat actacaaaaa caaacatcca aaaatctaat ttccactctt  1200
caagatctta ttaaggacat aaacccacaa acaaataagt tcaagatcga gttactggaa  1260
aaattcattt cggagttaga tgctttttat aaagaagaaa gtactttgat gaaaaactca  1320
tcggaattat ctagcacggt gtctatcctt aagacaatac tagaggacat gaaggagttg  1380
catgcaagtc agacgcaaac ttcggaggca gctatagctg cctggaataa ggaatatgta  1440
tataatgagg accctaagaa gaatttagac ccggattatg atgtaacaaa tccacatgca  1500
ttttatgccg atgcgaataa tgacgggata accaattatg attctatgca gggttttacg  1560
gttacatccg atggacaaat acagccttat ggaatgagga aggattttcc aacctattat  1620
tgtaattatc gtcttaaaag cacaacagga gatccgttta cagacacgaa taaattaatc  1680
ggttccggta ccgttgaacg agtggctaat atatcagaat tggcacgaaa cccgttagta  1740
gcagcgtatc cacatataaa tgtgaacatg gttggttttc agttaatccc agaaatcact  1800
aagactgaag gagtcgcaaa aacctattca ttttctgtaa gtaattctcg aacagattcg  1860
cagacaacta gtactgggca aacacatgga acggaagagg cgatacacgg agagatatca  1920
atatcagaaa acccctcaat tggaggggga ggctcgaaga gttggtcgaa cagcttatca  1980
aatgagatgt ccacttcaaa cactacagaa gtaaacacca ccaatggcaa agatgagtct  2040
acgtcttttc aaaagagttt taacacagca aattacgcga tgtttaatgg tttggtaaga  2100
tatcgaaatt caggaactgc tggtgtcagt aagttattac caaccttcaa ttttaattac  2160
catgatggaa ataaaatgga acctcttgtt actgtgaagc cagcaaaaga tggatcggca  2220
gaagtcggat tacttcagcc agatgcctcg tatcctcctg atgatcagaa aaccccttta  2280
gttattaaat caactgatgc ttttaatgca aatcaaattc aggcgtctca atcacaagtt  2340
caggccatat tgtcagggcg cccaatgagt ttaagtttgc tacaatatga tggttatata  2400
ccaaatgggg agccaacttc caatacccga tgggtacagc atttagataa aatacaagag  2460
catacagcct attggaccct gattacaccg gagggggaca tgtatgatag acgaattgca  2520
gcaccaagag agaacgattt aggatacaag ggcatcaatc cagacaaact aggcaaactt  2580
cccttctctt atgaagatat cgataaagct catcgcttga caattggaga ggccataaca  2640
cttgcattca gtgatgatcc atcacaaaaa tttgtgaaaa caaataagaa tggaattaag  2700
tatgatttgc aatcaaagaa tgtgaaaatt acgatgtcta ggcagaccaa agaggctcta  2760
aagaaacaac tggattttgc aaagacggag gtagaagaaa cacaatttca tttgaaaaag  2820
ttagagcggg atgaagcaga acaatacaaa aagatagaga atgaatttaa gaagttacaa  2880
atgaaagacg aagatagaaa agaatggtta tacaatttcc atcagaacaa accggtacaa  2940
aaaaaactgg aaaccccttga acaaaacaaa caatttatag gggatcaact cgagcatatc  3000
aaaccaaaaa gcgacaaagg tttgcaactt gccgcagcgg atgtcaacaa acttcaaaca  3060
caacttgacc agataaatga cgcgattgac aaactagagg cagaacagat ggggtatcaa  3120
gagaagatgg acaatcttct gaagcaggta ggaaaaacgt tgaatcaaaa acaaattgat  3180
gattggacaa aaaagataac aaaaaagata gcaaacatgg atcttgtaca agagtggatt  3240
cagcagcaac gtgcaaaggg acaggcctat ttgggcgaaa tgaagaagac gctcgaaaaa  3300
aagaattttt atgattatga acttctacaa ggaatgcgct tgattataca aattccacct  3360
attgtaacgg caacattcaa aaatgctacc acagaagata agcacacgta tcaagaactg  3420
tacctgaaaa atcatttcct acaagaaaag ctaaagtatc acattaaatt acttccgcct  3480
tcatcgacaa caacgctaaa agatgcgcca aaattgggtt cttttactcc agctacagaa  3540
aagaacgtat ttggatataa agaaggggta ctagaaccaa acgcagagca aaatacgaag  3600
attccacatc tttctaataa cgatcggatt gaagtgtgga ttcaaaaaga tggagaaaaa  3660
gactatagcc ttctgatttc aaaaacggta ggacaaatac caggtttccg agctgacaag  3720
ccaaaagtaa acacaacaaa actgacagag aacttcacat tccagacatt taaagtggat  3780
tggtcttacc cgaaagcgtg taatggcgta gcactctcta ttccttcccc tgatatatta  3840
aaagagtttc tatcctttac attagaggta acggacccta ctaccaacaa aacggctagt  3900
tatggacctg tactggcatc agaaataaga aaaaatattg tacctgaaaa gaacgcggca  3960
aaacagagct gtacctttga cttttctctt tttaaggaat ttgatatgaa aaaaaattac  4020
tggggatata tgttcacact gaaaggaaaa ttagatgaag cggtaccgag cggttgggaa  4080
aagaaacaac ctgtttctcg tcctaaagat gagaagggca agatgaaaaa cggtgttaca  4140
ttagtaccta catttgaaga gccgaggaca attgagttat gtaaacaaat tttccctgga  4200
aaaatgttta gtctagaaca gtatatgaac gcttttaaaa ataaaggaac actttctagt  4260
cctctaacaa atcagaagtc aaaagtaaat ggggaccatg tcacatttaa tagcgtatat  4320
```

```
ccggaattcg taattgaaag acagggagaa ctttctaatt atccacttct tcttgctggt  4380
attaaaaaag ttacttgcat ctttaagaac acggcaaaga cagaagtaat cactccaacc  4440
gacacacagt ttacaatgaa gaataatgca ttacatgtct gctttaatac caaaatagat  4500
gtaacacaaa aagaagaacc tgacggatgg aaagttgcag gagaggttgg gaaaggcgct  4560
ttattaagcg ccttgattcc ctcatcagtc gagaatatta agcatgaatt caataaatac  4620
agcacatata atgcagaagt agacggtttg atcaagtcag acaaatacga taaaatcttt  4680
aaggttcagc ttactgtgga taaagatata ttgacagata acaatcacaa agatcaagtg  4740
tttacgattt tcgagacaaa gata                                         4764

SEQ ID NO: 28          moltype = AA  length = 1588
FEATURE                Location/Qualifiers
source                 1..1588
                       mol_type = protein
                       organism = Bacillus thuringiensis
SEQUENCE: 28
MATTNSVSQN SFDLAPLGLY GIFYKKALFQ DMILGVQGEN DGGIFHFMSP QKYQSDLHLT  60
SFESARWVGR LKISEAGDYL FSSSDKWRSC MKIWKQVTFQ VSPKVLKQMK CTEDKDDKIY  120
TIPEKTDPNA KNAFRVTCKQ GVYQVLKEDN EDDNWNVEIR VPKTSNGETY SGTISYLMQQ  180
GDLTGHLEEG IYKIRVEYMP LIPIVANENI FTLYWQTPTI LKKSGGDPAK NTVIPTENLR  240
GPDCLDSDYF PTHITDNLFN SKQYMILDSE EIQSLVSSNQ HPETQTIVSY NRISADTELT  300
DESNTDESKG ADRAINITLD QLKAMTLIQN RIKQIGNDQN VMEEQMKRWA KARKDENIAF  360
NMETMIQMLW KEKAPKFIQQ LKNSLSILQK QTSKNLISTL QDLIKDINPQ TNKFKIELLE  420
KFISELDAFY KEESTLMKNS SELSSTVSIL KTILEDMKEL HASQTQTSEA AIAAWNKEYV  480
YNEDPKKNLD PDYDVTNPHA FYADANNDGI TNYDSMQGFT VTSDGQIQPY GMRKDFPTYY  540
CNYRLKSTTG DPFTDTNKLI GSGTVERVAN ISELARNPLV AAYPHINVNM VGFQLIPEIT  600
KTEGVAKTYS FSVSNSRTDS QTTSTGQTHG TEEAIHGEIS ISENPSIGGG GSKSWSNSLS  660
NEMSTSNTTE VNTTNGKDES TSFQKSFNTA NYAMFNGLVR YRNSGTAGVS KLLPTFNFNY  720
HDGNKMEPLV TVKPAKDGSA EVGLLQPDAS YPPDDQKTPL VIKSTDAFNA NQIQASQSQV  780
QAILSGRPMS LSLLQYDGYI PNGEPTSNTR WVQHLDKIQE HTAYWTLITP EGDMYDRRIA  840
APRENDLGYK GINPDKLGKL PFSYEDIDKA HRLTIGEAIT LAFSDDPSQK FVKTNKNGIK  900
YDLQSKNVKI TMSRQTKEAL KKQLDFAKTE VEETQFHLKK LERDEAEQYK KIENEFKKLQ  960
MKDEDRKEWL YNFHQNKPVQ KKLETLEQNK QFIGDQLEHI KPKSDKGLQL AAADVNKLQT  1020
QLDQINDAID KLEAEQMGYQ EKMDNLLKQV GKTLNQKQID DWTKKITKKI ANMDLVQEWI  1080
QQQRAKGQAY LGEMKKTLEK KNFYDYELLQ GMRLIIQIPP IVTATFKNAT TEDKHTYQEL  1140
YLKNHFLQEK LKYHIKLLPP SSTTTLKDAP KLGSFTPATE KNVFGYKEGV LEPNAEQNTK  1200
IPHLSNNDRI EVWIQKDGEK DYSLLISKTV GQIPGFRADK PKVNTTKLTE NFTFQTFKVD  1260
WSYPKACNGV ALSIPSPDIL KEFLSFTLEV TDPTTNKTAS YGPVLASEIR KNIVPEKNAA  1320
KQSCTFDFSL FKEFDMKKNY WGYMFTLKGK LDEAVPSGWE KKQPVSRPKD EKGKMKNGVT  1380
LVPTFEEPRT IELCKQIFPG KMFSLEQYMN AFKNKGTLSS PLTNQKSKVN GDHVTFNSVY  1440
PEFVIERQGE LSNYPLLLAG IKKVTCIFKN TAKTEVITPT DTQFTMKNNA LHVCFNTKID  1500
VTQKEEPDGW KVAGEVGKGA LLSALIPSSV ENIKHEFNKY STYNAEVDGL IKSDKYDKIF  1560
KVQLTVDKDI LTDNNHKDQV FTIFETKI                                     1588

SEQ ID NO: 29          moltype = DNA  length = 1944
FEATURE                Location/Qualifiers
source                 1..1944
                       mol_type = other DNA
                       organism = Bacillus thuringiensis
SEQUENCE: 29
atgaaacaaa ataaaaataa tatgcgagga gaattatgta tgaaatacaa agatcgaaca  60
cctgcaaaac gtaaatacaa acaagcatta cttgctacag tagcaagtat gaccttagga  120
gtaagtacat taggaagtat gccttctgca ttcgctgatg aaaatacagc aaatatccca  180
caagcaactt ctgcatcagc aactgatgaa cccgttttca aaagagaaag caatggagct  240
attacagttt taaaagacaa actattcaat atagaaacct taaaagcagt tggttcatta  300
ggtggagata cattaaagca agcctgggct gattctaaag tagatggtgg gaactttaac  360
aacactttta gaactttagc catgggatca gcagcaataa ttccatatgg tggagtagtc  420
ctttctccac taattgggct actatggtca gcggatacga cagatgaaca gaatcggtta  480
aacaaattga agcaggagat ttttgagcaa acgcatacac aaattacaaa gcatgatttg  540
gaagaacttg aacaaaaact aaagaaacta tatacagatt tagaggaatt tgaaaaaaca  600
ataaatccta acggcagaaa acttgctgca gcaccttcag taggtgataa agcagctgcc  660
attcgatcgc aagcggaatt tattcataac gattttaaaa accttatatc agaatctcaa  720
aaaccgtcat ataaagaagc tgaacttcct atttttatga ttgcagcaac ggctcacttg  780
aacttcttgc acttcatgga acttcacggt aaagatccta aaataaacta tagccatgac  840
ggactcgaac aaatgttttt aaaagatcaa aaacgagtcc gtgaggaata cgtcaaatac  900
gcaaacaaca tcgctcagaa ggatttagat cgtgcagatc ggtttgccac aaaaggagtg  960
ccagagctgc ttcatacgcg cgccaacgct gacactctcg gagcccgtat tatgacatat  1020
agtattaaga aagctatcca aggagagaac gaaaaccttg aaatagcatt aaataagacc  1080
ataaataata tagctttcaa acaagcagca aacatcaaat ctgagtggac actggatcaa  1140
aatggacgac ctttctacta caggctagat ggtaatatac aaactggatg gaaagaaatt  1200
tcaacttcat ttgccactag atatgacttc cttggtgaaa aatggttaaa agaacaagga  1260
ctttcatatt caaagtatta cttcagccct gaaaaaactg acaaattcga aaaaggtgag  1320
atgtatagag acacgacaca aactattaat gggaaaactt atcagtttag taaagatggt  1380
aagtgtctaa atccagatgg agtacaaaaa actggttggg ttcagcttgg ggatacatgg  1440
tattatgtaa gccctacaga cagtactaaa aactcctcag gcgaagtatt taaacagggg  1500
aaagtagtaa ccggaaaggt tgaaattaaa gggaaaactt attacttcaa acctgccaca  1560
ggagaaatgg cgactggatg gaccaaaact ggagataagt gttattactt cagtccagaa  1620
gataacacta aaaactatga cggcaccaca tttaacaaag gtgaaatgac gactggatgg  1680
atgcagatta cgagacttga atcgagcaaa aaaattaccg attattatta cttcagtcct  1740
acagacaacg ctacaaacaa ctatcaaaag gggaaaacat ttgctaaagg acaaatgtgg  1800
```

-continued

```
actggatgga tgcaatatac taaaaaagat aatccagcta atggaaatga taagtggtac  1860
tacttaaatg atagtactgg agctatgctt catgatacta ctactcccga cggctataaa  1920
gtcgataaga aaggtgtaca aaag                                          1944

SEQ ID NO: 30          moltype = AA  length = 648
FEATURE                Location/Qualifiers
source                 1..648
                       mol_type = protein
                       organism = Bacillus thuringiensis
SEQUENCE: 30
MKQNKNNMRG ELCMKYKDRT PAKRKYKQAL LATVASMTLG VSTLGSMPSA FADENTANIP  60
QATSASATDE PVFKRESNGA ITVLKDKLFN IETLKAVGSL GGDTLKQAWA DSKVDGGNFN  120
NTFRTLAMGS AAIIPYGGVV LSPLIGLLWS ADTTDEQNRL NKLKQEIFEQ THTQITKHDL  180
EELEQKLKKL YTDLEEFEKT INPNGRKLAA APSVGDKAAA IRSQAEFIHN DFKNLISESQ  240
KPSYKEAELP IFMIAATAHL NFLHFMELHG KDPKINYSHD GLEQMFLKDQ KRVREEYVKY  300
ANNIAQKDLD RADRFATKGV PELLHTRANA DTLGARIMTY SIKKAIQGEN ENLEIALNKT  360
INNIAFKQAA NIKSEWTLDQ NGRPFYYRLD GNIQTGWKEI STSFATRYDF LGEKWLKEQG  420
LSYSKYYFSP EKTDKFEKGE MYRDTTQTIN GKTYQFSKDG KCLNPDGVQK TGWVQLGDTW  480
YYVSPTDSTK NSSGEVFKQG KVVTGKVEIK GKTYYFKPAT GEMATGWTKT GDKCYYFSPE  540
DNTKNYDGTT FNKGEMTTGW MQITRLESSK KITDYYYFSP TDNATNNYQK GKTFAKGQMW  600
TGWMQYTKKD NPANGNDKWY YLNDSTGAML HDTTTPDGYK VDKKGVQK                648

SEQ ID NO: 31          moltype = DNA  length = 1809
FEATURE                Location/Qualifiers
source                 1..1809
                       mol_type = other DNA
                       organism = Bacillus thuringiensis
SEQUENCE: 31
atgaataaga aattgtacaa gaaattctta ttatcaatga tgattgctgg aatggtaaca  60
agtaatatag taccacttca tactttcgcg gcagaacaaa aagtccatac aactatatcg  120
caagaaacca ttcataatta ttcacttggt cctgagggct ttcaagatgt actagcacca  180
gcaatgtcta atgtacttgt tatggattca tatgccaaaa caatacgtaa tcaacaagag  240
acagacctta gtggtataag ttctcttaat agttatttac gagcaaacat gttgaagcac  300
caggacgatg caaaaaaaaa cgcgacctat tggttagata atcttaaacc acgtattatg  360
aatacgaatc aaaacattgt aaattataat gaaacatttc aaacgcacta tagtatttta  420
ctagctgcaa tagatcaaaa agatactgaa aaattgaaaa ctgagctcga aaaattgtat  480
caaagtatat tgactaataa aagtgaagtt aacgagctat tggaacagct gaaaacattc  540
cgaaataaaa tgaaagcaga tacgcaaaac tttaaacaag atacaaatca attaacgact  600
attttagcta gtacaactgc aggtattcca tatttagaac agcgaattaa tgggtataat  660
gagtctatca aaaaaagcaa tgatcaaatt attgcaggtt cagtactttg cgcgacgtta  720
ataacgtgta tcattggtgg accgctgatt gcaacagcaa aagtaatat tgcatctgct  780
gagcgagaaa tagaaatttt aaaagcacaa atttctgggg cacaagcaga aatagctatt  840
ataactgatg caaaaaataa gactacgaat atggcggaaa caattgacac agctattact  900
tctatacaga aatgtctaa tagttgggat actgtagcag caaaatataa taatttagta  960
aaaaatatca catttattac cccagaagaa tttgctttta taaaagcaga tcttaataca  1020
gcaaaagata gctggcaaga tcttaagaat tatgctgata aattatatga atcggtgaaa  1080
attgcggaga aagaagagca ggatcttatg gatcgacttc gtccgtcaag tgttcaatat  1140
ttctacaaac cgatacataa tgcctataca tttgaaataa aaacgggagc aaatgcacca  1200
aatgcgtcct ataaagttat gaatttaaca aaacggacta ctcataatat gtggagcgga  1260
ggaccaaatg caagcatgtg gattgaccgg cttccattaa acttcaaaga ccaatatgcg  1320
gtaatagcaa cggtcaatgg aatggattat gtcatatata aagaagtagg agaaaacatt  1380
cctggagcta atttgaatgg tacctatcaa ctattttctg cgttaaataa tagtagcgtt  1440
atagatatgg atcgatcaac gaataatgtt accttatgga gcaataacgg cggtaatcat  1500
caaaaatgga agttagtata tgattcaaat aaaaaggcct atcaaattaa aagtgtaaca  1560
aatgaaaatt taatattagc ttggaatgac tatcaaggtt ctaacaatgt ttttgctaca  1620
cctaaccaat actatgaaga gcattattgg atagttgaag atgcaggaaa tggatatttt  1680
tatttaaaaa ataagaaaaa ctctaggtat ttagatgtaa ctggttctgg tactaaaaat  1740
ggaacaaata ttatagtata tccatttaca gctagtaata atcaaaaatt caaattacag  1800
agactaaat                                                           1809

SEQ ID NO: 32          moltype = AA  length = 603
FEATURE                Location/Qualifiers
source                 1..603
                       mol_type = protein
                       organism = Bacillus thuringiensis
SEQUENCE: 32
MNKKLYKKFL LSMMIAGMVT SNIVPLHTFA AEQKVHTTIS QETIHNYSLG PEGFQDVLAP  60
AMSNVLVMDS YAKTIRNQQE TDLSGISSLN SYLRANMLKH QDDAKKNATY WLDNLKPRIM  120
NTNQNIVNYN ETFQTHYSIL LAAIDQKDTE KLKTELEKLY QSILTNKSEV NELLEQLKTF  180
RNKMKADTQN FKQDTNQLTT ILASTTAGIP YLEQRINGYN ESIKKSNDQI IAGSVLCATL  240
ITCIIGGPLI ATAKSNIASA EREIEILKAQ ISGAQAEIAI ITDAKNKTTN MAETIDTAIT  300
SIQKMSNSWD TVAAKYNNLV KNITFITPEE FAFIKADLNT AKDSWQDLKN YADKLYESVK  360
IAEKEEQDLM DRLRPSSVQY FYKPIHNAYT FEIKTGANAP NASYKVMNLT KRTTHNMWSG  420
GPNASMWIDR LPLNFKDQYA VIATVNGMDY VIYKEVGENI PGANLNGTYQ LFSALNNSSV  480
IDMDRSTNNV TLWSNNGGNH QKWKLVYDSN KKAYQIKSVT NENLILAWND YQGSNNVFAT  540
PNQYYEEHYW IVEDAGNGYF YLKNKKNSRY LDVTGSGTKN GTNIIVYPFT ASNNQKFKLQ  600
RLN                                                                 603

SEQ ID NO: 33          moltype = DNA  length = 2403
```

| FEATURE | Location/Qualifiers |
|---|---|
| source | 1..2403<br>mol_type = other DNA<br>organism = Bacillus thuringiensis |

SEQUENCE: 33

```
atgaaaaaga aacaaaaaac actctctatg acagtagcta caggtgtact tgctggtaca    60
tacattccaa ctgcatacaa ggtatttgca gaaactgaac aaaaagaaga tttcaaagaa   120
aatcaaacaa aaaatagtga tcaaaataat cttctatttg attcacgtgg tttgtttgaa   180
aaccccttaca aaggggtaac tgttgagagt tttttaaatg catttaatag taatcagttc   240
aaaccgctat taacccatat acatcaaaat aaagatgcgt ggctcaggtac tattgctttt   300
ctaaaaggaa tgatgaccac aggattatct ttattaccac caccagctag tctattagga   360
agtatttggt atgtatttat gcctggctct agcgttcaag atgatatgtg gatgcaatta   420
gtaaaataca ttgatgaaca aatagatagc aatataaatg attatcataa atatcttatg   480
agtgcagaat gtaaaggttc tatgacagcg ataaaagaat atcagcgagt gctgcaaata   540
tataatgaca gtaaaaatag tttgacaaga gtcgaagagc ctggaacacc ggtaatcgag   600
gctgttcggg cagcggatag ggatttgaaa aagtttatta ctattattca gaccccctgaa   660
aaaagcagtg attctgtgta tcaacaatta acagctccaa tctttgtaca agctgtaaat   720
gtccatctcc tattactgag agacatgatt ctatatggag aagaggcggg aatgataaa   780
aatcaatggc aaggatatag ggatcaactg aaagaactta ttcaagaata tacgaattac   840
gctatgaaag tatataacga tggattgaaa aaagaaaaa atgaagctga acagattaat   900
acccaagaaa aatataggaa tactgacagt tggaatcata ttaatgaata tgtaaggaa   960
tatcattaa gcgttctaga ctttgtagca ttgtttccat ctaccgatcc tagtaatatt  1020
ctaaaggaac aatgcaaaaa aaattctagg caaatttatt cagatattgg aaggaaagtc  1080
caaccaaatg aaaaaacatg gcaatatata caacagatct tagactccca gaatataaaa  1140
ggtgaactga aacagcttga tatacgatgt tggggtcgta ttgatgccat caaccatgg  1200
tatgataatc gtgtggttgg tggaaatatg tatcatactc ctggatggt tggaaatacg  1260
aatggaggaa ctttaagaga gcgcattcat tccgcttcta atcctataac taaaattacg  1320
atgggatcag aaattactcc taattatctc gacattaccc atgatgacag aaagacatac  1380
cctcgatttg gttcaaccca ctctgggatt ggaaaggaat ctactttga atttcctaat  1440
caaaaggttt ctcttgttca cgcatttaac agaaacactc aacctgggtt tgaaggtatt  1500
gatgcagtag tatttggatt tagcgacaaa aaagttgatc ttagacacgc tttgatgaca  1560
aatatgataa attcaatccc agctgagatg tataataggg gaattagtaa tttcaaacca  1620
caaattgaac ctacacatgc ggcgcaaaag gcaatgaaaa cagatactac taattcttat  1680
ttagaatata gcgtagaaaa ttttaaagag caagaatata aaattagata taggggttgca  1740
gctaacgaga atgctaaaat tagtctttca cacagaagta gtgccagtaa taatttcaca  1800
aaaataggtg acacattaat ccctactaca ggacatgcag gagacactgt aaaaggtgaa  1860
tgtggtcatt acaagattgt agaaggaccc actgtcaaat aaaatgggg aacaaatgaa  1920
ttgaaactgg aaaatgcaca agggaaattt tctttagctg aaattgaatt agaatctgtc  1980
gaaaaggatg aagttatagc cgaggataat tttgataatc aacgattaaa ttgggtaaac  2040
ataggtggta ttgtagatga aggtatgata ggaaaagctg gtatggttgg tacaaatgga  2100
gatacttgga cgtatattca agatcgagta gcaacaaatt ctaggtatac cttgagcatg  2160
aaagtaaaat taaattccga tgatgaaaat gcaaggaaaa aggtaacgat attcacagat  2220
aatgcaaatc atgagcgaat tacaaaaaca gtcgagctta ggggagggc aggctatcaa  2280
gaaataaagc tagaatttat ttcaaaaaga ggttctagta acactcatgt tggcatccaa  2340
acattaaatg gaacatctag tgtattattt gatgatgtta agttatcgg tgcaaaaaat  2400
ggt                                                              2403
```

| SEQ ID NO: 34 | moltype = AA   length = 801 |
|---|---|
| FEATURE | Location/Qualifiers |
| source | 1..801<br>mol_type = protein<br>organism = Bacillus thuringiensis |

SEQUENCE: 34

```
MKKKQKTLSM TVATGVLAGT YIPTAYKVFA ETEQKEDFKE NQTKNSDQNN LLFDSRGLFE    60
NPYKGVTVES FLNAFNSNQF KPLLTHIHQN KDAGSGTIAF LKGMMTTGLS LLPPPASLLG   120
SIWYVFMPGS SVQDDMWMQL VKYIDEQIDS NINDYHKYLM SAECKGSMTA IKEYQRVLQI   180
YNDSKNSLTR VEEPGTPVIE AVRAADRDLK KFITIIQTPE KSSDSVYQQL TAPIFVQAVN   240
VHLLLLRDMI LYGEEAGMDK NQWQGYRDQL KELIQEYTNY AMKVYNDGLK KRKNEAEQIN   300
TQEKYRNTDS WNHINEYVRE YTLSVLDFVA LFPSTDPSNI LKEQCKKNSR QIYSDIGRKV   360
QPNEKTWQYI QQILDSQEYK GELKQLDIRC WGRIDAIQPW YDNRVVGGIL YHTPGWVGNT   420
NGGTLRERIH SASNPITKIT MGSEITPNYL DITHDDRKTY PRFGSTHSGI GKESTFEFPN   480
QKVSLVHAFN RNTQPGFEGI DAVVFGFSDK KVDLRHALMT NMINSIPAEM YNRGISNFKP   540
QIEPTHAAQK AMKTDTTNSY LEYSVENFKE QEYKIRYRVA ANENAKISLS HRSSASNNFT   600
KIGDTLIPTT GHAGDTVKGE CGHYKIVEGP TVKLKWGTNE LKLENAQGKF SLAEIELESV   660
EKDEVIAEDN FDNQRLNWVN IGGIVDEGMI GKAGMVGTNG DTWTYIQDRV ATNSRYTLSM   720
KVKLNSDDEN ARKKVTIFTD NANHERITKT VELKGGAGYQ EIKLEFISKR GSSNTHVGIQ   780
TLNGTSSVLF DDVKVIGAKN G                                           801
```

| SEQ ID NO: 35 | moltype = DNA   length = 3561 |
|---|---|
| FEATURE | Location/Qualifiers |
| source | 1..3561<br>mol_type = other DNA<br>organism = Bacillus thuringiensis |

SEQUENCE: 35

```
atgaatcaaa ataataatga atatgagatt atagatgcaa atccgtcaac ttattccaat    60
tgtccatcca acaaaaataa ctttagatat ccttacgcaa ataatccaaa ccaagcatta   120
caacatacca attacaaaga ttggattaat atgtatcaag aaaatcagca atatcgtgag   180
aatcttgagg tttttaatat tgatataccct gcagcagttg gtgcaggtat tattgtaata   240
ggtactaaa tgactgcttt tgccacttta gtaccaggtg gaattgtact gatatctttc   300
```

```
gggacattat tacctatctt ttggccatca acaacagagt ttaaaacggt ttggggagcag   360
tttatgacac atggtgaaac aattatcgga caaaatttac aacccgataa acgaaatgac   420
gtcatgctaa aattagaagg ccttagaaac gttttaaaaa cctatgaaga acacctccaa   480
acatggaaaa acaatccaac tccaaaaaac gccaacgatg tactaaatca aatcgctata   540
gttcattctc attttgaatc agatatgcct acaattcaag ggaaaccgat agttccaggt   600
agttctgatt atagagtaat actattatct gccatgcac  acgctgcaaa tttacatcta   660
aatttgttaa accaagcagc ccgatttcaa gatcgtttga acgctaccca acaattctct   720
tattcaggca atctatcaag agctattgat tatcgtggaa aattagaaga atatatagaa   780
aaatatatta atgaatgtac agaaacctat aaattaggct taaataaact taaaaattcc   840
cctgaaatct catgggatat ttataatacg tatcgtagag aaatgacgct tactgtatta   900
gatcttgttg cgcttttttcc agattataat gtacttaact atccagtagg aactaaatca   960
gaacttacta gaaaaatcta ttcaaatact tttggaccac gtcttatag cggaaaagaa   1020
gatcttacta taagaagaa tttattcaca catcaacctg atttgtttac aatactaaga   1080
tcatttacct ttaatgaaag cgaagaaata gaatattatt atctatccgg tattataaat   1140
aggcataatt acattaattc ttctgctatt atagaaagac atttggaga ttcaagtaag   1200
cctgtacaaa atctaaaaat tattcctaaa aaataattc gagttcattt cgcaagagct   1260
gcaattataa ttagtgcggg tacggctgtt tttcaaatca caattttaaa tttattttat   1320
ggggaaggac cacaggatta ttactcatat atatctggta aaccagcacc tgagctacaa   1380
tccacagatc ttaagtttcc tgatcacaat ttacattcta tttcaatatt tccaaggaac   1440
actgaacttg gtaatacgtt tgaagtatat ttattcactt ggacacattc tggtgtttct   1500
actaacaatc aaatatatga agatgtaatc acccaaatac cagctgtgaa aggtaatgtt   1560
atccaagctg gaacaaaccc taaccccaac ttggattcac aagttattcg cggtcctggt   1620
ttcacaggag agatttagt ccgtcttaga tccaaaatga tccttacgat ccaatcacct   1680
agatcacaaa atacaacttc aaccttttat tatatccgta ttcattacgc gtcaaatagc   1740
actactttaa ttactataaa cattccagct ttaagaatta atcaaaacat gcatttacct   1800
gcaaccttta ctcatgtcac tgttcctgat taaaaatata cagaatttaa atatttacaa   1860
tttaacgccc cagtgaaat cccctccaaat gaaacaatag atatagaact ttttggaacc   1920
agtggttcag agttgttact gattaataaa attgaattta ttccagtaac cccgtctgtc   1980
aaacaaatgc acgaagaaca aagatttcaa aaaacaaaac aaagtataag ctcattattt   2040
actactgaca gaaataacat tttgaaatta gaaagtacag attatcaaat tgatcaaatt   2100
gcaaatttga cagaatctat atcagaggaa ttatacccaa aagaaaaaat gatcctatta   2160
gataaagtaa aatatgcaaa acatttaagt caatcacgaa atttactcga taatggaaat   2220
tttgaatcta caatgggatg gacaacaagt cataacatta ctattcaaac agataatcca   2280
attttcaaag aacaatatct tcatatgcca ggagcaagaa caacagaat tggcaataca   2340
atctttccaa cttatgttta tcaaaaaatt gatgaatcaa aattaaaacc atatactcgt   2400
tatatcgtca gaggatttat tggaagtagt aaaggtttag aaatacttgt cagaagatat   2460
aacaaaaaag tccatacaat catgaatgta cccaatgatc taaccaacat aatgtcttat   2520
gaagaatcca attcatgtaa cccatgtgaa ccgcaatcgt attctgttat gagtgaaaaa   2580
gactataaaa tgagccaaat atcacaaaat ccgacaatat tacgtacgac atcagatttc   2640
aatcaacata catgtgactg tgaaacaaac acagtaaatt cagcctatca tgcctctcat   2700
gtattttcaa attctattga tacaggaaat ttagatttca atcaaaatct tggtattgga   2760
atcctattta gaatctctaa tccagatgga tatgcaacat taagtaatct agaagtaatt   2820
gaggaaaaaa cattagtggg agaagaaatc aatcaagtta aagaaaaaga aaacagatgg   2880
aaaaacgatt tagattataa acgaaatgaa acagaacagg cgttttcacg agcgcaacag   2940
gcagtaaatc gttttattat aaatacccaa cattctatgt tgaaaatcga aacaactatg   3000
caagatattc tgatagccga taatcttatc gattctatcc catatgtgta caacaaatgg   3060
ttaccaaatg aaccaggtat gaattataat atgtttcaaa tttaaaaaa tcagatttca   3120
caagcatatt ctttatatga aaatagaaat atgattcaaa atggtaattt cataaatggt   3180
ttaacaaatt ggtatgcatc atcagatgca gaaatacaac aaatagatgg tatatccgta   3240
cttgttctcc cgaattggag tacacaagta tctcaacaaa atatacagtt acaaccaaat   3300
cataaaatata tgttacgtgt cacagcaaaa aagaaggaa tgggaaatgg atatgtaaaa   3360
gtgagtgatt gtgcaaatca tgtagaaaca ctaactttta aatccagtga tatcaataac   3420
aacaatatgt ggaatgaatc tataggatat atgaccaaaa caatgtatgt cactccacat   3480
actagtcaag tacgcattga tataggagaa acagaaggta cttttaaaat caatagtgtg   3540
gaattgattt gtatgaagaa t                                              3561

SEQ ID NO: 36         moltype = AA   length = 1187
FEATURE               Location/Qualifiers
source                1..1187
                      mol_type = protein
                      organism = Bacillus thuringiensis
SEQUENCE: 36
MNQNNNEYEI IDANPSTYSN CPSNKNNFRY PYANNPNQAL QHTNYKDWIN MYQENQQYRE    60
NLEVFNIDIP AAVGAGIIVI GTIMTAFATL VPGGIVLISF GTLLPIFWPS TTEFKTVWEQ   120
FMTHGETIIG QNLQPDKRND VMLKLEGLRN VLKTYEEHLQ TWKNNPTPKN ANDVLNQIAI   180
VHSHFESDMP TIQGKPIVPG SSDYRVILLS AYAHAANLHL NLLNQAARFQ DRLNATQQFS   240
YSGNLSRAID YRGKLEEYIE KYINECTETY KLGLNKLKNS PEISWDIYNT YRREMTLTVL   300
DLVALFPDYN VLNYPVGTKS ELTRKIYSNT FGPRLYSGKE DLTIQEDLFT HQPDLFTILR   360
SFTFNESEEI EYYYLSGIIN RHNYINSSAI IERPFGDSSK PVQNLKIIPK KIIRVHFARA   420
AIIISAGTAV FQITILNLFY GEGPQDYYSY ISGKPAPELQ STDLKFPDHN LHSISIFPRN   480
TELGNTFEVY LFTWTHSGVS TNNQIYEDVI TQIPAVKGNV IQAGTNPNPN LDSQVIRGPG   540
FTGGDLVRLR SKMILTIQSP RSQNTTSTFY YIRIHYASNS TTLITINIPA LRINQNMHLP   600
ATFTHVTVPD LKYTEFKYLQ FNAPVEIPPN ETIDIELFGT SGSELLLINK IEFIPVTPSV   660
KQMHEEQRFQ KTKQSISSLF TTDRNNILKL ESTDYQIDQI ANLTESISEE LYPKEKMILL   720
DKVKYAKHLS QSRNLLDNGN FESTMGWTTS HNITIQTDNP IFKEQYLHMP GARTTEIGNT   780
IPPTYVYQKI DESKLKPYTR YIVRGFIGSS KGLEILVRRY NKKVHTIMNV PNDLTNIMSY   840
EESNSCNPCE PQSYSVMSEK DYKMSQISQN PTILQYTSDF NQHTCDCETN TVNSAYHASH   900
VFSNSIDTGN LDFNQNLGIG ILFRISNPDG YATLSNLEVI EEKTLVGEEI NQVKEKENRW   960
KNDLDYKRNE TEQAFSRAQQ AVNRLFINTQ HSMLKIETTM QDILIADNLI DSIPYVYNKW  1020
```

```
LPNEPGMNYN MFTDLKNQIS QAYSLYENRN MIQNGNFING LTNWYASSDA EIQQIDGISV 1080
LVLPNWSTQV SQQNIQLQPN HKYMLRVTAK KEGMGNGYVK VSDCANHVET LTFKSSDINN 1140
NNMWNESIGY MTKTMYVTPH TSQVRIDIGE TEGTFKINSV ELICMKN           1187

SEQ ID NO: 37           moltype = DNA  length = 1968
FEATURE                 Location/Qualifiers
source                  1..1968
                        mol_type = other DNA
                        organism = Bacillus thuringiensis
SEQUENCE: 37
atggaaaaca tgaagaaaca attagcgaat gttataactg gtacactatt agctcctatg   60
tttttaaacg gagatataaa ttctgtttac acggattgtc aaacaaaaca tgggcttaca  120
gctcaggaga tcaagagaa agaagtagat cgaaaaggac tttttggata ttacttttaaa  180
ggtaaagatt ttaataatct tactgtattt gcaccaacgc gtgataatgt cctttgtttat  240
gatcaactga cagcaaatac attactaaat caaaaacaaa aaagctatca gtctattcga  300
tggattggtt taattcaaag caaagaaaca ggtgatttca catttaactt atcaaatgat  360
gaacatgcgt tgatagaaat tgatggaaaa gtcgtctcta ataaggtaa agaaaaacaa   420
gttatccatt tagaaaaagg acagtttgtt cctatcaaaa tagaatatca agctgagaaa  480
ccatttaata cggaatgtca aacctttaaa aaccttaaac tttttaaagt agataatcag  540
caacagcctc atcaaatcca actagatgaa ttaagaaagc ctgaatttaa caaaaaagaa  600
gcacaagaat ttctaacaaa gacaacaata acaaatctag ttacacaaaa agtaaagagt  660
aacagagatg aagagacgga caaagtggaa gactctatcc cagacagttg caaagaaaat  720
gggtatacca tccaaaataa aattgccatc aaatgggatg attcactaac aagtaaagga  780
tataagagaa tcatttcaaa tccacacgat actcacatga ttgtagggcc ttattgtaat  840
tatgaaaaag cagtaagaga tatagattta tcaaatgcaa agaaaaatt taacccattg  900
gttaccactt ttcaagtgt agttagtata gaaaaattta tattattatc aaatgaggat  960
ttaacaaata gcgtagagct tcattcatcc tcaaattgct cgtatataaa taagaaggg  1020
gattcagttg aaacagaaat cggaaaagaa ggctttttct ttggagtaag tgtaaactat 1080
caacaatctg aaacagttgg gtatgaatgg gaacgtctta catggaatat ttttcaattt 1140
aatactgcat cagcaggcta tttgattcga atgttcgaga caataacggt ggagcaagaa 1200
cccatctatt atgtaaagcc tacatcgagt ttcgtattaa ataaaatac catcaaagtg 1260
ataacagtaa aatcgaattt gactacatta agtatatctc cggacagat ttataaaaaa 1320
caaggtcaaa atggaatcgt aataacatcg atggacgatt ttaacgctca gtcgattaca 1380
gtaattaagc agcagttagg tgtattaaat aataaacctg ttatattaga gacaggcgtt 1440
attgtgaaat gggtacatga atgaatgat gtgacacaac gaatcgaagt taaaactgat 1500
tctattatcg ccaataatgg aaaacgtgtg gctgcaaaat tttatacaga cctagaagat 1560
aaaaaaacag aattgatgtt aataaatata ctaaaacttt catcttcaaa tattacaatt 1620
gtattattcg aatgtaaaaa taaaaaagta tatgaatcga ttgttataat ttatctagat 1680
gaaaatgcgg aaagagaagt caaaaaacat ataaatggg tttaagaat                    1740
gtaaaccatt tatataatgt aaaattgaca gtaaagatga attttacgtt caaaatggcc 1800
actttgtatg acgtggaaga tggagcaaat gctgggtatt tagtgagatg gaataatgtg 1860
agtattggg acgaaattcg tactggtgaa ttagtggcgg tttcatacca tagctacagc 1920
tatcttcaaa ggcgaaaagt aaagatgcta tccttcactt ggatcaag              1968

SEQ ID NO: 38           moltype = AA  length = 656
FEATURE                 Location/Qualifiers
source                  1..656
                        mol_type = protein
                        organism = Bacillus thuringiensis
SEQUENCE: 38
MENMKKQLAN VITGTLLAPM FLNGDINSVY TDCQTKHGLT AQENQEKEVD RKGLFGYYFK   60
GKDFNNLTVF APTRDNVLVY DQLTANTLLN QKQKSYQSIR WIGLIQSKET GDFTFNLSND  120
EHAVIEIDGK VVSNKGKEKQ VIHLEKGQFV PIKIEYQAEK PFNTECQTFK NLKLFKVDNQ  180
QQPHQIQLDE LRKPEFNKKE AQEFLTKTTI TNLVTQKVKS NRDEETDKVE DSIPDSCKEN  240
GYTIQNKIAI KWDDSLTSKG YKRIISNPHD THMIVGPYCN YEKAVRDIDL SNAKEKFNPL  300
VTTFPSVVSI EKFILLSNED LTNSVELHSS SNCSYINKEG DSVETEIGKE GFFFGVSVNY  360
QQSETVGYEW GTSTWNIFQF NTASAGYLIR MFETITVEQE PIYYVKPTSS FVLNKNTIKV  420
ITVKSNLTTL SISPGQIYKK QGQNGIVITS MDDFNAQSIT VIKQQLGVLN NKPVILETGV  480
IVKWVHEMND VTQRIEVKTD SIIANNGKRV AAKFYTDLED KKTELMLINI LKLSSSNITI  540
VLFECKNKKV YESIVIIYLD ENAEREVKKH INDTIGGFKN VNHLYNVKLT VKMNFTFKMA  600
TLYDVEDGAN AGYLVRWNNV SIGDEIRTGE LVAVSYHSYS YLQRRKVKML SFTWIK      656

SEQ ID NO: 39           moltype = DNA  length = 1641
FEATURE                 Location/Qualifiers
source                  1..1641
                        mol_type = other DNA
                        organism = Bacillus thuringiensis
SEQUENCE: 39
atggaacaca cagacaaaaa tagaaacgag ccacagcaag ccacacctaa tccacaaggt   60
gctagcggta taagaagtaa tgcctcaata tccgctgatg agaaagacaa gaatgctatt  120
cagcaaaaaa gtcctaacac ctattatgag ggtacacaaa aaatctgggt cctctagca   180
caatttgata catgggtaca agatcttggg aaaaggaatt ataaacacac agttgctatg  240
gcagaaaagc tactaccaac aatctataaa gatttaaata gaggaaattt caacaatact  300
gcaaggtgca ttactatgtt atctctacagc ttaattccat atggagtggc attcatttct  360
ccaataattg ggattctttg gccggagaac ggggccaaata taaagaaat gctgcaggaa  420
atggaaata aacttgttag aataatggat gaaaaaattg aagccaaaga tttagatgat  480
cttgaggctg cagtaaaagg attgatggta actctaaaag aatttgaaaa ctcattgcag  540
ggtaatatag tggtgaaaa ttattctgcc ccagctgatg tagactcact taaccgaggt  600
cgtataacag ccattcaaaa gggggtttaac gatcttatta gtgcagctag taaaccgagg  660
```

```
tttaaaatas cagaacttcc tatatataca attattgcaa ctgctcactt gaatttcttg    720
catactgtgg aaaaacaggg aacttcacct aaaataaact acacagaagc agccttaaaa    780
gattttctac aaaatatgaa gaagaatcac aaggattatg caaattatat agaaaaaacg    840
tttaagaag gagaaactag aatcgatagt aaactagaag acaagcaaca aatagaaaaa    900
gaattagata aagtacacga acagttatca gcacttggtc ccaaacctaa gaatcacact    960
cacatagaag aaaatagata tataaataag aaggaggaac tttacgaacg agcaaggtct   1020
cttaaggaaa ggttgtctaa atataatgaa ttaatgtatc aaaagagtga tttttatagc   1080
aagacaaagg gtagcacagc attccaaata gcatcaacag gaaaaacaac agcaaatcca   1140
agttgggtta atacagaagg atcgtgggtt cacaatgggt tttggtatta tattgatgca   1200
aaagggcaag tgaaaaccgg ttggttcaat aataaggcac ctgatggtaa ggatagatgg   1260
tattacctta gcactggaac aactggtctc gacagtgtaa gggggaattc tcttcttccc   1320
aaaggaacaa tgctaactgg ttggttccac gatacgcgta aagataagca gatgatcggt   1380
gtgaatacga agactactaa tgaatactgg tattacctca gcccgaaaaa aaatcttaaa   1440
aattctgccg gagaactatt taatctagga cagatgatga caaatgggt tgaaattaag   1500
gatacaaaga ctggtgaacc acaatgtat tattttaacc ctgaagacgt agtatgata   1560
catgataaaa aagcggtaca aattggtaac ctaaaatatg attttgattc caatggtgtg   1620
tgtacaacgc ctaacggtta c                                             1641

SEQ ID NO: 40        moltype = AA   length = 547
FEATURE              Location/Qualifiers
source               1..547
                     mol_type = protein
                     organism = Bacillus thuringiensis
SEQUENCE: 40
MEHTDKNRNE PQQATPNPQG ASGIRSNASI SADEKDKNAI QQKSPNTYYE GTQENLGPLA    60
QFDTWVQDLG KRNYKHTVAM AEKLLPTIYK DLNRGNFNNT ARCITMLSTA LIPYGVAFIS   120
PIIGILWPEN GPNIKEMLQE MENKLVRIMD EKIEAKDLDD LEAAVKGLMV TLKEFENSLQ   180
GNIGGENYSA PADVDSLNRG RITAIQKGFN DLISAASKPR FKITELPIYT IIATAHLNFL   240
HTVEKQGTSP KINYTEAALK DFLQNMKKNH KDYANYIEKT FKEGETRIDS KLEDKQQIEK   300
ELDKVHEQLS ALGPKPKNHT HIEENRYINK KEELYERARS LKERLSKYNE LMYQKSDFYS   360
KTKGSTAFQI ASTGKTTANP SWVNTEGSWV HNGFWYYIDA KGQVKTGWFN NKAPDGKDRW   420
YYLSTGTTGL DSVRGNSLLP KGTMLTGWPH DTRKDKQMIG VNTKTTNEYW YYLSPEKNLK   480
NSAGELFNLG QMMTKWVEIK DTKTGEPQWY YFNPEDGSMI HDKKAVQIGN LKYDFDSNGV   540
CTTPNGY                                                             547

SEQ ID NO: 41        moltype = DNA   length = 1371
FEATURE              Location/Qualifiers
source               1..1371
                     mol_type = other DNA
                     organism = Bacillus thuringiensis
SEQUENCE: 41
atgaattctg gtcaaagaaa taatgagtgg aacaatcaaa atatgtttga tgaacacatg    60
aatcaaacga ttaataaaga taaatcgtgc cattgtaact cagttgtaac tggcacgcta   120
tttacagaaa ataacaatcc acctcaacca aatttacctg atgaaagtaa aagatttcaa   180
acgattactt tttcttattc ttctcacaat cgtggtttag atgctttaag aactcgacct   240
ggagatcttt taggtaatga tttgggagaa ttttgtcgta atgtaacact tcaaaatcaa   300
gtagtaaatg attgggtcca tggaaatgga aatcgacaac gatttatatt ttaccataca   360
gatagtggaa gatttgtaat agcaaatcaa gcatatgggg aagttttaac gattgtgcct   420
aataataatc attcaacagt tactcgattg tataatggtg aatcagtca gttattcaga   480
aaagtttcag atacgagtgg taattttaat ctagtaagtg ataataacaa ttatactata   540
tcagcatgtg gtacagccga tcaggtggat tcgtggataa gaattacagt gggtcttcct   600
actgttccga gcaatcactc aagtttttta cttagacata tagagtctca aaatagacct   660
gtaacttttc atccactatc acctccaaca caattagttg ccccgccacc attaacatca   720
ctgactgata ctggtcttaa cccaaatata gcaccaagag caattttagg aaacacatta   780
ataccttgta tattaataaa tgatattatt ccactagatc aaagaatcag agatcatcca   840
tattatattt taacacgtaa tgtatattgg tatagattat ggacagatac aatccctgca   900
ggatcgactg ttaataaaat tgaaataacc ggaatgcatt cagatgtaca agaaaacatg   960
aaaaatacat tagatatgtc aataggagca gattgggggt tgcaattttt tcaaaagaca  1020
aatccgttta aacaacaaat tagtagtggg ttaaataaca atccttctca cactattaca  1080
cctttaggat tacgggaaga cgaagtaccg tatacaaatc gtacgtttga gagtgtgaga  1140
tatataaggt atgtaaaagc atatgaatat gtattaacac gttctgataa acaaccgta   1200
ggaactccat ggacttacta cgattataat agtatgttgt tacaaacata tcctacgaat  1260
caattcataa taatggaaaa tgataaaata gtaagatgtg ataatagtta tgatttatct  1320
gtatggaaaa ccccaatgaa aatacgagat ggtgaaatta tcgaaagaaa a            1371

SEQ ID NO: 42        moltype = AA   length = 457
FEATURE              Location/Qualifiers
source               1..457
                     mol_type = protein
                     organism = Bacillus thuringiensis
SEQUENCE: 42
MNSGQRNNEW NNQNMFDEHM NQTINKDKSC HCNSVINGTL FTENNNPPQP NLPDESKRFQ    60
TITFSYSSHN RGLDALRTRP GDLLGNDLGE FCRNVTLQNQ VVNDWVHGNG NRQRFIFYHT   120
DSGRFVIANQ AYGEVLTIVP NNNHSTVTRL YNGESSQLFR KVSDTSGNFN LVSDNNNYTI   180
SACGTADQVD SWNRITVGLP TVPSNHSSFL LRHIESQNRP VTFHPLSPPT QLVAPPPLTS   240
LTDTGLNPNI APRAILGNTL IPCILINDII PLDQRIDHP YYILTRNVYW YRLWTDTIPA    300
GSTVNKIEIT GMHSDVQENM KNTLDMSIGA DWGLQFFQKT NPFKQQISSG LNTNPSHTIT   360
PLGLREDEVP YTNRTFESVR YIRYVKAYEY VLTRSDKTTV GTPWTYYDYN SMLLQTYPTN   420
QFIIMENDKI VRCDNSYDLS VWKTPMKIRD GEIIERK                             457
```

```
SEQ ID NO: 43          moltype = DNA  length = 870
FEATURE                Location/Qualifiers
source                 1..870
                       mol_type = other DNA
                       organism = Bacillus thuringiensis
SEQUENCE: 43
atgcaaaaga aaataatatt gtgtggtgtg atggctagta ctttattagg tacgggtatt  60
ttttctaata ctgcaagtgc tactgaaatt cagaaaaata gagaagatat tgtagattat  120
aagaatgttg gtcaacaagg ggcaatagaa gatattgata gaaaaattga tagtatgata  180
gatgccattc ctccgtatat tgaaactaag tggcggaggc taggggatgg aacagttaaa  240
atatccggag taaatattga aaaaagtaat gttacaaata ccataccttt atttttagga  300
tcaaatacat ttataaatga tacagatcga gaaatgacat ataatactag tacttttagt  360
gaagaaatta caacaaccac atctactcaa atcgaaaatg gctttaaaac tggacttgct  420
gcagaaggaa aagttggaat tccatttgta gctgaaggca aaatcacaac tactcttgaa  480
tataattttg ctaatacaaa tacaaataca gatagtatta ctaagacaat tacagctcct  540
tcacagcctg ttccggttaa gccacattca ataaccaaag cggaagttta tttcgaaaag  600
aaatctactt ctggaaatgt agaaatattt gcagatgttg cccaactgat aatagcaggt  660
cgcactataa caaatatagg taatggacta gatatgacaa ctaacacata tggtttaatt  720
aaaactcctg ataatccaca tacagttcgt gtaaagggaa gtgggaaatt tactactgaa  780
tatgctacag acttaattgt aaaaacgtat gacgtaacat caggtgaaaa atctgctaaa  840
ttgatagatt ctaaaagaat ttccataaat                                   870

SEQ ID NO: 44          moltype = AA  length = 290
FEATURE                Location/Qualifiers
source                 1..290
                       mol_type = protein
                       organism = Bacillus thuringiensis
SEQUENCE: 44
MQKKIILCGV MASTLLGTGI FSNTASATEI QKNREDIVDY KNVGQQGAIE DIDRKIDSMI  60
DAIPPYIETK WRRLGDGTVK ISGVNIEKSN VTNTIPLFLG SNTFINDTDR EMTYNTSTFS  120
EEITTTTSTQ IENGFKTGLA AEGKVGIPFV AEGKITTTLE YNFANTNTNT DSITKTITAP  180
SQPVPVKPHS ITKAEVYFEK KSTSGNVEIF ADVAQLIIAG RTITNIGNGL DMTTNTYGLI  240
KTPDNPHTVR VKGSGKFTTE YATDLIVKTY DVTSGEKSAK LIDSKRISIN             290

SEQ ID NO: 45          moltype = DNA  length = 672
FEATURE                Location/Qualifiers
source                 1..672
                       mol_type = other DNA
                       organism = Bacillus thuringiensis
SEQUENCE: 45
atggcggcaa caaatttatt gattgggcga attaaaaaca tatatctctt ttttcaacat  60
aaaaatataa agaagttcat ttacatcaaa ctctaccctg atgaaggagg caaaacaaaa  120
atggaaaatg tttatcaaaa ccacagcaaa catgagccac aacaaaatcc ttccccaaca  180
cagcattctc acttttcaaa tccaatacat gatcatgaaa aaaatcatgt attacctttt  240
tctattttgg tcaatattcc aaaaggattt catatacaaa aacaaacaga ccccaaattg  300
gtatacgact taagctacct ttctatgacg aaagaaattt gtaaaaaatc cattgaagtt  360
gatcattgtg gttgcgtaga tgtggattta catgtattaa aaataaaagg ttgtttatcc  420
tttttactca atttatgtat agaaccgatt cacaaacaaa aaatctgctc cacagatgct  480
aaagatgact ccatttttctt gtgttgtcaa gatacattat atgtagatca catattaaaa  540
tatagtgtcg gaaaattacc ttattatgtg attgatgagg atcatattca agtacgaaaa  600
ttagaaatac aagtgttaga tgattctcct caagtcgcaa aaatttcagg tgtcttttat  660
tttgaatatg aa                                                      672

SEQ ID NO: 46          moltype = AA  length = 224
FEATURE                Location/Qualifiers
source                 1..224
                       mol_type = protein
                       organism = Bacillus thuringiensis
SEQUENCE: 46
MAATNLLIGR IKNIYLFFQH KNIKKFIYIK LYPDEGGKTK MENVYQNHSK HEPQQNPSPT  60
QHSHFSNPIH DHEKNHVLPF SILVNIPKGF HIQKQTDPKL VYDLSYLSMT KEICKKSIEV  120
DHCGCVDVDL HVLKIKGCLS FLLNLCIEPI HKQKICSTDA KDDSIFLCCQ DTLYVDHILK  180
YSVGKLPYYV IDEDHIQVRK LEIQVLDDSP QVAKISGVFY FEYE                   224

SEQ ID NO: 47          moltype = DNA  length = 1131
FEATURE                Location/Qualifiers
source                 1..1131
                       mol_type = other DNA
                       organism = Bacillus thuringiensis
SEQUENCE: 47
atggttacag caatattagc aagtccttcc aactatgtaa gtgtttacgc ggagaaggtg  60
cagtctaaat cagagtcaac atatgtacaa aatgtcaaaa atgcgaatac attatcacat  120
tcgattagaa cgttaggttc acaatcacct ttagcacaag catatggatt aattatttta  180
cagcaaccaa ccattaaagg gactggtatg agcagtttaa cgaatcacca agaatttgta  240
aaaaatcatg ttcgcgaatg gttagatgaa tataatccta agttagttga cttaaatcaa  300
gatatgcagc gttttagtac aagattcaat ggttattatg gtacattata tgatttagcg  360
ggaacggtaa atacagatgc ggaaacaaaa gtgagttttg caaatgcttt taatagacta  420
caacaggacg tacaaactat ccaagatagt atgaaccaaa ccttattgca gctaaatcgt  480
```

```
tttaatgatt tattgcttca agataacaaa gggttttctg aaaaagcaaa agtagcaatt  540
caatccttag aggggtcaga tggaactgtt acacagctaa gggctgatat taaaagactt  600
caagaagaga tactggtaga actcgcaaaa attttaaata gaccaaatga agttcgtaac  660
ggcgttataa atattgggaa gcaagtcttt acgattgcgg gcggagcagc tcagactcaa  720
actatagatt ttatctctat ttcatctctt ggtggtggaa ttttagatct tttcgacagc  780
caaacagctg cttctgctag gctcattgag cagaaacaaa aagaattact accactaatt  840
cagcagttag cagaaaccca aattcaagtg actgaaatga cttttattga ggatcaaatg  900
aatgggttta ctgagatgat taagaggcaa attactactt ttgagtattt gatgaatgat  960
tggaaagcgt taaatgatac aatgatccaa atccaactcg atctaagtgc aggggcacat  1020
atggatagtg ttggattgca aaatcaatta attcagctca aagaattcag tgatgaactg  1080
tatttgcaaa caaaaaagtt tgaaaatttc atttcaaatg taacaataaa t           1131

SEQ ID NO: 48          moltype = AA  length = 377
FEATURE                Location/Qualifiers
source                 1..377
                       mol_type = protein
                       organism = Bacillus thuringiensis
SEQUENCE: 48
MVTAILASPS NYVSVYAEKV QSKSESTYVQ NVKNANTLSH SIRTLGSQSP LAQAYGLIIL  60
QQPTIKGTGM SSLTNHQEFV KNHVREWLDE YNPKLVDLNQ DMQRFSTRFN GYYGTLYDLA  120
GTVNTDAETK VSFANAFNRL QQDVQTIQDS MNQTLLQLNR FNDLLLQDNK GFSEKAKVAI  180
QSLEGSDGTV TQLRADIKRL QEEILVELAK ILNRPNEVRN GVINIGKQVF TIAGGAAQTQ  240
TIDFISISSL GGGILDLFDS QTAASARLIE QKQKELLPLI QQLAETQIQV TEMTFIEDQM  300
NGFTEMIKRQ ITTFEYLMND WKALNDTMIQ IQLDLSAGAH MDSVGLQNQL IQLKEFSDEL  360
YLQTKKFENF ISNVTIN                                                  377

SEQ ID NO: 49          moltype = DNA  length = 1545
FEATURE                Location/Qualifiers
source                 1..1545
                       mol_type = other DNA
                       organism = Bacillus thuringiensis
SEQUENCE: 49
atgaaattaa tatcaaaaat agtaatgacc gcgttaatag tattgagtac atttacattc  60
aacttaggtg gacaatttga taaaagtttt ctttctgcct caaaagcata tgcggatgta  120
atcaaggcac ttccacaaaa tgcttcaaag atagagttag attatgctcc tgtgtatgac  180
tacgacacag atgggtgtta tgcgactgca gcaatttctc cagatggtac gactaaccct  240
ggtctaagtt tgggcggttc cccggaaagt gtctgtagag atgttaaccg actggaaaat  300
tcaaacactt attctcgggc caaatcaaat aatggttgga ctgccattat gtatgcgagt  360
tactttgaga aagatcaaca aacttcgggc cctgttgcgc ttggacatcg acatgactgg  420
gaacacacaa tagtttgggt taaagatagt caggttcaat atgtaactta ttcagcacat  480
ggtaattggt acactaatcc tcgctcaaac gttagattcg atggaaacca cccgaaaatt  540
gtataccata aggacggcgg cttgacacat gcttttcgcc tggctaatag caatgacgag  600
ccgccagaaa actattatca ccagtggctc caactaccaa tggttggttg gaatggctat  660
ccaagcccaa atattcgtga aaaactaatg actacgaact ttggagatgc aacacttgag  720
atcaaagatg gaagatttga aaaagccctt gctaacgcaa agccccccat taactttgac  780
ccttatgcac cggaactgga agatggtggt acgtatcaaa tagtttctac tttaaataat  840
agtagtgtcg ttgacttaaa tcaagcagat ggaaatgttc tgttgtggca aaatggcaac  900
gctaataatc aaaaatggaa gctagtatat gattcaagta aatcagcata ccaacttaaa  960
aatatagcaa atcaaaattt agtattagct tggaatgatc ttaatggttc taataatgta  1020
gttgctacat ctaatcaaaa taaggaagag caatattgga taccaacaga agcaggaaat  1080
ggatattatt atgtaaggaa taagaaggat caaaacaaag tgttagatgt aagtggttat  1140
ggtactgcaa atggaacaaa tgttacagta tataatttcc atggtggtaa taatcaaaca  1200
ttccaattgt ctaatgtaac agggactttta acaagagaag tggagtcact ctataaggca  1260
cagcctggtc aaaccagtag atcaagtaat aatttttcac ttgaacatct cgcggcaggt  1320
accaaagtac gagttgtttt agaaggaaca ggtgctacct ctttgtcatt taacatttca  1380
agagataaat caggtgcaga ctctagaatt tggtcaaatg ttagagatgg ttctgttcta  1440
acgatccttt caggagatga tagaaaaaat ttgtatatct ctggtcctcc tagcggatat  1500
acttctaacg gtacatttaa agtgaaattc tacgctcttc caaac                  1545

SEQ ID NO: 50          moltype = AA  length = 515
FEATURE                Location/Qualifiers
source                 1..515
                       mol_type = protein
                       organism = Bacillus thuringiensis
SEQUENCE: 50
MKLISKIVMT ALIVLSTFTF NLGGQFDKSF LSASKAYADV IKALPQNASK IELDYAPVYD  60
YDTDGCYATA AISPDGTTNP GLSLGGSPES VCRDVNRLEN SNTYSRAKSN NGWTAIMYAS  120
YFEKDQQTSG PVALGHRHDW EHTIVWVKDS QVQYVTYSAH GNWYTNPRSN VRFDGNHPKI  180
VYHKDGGLTH AFRLANSNDE PPENYYHQWL QLPMVGWNGY PSPNIREKLM TTNFGDATLE  240
IKDGRFEKAL ANAKPPINFD PYAPELEDGG TYQIVSTLNN SSVVDLNQAD GNVLLWQNGN  300
ANNQKWKLVY DSSKSAYQLK NIANQNLVLA WNDLNGSNNV VATSNQNKEE QYWIPTEAGN  360
GYYYVRNKKD QNKVLDVSGY GTANGTNVTV YNFHGGNNQT FQLSNVTGTL TREVESLYKA  420
QPGQTSRSSN NFSLEHLAAG TKVRVVLEGT GATSLSFNIS RDKSGADSRI WSNVRDGSVL  480
TILSGDDRKN LYISGPPSGY TSNGTFKVKF YALPN                              515

SEQ ID NO: 51          moltype = DNA  length = 2385
FEATURE                Location/Qualifiers
source                 1..2385
                       mol_type = other DNA
```

```
                        organism = Bacillus thuringiensis
SEQUENCE: 51
atgaaccaaa atcacaacaa aaatgaatat gaaatcatgg atacaggtgg catgagctat    60
aaaccaaggt accccccttgc gaatgcacca ggttcagaat tccaaacaat gaattacaaa   120
gattggatgg atatgtgtga atttggggaa tcaggagat tatttgcagg ttcaaatact    180
gctaggaatg gagttattat cggtacaggt attgcatggg cagtccttgc actagttcca   240
gctgttggtc ctggattatc agcaatagcg ggcatattaa atgtagtaat tccatactta   300
tggcctgaag aggcaggacc acccggaact tcccaagcgc aatttacgtg ggatcagctg   360
atgagtgcgg caggagaact tattgatcaa aaaatttcag acctagttag aaccaatgct   420
attaatacat tacgaatatt acaatcacgt gtaagagact atcaacaagc aatctgtaat   480
ttaaaaaaag acccaaataa cgaagcatac aaagcggacg taagaaggga atttaatgat   540
gctgacgatc aggcgaaatc cgctattatc gaattacaaa ctatcggcta tgaaattcca   600
ttattatcta gttatgcgca agctgccaat ttacacttac ttttattacg agatgttgtc   660
caatacggag agagttgggg attttccacca cttgaagtcc aacaatatta ttctaacact   720
agcgcagtag gaaaccgggg catgttagaa ctattagaag tatatactga gcattgtatt   780
gagtggtata ataaaggttt aaataaatta aggcaagaag ccgtaattc acctgaagaa    840
tggaataagt tcaatgattt ccgtagggac atgaccataa tggcactaga tattgtatca   900
ttatggccaa cttatgatcc gaaattctat gcatattca caaaatcaca gcttacacgg   960
agtgtgtata caccaatgtc tgggagactt cttcgcggtt tgaggatcg tgagaatgct  1020
gtaatcccc ctccgtctct atttttcatgg ctacgtgagg taacgttctt tagaagagca  1080
tttcctgttc ctactaatca ggatgcgcta tttacgcagt atgctggtta taaaatgtcg  1140
tttcaaaata ctttagatag tacgttacag gaaacaccag tgttcggcac aacaagcaa   1200
gaagttaatg ttgtaaagat aggtgaggag cctaatttg aagtttataa aatgagaaac   1260
attatactgg caccagaagc tagcagaacg tttcaatctc ctcaaacatt tgattttcac   1320
tttactccat caggaacgtt tgaaacagtt ggaatcaatt atgccgatat acaggaagag   1380
ccaacaaata ctacgaatca aggacttgct tgtaacagtg ataataaacc ttgtgatcct   1440
tgtacttcta cgactcccttg tccaactggg cctatcaata ctactattcc ttgtgatagc  1500
cttagtctt tatgtcatcg actgtcatgg atgggtagta ttattggtgc taatccagga   1560
agtataatcc aacttaccta cggctggacc cacataagtg cagatgcaac caataggata   1620
gacactgaaa agattaccca aattccagcg gtgaaggctt ctggtggaga taatttccaa   1680
gttataaaag gacctggcag cacaggagga gatttagttg cattgaccac ctattctaag   1740
ataatgatac cggtgactgc cccaggaacc aaagcatatc acattagaat tcgttatgca   1800
tgtataggag ctgttcggtt aagaattgga acatttaaca ataatgcatg gatatatagc   1860
gactatgata tacttagcac gtattctgat agtcagttaa cctattcttc atttggatat   1920
gagttcattg gtatgtacc aacaacatct acagatatta aaatatctat tgaaaaataa   1980
gctccatttg aaataccctat catcctcgac aaaatcgaat tcattccaat tgaaaaatct   2040
ttggaagaat atcaagcgaa tcagaatcta gaaaaagcgc ggaaggcagt gaatgccttg   2100
tttaccaatg atgcgaaaaa tgccttgaaa ttgaacatca cggattatgc tgtagatcaa   2160
gctgctaacc tagtcgattg tgtatctgac gaaatctctt cacaagaaaa aatgatttta   2220
cttgatcaag tcaaatttgc gaaacgactt agtcaagcac ggaatctatt gaactctgga   2280
gattttgaat ccccagactg gtccggagag aatggatgga agacaagtaa tcatgtccat   2340
gtctctgcag ataatccgat ctttaaagga cgttatctcc atatg                 2385

SEQ ID NO: 52         moltype = AA   length = 795
FEATURE               Location/Qualifiers
source                1..795
                      mol_type = protein
                      organism = Bacillus thuringiensis
SEQUENCE: 52
MNQNHNKNEY EIMDTGGMSY KPRYPLANAP GSEFQTMNYK DWMDMCEFGE SGELFAGSNT    60
ARNGVIIGTG IAWAVLALVP AVGPGLSAIA GILNVVIPYL WPEEAGPPGT SQAQFTWDQL   120
MSAAGELIDQ KISDLVRTNA INTLRILQSR VRDYQQAICN LKKDPNNEAY KADVRREFND   180
ADDQAKSAII ELQTIGYEIP LLSSYAQAAN LHLLLLRDVV QYGESWGFSP LEVQQYYSNT   240
SAVGNRGMLE LLEVYTEHCI EWYNKGLNKL RQEAGNSPEE WNKFNDFRRD MTIMALDIVS   300
LWPTYDPKFY AYSTKSQLTR SVYTPMSGRL LRGFEDRENA VIPPPSLFSW LREVTFFRRA   360
FPVPTNQDAL FTQYAGYKMS FQNTLDSTLQ ETPVFGTTSQ EVNVVKIGEE PNFEVYKMRN   420
IILAPEASRT FQSPQTFDFH FTPSGTFETV GINYADIQEE PTNTTNQGLA CNSDNKPCDP   480
CTSTTPCPTG PINTTIPCDS LSLYSHRLSW MGSIIGANPG SIIQLTYGWT HISADATNRI   540
DTEKITQIPA VKASGGDNFQ VIKGPGSTGG DLVALTTYSK IMIPVTAPGT KAYHIRIRYA   600
CIGAVRLRIG TFNNNAWIYS DYDILSTYSG SQLTYSSFGY EFIGYVPTTS TDIKISIENI   660
APFEIPIILD KIEFIPIEKS LEEYQANQNL EKARKAVNAL FTNDAKNLAK LNITDYAVDQ   720
AANLVDCVSD EISSQEKMIL LDQVKFAKRL SQARNLLNSG DFESPDWSGE NGWKTSNHVH   780
VSADNPIFKG RYLHM                                                    795

SEQ ID NO: 53         moltype = DNA   length = 2932
FEATURE               Location/Qualifiers
source                1..2932
                      mol_type = other DNA
                      organism = Bacillus thuringiensis
SEQUENCE: 53
atgtatttat tcgtcctcat tctgcatgag ggcttacaca tagtatacga gggaggttta    60
tatatgaatc aaaactacaa caacaatgac tatgagatca taaatggcga ttacaggtac   120
gatacacaaa ggtatccttt tgcggaagcg ccagatttag cagtacaaaa catgaattat   180
caagatgtga tgaacccatg tatgggaagc acttatacta cagatccaca attacaggtc   240
cgagaatctg tcagtaaagc tgcagacgtt gtactgcagc ttctcagttt aggtgcccca   300
ggactagctg cagctggagg agttatccaa tcgatatttg gattactttg gccagcacca   360
aataaccaag acgtctggca gggatttata ggggcggtag aaacgctcgt atctcaatca   420
attgacacac ttgtacgaga tacagcaatt aggcaattag agggcctaca aacatcttg   480
gaagaatatg aaattaaccct tcagatttttt aaggactacc cagataaccc agtacacgca   540
```

```
gaggcattac gaattctagc ttttgatata gatggtgcat ttgagcaggc aatgcctgaa    600
tttacgatta ccaatcatga agtaacatta ttacccatat atgcacatgc ggccaatctc    660
catttagcct ttatacgaga cgttgtcatg catggactta catggggtat gtcacagcaa    720
caaataaact cctttacat gtatgattgt ggggcctag aatatcttac ggaagaatat    780
acagattatt gtgtgaagtg gtataaaaac ggtcttgaca aagcctacta cttaggaccg    840
aattcaagag attacaacaa atatccatat ctagaagatt atccaagtta tgccagtcaa    900
tacctatatt acgatccagt ggttgattgg aatctatata tgattaccg aagatctatg    960
accttatgg tgttagattt agtagcgata tggccaacat atgatccatt cctatattcg   1020
gttcctgttg caactcagtt atcacgagaa gtatattcta tagcatatgg gaaagtgggt   1080
tctagctgga aaagtcagga tgttgttgag actacttatg tccgtccacc tcatctcgtt   1140
acgtggttaa agaaatagc cattcatatg tcatctaatc cttcttccta tctatttgat   1200
caatttgcag gtgtaaaaat caaactgtcc cttacaggct catctagtac acgggaggac   1260
ggttttcctc ctcttcgatc atactcttct gatcaaagag ttacgtctag taacattggt   1320
ggtctgagaa taggaactgg taatgttata tgcgcagttg atttttctgaa tccttcagga   1380
tcatcgatta aggcgcttgg atattgtgag tcggttggat tccaagaaaa tattgttgta   1440
catgatgcag gtatcgatac cccttcaagt acgaacccag cctccatcg tttatcctat   1500
ataaatgcga tagacgcaag ctttactggt tatccaggtg tggtgaaaca tgggctatca   1560
tcatggggat ttggttggac aacataacagt ttaacaccac aaaaataacat atctgtggat   1620
cgaatatctc aatttccggc ggtgaaagcc tttgatatat cagatacggg accaggtaaa   1680
gtcatcaaag gtcctggtca tacaggaggt gatttagtat ctcttccttc aggaggtgca   1740
cgggcgaagt tgcgtttgat tccagaacag caaggaaaat cctataaagt gagaatccgt   1800
tatgcatgtc ctggaactgc gcaactatgg gtggagaaag ggaccgggaa tttttacggt   1860
caaacatata ctgttaacgc gacgtatacc gatgggtat tagattataa tgcatttaaa   1920
ttcttggatg tatataactt ctacactgga gagcctaatt tgaaatat tatacaaaac   1980
acaggaaatt caactattat catcgacaaa atcgagttca ttccgataga aggatcagtg   2040
gaagaaatatg aagcgggtca agattagaa aaagcacgga agctgtgaa tgccttgttt   2100
accaatgatg cgaaaaatgc attacaattg aatatcactg gttatgatgt cgatcaggct   2160
atgatgcaag tggaaatat acctgatgat atgttccaaa agaaaaaat gatttatg   2220
aatcttgtga acatgccaa gcgtctgagt caagctagaa atctgttgaa atatggtgat   2280
tttgaatccc catatgtggg aaggtgaag ggatgaaag caaataataa tgttacgtg   2340
acatcagatg atcgagggt tagccgctat tgaatatgc caggtgcaaa tgtggtaggg   2400
gaacaggtag tcccaacgtt tgtgtatcaa aaagtggatg aatcgaagtt aaaaccgtat   2460
acacgttatt tagtacgagg atttgtgaga cactagtaaa agttagaact gtttgtgaga   2520
cgatatggtc aagaagttca tgcggatttt ccacgcagtc tgatgacac atgtaatcag   2580
acatcgaata tggcaaacgg atatgatgtg agtactgtac catatactac gatgtcacaa   2640
gaaggatctt gtaaccata tcgtagtgaa tatacgtcaa aggcattagt gatgatggat   2700
ccaactacca acggtagcta tgaggaaaaa cgacattttg tctttcacat tgatgtaggt   2760
gcaatcgacc cgcgagcgaa tcttggtata gatattggct ttaaaatctc ttctccaaca   2820
ggtatggccc agttaaacaa tgtagagatt atagaagcga agccattaac gggcgaagca   2880
ttagctcgtg tgaaaaaacg ggaacagaaa tggaaaagag agctggaaca ga            2932

SEQ ID NO: 54              moltype = AA  length = 977
FEATURE                    Location/Qualifiers
source                     1..977
                           mol_type = protein
                           organism = Bacillus thuringiensis
SEQUENCE: 54
MYLFVLILHE GLHIVYEGGL YMNQNYNNND YEIINGDYRY DTQRYPFAEA PDLAVQNMNY    60
QDVMNPCMGS TYTTDPQLQV RESVSKAADV VLQLLSLGAP GLAAAGGVIQ SIFGLLWPAP   120
NNQDVWQGFI GAVETLVSQS IDTLVRDTAI RQLEGLQNIL EEYEINLQIF KDYPDNPVHA   180
EALRILAFDI DGAFEQAMPE FTITNHEVTL LPIYAHAANL HLAFIRDVVM HGLTWGMSQQ   240
QINSFYMYDC GGLEYLTEEY TDYCVKWYKN GLDKAYYLGP NSRDYNKYPY LEDYPSYASQ   300
YLYYDPVVDW NLYNDYRRSM TLMVLDLVAI WPTYDPFLYS VPVATQLSRE VYSIAYGKVG   360
SSWKSQDVVE TTYVRPPHLV TWLKEIAIHM SSNPSSYLFD QFAGVKIKLS LTGSSSTRED   420
GFPPLRSYSS DQRVTSSNIG GLRIGTGNVI CAVNFLNPSG SSIKALGYCE SGGFQENIVV   480
HDAGIDTPSS TNPASHRLSY INAIDASFTG YPGGGEHGLS SWGFGWTHNS LTPENTISVD   540
RISQFPAVKA FDISDTGPGK VIKGPGHTGG DLVSLPSGGA RAKLRLIPEQ QGKSYKVRIR   600
YACAGTTQLW VEKWTGNFYG QTYTVNATYT DGVLDYNAFK FLDVYNFYTG EPNFEIIIQN   660
TGNSTIIIDK IEFIPIEGSV EEYEAGQDLE KARKAVNALF TNDAKNALQL NITGYDVDQA   720
MMQVENIPDD MFQKEKMILL NLVKHAKRLS QARNLLKYGD FESPYWLGEN GWKANNNVTV   780
TSDDRGVSRY LNMPGANVVG EQVVPTFVYQ KVDESKLKPY TRYLVRGFVR HSKELELFVR   840
RYGQEVHADF PRSLMDTCNQ TSNMANGYDV STVPYTTMSQ EGSCNPYRSE YTSKALVMMD   900
PTTNGSYEEK RHFVFHIDVG AIDPRANLGI DIGFKISSPT GMAQLNNVEI IEAKPLTGEA   960
LARVKKREQK WKRELEQ                                                  977

SEQ ID NO: 55              moltype = DNA  length = 2956
FEATURE                    Location/Qualifiers
source                     1..2956
                           mol_type = other DNA
                           organism = Bacillus thuringiensis
SEQUENCE: 55
atgaagataa ataatcagaa ccaatgcata ccatataatt gcttaagtaa tcctgaggaa     60
gtacttttgg atggggagag atattaccct gatatcgatc cactcgaagt ttctatgtcg    120
cttttgcaat ttcttctaaa taactttgtt ccaggggggg ggttttattc aggattaatt    180
aataaaaatat ggggggcttt gagaccatct gaatgataat tatttcttgc acagattgaa    240
cagttgattg atcgaagaat agaagcagca gtaagagcaa aagcaatcgc tgaattagaa    300
ggtttaggga gaagttatca actatatgga gaggcattta agagtgggaa aaaaactcca    360
gataacacag cggtccggtc tagagtaact gagagatttc gtaataattga tgctcaaatt    420
gaagcaaata tcccttcgtt tcgggtttcc ggatttgaag tgccacttct atcggtttat    480
```

```
acccaagcag ctaatttgca tctcgctcta ttaagagatt ctgttgtttt tggagagaga    540
tggggattga cgactacaaa tgtcaatgat atctataata gacaagttaa gagaattgat    600
gaatatagcg atcattgtgt agatacgtat aaaacagaat tagaacgtct agagtttagc    660
tctatagcgc aatggagaat atataatcag tttagaaggg aattgacact aacggtatta    720
gatattgtcg ctctttttcc gaactatgat ggtagactgt atccgattcg aacaatttct    780
caattgacaa gagatattta tacatcccca gtaagcgaat tttattatgg tcccatttat    840
aattataata tagttggtcg ccttactgaa cagcagctaa ggcgaccaca tcttatggac    900
ttctttaact ccatgatcat gtatacgtca gataatagac gagaacatta ttggtcagga    960
cttgaaatga aggctactga tacttcagga aaccaagtgt cattcccttt agctgggact   1020
agagggaatt cagctccacc agtaactgtt agaaataatg gtgagggagt ttatagaata   1080
ttatcagagc catttattc atcacctttt ctaggcacca gtgtgctagg aagtcgtggg   1140
gaagaatttg cttttgcatc taatactact acaagtctgc catctacaat atatagaaat   1200
cgtggaacag tagattcatt agtcagcata ccgccacaag attatagcgt accaccgcac   1260
aggggtata gtcatttatt aagtcacgtt acgatgcaca atagttctcc tatattccac   1320
tggacgcatc gtagtgcaac ccctagaaat acaattgatc cagatagtat cactcaaatc   1380
ccagtagtta aggcttcgca cctctctggt ggttcagtta taaagggcc tggacataca   1440
ggtggagatt taataagcct acctgtaaat aactttactc atttccgaat cccatttcag   1500
gcaaacactc cacaaaggta tcgtattaga attcgttatg cggcagactc agatgggact   1560
ttggatagtg gagttttctt aagtgcagca gcagggatg gttttaatac aacttctttat   1620
agggccacaa tgagccctgg aggttcctta acatctcgtg attttcaatt tttagattta   1680
aacacatcgt ttacctccga tgtagcatct aacttatggt tacattttat acgttatata   1740
cgaccaggga atttgtatat agatagagcg gaatttatcc cagtggatgc aaccttcgag   1800
gcaggttata atttagaaag ggcgcaaaag gcggtgaatg ccctgtttac ttctacaaac   1860
caaaaaggat tacaaacaga tgtgacggat tatcatattg atcaagtatc caatctagtt   1920
gattgtttat ctgatgagtt ttgcttagat gaaaagcgag aattgtccga gaaagtcaaa   1980
caggcgaagc gactcagtga tgagcgaatt ttactccagg attcaaattt cagaggcatc   2040
aataggaac aagaccgtgg atggagagga agtacgcata ttactatcca aggaggaaat   2100
gatgtattca agaaaatttt tgttacacta ccaggtgcct ttgatgcgtg ttatccaacg   2160
tatttgtatc aaaaaataga tgaatctaaa ttaaaagcct atacacgtta tgaattaaga   2220
ggatatatag aagtagtca agatttggat atttacttga tccgttacaa tacgaaacat   2280
gaaacattaa atgttccagg tactaagtct ccatggtcgc tttgtacgga gagcccactt   2340
ggaaagtgtg ggaaccaaa tcgatgcgca tcacaaatag aatggaatcc tgatctagac   2400
tgctcttgca gagacggaga aaaatgtgcg catcattcgc atcatttctc cttggacatt   2460
gatgttggat gtacagattt gaatgagaac ctaggtatat gggtgatatt caagattaag   2520
acacaggatg gtcatgcaag actaggaaat ctagaatttc tcgaagagaa accgttatta   2580
ggagaagcgt tagcccgtgt gaagagagcg gagaaaaaat ggagagacaa acgtgaaaaa   2640
ttgcaatcag aaacaaatat tgtttataaa gaagcaaaag aagctgtaga tggtttattc   2700
gtagattccc aatatgagag attacaagct gatacgaata tcgccatgat tcatgcggca   2760
gataaacacg ttcatcaaat ccgagaggtt tatttcccag agctctctgt gattccaggt   2820
gtcaatgcag cgattttcga agaattagaa ggccgtattt tcacagcgta ttccctatat   2880
gatgcgagaa atgtcattaa aaacggtgat ttcaataatg gcttatcatg ctggaacgtg   2940
aaagggcatg tagatg                                                   2956

SEQ ID NO: 56           moltype = AA  length = 985
FEATURE                 Location/Qualifiers
source                  1..985
                        mol_type = protein
                        organism = Bacillus thuringiensis
SEQUENCE: 56
MKINNQNQCI PYNCLSNPEE VLLDGERILP DIDPLEVSMS LLQFLLNNFV PGGGFISGLI    60
NKIWGALRPS EWELFLAQIE QLIDRRIEAA VRAKAIAELE GLGRSYQLYG EAFKEWEKTP   120
DNTAARSRVT ERFRIIDAQI EANIPSFRVS GFEVPLLSVY TQAANLHLAL LRDSVVFGER   180
WGLTTTNVND IYNRQVKRID EYSDHCVDTY KTELERLEFS SIAQWRIYNQ FRRELTLTVL   240
DIVALFPNYD GRLYPIRTIS QLTRDIYTSP VSEFYYGPIY NYNIVGRLTE QQLRRPHLMD   300
FFNSMIMYTS DNRREHYWSG LEMKATDTSG NQVSFPLAGT RGNSAPPVTV RNNGEGVYRI   360
LSEPFYSSPF LGTSVLGSRG EEFAFASNTT TSLPSTIYRN RGTVDSLVSI PPQDYSVPPH   420
RGYSHLLSHV TMHNSSPIFH WTHRSATPRN TIDPDSITQI PVVKASHLSG GSVIKGPGHT   480
GGDLISLPVN NFTHFRIPFQ ANTPQRYRIR IRYAADSDGT LDSGVFLSAA AGDGFNTTSY   540
RATMSPGGSL TSRDFQFLDL NTSFTSDVAS NLWLHFIRYI RPGNLYIDRA EFIPVDATFE   600
AGYNLERAQK AVNALFTSTN QKGLQTDVTD YHIDQVSNLV DCLSDEFCLD EKRELSEKVK   660
QAKRLSDERN LLQDSNFRGI NREQDRGWRG STHITIQGGN DVFKENFVTL PGAFDACYPT   720
YLYQKIDESK LKAYTRYELR GYIEDSQDLD IYLIRYNTKH ETLNVPGTKS PWSLCTESPL   780
GKCGEPNRCA SQIEWNPDLD CSCRDGEKCA HHSHHFSLDI DVGCTDLNEN LGIWVIFKIK   840
TQDGHARLGN LEFLEEKPLL GEALARVKRA EKKWRDKREK LQSETNIVYK EAKEAVDGLF   900
VDSQYERLQA DTNIAMIHAA DKHVHQIREV YFPELSVIPG VNAAIFEELE GRIFTAYSLY   960
DARNVIKNGD FNNGLSCWNV KGHVD                                        985

SEQ ID NO: 57           moltype = DNA  length = 1947
FEATURE                 Location/Qualifiers
source                  1..1947
                        mol_type = other DNA
                        organism = Bacillus thuringiensis
SEQUENCE: 57
atggagagaa ataatcagga tcaatgcatt ccttataatt gtttgaataa tcctgaggtt    60
gggatattag atattgaaaa tttcaatctc gaacttgtat cgcaagtcag cgtggggctc   120
acacgttttc ttttggaagc atctatccct ggggcaggtt ttgcattggg tctattcgac   180
atcatttggg gtgctctagg cgtcgatcaa tggagcttat ccttgcgca aattgagcaa   240
ttaattaatg aaagaataac aacagtgaaa aggaatagag cgattcaagc attaagtgga   300
ctatcgagta gttatgaagt atatattgag gcattaagag aatgggagaa tgatctggat   360
```

-continued

```
aatccagctt cacgagatag agtggttgca cgttttcgtg caacagataa ttctctaata  420
acagatatac ctctattgga aattccaggt tttgagatag ctactttatc agtctatact  480
caagcggcga atctacattt agctttgtta agagatgccg tttactttgg agaaagatgg  540
ggattaacac aaacaaatat tgaagatctg cacacaagac tcacgagata tattcaagaa  600
tactcagacc attgcgcaag atggtataat caaggtttga ataatattgg agggataaat  660
acaagatatt tggacttcca aagagaatta acaatttcgg tcttagatat tgtcgctctt  720
ttcccaaatt acgacatccg aacatatcca attccgacac aaagccaatt aacaagggaa  780
atatatacat ctcccgtcgt tgcacctggt gtaaattgga ttttaagtat atcgaatgta  840
ttgagagccc ctcatctgat ggattttttt gatcgaataa ttatttatac tggtacagtt  900
agaagtacac cacattggga agggcatgaa gtcatatcta gaagaacagg gcaaggaaat  960
gagatacgct cgcctttata tggagtggct gcaaacgcag aaccaccagt tactataaga  1020
cctacaggat ttactgatga gcaaagacaa gtgtatagag tactatcacg tgttgcttct  1080
tttagaaatt caggaaccaa ctttagtctg gtagatgcag catcattcct aactatattt  1140
agcgctagct caatctatag aaatggtttt gggtttaatg ctgatactat tgatgaaatt  1200
ccaattgagg ggactgatcc atatattgga tatagccatc gattatgcca tgttggattt  1260
actgcgtcat ctccatttat ctcccagtat gcaagggcgc ccgtattttc ttggacgcat  1320
cgtagtgcga cttttacaaa tacaattgat ccagagagga ttacgcaaat accaatggta  1380
aaagcataca atcttcatgc aggtgccact gttgttagag gacccgggtt tacaggtggt  1440
gatctcttac gaagaacgaa tactggtaca tttgcagata taagagtaaa tattactggg  1500
ccattatctc aaagatatcg tgtaagaatt cgctatgctt ctacgacaga tttacaattt  1560
ttcacgagaa tcaatggaac ttctgtaaat caaggtaatt tccaaagaac tatgaataga  1620
ggggataatt tagaatctgg aaactttagg actgcaggat ttagtacgcc ttttagtttt  1680
tcaaatgcgc aaagtacatt cacattgggt actcaggctt tttcaaatca ggaagtttat  1740
atagatcgaa ttgaatttgt cccggcagaa gtaacattcg aggcagaatc tgatttagaa  1800
agagcgcaaa aggcggtgaa tgccctgttt acttctacaa gccaactagg gctaaaaaca  1860
aatgtaacgg gttaccatat tgatcaagtg tccaatttag ttgcgtgttt atcggatgaa  1920
ttttgtctgg atgaaaagag agaattg                                    1947
```

```
SEQ ID NO: 58          moltype = AA  length = 649
FEATURE                Location/Qualifiers
source                 1..649
                       mol_type = protein
                       organism = Bacillus thuringiensis
SEQUENCE: 58
MERNNQDQCI PYNCLNNPEV GILDIENFNL ELVSQVSVGL TRFLLEASIP GAGFALGLFD  60
IIWGALGVDQ WSLFLAQIEQ LINERITTVE RNRAIQALSG LSSSYEVYIE ALREWENDLD  120
NPASRDRVVA RFRATDNSLI TDIPLLEIPG FEIATLSVYT QAANLHLALL RDAVYFGERW  180
GLTQTNIEDL HTRLTRYIQE YSDHCARWYN QGLNNIGGIN TRYLDFQREL TISVLDIVAL  240
FPNYDIRTYP IPTQSQLTRE IYTSPVVAPG VNWILSISNV LRAPHLMDFF DRIIIYTGTV  300
RSTPHWEGHE VISRRTGQGN EIRSPLYGVA ANAEPPVTIR PTGFTDEQRQ VYRVLSRVAS  360
FRNSGTNFSL VDAASFLTIF SASSIYRNGF GFNADTIDEI PIEGTDPYIG YSHRLCHVGF  420
TASSPFISQY ARAPVFSWTH RSATFTNTID PERITQIPMV KAYNLHAGAT VVRGPGFTGG  480
DLLRRTNTGT FADIRVNITG PLSQRYRVRI RYASTTDLQF FTRINGTSVN QGNFQRTMNR  540
GDNLESGNFR TAGFSTPFSF SNAQSTFTLG TQAFSNQEVY IDRIEFVPAE VTFEAESDLE  600
RAQKAVNALF TSTSQLGLKT NVTGYHIDQV SNLVACLSDE FCLDEKREL              649
```

```
SEQ ID NO: 59          moltype = DNA  length = 2358
FEATURE                Location/Qualifiers
source                 1..2358
                       mol_type = other DNA
                       organism = Bacillus thuringiensis
SEQUENCE: 59
atgaacaaga ataatactaa attaagcaca agagccttac caagttttat tgattatttt  60
aatggcattt atggatttgc cactggtatc aaagacatta tgaacatgat ttttaaaacg  120
gatacaggtg gtgatctaac cctagacgaa attttaaaga atcagcagtt actaaatgat  180
atttctggta aattggatgg ggtgaatgga agcttaaatg atcttatcgc acagggaaac  240
ttaaatacag aattatctaa ggaaatatta aaaattgcaa atgaacaaaa tcaagtttta  300
aatgatgtta ataacaaact cgatgcgata aatacgatgc ttcgggtata tctacctaaa  360
attacctcta tgttgagtga tgtaatgaaa caaaattatg cgctaagtct gcaaatagaa  420
tacttaagta aacaattgca agagatttct gataagttgg atattattaa tgtaaatgta  480
cttattaact ctacacttac tgaaattaca cctgcgtatc aaaggattaa atatgtgaac  540
gaaaaatttg aggaattaac ttttgctaca gaaactagtt caaaagtaaa aaaggatggc  600
tctcctgcag atattcttga tggtttaact gagctaactg aactagcgaa aagtgtaaca  660
aaaaatgaag tggatggttt tgagttttac cttaatacat tccatgacgt aatggtagga  720
aataatttat tcggacgttc agctttaaaa accgcttcgg aattaatcgc taaagaaaat  780
gtgaaaatta gtggcagtga ggtaggaaat gtatataatt tcttaattgt attaacagct  840
ctgcaagcaa aagcttttct tactttaaca acatgccgaa aactattagg ccgagcagat  900
attgattata cttccattat gaatgaacat ctaaataagg aaaaagagga atttagagta  960
aacatccttc ctacactttc taatactttt tctaatccta cctatgcaaa agctaaagga  1020
agcgatgaag atgcaaagat gattgtggaa gctaaaccag gatatgcttt ggttggattt  1080
gaaatgagca atgattcaat aacagtatta aaagcatatc aggctaagct aaaacatgat  1140
tatcaagttg ataaggattc gttatcggaa attgtctatt gtgatatgga taaattattc  1200
tgctcggatc gatctaaaca aatatattat acaaataaca tagcatttcc taatgaatat  1260
gttattacta aaattacttt cactaaaaaa atgaacactt taagatatga ggtgacagct  1320
aacttttatg attcttctac tgggaatatt gatttaagta agaaaaaaat agaatcaagt  1380
gaagcgaagt atagtacgtt aagtgctagt aatgatgggg tttatttgcc gttaggtatt  1440
attagtgaaa cattcttgac tccaattaac gggtttgggc tcgtagtcga tgaaaggtca  1500
agattagtaa atttaacatg taaatcatat ttaagagagg tattgttagc aacagactta  1560
aagaataaag atactcaatt gattgtccca cctaatggct ttattagcaa tattgtaaaa  1620
```

```
aacgggact taaagggaga caatttagac ccgtggaaag caaataataa aaatgcgtat  1680
gtaaatcata caggtggtgt gaatggaact aaagctttaa ctgttcatgg ggatggtgag  1740
ttctcaaatt ttattggtga taagttgaca tcgaaaacac aatatgtatt tcaatatact  1800
gtaaaggaa aggcttctat ttatttaata gataaaaaa atggcgatgt catttacgaa  1860
gatacaaata acgatttaga agattttcag acttttatta aacgttttac taccggaacg  1920
aattttcag gagcttattt gattttaat agtcaaaatg gcgatgaagc ttttggagac  1980
aactttatta tctcagaaat taggccttta gaagagttat taagtccaga attaataaaa  2040
tcggatgcct gggttcgatc tcagggtgct tctggtagtg gaaactctct ctttattagt  2100
agtaatacaa atggaacctt tagacaaaat cttccgctag aaaactattc aacttatagt  2160
atgaacttta atgtgaatgg gtttggcaag gtgacaataa gaaattctcg cgaagtagta  2220
tttgaaaaaa catatcatca gtttacacct atagatattt ctgaaaaatt cacaacaacc  2280
aataatactg gattatatgt agaactttct cgtggcactg ggtctgggac tataaatttc  2340
cgagactttt caattaaa                                               2358

SEQ ID NO: 60           moltype = AA  length = 786
FEATURE                 Location/Qualifiers
source                  1..786
                        mol_type = protein
                        organism = Bacillus thuringiensis
SEQUENCE: 60
MNKNNTKLST RALPSFIDYF NGIYGFATGI KDIMNMIFKT DTGGDLTLDE ILKNQQLLND   60
ISGKLDGVNG SLNDLIAQGN LNTELSKEIL KIANEQNQVL NDVNNKLDAI NTMLRVYLPK  120
ITSMLSDVMK QNYALSLQIE YLSKQLQEIS DKLDIINVNV LINSTLTEIT PAYQRIKYVN  180
EKFEELTFAT ETSSKVKKDG SPADILDGLT ELTELAKSVT KNEVDGFEFY LNTFHDVMVG  240
NNLFGRSALK TASELIAKEN VKISGSEVGN VYNFLIVLTA LQAKAFLTLT TCRKLLGRAD  300
IDYTSIMNEH LNKEKEEFRV NILPTLSNTF SNPTYAKAKG SDEDAKMIVE AKPGYALVGF  360
EMSNDSITVL KAYQAKLKHD YQVDKDSLSE IVYCDMDKLF CSDRSKQIYY TNNIAFPNEY  420
VITKITFTKK MNTLRYEVTA NFYDSSTGNI DLSKKKIESS EAKYSTLSAS NDGVYLPLGI  480
ISETFLTPIN GFGLVVDERS RLVNLTCKSY LREVLLATDL KNKDTQLIVP PNGFISNIVK  540
NGDLKGDNLD PWKANNKNAY VNHTGGVNGT KALTVHGDGE FSNFIGDKLT SKTQYVFQYT  600
VKGKASIYLI DKKNGDVIYE DTNNDLEDFQ TFIKRFTTGT NFSGAYLIFN SQNGDEAFGD  660
NFIISEIRPL EELLSPELIK SDAWVRSQGA SGSGNSLFIS SNTNGTFRQN LPLENYSTYS  720
MNFNVNGFGK VTIRNSREVV FEKTYHQFTP IDISEKFTTT NNTGLYVELS RGTGSGTINF  780
RDFSIK                                                            786

SEQ ID NO: 61           moltype = DNA  length = 2445
FEATURE                 Location/Qualifiers
source                  1..2445
                        mol_type = other DNA
                        organism = Bacillus thuringiensis
SEQUENCE: 61
atgggaaata ggagggaatt tatgaataac gaaacacaaa atcaatgcat cccttataat    60
tgtttaagta accctgaagt ggagatatta ggaggagaca tagtagctgg tattctgcca   120
atacaaatct ctctatcgtt aacgcgtttc cttgctggcg aatttatccc aggagtggga   180
gttgcacttg ggttatttga tttaaatatg ggatttataa gtcctcctga ttgggatcaa   240
tttcttgtac ggattgaaca attaattgat caaagaatag aagaattaga aagaactaga   300
gcactctctg cattacaagg actagcgaat agtatgggta tgtatgttga agcgcttaga   360
gcgtgggagg ctgatcctaa taatgaagca ttaaaggaag atgtgcgtac tcgatttact   420
agtattgatg gtgatttaat agcagagatt cctagattta gacttagagg ttatgaggtt   480
cctctgttat cggtatatgt tcaagcaact aatttacatt tatctatgtt aagagattct   540
gtaagtcttg ggctgcggtg gggatttgat attgccacta ttaataatca ttataacaga   600
ttaattaata atattcgtga gtatacagat tatagtgtga gcacataaa tataggatta   660
gaacgcttaa ggggaactcg tgttcaagat tgggtaaagt ttaatcagtt taggagggaa   720
ctaacactta ctgtgttaga tattgtttct ctttttccaa actatgatgt cagaacatat   780
ccaattcaaa cagtatcaca attaactaga gaaatttata caaatcctgt atttgaaaat   840
tcaccagtta atattaatct tgttaatggc tttaatagag ttgagtacgg agtccgacaa   900
cctcatctta tggatcacct catgaatgta tctatttctg aagaagatta tagagggagc   960
accttttggg gaggtcactc tattgcctcc gtagatacgg tggtaatctt gtcggtttc   1020
ccgttttatg gtaatttcga tagattttcg tttcaaacaa tcaacgctca acaattccct  1080
cttttttagaa cgttatcaga tcctgtttat aacctcagta catctggagg gagaaacaga  1140
ctatttgctc ttgaagggat aggatttcaa caggctgtaa cgggaaccac acgagctttt  1200
aggagagtcg gaacaataga ttctcttatt gaaataccac tcaagatgaa agtgaagta   1260
ccttggaatg gctatagtca tgtattaaat catattacat ttataaattg gccagctgtt  1320
ttcctacaag gggaaagaat agcttctcca atgttttctt agacacatcg tagtgcagat  1380
cgtatcaata gaattattcc agatgttatc aatcaaattc cagctgttaa aggcagctct  1440
attattaatg gaactgtaat ttcaggacca ggatttactg gaggagattt agttagatta  1500
gaaaataatg catccttga aattccagtg caatttcaaa aacatctac aaattatcga   1560
gttcgtgtac gttatgcctc cacctctcaa gcatctataa gtgtagtttt tggaaatata  1620
gatcatccta gtaccatacc agccacagct gaatcattag acaatctaca atataacgat  1680
tttgattatt tgatgttat tggtactttc ttaccttcat taggcggtag tttagctttt  1740
agaactttaa gttcgaatgc aaatgtggta ataagatagat tcgaatttat cccagttact  1800
gcaacatttg aggcagaata tgatttagaa aaagcgcaag aggcggtgaa tgctctgttt  1860
acttcttcca atcaaataggg gttaaaaaca gatgtgacag actatcatat tgatcaagtg  1920
tccaatctag ttgaatgttt atcggatgaa ttctgtcttg atgaaaaag agaattgtcc   1980
gagaaagtca aacatgcgaa gcgactcagt gatgagcgga atttactaca agatcaaaac  2040
ttcagaggca ttaatgggca accagaccgt ggctggagag aagcatggg tattaccatc  2100
caaggaggag atgatgtatt caagagaat acgtcacac taccaggtac ctttgatgag   2160
tgctatccaa cgtatttgta tcaaaaata gatgagtcga aattaaaagc ctatacccgt   2220
tatcaattaa gaggatatat cgaagatagt caagactag aaatctattt gattcgttac   2280
```

```
aatgcgaaac atgagacatt aaatgttccg ggtacgggtt ctttatggcc gctttcagtc  2340
gaaagtccaa ttggaaagtg cggagaaccg gatcgatgcg caccacatat tgaatggaat  2400
tctgatctag attgttcctg tagagatgga gaaaaatgtg cacat                  2445

SEQ ID NO: 62          moltype = AA  length = 815
FEATURE                Location/Qualifiers
source                 1..815
                       mol_type = protein
                       organism = Bacillus thuringiensis
SEQUENCE: 62
MGNRREFMNN ETQNQCIPYN CLSNPEVEIL GGDRSAGILP IQISLSLTRF LAGEFIPGVG  60
VALGLFDLIW GFISPSDWDQ FLVRIEQLID QRIEELERTR ALSALQGLAN SYGVYVEALR  120
AWEADPNNEA LKEDVRTRFT SIDGDLIAEI PRFRLRGYEV PLLSVYVQAT NLHLSMLRDS  180
VSLGLRWGFD IATINNHYNR LINNIREYTD YSVSTYNIGL ERLRGTRVQD WVKFNQFRRE  240
LTLTVLDIVS LFPNYDVRTY PIQTVSQLTR EIYTNPVFEN SPVNINLVNG FNRVEYGVRQ  300
PHLMDHLMNV SISEEDYRGD TFWGGHSIAS VDTGGNLVGF PFYGNFDRFR FQTINAQQFP  360
LFRTLSDPVY NLSTSGGRNR LFALEGIGFQ QAVTGTTRAF RRVGTIDSLI EIPPQDESEV  420
PWNGYSHVLN HITFINWPAV FLQGERIASP MFSWTHRSAD RINRIIPDVI NQIPAVKGSS  480
IINGTVISGP GFTGGDLVRL ENNAYLEIPV QFQTTSTNYR VRVRYASTSQ ASISVVFGNI  540
DHPSTIPATA ESLDNLQYND FDYFDVIGTF LPSLGGSLAF RTLSSNANVV IDRFEFIPVT  600
ATFEAEYDLE KAQEAVNALF TSSNQIGLKT DVTDYHIDQV SNLVECLSDE FCLDEKRELS  660
EKVKHAKRLS DERNLLQDQN FRGINGQPDR GWRGSMGITI QGGDDVFKEN YVTLPGTFDE  720
CYPTYLYQKI DESKLKAYTR YQLRGYIEDS QDLEIYLIRY NAKHETLNVP GTGSLWPLSV  780
ESPIGKCGEP DRCAPHIEWN SDLDCSCRDG EKCAH                              815

SEQ ID NO: 63          moltype = DNA  length = 1839
FEATURE                Location/Qualifiers
source                 1..1839
                       mol_type = other DNA
                       organism = Bacillus thuringiensis
SEQUENCE: 63
atggctcagg atccctttag ttttcaacat aaatcattag atactataca aaaagaatgg  60
acggaatgga aagagatga tcatagttta tatgtagctc ctgttgttgg aactgttgca  120
atttttctgc taaagaaatt ggggggttc gctgcaaaaa ggatattgaa tgggttatgg  180
gatttagtat ttcctaatga taataccaaa ctaatgcaag atattttaag agagacagaa  240
aaatttctaa accaaagact taatgcagac actctttctc gagtaaatgc agaattggag  300
gggcttcaaa aaaatgtagc ggagtttaat agacaagtgg ataattttt aaatcctaat  360
cgaaacccga ctcttttatc aataacttct tcagttaata caatgcaaca attgttccta  420
aatagattaa cgcagttcca gttacgagga tacgagctgt tattattacc tttatttgca  480
caagcagcca atttacatct ttcctttatt agggacgtta ttctgaatgc agaggaatgg  540
gggatttcag cagcaacgtt acgcacatat cgaggttacc taaaagacta tacaaaagaa  600
tactctaatt attgtataaa tacgtatcaa accgcattta aaagttaaa tactccttta  660
cacgaaatgt tagagtttag aacatatatg tttttaaatg tatttgaata tgtatccatt  720
tggtcattgt ttaagtatca gagtcttctg gtatcttctg gcgcaaattt atatgctagt  780
ggtagtgggc cacagcagaa acaatcattt agcgcgcaga actggccatt tttatattcc  840
cttttccaag tgaattctaa ttatgtatta actggtttta gtggttttag gaattctttt  900
accatgccta atattggtgg tttccccggt tctactacaa ctcacgcatt gtttagtgcg  960
agggctaatt atagtggagg aatttcatct ggtatcatag ggatgactaa tagtaatcac  1020
aactttaatt gtagcaccgc ttctttacaa acaccatata ctagaagttg gctggattca  1080
ggtagagatc aacatgccat taatacttt acagattggc agacagaatg ttttcaaaca  1140
acttcggatt cctggtgtgg tgcctttgtc ccccgtggta atacgaatta tttcccagat  1200
tattttattc gtaatatttc tggagtttct ttagttgtcg ggaatgaaga tttaagaaga  1260
ccgttacact ataatgaaat aagaaatata gcaagtcctt ccggaacccc tggtggaggg  1320
cgagcttata tggcatctgt gcacaacaga aaaaataata tctatgccgc tcatgaaaat  1380
ggtactatga ttcatttggc gccggatgat aatacagggt ttattatatc gccgatacat  1440
gcaacacaag taaatacgca gaatcgaaca tttatttccg agaaatttgg aaatcaaggt  1500
gattccttac gatttgaaca aacaaacaca acagctcgat acacatttag gggaaagggc  1560
aatagttata atctgtattt aagagtatca tctttaggaa attccactat tcgagttacg  1620
ataaacggta aggtttatac tgttccaaat gttaatacca ctacaaataa tgatggggtt  1680
attgataatg gatcacgttt ttcagatgtt tacatcggta acgtagtagc aaatgataag  1740
acgaatgtac cgttagatat aaatgtgaca tttaattctg gtactcaatt tgagcttatg  1800
aatattatgt gtattccaac taatattaca ccactttat                          1839

SEQ ID NO: 64          moltype = AA  length = 613
FEATURE                Location/Qualifiers
source                 1..613
                       mol_type = protein
                       organism = Bacillus thuringiensis
SEQUENCE: 64
MAQDPFSFQH KSLDTIQKEW TEWKRDDHSL YVAPVVGTVA IFLLKKLGGF AAKRILNGLW  60
DLVFPNDNTK LMQDILRETE KFLNQRLNAD TLSRVNAELE GLQKNVAEFN RQVDNFLNPN  120
RNPTLLSITS SVNTMQQLFL NRLTQFQLRG YELLLLPLFA QAANLHLSFI RDVILNAEEW  180
GISAATLRTY RGYLKDYTKE YSNYCINTYQ TAFKKLNTPL HEMLEFRTYM FLNVFEYVSI  240
WSLFKYQSLL VSSGANLYAS GSGPQQKQSF SAQNWPFLYS LFQVNSNYVL TGFSGFRNSF  300
TMPNIGGFPG STTTHALFSA RANYSGGISS GIIGMTNSNH NFNCSTASLQ TPYTRSWLDS  360
GRDQHAINTF TDWQTECFQT TSDSWCGAFV PRGNTNYFPD YFIRNISGVS LVVGNEDLRR  420
PLHYNEIRNI ASPSGTPGGG RAYMASVHNR KNNIYAAHEN GTMIHLAPDD NTGFIISPIH  480
ATQVNTQNRT FISEKFGNQG DSLRFEQTNT TARYTFRGKG NSYNLYLRVS SLGNSTIRVT  540
INGKVYTVPN VNTTTNNDGV IDNGSRFSDV YIGNVVANDK TNVPLDINVT FNSGTQFELM  600
```

-continued

```
NIMCIPTNIT PLY                                                      613

SEQ ID NO: 65           moltype = DNA  length = 2067
FEATURE                 Location/Qualifiers
source                  1..2067
                        mol_type = other DNA
                        organism = Bacillus thuringiensis
SEQUENCE: 65
atgaaaccaa agaatcaaaa taagtatcaa agtttatcga aaaatgcgac agttgataaa  60
atctctacgg attcactaaa aaatgaaaca gatagagaat tgaaaaatat ttataatgaa  120
gattgtttga gaatgtctga gcatgaaagt atggagccgt ttgttagtgc atcaacaatt  180
caaacgggga ttggtattgc tggtaaaatc cttggtaacc taggcgttcc ttttgctgga  240
caagtagcta gcctctatag ttttatccta gatgagcttt ggcccaaagg gaaaagccaa  300
tgggaaatct ttatggaaca tgtagaagag cttattgctc aaaaaatatc gacttacgcc  360
agaaacaaag cacttgcaga tttaaaagga ttaggggatg ctttggctgt ctaccatgag  420
tcgctggaaa gttggattaa aaatcgcaat aacacaagag ccagaagtgt tgttaagaac  480
caatacatcg ctttagaact tatgtttgtg caagcgttgc cttcttttgc agtgtctgga  540
gaggaagtac cactattacc aatatatgct caagctgcaa atttacactt gttgctatta  600
agagatgcgt ctatttttgg aaaagagtgg ggattatccg actcagaaat ttccacattt  660
tataatcgcc aatctggaag gtcgagggaa tattctgacc actgcgtaaa atggtataat  720
acaggcctaa atcgcttgag gggaacaaat gccgaaagtt gggtacgtta taatcaattc  780
cgcagagaca tgactttaat ggtactagat ttagtcgcac tattcccaag ctatgataca  840
catatgtatc caattaaaac tacagcccaa cttacaagag aagtttatac aaatccaatt  900
ggtgtcgtag gaggagtttc ttggtttgaa aacgccgctt ctttcgccgc tatagaaaac  960
gcagttattc gacaacctca tctatacgat tttatgactg accttaccat ttacacgaga  1020
ctaagtcgag cactccctcg ttatatgaat ttgtgggcgg ggcatagaat caattttaat  1080
acaattcgtg gttctactag tcgcgaaatg gtgtatggag ctattactaa tccagttagt  1140
actactcccc tttcatttgt caatcaagat atttatagaa ctcaatcaat agctggagta  1200
cttctcaatc tttcaagcag attttacggc gtacctagag ttgattttga tataagaaat  1260
cgtaactatc ctaatataat caatagacta acttataatc ctggatacgc agaaattgca  1320
actcaagtaa aagattcaga aactgaatta ccgcctgaaa caacagaaca gccaaattat  1380
gaagctgcta gtcatctgct atgtcatatt ggaatgcctc caacggggtc cggaactggt  1440
tcagcaactc ctccagtata ttcttggaca caccggagtg cgggtcgtac gaatatcatt  1500
aattcggata gtattacaca aatcccatta gtaaaggcta ataaccttca ttcaggcgct  1560
actgtcgtca agggcccagg atttacagga ggagacatac tccgaagaac tagcgcgggt  1620
acatttgtgg atttaccagt taatcttatt agttggcaat tatcacaaag ttatcgcgta  1680
aggatacgtt atgcttctac tacggattta caatttcata cgtcaattaa cgggagagca  1740
attaatcagg ggaatttttc agcaactatg aatagaggag atgccttaga atctagaacc  1800
tttagaactg tagggtttac tactcctttt aacttttcag atgcgcaaag tacattcaca  1860
ataagtgctt ggaacttctc ttcaagtaac gaagtttata tagatagaat tgaatttgtt  1920
ccagcagaag taacattaga ggcagaaagt ttagaaagag cgcaaaaagc ggtaaataat  1980
ctgtttactc caacagacgt gacggactct catatagacc aagtatccaa tctagtagag  2040
catctatcgg acgaactctg tctcaat                                       2067

SEQ ID NO: 66           moltype = AA  length = 689
FEATURE                 Location/Qualifiers
source                  1..689
                        mol_type = protein
                        organism = Bacillus thuringiensis
SEQUENCE: 66
MKPKNQNKYQ SLSKNATVDK ISTDSLKNET DRELKNIYNE DCLRMSEHES MEPFVSASTI  60
QTGIGIAGKI LGNLGVPFAG QVASLYSFIL DELWPKGKSQ WEIFMEHVEE LIAQKISTYA  120
RNKALADLKG LGDALAVYHE SLESWIKNRN NTRARSVVKN QYIALELMFV QALPSFAVSG  180
EEVPLLPIYA QAANLHLLLL RDASIFGKEW GLSDSEISTF YNRQSGRSRE YSDHCVKWYN  240
TGLNRLRGTN AESWVRYNQF RRDMTLMVLD LVALFPSYDT HMYPIKTTAQ LTREVYTNPI  300
GVVGGVSWFE NAASFAAIEN AVIRQPHLYD FMTDLTIYTR LSRALPRYMN LWAGHRINFN  360
TIRGSTSREM VYGAITNPVS TTPLSFVNQD IYRTQSIAGV LLNLSSRFYG VPRVDFDIRN  420
RNYPNIINRL TYNPGYAEIA TQVKDSETEL PPETTEQPNY EAASHLLCHI GMPPTGSGTG  480
SATPPVYSWT HRSAGRTNII NSDSITQIPL VKANNLHSGA TVVKGPGFTG GDILRRTSAG  540
TFVDLPVNLI SWQLSQSYRV RIRYASTTDL QFHTSINGRA INQGNFSATM NRGDALESRT  600
FRTVGFTTPF NFSDAQSTFT ISAWNFSSSN EVYIDRIEFV PAEVTLEAES LERAQKAVNN  660
LFTPTDVTDS HIDQVSNLVE HLSDELCLN                                     689

SEQ ID NO: 67           moltype = DNA  length = 2223
FEATURE                 Location/Qualifiers
source                  1..2223
                        mol_type = other DNA
                        organism = Bacillus thuringiensis
SEQUENCE: 67
atgagtccaa ataatcaaaa tgaatatgaa attatagatg cgacaccttc tacttctgta  60
tccaatgatt ctaacagata ccctttttgcg aatgagccca caaatgcatt acaaaatatg  120
aattataagg attatttaag aatgtctgag gggtatgata gtgaatattc tggttcacct  180
ggagcacttg ttagtggaaa acaagcaatt aaggttggaa tcgatattgt cggcaacata  240
ttaggtaagt taggagttcc gtttgttcct cagatagtaa gtttttataa ttttattctc  300
gatcagctat ggccatcaaa ttctgtgagt gtatgggaac agattataac gctagtggaa  360
gaacttgtag atcaaaaaat aacagaatat gcaagaaata aagcactcgc tgaattaaaa  420
ggattaggag atgctttggg tgtatatcag caatcacttg aagcatggtt ggaaaatcgc  480
aatgacacga gagctagaag tgttgtttct aatcaattta tagctttaga actggatttt  540
gttggagcaa ttccatcctt tgcagtatcc gggcaggaag taccattatt agcagtatat  600
```

```
gcacaggctg tgaacatgca cttattgtta ctaagagacg cttctatttt tggagaagag  660
tggggattca catcatctga aatttccact tactacaacc gtcaagtgca actcacttct  720
caatattccg attattgtgt gaagtggtac gataccggtt tacagaaatt aaaaggtacg  780
agcgctgaga gttggctgga gtatcatcaa ttccgcagag agatgacttt catggtatta  840
gatttggttg cattatttcc aaactacaat acacacacgt atccacttga aacaaaggct  900
caacttacac gagaagtata taccgatccg atcgccttta atctttctgg ggcagcgggt  960
ttttgtagac cttggtcaaa gtatactggt atttcctttt cggagattga aaatgctgta  1020
attcgtccac ctcatttatt taatgtactc agtagtttag aaattaatac agttaggggg  1080
acaattttag gtagcactac agcgtaccta aactattggt caggtcattc tctacaaatat  1140
aattttatag gtaatacaac agtcagggaa agtaattatg gatatcttac ttcagaaaaa  1200
actaggattc aattagacac tagagatatt tttgaaatta attcaactgc cgctagctta  1260
gcgaattact atcaagagac ttatggtgtg ccagaatcta ggttccattt ggtgagatgg  1320
gctagcccat attatacatc atctcatctt tattctaaaa cacatacaac tggagaaggt  1380
tgtacacaag tttatgaatc aagtgaggaa atacctgtag acagaaccgt accggtaaat  1440
gaaggttata gtcacagact atcgtatgtc accgctctct tttccagaa atttattaat  1500
actttttata caaatggaac tctacctgtc tttgtttgga cacatcggag tgcggatctc  1560
accaatacaa tttatccgga taaaatcacg caacttccaa tagtaaaatc atacacttta  1620
ccttcaggta cttccgtaat acagggtcct ggatttacag gaggaaatat attaaaaaga  1680
acaagcactg gcagaatagg aactttcga attaacttaa ccggaccatt gacacaaaga  1740
tatcgtgtaa gaattcgtta tgcttcttct agtgatataa atttccgtgt aattcatgcg  1800
ggtaagacgg ttaatgagta ttcctttagt aaaactatga atcaaggagc atctttaaca  1860
tatgaaacat ttaaatttgc tagctttact acgcctttca gatttgaaaa tacttcaggt  1920
gaaataggga tagatgtgta taattttctc tcaagtggag aagtttatgt agaccgaatc  1980
gaagtcatcc cagtagatgc gacatatgaa gcggaacaag atttagaggc ggcaaagaaa  2040
gcagtgaatg ccttgtttac gaatacaaaa gatggcttac gaccaggcgt aacggattat  2100
gaagtgaatc aagcggcaaa cttagtggaa tgcctatcgg atgatttgta tccaaatgaa  2160
aaacgtttgt tatttgatgc ggtgaaagag gcaaaacgac tcattcaggt acgcaactcg  2220
ctt                                                                2223
```

```
SEQ ID NO: 68          moltype = AA  length = 741
FEATURE                Location/Qualifiers
source                 1..741
                       mol_type = protein
                       organism = Bacillus thuringiensis
SEQUENCE: 68
MSPNNQNEYE IIDATPSTSV SNDSNRYPFA NEPTNALQNM NYKDYLRMSE GYDSEYSGSP  60
GALVSGKQAI KVGIDIVGNI LGKLGVPFVP QIVSFYNFIL DQLWPSNSVS VWEQIITLVE  120
ELVDQKITEY ARNKALAELK GLGDALGVYQ QSLEAWLENR NDTRARSVVS NQFIALELDF  180
VGAIPSFAVS GQEVPLLAVY AQAVNMHLLL LRDASIFGEE WGFTSSEIST YYNRQVQLTS  240
QYSDYCVKWY DTGLQKLKGT SAESWLEYHQ FRREMTFMVL DLVALFPNYN THTYPLETKA  300
QLTREVYTDP IAFNLSGAAG FCRPWSKYTG ISFSEIENAV IRPPHLFNVL SSLEINTVRG  360
TILGSTTAYL NYWSGHSLQY NFIGNTTVRE SNYGYLTSEK TRIQLDTRDI FEINSTAASL  420
ANYYQETYGV PESRFHLVRW ASPYYTSSHL YSKTHTTGEG CTQVYESSEE IPVDRTVPVN  480
EGYSHRLSYV TALFFQKFIN TFYTNGTLPV FVWTHRSADL TNTIYPDKIT QLPIVKSYTL  540
PSGTSVIQGP GFTGGNILKR TSTGRIGTFR INLTGPLTQR YRVRIRYASS SDINFRVIHA  600
GKTVNEYSFS KTMNQGASLT YETFKFASFT TPFRFENTSG EIGIDVYNFL SSGEVYVDRI  660
EVIPVDATYE AEQDLEAAKK AVNALFTNTK DGLRPGVTDY EVNQAANLVE CLSDDLYPNE  720
KRLLFDAVKE AKRLIQVRNS L                                            741
```

```
SEQ ID NO: 69          moltype = DNA  length = 2448
FEATURE                Location/Qualifiers
source                 1..2448
                       mol_type = other DNA
                       organism = Bacillus thuringiensis
SEQUENCE: 69
atggcaaaga ctaactctta caaaaaatta atcgctggta caatgacagc agcaatggta  60
gcaggcgttg tatctccagt agcagcagca ggtaaatcat tcccagacgt tccagctgat  120
cactgggcat tagattctat taactactta gtagaaaaag gcgcaattaa aggtacagat  180
caaggtacat tcgctcctga acaagaagta actcgtgcag aagcagctac aatgatggct  240
atcacattaa acttaccaat cgaagagaac gctaaaccaa cttacaaaga tgctcaaaac  300
cactgggctt caaaatacat cgcagctgta gaaaaagctg gtgtagttgc aggtaaaggc  360
gacggcacat tcgctccaga cggaaaaatc aaccgcgttt caatggcagc aatgcttgta  420
ccagctttca aattagacac taaagtagct ggtactccag aaactaaatt cgaagattta  480
aaacctagct ggggtaaaga caaagctaac atcctagttg aattaggaat ttctgcaggt  540
actacaacta ctacttggga gcctgaaaaa actgtaacta aagcagaagc agctcaattc  600
attgctaaga ctgacaagca gttcggacaa aagaagaag ctaaagttga gtctattaaa  660
gcaatcaatg ctaaagagat cgaagttaaa cttggcgcta cagtgaaaga agaagatgtg  720
aagaacgcga aattcactct ttctcaagga actaacgcaa cagcagttac tacaaaaatc  780
ggtgaagata aaaaatctgt aatcgtaact ttagatggag atgcaaaact taaaaataaa  840
gaagcatacg ttctaactgt tgaaggctta aaagctgctg atggtaaaga aattccaaaa  900
gcattagaag ttatcttctt taatgacgaa gtagctccaa ctgtatctac agtgtctact  960
ccagacggaa aagttaaagt agtatttagt gaaaaattag atacagcaaa agctgtaact  1020
gtaatcgtta atggtcaaaa agtagacgga aaagttgaaa ataatacttt cacttctact  1080
aacactttaa accttgagaa cggtaaagaa ttctcagtta tcgtaacggg tgctcaagat  1140
ttatcaggta acgaaatgga aatgtacgaa ggtaaagcta cttacaaagt agaaaaagac  1200
gttacagctc cagaagtaaa agaaattaaa gtaaaagacc ttgctaatgg tacagctaca  1260
ttagaagcta catttacaga ggaactttct gcacaaggta cagtagttgt aaaaaaaggt  1320
aatacagtag taaaagaggc tacaattgct cttgatcaag ataaaacaaa agcgcttgtt  1380
acagtaccgg gtgctcttac agataaagaa acagctgcag atcttacagt tgaatttgtt  1440
```

-continued

```
ggctacaaag atttagcaaa caatgtaggt actaaagtat ctaaagcagt aaaagttaca  1500
aaagatgttg tagctcctaa cttagttaaa gttgtggcag atcaaaataa agaagctaca  1560
tttacttttg ataaagatgt aactaaacaa gacggaaaaa ttcgtgtaat caatttagat  1620
acaagcagag atgtaactgg tgaagtgaca atcgaagcag caaaagacaa cagcaaaggt  1680
attacattaa cattcccagc aaaaggtaac tacaaagtag ctgctacaaa aggtcttgta  1740
aaagatgcag ctggtaatga gtctgcagca tttactaaag aagtgaaagt tgtagaaaaa  1800
gaatctgaaa aagaaacaga taaagtagct ccagcagtaa caggcgtggc ttttgataaa  1860
gctacaaata aaattacagt aaactttgat aaagaagtaa aaggtggcca agtagctgaa  1920
tcagcttcta atgtaaacaa ttacacatta gctggtgcta aattaccaga aggtgctcta  1980
atcgtattag acggtacaaa tgcagttatt gagttaccat ctacatttac tttcgaaaaa  2040
tcagaaacag ttaaatttac agtagctaat gttgcaaaca aagacggagt gaaaatgggt  2100
acgaaaaacc tattattaaa cgttgtagat acaaaagctc ctgaattcca gtcagctaaa  2160
attacaaaag ttgacgctaa agaaattact ttaacattct ctgaagctgt gaacgttgat  2220
gcaactgact ttgttattga cctaaatggt gtggcgttaa cagtagcaaa agctgatgac  2280
aaagcagcta aagaagtagt acttaaagta acagctccaa cagatgttaa cttagcaact  2340
ggtacattaa cacttaaaac taaagaactt aaagataatg caactttaaa tacagttgat  2400
acagcagcta acaaacttgt tgctttcaaa ccagtaacag tagctcgc              2448

SEQ ID NO: 70           moltype = AA  length = 816
FEATURE                 Location/Qualifiers
source                  1..816
                        mol_type = protein
                        organism = Bacillus thuringiensis
SEQUENCE: 70
MAKTNSYKKL IAGTMTAAMV AGVVSPVAAA GKSFPDVPAD HWALDSINYL VEKGAIKGTD  60
QGTFAPEQEV TRAEAATMMA ITLNLPIEEN AKPTYKDAQN HWASKYIAAV EKAGVVAGKG  120
DGTFAPDGKI NRVSMAAMLV PAFKLDTKVA GTPETKFEDL KPSWGKDKAN ILVELGISAG  180
TTTTTWEPEK TVTKAEAAQF IAKTDKQFGQ KEEAKVESIK AINAKEIEVK LGATVKEEDV  240
KNAKFTLSQG TNATAVTTKI GEDKKSVIVT LDGDAKLKNK EAYVLTVEGL KAADGKEIPK  300
ALEVIFFNDE VAPTVSTVST PDGKVKVVFS EKLDTAKAVT VIVNGQKVDG KVENNTFTST  360
NTLNLENGKE FSVIVTGAQD LSGNEMEMYE GKATYKVEKD VTAPEVKEIK VKDLANGTAT  420
LEATFTEELS AQGTVVVKKG NTVVKEATIA LDQDKTKALV TVPGALTDKE TAADLTVEFV  480
GYKDLANNVG TKVSKAVKVT KDVVAPNLVK VVADQNKEAT FTFDKDVTKQ DGKIRVINLD  540
TSRDVTGEVT IEAAKDNSKG ITLTFPAKGN YKVAATKGLV KDAAGNESAA FTKEVKVVEK  600
ESEKETDKVA PAVTGVAFDK ATNKITVNFD KEVKGGQVAE SASNVNNYTL AGAKLPEGAL  660
IVLDGTNAVI ELPSTFTFEK SETVKFTVAN VANKDGVKMG TKNLLLNVVD TKAPEFQSAK  720
ITKVDAKEIT LTFSEAVNVD ATDFVIDLNG VALTVAKADD KAAKEVVLKV TAPTDVNLAT  780
GTLTLKTKEL KDNATLNTVD TAANKLVAFK PVTVAR                            816

SEQ ID NO: 71           moltype = DNA  length = 3522
FEATURE                 Location/Qualifiers
source                  1..3522
                        mol_type = other DNA
                        organism = Bacillus thuringiensis
SEQUENCE: 71
atgaacgaaa ccgtcgagga cgacgagaaa aaacgagcct ggcttgatac cgaaaaggtt  60
cagaccactg tcgctcaggt cacgaaactg gcagacggat cactcaagga actgggcgac  120
ggagcgcagt tttccgaggt gttctgggcg gatgcggtcg aaacatcgct ttaccagaca  180
caccccagag tgccggagct gcaaactcaa atggtgtgcc ggtacaagtt cgaatcaggc  240
cgcatctatg tgaagacctt gcgctaccac atgaccacaa ggggcgccaa taaagatagg  300
gcaaacatag atttgggcct gcaggccggt acatgggtgc gcaagaactc acctgacagc  360
atgctgcaag ataaccggtg gcacgattat gtggaatatg tcgactcccc gctcggtcct  420
cctgattttg gcgtgtcgct ggcaatccgg gttaactacg acggagaaaa caacgatgtt  480
gaaccccacg aagggtgggg ccttgatatt tatccagcac agaaaccgat tatcgaggtt  540
cccacttccg gaacctcgat cgatgtcgag aagccgttca ctgtatccgg tagaaacggg  600
cttgtccccg gcacaattca tttgaggcgg cagtctaaca atgctgaaat tccagtgggg  660
actgctcctg tccagaacaa cggggggtgg aatacctcca tcgtgttgcc gcccggcgtt  720
ttggatttct acgccgtaca aatcattggc aaccagaact ccggtaagtc caataccgtt  780
accctcaaaa ggtacgtggc accacgtatc gactctccgg caaacagtgc ggtactcaag  840
tcggccagcg gattgctgat caaaggccga ggcacgccag gcaatgtcat cgatgtgatg  900
accccggggg gcgccgtgtt acacgccacg acaaccgtca agcctgacga aacgtgggaa  960
gcatcattca accagtccaa ctaccctgac ggcggtcgcg tcgatatcac ggctggccac  1020
agaggcatgg atgattggac cgctgcgcaa ttcttcacct tgcttctgca gccgacaatc  1080
acgacgccat ccgaatcagc ggtgaccgat ccgagaggtc cgatagaagg ggggagggct  1140
gttccaggtg cgaccgtcga agtcctcaag gatttcgaac attcattcaa ggtcggccag  1200
ggcattgctg atgccaacgg aggatggagg gttacaacgt tcacccgcga catgccgccg  1260
ggccgcttta cggttgtggc gcagcaaacg gtacctggcg gcacttcgga agtgagtgtg  1320
gcccgttcgt tcaaagtccg ccccccaaca ccgagcacaa tcaacttcac ctacccgtcc  1380
ctcacctcca tcgagtttc cggcgcaggt tttaccggcg ccacggtcga gatcacgatt  1440
gtccgcggtc cgactggagc tacgccgcca cctgccgttg tcgtgaccgc aggcagttgg  1500
agaacgactt cacagtactg gcccatcggc gactacgatc tgaaggtcgt gcagaaggtt  1560
gacgacaatg ctggtggctg gattccctcg catgaatacc atttcaaggc ctcatcaaag  1620
ctaccaccgc cctctgctgt gagatacacc aatgacctct acactccgac attcatcggc  1680
gaaggtatcg caggggcatc tgtcgaggtc accgacaagg cgaccggcgc tgcgctcgct  1740
ccatcgacgc aggtcacgaa tcagggctgg ttgacccgtg ccttcgaggc gtgggcaccg  1800
ggttcgaccc gcaccgtgcg tgtggtgcag aggctcggtg cggcggtgtc ggacgctgtt  1860
gagctggtca tcaatatcga ccgtttccca ccgccgaccg agctggcttt taccgttgtc  1920
gactacaagc cgcgtatcac tggcagaggg atagccggcg ccacagtgca agtgacggac  1980
aagcagaacg gcgccgccat tgcaccaccc gcgcccgtga cgggccaggg ctggacggca  2040
```

-continued

```
gaggcatcga caccctggca gccgaatacc agcagaatcg tcctggtggt gcagtccaaa  2100
gacgctttcg cctccgatcc ggtggaaata accatctctg tgccgctgct ggcacccatc  2160
atcactgccg tcgaagacga tggactctcg ccgaaaatct ccggctcctg ctggcccggc  2220
gcgacactga gcctgaagta cagcgacagt gcgaccgagc acaaacctga tggaagcagt  2280
ggcacatgga ccttcaagcg cgacgccggg tttgctccgg acgagcagca caccgtgacg  2340
gtgatccaga ccgtcgccgg gcgaccgtcg ccgccagcct cgcaaacgtt ctcggtcagc  2400
ccggagaaac cggatatcac cgcgccgaat gaaaacgcag acacccacta cgacatgaac  2460
gtgcacggca tcaacggcta taacggtgcc acattgcaac tgcgggacgc gcaattcggg  2520
cggaatctgg gtgagccgaa acggctgacc gctcatggcg actggttcat cgagctgaaa  2580
aaactggagt tccgcaaata ccagatcgat gccgtgcaaa ccatcgccgg cagaccctct  2640
ctgcccagtg ctgtgcgcag ttttttgtc gtgctggtgc cgccggtcat cacggtgccg  2700
caggagcatc aatcgctggc gcgcacctcg acgcttcgtg gcaccggcga acccccttggc  2760
cacgtgacga tctggcgtga aagtccgagc gaaatcctgc tcgataaaat ctcgataggc  2820
gccaagggcg attggtttgc cgacgtaacg ttgccggtcg gcaactacaa agtgaaggcc  2880
cggcaattct tcgacgatca tgagtcgaag gaaagtcttg tgcgcagttt caaggtggtg  2940
cccgccgcgc cggttatcga aagccccggg cgaggtgtgc acgtcggtcg tcgggttgtt  3000
gtgtccggct tcggctaccc cggtgacaca gtgctggtga cgctgacggg cagcaagggt  3060
tcggtacgcg taagcgctcc ggtgctggag gatcgtacct ggtcgctgac gcttgaaacg  3120
gagcagtccg acggcactgc gcaactggtg gcggtgtcct cgtgtgatgg cttcgagtct  3180
gccccctcgg ctccacatcc agtagagctg ggcacttacc tgcccgctat cgatgagccg  3240
acgccgggaa gctggaaaga aaatccgctt cgcttcctcg gtaaaggccg cacgggcgtg  3300
gggcgcgtgg tgagctggtt cgaccctgat caagtcttga gcgaagacat tgccgtcacc  3360
gatcaaggct ggcgcggcga ggcatcgcac gccttgcgtc caggcggcca ctggtgccga  3420
ttccaacaga ccgtcaccga cgctgcggat ggctcgacca agtccgactg ggttgaaagc  3480
gagcgtttcg aggtgatttc gattccaccg ggagcaagac ca                    3522

SEQ ID NO: 72           moltype = AA  length = 1174
FEATURE                 Location/Qualifiers
source                  1..1174
                        mol_type = protein
                        organism = Bacillus thuringiensis
SEQUENCE: 72
MNETVEDDEK KRAWLDTEKV QTTVAQVTKL ADGSLKELGD GAQFSEVFWA DAVETSLYQT  60
HPRVPELQTQ MVCRYKFESG RIYVKTLRYH MTTRGANKDR ANIDLGLQAG TWVRKNSPDS  120
MLQDNRWHDY VEYVDSPLGP PDFGVSLAIR VNYDGENNDV EPHEGWGLDI YPAQKPIIEV  180
PTSGTSIDVE KPFTVSGRNG LVPGTIHLRR QSNNAEIPVG TAPVQNNGGW NTSIVLPPGV  240
LDFYAVQIIG NQNSGKSNTV TLKRYVAPRI DSPANSAVLK SASGLLIKGR GTPGNVIDVM  300
TPGGAVLHAT TTVKPDETWE ASFNQSNYPD GGRVDITAGH RGMDDWTAAQ FFTLLLQPTI  360
TTPSESAVTD PRGPIEGGRA VPGATVEVLK DFEHSFKVGQ GIADANGGWR VTTFTRDMPP  420
GRFTVVAQQT VPGGTSEVSV ARSFKVRPPT PSTINFTYPS LTSIEFSGAG FTGATVEITI  480
VRGPTGATPP PAVVVTAGSW RTTSQYWPIG DYDLKVVQKV DDNAGGWIPS HEYHFKASSK  540
LPPPSAVRYT NDLYTPTFIG EGIAGASVEV TDKATGAALA PSTQVTNQGW LTRAFEAWAP  600
GSTRTVRVVQ RLGAAVSDAV ELVINIDRFP PPTELAFTVV DYKPRITGRG IAGATVQVTD  660
KQNGAAIAPP APVTGQGWTA EASTPWQPNT SRIVLVVQSK DAFASDPVEI TISVPLLAPI  720
ITAVEDDGLS PKISGSCWPG ATLSLKYSDS ATEHKPDGSS GTWTFKRDAG FAPDEQHTVT  780
VIQTVAGRPS PPASQTFSVS PEKPDITAPN ENADTHYDMN VHGINGYNGA TLQLRDAQFG  840
RNLGEPKRLT AHGDWFIELK KLEFRKYQID AVQTIAGRPS LPSAVRSFFV VLVPPVITVP  900
QEHQSLARTS TLRGTGEPLG HVTIWRESPS EILLDKISIG AKGDWFADVT LPVGNYKVKA  960
RQFFDDHESK ESLVRSFKVV PAAPVIESPG RGVHVGRRVV VSGFGYPGDT VLVTLTGSKG  1020
SVRVSAPVLE DRTWSLTLET EQSDGTAQLV AVSSCDGFES APSAPHPVEL GTYLPAIDEP  1080
TPGSWKENPL RFLGKGRTGV GRVVSWFDPD QVLSEDIAVT DQGWRGEASH ALRPGGHWCR  1140
FQQTVTDAAD GSTKSDWVES ERFEVISIPP GARP                             1174

SEQ ID NO: 73           moltype = DNA  length = 2100
FEATURE                 Location/Qualifiers
source                  1..2100
                        mol_type = other DNA
                        organism = Bacillus thuringiensis
SEQUENCE: 73
atgaatggag gagagaatat gaatcaaaat aatcaaaatg aactgcaaat aatagattct  60
tcatccaatg attttagtca atcaagcagg tatccaagat atccattagc taaagagtca  120
aattataaag attggctagc tagttgtgat gaatccaatg tagatacatt atcagctaca  180
agtgatgtaa aggattcagt ctccagggtt ttgggtattg tgaatcagat tttggatttt  240
ctaggtcttg gatttattgg aacaggtctt ggtgtactag gtgatttatt taattcattt  300
tggccatcaa ataataatgc ggtttgggag gcttttctac gtagtgttga agaacttatt  360
aatgaacgag taagggaaac tgagaggtcc cgtatcgtag cccaatttac gggcctaaga  420
agtgttctgt tgaattataa tggtgctctt caggattggg ataaagatcg taataatccc  480
gaacttagag atgaaataag aagccgcttt gctaatgcag atgatatttt tgcaaatcgt  540
atggatgaat ttagcataaa agggtttgaa gtacaatcgc tagctgtata tgcacaggct  600
gcaactcttc atttattatt attaagggat ggggttctta atggactgca atggggattc  660
aatatcgcta cggttaaccg tctttataac agattggtag aaaagagtgg taaatataca  720
gatcattgta catccttttta taggcagggt ttgcaggagt taaggaacag agggaattgg  780
aatgcattca atacttatcg cagaaacatg actattcaag tattggatgt catttcttta  840
ttttcaaatt atgatcctcg cctatatgaa attaatacaa acacacaact tacaagagaa  900
atatacactg aaccacttgc tggtcctgga tggcttaatt ctcattccaa tccaactcaa  960
ttccaacaaa tagaaaatga tcttattcgc tcaccttcag tattttctaa tctacagatt  1020
ctttttatgg aagctggttt tgcattccac gatatccaga cacctagaca aacagtatta  1080
agaacactta cgcagagttt gaatacgggg cgtactggta tcatcgtaac tccttggcaa  1140
ggtgcactta atcctagtgt ttcacaacga ctgcaggtgc aatttgaaaa taggaatgtt  1200
```

-continued

```
tttaatatca attcagtagt agcttggcaa acttctaatc caaacagctc attatttggg  1260
gtccaacaag ccatttttaa ctttgtgtac gaaggcggaa acgcagcttc gacaacacaa  1320
ttcaatctac caagtgctag atatttaacg tctataacgt ctaatatacc aggaacaaac  1380
tcaacaactc caaccggttc agattatacc catagactat cttcgataac ttcaacttca  1440
gtaggaacgt ggcagagaga tagaacgaat attatggcat atggatggac tcatgttagt  1500
gcagagcgta ctaataggat tataccgaat agaattacac aaattccagc tgtaaaagga  1560
tcactgtcta gtgataatcc accaaaccaa ttacgaacac gtgtagaaag tggccctggt  1620
catactgggg gaggactcgt agttatgggc ggaggaacta gtgtattaca gatgagaatc  1680
acttcttcag caaggcaaag gtatgatatg cgtttacgtt atctagctct tgctccagct  1740
gctgttgaag taagaattcc ggaattaggg gagcatgtta ggtttcagat gccaatgact  1800
gcaacggggt tgactgcgcc tctaccatac tgccatttgc gatatgtgga tatcccgctg  1860
aggtttgaga cacccaatgg tgaaaatact tggacgtttg aactacggac tatgaatgca  1920
gcagttgcaa ttgacagggt cgaattcata ccagttaatg ctacagcttt agaatatgaa  1980
ggaaaacgac atctagaaaa agcaaagaaa gccgtgggtg atctgtttat caataatgga  2040
aaagaggctt taaaagtaga tacgacggat tatgatgtgg atcaagctgc aaatctagta  2100

SEQ ID NO: 74          moltype = AA  length = 700
FEATURE                Location/Qualifiers
source                 1..700
                       mol_type = protein
                       organism = Bacillus thuringiensis
SEQUENCE: 74
MNGGENMNQN NQNELQIIDS SSNDFSQSSR YPRYPLAKES NYKDWLASCD ESNVDTLSAT  60
SDVKDSVSRV LGIVNQILDF LGLGFIGTGL GVLGDLFNSF WPSNNNAVWE AFLRSVEELI  120
NERVRETERS RIVAQFTGLR SVLLNYNGAL QDWDKDRNNP ELRDEIRSRF ANADDIFANR  180
MDEFSIKGFE VQSLAVYAQA ATLHLLLLRD GVLNGLQWGF NIATVNRLYN RLVEKSGKYT  240
DHCTSFYRQG LQELRNRGNW NAFNTYRRNM TIQVLDVISL FSNYDPRLYE INTNTQLTRE  300
IYTEPLAGPG WLNSHSNPTQ FQQIENDLIR SPSVFSNLQI LFMEAGFAFH DIQTPRQTVL  360
RTLTQSLNTG RTGIIVTPWQ GALNPSVSQR LQVQFENRNV FNINSVVAWQ TSNPNSSLFG  420
VQQAIFNFVY EGGNAASTTQ FNLPSARYLT SITSNIPGTN STTPTGSDYT HRLSSITSTS  480
VGTWQRDRTN IMAYGWTHVS AERTNRIIPN RITQIPAVKG SLSSDNPPNQ LRTRVESGPG  540
HTGGGLVVMG GGTSVLQMRI TSSARQRYDM RLRYLALAPA AVEVRIPELG EHVRFQMPMT  600
ATGLTAPLPY CHLRYVDIPL RFETPNGENT WTFELRTMNA AVAIDRVEFI PVNATALEYE  660
GKRHLEKAKK AVGDLFINNG KEALKVDTTD YDVDQAANLV                        700

SEQ ID NO: 75          moltype = DNA  length = 1977
FEATURE                Location/Qualifiers
source                 1..1977
                       mol_type = other DNA
                       organism = Bacillus thuringiensis
SEQUENCE: 75
atgaattcat atgaaaataa aaatgaatat gaaatattgg aatcttcatc aaataacaca  60
aatatgccaa acagatatcc ttttgcaaat gatccaaata tttttcctat tatcctgaac  120
gattgtccgg gaaaaccatg gcaagatacg tggaaatcaa tctcgaattt cataagtgtt  180
atggtaagca tggcaggatt cataagctca cctggtctac taattggaat tcctgcacta  240
ttgggaatag taaacctact aattccatct tctggtccat ctgtggcagc actttctata  300
tgtgatttat tatctataat tcgtaaagag gtagacgaga gtgttttaaa tgacgcggtt  360
gcagatttta acggtaaatt gactaattat aaagagtatt atctttcttc tcttcaggag  420
tggcttagtg caggtaaacc aaatgatagc agacttagta atgtagttga gtatttcaaa  480
aagtctgaag aaggtttcaa tgaaattcta gcagggtcat tatcaaggca gaatgctcaa  540
atattattat tgcctacgtt tacgcaagct gcaaatgtac agttattact attaagggat  600
gcagttcaat ataaaaaaga atggggagca ttgttgagtg cggagaaagt aggatcggaa  660
ttaatatcac ctactattga ttatggtcag cgattaaaag ataaaatagc acagtatacc  720
aagtattgtg tattttggta tcaggaggtt ttaaatcaga taaaagaggg gggggcatat  780
gctgaaactt ggttgaaatt taataaattt cgtagagaaa tgacgttagc ggtattggat  840
attatcgctc tatttccaat ttatgatttt gcaaaatatc cattaggaac aaatgtagag  900
ttaactaggg aaatttatac agacccagtg ggatattcag gggaaatta tcgttgggaa  960
gggcttttta gctttaattc gctagaagct aatggaacac ggggacctgg tttagttact  1020
tggcttcaag ctatagatat atatagtcat tctgttaata ttctacctgg ttatagttat  1080
cttaccggct ggggaggaac tcgtcattat gaagactaca caaagggtaa cggtgctttt  1140
caacgtatgt ctggaactac gagtaatgat ccacatccta ttagtttcgg cactaccgat  1200
atatttaaaa ttagttcatt agctagagtt gaattgcaac catttgttgg gtattcaatc  1260
ccacggtatc gtacttcacg tgcagaattt tttccgacaa cactaaatac tttactatat  1320
gagagaaaca gttctgggta ctcacagaca attgaatctg tgttaccagg tattgataag  1380
gatcgatcac ctagtcctac aaattactct catagattat caaatgcggc atgtgttcaa  1440
tatgaaacct ccgtagttaa cgtatttggt tggacacata caagtatgac aagaaataat  1500
ccaatttatc cagataaaat tacacaaata ccggctgtga aagcatttgc tttagaaaac  1560
gacgcttatg ttagcgctgg acctggtgat acaggaggag atgtagtaac gttaggatat  1620
cttggacgtt taaaaatacg tttaactcct gcagccacaa ataaagacta ccttgttaga  1680
attcgctata aaagtgcatc aaatggtcgg ataaacgtac aaagatggtc gccgagttct  1740
actataggta attattatta tgttccaaat acaggtcctg gtgattcatt tggctatttg  1800
gaaaccttag ttactacatt tcatcagcca ggtgttgaaa taattataca gaatcatgat  1860
gtctctatta tcattgacaa agttgaattt atcccacagg attctacggc tttagaatat  1920
gaaggaaaac aaagtctaga aaaggcacaa aatgtagtga atgatttatt tatcaat     1977

SEQ ID NO: 76          moltype = AA  length = 659
FEATURE                Location/Qualifiers
source                 1..659
                       mol_type = protein
```

```
                        organism = Bacillus thuringiensis
SEQUENCE: 76
MNSYENKNEY EILESSSNNT NMPNRYPFAN DPNIFPIILN DCPGKPWQDT WKSISNFISV    60
MVSMAGFISS PGLLIGIPAL LGIVNLLIPS SGPSVAALSI CDLLSIIRKE VDESVLNDAV   120
ADFNGKLTNY KEYYLSSLQE WLSAGKPNDS RLSNVVEYFK KSEEGFNEIL AGSLSRQNAQ   180
ILLLPTFTQA ANVQLLLLRD AVQYKKEWGA LLSAEKVGSE LISPTIDYGQ RLKDKIAQYT   240
KYCVFWYQEG LNQIKEGGAY AETWLKFNKF RREMTLAVLD IIALFPIYDF AKYPLGTNVE   300
LTREIYTDPV GYSGGNYRWE GLFSFNSLEA NGTRGPGLVT WLQAIDIYSH SVNILPGYSY   360
LTGWGGTRHY EDYTKGNGAF QRMSGTTSND PHPISFGTTD IFKISSLARV ELQPFVGYSI   420
PRYRTSRAEF FPTTLNTLLY ERNSSGYSQT IESVLPGIDK DRSPSPTNYS HRLSNAACVQ   480
YETSVVNVFG WTHTSMTRNN PIYPDKITQI PAVKAFALEN DAYVSAGPGD TGGDVVTLGY   540
LGRLKIRLTP AATNKDYLVR IRYKSASNGR INVQRWSPSS TIGNYYYVPN TGPGDSFGYL   600
ETLVTTFHQP GVEIIIQNHD VSIIIDKVEF IPQDSTALEY EGKQSLEKAQ NVVNDLFIN    659

SEQ ID NO: 77           moltype = DNA  length = 1962
FEATURE                 Location/Qualifiers
source                  1..1962
                        mol_type = other DNA
                        organism = Bacillus thuringiensis
SEQUENCE: 77
atgaattctt atcaaaatac aaatgaatat gaaattctgg atggttcccc gaataacaca     60
aatatgtcaa acagatatcc ttttgcaaaa gatccaaata tatttcctat taacctggac    120
gcttgtcagg gaaggccatg gcaagatacg tgggaatcag tctcggatat agtaactatt    180
gggacatacc ttatacaatt cttgctagaa cccgtatagg gtggaattcc tgtaatattg    240
tcaataataa acaaactcat tccgtcttct ggtcaatctg tggcagcact ttctatatgt    300
gatttattat ctataattcg taaagaggta gacgagagcg ttgttaagtg aggggttgca    360
gattttaagg gtgaaatgac tgcttatcga gattattatc ttccttatct tgaggattga    420
cttacagata aatcaaatcc tgaaaaactt gctgacgtag ttaaacagtt ccaagcacgg    480
gaagaagatt tcactaaact tttagcaggg tcattatcaa gacagaaagc tgaaatatta    540
ttattgccta cgtatgtgca agctgcaaat gtgcatttat tactattaag ggacgcagtt    600
aaatataaaa aagaatgggg actagtgtgt ccaccgttgt atccagggtc agggagaact    660
gattgtaacg agcggttaaa agcgaaaata aaagagtata ctaattattg tgtagagtgg    720
tataacaagg gtttagatca gataaaacag gcgggtacaa gtactgaaac ctggttgaaa    780
tttaataaat ttcgtagaga aatgactttg gcggtattgg atgttattgc tatatttcca    840
acttatgatt ttgaaaaata tccattagca acaaatgtag aattaactag ggaagttttat   900
acagatccag tggggtattc aggaagcagt attcgttggg aaaggacttt tcccaatgct    960
tttaatacgc tagaagctaa tggaacacgg gacctggtt agttacttg gcttgaagtt     1020
ttaggtatat ataatcatga ttttcaggat tacgcgttt attttagcgg ctgggtagga    1080
agtcgtcatt ctgaagacta cacacggggt aacggtactt tttcacgtat atctggaact   1140
acgagtaatg atatacgcaa tcagactttt tactctcgcg atgtatttaa aattgattca   1200
ttaggtatct atgaaacaag agcagagctt ggatacacac ggcaacggtt ttgtgtttca   1260
cgtgcagtat ttagttcaac actatataac tacgtgtatg atgcaagaaa taatgggcaa   1320
ggccgaatga caattgaatc tatgttacca ggtattaaga atccaatacc tagttctcaa   1380
gattactctc atagattatc aaatgcggca tgtgttcaat taacgactc cagaattaac    1440
gtatatggtt ggacacatac aagtatgaca aaaacaatc caatttatac agataaaatt   1500
tcacaaatac cggcggtgaa agcatttgct ttagaatcag cgcttatgt tagccgtgga    1560
cctggtcata caggaggaga tgtagtaacg ttaccaaata gaggcgtttt aaaaatacgt   1620
taacttctgc cacccacgaa taaaaattac cgtgttagag ttcgctatgc aacttcttat   1680
ggagctgatt taatggtaca aaggtggtcg ccgagtggca atcatgcaag tggttatttt   1740
agtggttcac ctacgggttc ttatcctaca tttggatata tgaatacttt agttactaca   1800
tttaatcaat caggtgttga aataattata gaaaatcgac attatagcaa cattatcatt   1860
gacaaaatcg aatttatccc agatgatata acaactttag aatatgaggg agaacgggat   1920
ctagaaaaaa caaaaaacgc ggtgaacgat ttgtttacca at                      1962

SEQ ID NO: 78           moltype = AA  length = 654
FEATURE                 Location/Qualifiers
source                  1..654
                        mol_type = protein
                        organism = Bacillus thuringiensis
SEQUENCE: 78
MNSYQNTNEY EILDGSPNNT NMSNRYPFAK DPNIFPINLD ACQGRPWQDT WESVSDIVTI    60
GTYLIQFLLE PGIGGIPVIL SIINKLIPSS GQSVAALSIC DLLSIIRKEV DESVLSDGVA   120
DFKGEMTAYR DYYLKQPYLE DWLTDKSNPEKL ADVVKQFQAR EEDFTKLLAG SLSRQKAEIL  180
LLPTYVQAAN VHLLLLRDAV KYKKEWGLVC PPLYPGSGRT DCNERLKAKI KEYTNYCVEW   240
YNKGLDQIKQ AGTSTETWLK FNKFRREMTL AVLDVIAIFP TYDFEKYPLA TNVELTREVY   300
TDPVGYSGSS IRWERTFPNA FNTLEANGTR GPGLVTWLEV LGIYNHDFQD ITVYFSGWVG   360
SRHSEDYTRG NGTFSRISGT TSNDIRNQTF YSRDVFKIDS LGIYETRAEL GYTRQRFCVS   420
RAVFSSTLYN YVYDARNNGQ GRMTIESMLP GIKNPIPSSQ DYSHRLSNAA CVQFNDSRIN   480
VYGWTHTSMT KNNPIYTDKI SQIPAVKAFA LESGAYVSRG PGHTGGDVVT LPNRGRLKIR   540
LTSAPTNKNY RVRVRYATSY GADLMVQRWS PSGNHASGYF SGSPTGSYPT FGYMNTLVTT   600
FNQSGVEIII ENRHYSNIII DKIEFIPDDI TTLEYEGERD LEKTKNAVND LFTN          654

SEQ ID NO: 79           moltype = DNA  length = 1665
FEATURE                 Location/Qualifiers
source                  1..1665
                        mol_type = other DNA
                        organism = Bacillus thuringiensis
SEQUENCE: 79
atgggaggaa caaatatgaa tcattttcaa aacgttattc cagaacttgt aaactcttgt     60
```

```
cctcctgatg attgcgatta ctataacatc ctagtattat ctagttatgc acaagtagca  120
aacttacatc tgactgtatt aaatcaagcc gtcaaatttg aagcgtattt aaaaaataat  180
cgacaattcg attatttaga gcctctgcca acagcaattg attattatcc agtattgact  240
aaagctatag aagattacac taatcattgt gtaacaactt ataaaaaagg attaaattta  300
attaaaacga cgcctgatag taatcttaat ggaaatataa actggaacac atataataca  360
tatcgaacaa aaatgactac ttccgtatta gatcttgttg cactgtttcc taattttgat  420
gtaggtaaat acccaatagg tgtccaatcg gaacttacta gagaaattta tcaggtactt  480
aacttcgaag aaagccccta taaatattat gactttcaat atcaagagga ttcacttaca  540
cgtagaccgc atttatttac ttggcttgat tctttgaatt tttatgaaaa agcgcaaact  600
actcctaata atttttcac cagccattat aatatgtttc attacacact tgataataaa  660
tcccaaaaat ctagtgtttt tggaaatcaa aatgtaactg atagattaaa atctcttgat  720
ttggcaacaa atatttatat ttttttatta aatgtaacaa gtttagataa taaatatcta  780
aatgattata ataatattag taaaatggat ttttttataa ctaatggtac tagacttttg  840
gagaaagacc ttacagcagg atctggacaa ataaattctg atgtaaataa aaatattttc  900
ggtttaccaa ttcttaaacg aagagagaat caaggaatcc ctaccctttt tccaacatat  960
gataactata gtcatatttt atcatttatt aaaagtctca gtatccctgc cacatataaa  1020
actcaagtgt atacgtttgc ttggacacac tctagtgttg atcctaaaaa tacaatttat  1080
acacatttaa ctacccaaat tccagctgta aaagcaactt tacttgggac tgccactact  1140
gaactttcta aggttgttca agggcctggt catacaggag gggatttaat tgattttaaa  1200
gatcgtttca aaattatatg tcaacattca aattctcaac aatcgtactt tgtaagaatt  1260
cgttatgctt caaatggaag cgcaaatact cgtgctgcta taaatcttag catcccaggg  1320
gtagcagaac ttgatatggc actcaaccca actttttctg gcacagatta tacgaattta  1380
aaatataaag attttcagta cttagaattt ttggatgagg tgaaatttgg tccaaatcaa  1440
aacctttctc ttgtgtttaa tcgtttggat gtatatacaa acacaactgt acttattgat  1500
aaaattgaat ttctgccaat tactcgttct ataagagagg acagagagaa acaaaagtta  1560
gaaacagtac aacaaataat aaatacattt tttgtaaatt ctataaaaaa cactttaaaa  1620
tcagaaatta cagattacga tattgatcaa gcagctaaat tagta                1665

SEQ ID NO: 80          moltype = AA  length = 555
FEATURE                Location/Qualifiers
source                 1..555
                       mol_type = protein
                       organism = Bacillus thuringiensis
SEQUENCE: 80
MGGTNMNHFQ NVIPELVNSC PPDDCDYYNI LVLSSYAQVA NLHLTVLNQA VKFEAYLKNN  60
RQFDYLEPLP TAIDYYPVLT KAIEDYTNHC VTTYKKGLNL IKTTPDSNLN GNINWNTYNT  120
YRTKMTTSVL DLVALFPNFD VGKYPIGVQS ELTREIYQVL NFEESPYKYY DFQYQEDSLT  180
RRPHLFTWLD SLNFYEKAQT TPNNFFTSHY NMFHYTLDNK SQKSSVFGNQ NVTDRLKSLD  240
LATNIYIFLL NVTSLDNKYL NDYNNISKMD FFITNGTRLL EKDLTAGSGQ INSDVNKNIF  300
GLPILKRREN QGIPTLFPTY DNYSHILSFI KSLSIPATYK TQVYTFAWTH SSVDPKNTIY  360
THLTTQIPAV KATLLGTATT ELSKVVQGPG HTGGDLIDFK DRFKIICQHS NSQQSYFVRI  420
RYASNGSANT RAAINLSIPG VAELDMALNP TFSGTDYTNL KYKDFQYLEF LDEVKFGPNQ  480
NLSLVFNRLD VYTNTTVLID KIEFLPITRS IREDREKQKL ETVQQIINTF FVNSIKNTLK  540
SEITDYDIDQ AAKLV                                                  555

SEQ ID NO: 81          moltype = DNA  length = 2484
FEATURE                Location/Qualifiers
source                 1..2484
                       mol_type = other DNA
                       organism = Bacillus thuringiensis
SEQUENCE: 81
atgacaactt tatctgattt atattcccct ataccttata acgttatggt aactccgcca  60
ttaaaagaag gaaaatattg ggatcaattt aaagcgttaa taaaagaact aaaaggcgga  120
tggaacgaat tcgaaaaaac tggatatagc aaaccttatc tatctgctat tgatgaggcc  180
cttaaaatat ataaaggtgg agacgtagat tataccgctt tagttaaatc attcttatct  240
attggatcaa ctcttggtga attcattcca ggtggtacta ttattgttcc catttttaat  300
gggttagtgg atcttatttt tccgcactta tttggatcaa aagaggcgga caacaacaca  360
aaattcttta atatgataat cgcagaagta gctaaaatga tagataaaag catccaagat  420
cttgtcatag agttagacac taacacgatt aatggaatcg gtgaagctgc aaaacttctt  480
caaactgaaa tacaaactgc cataggagca ccggctgcag tgtttggtcc aaagttagat  540
gcagcagccc tacaactaga ttcttgctcc acttcacctt gtaaaacacc taccgtagac  600
gctttaaaga aggttgaaaa ccaatttata gcttccacta ccactatcgc tacaaacata  660
ccatcacttc ttctgaagac cggatctgac cgtaatgcac agcgtcaaac ggttatgtta  720
acgttaccga tgtatgtaac aggtgcaaca ttacatttat ctctcataca agggtatatt  780
caatttatgc aacaatggaa agatgtgtat gccgccaatc taagcagtgc tatatctacc  840
ttgcagagat atattcagca atattccaac accgtattaa atatgtataa tgactataac  900
aaagacgtaa ttcctgggat aaataacaaa gacatattaa ataaatatat ccaatacaat  960
cgagtgatgg cgacacaagt atttgatatg gtctccatgt ggtcttcttt ctttccagca  1020
gactacccttcaacatttaa cacagaccaa actcgtatcg catttggaaa tatcgctgga  1080
ccaacagaag accaacctac ccttcatttt gatctctatg atgtttacag taagaaatta  1140
ccaaataatg atatttttaa ttatttttat aatgggatgc aattaaacac atttgaactt  1200
gctggggctc atagtgcaga ttataatcgt gtgtatacta cagggataaa tgcaaggtac  1260
aacacttata atacaaccaa tagcattgca caatatgctt atacaggtcc ttatattaag  1320
aatttttccg aacaagacgt attgaactta actaatatta atatactctc tgtaaaaact  1380
aaatatcaag atattaataa attaatttat aattgtcaaa gctataatcc tgaggcttcc  1440
cgtggttatc aacttaacgg ctgtgattat agtgctggat acacaccaca agtccagcct  1500
aaaaatgtat acgtatcagc caacgtaccg tttagtaatc aaaaaattca agcgatttat  1560
ccagttgcca gtactgatgt ttggggaggt aaagacaaac gtggttatct ttatacactt  1620
gtcgattatg atttatttcc tcaaaatgtt atagggcaac ccaatgaaga tggacttatt  1680
```

```
agccaaatga ttcaagggtt ccctgcagaa aaaggtttta taagtaataa tataggtact  1740
ttacaactgg ttcctgaacc aattaatagt gccgcagctg tcaacttaaa attccaacaa  1800
atattatcat taccaattac taatctaacc gttcaaaact atcaaattcg tgttcgatat  1860
gcaaataaat cagacaatac aatttatttc cgtgttgaaa cacctaatgg aaatctaaac  1920
agtggtccac aaacgcttaa aaatgcgcaa gatactacaa atataactat taaaggtaat  1980
aacggagact acactttaca aacattggca gataaagttt ttcttccttc cggaaattta  2040
accgtacatt ttcaaaataa tagtaattca gatctctttt tagatcggat tgaatttgtt  2100
ccactaccte taaaacaaga agttctaaaa cctacagata ttaatatttt caaaggaagt  2160
cctgatccaa ttgtttggga atcacaagat aaagaagcag ttagtgctgt tttaaatgta  2220
agagaggaat ttggaatgcc tgttactaat tttgtattcg actttttattt aaataatgta  2280
cttcaattt cagaagatat aattggtgga gaaaaaactt atatgcataa tgggaaaacc  2340
tcaataaaa ttacaggtag aaataccaat ccagtagtga taagtgatac gttaattata  2400
tcaggaatca ttaatgaaga atattctcga agttcaaata ttttttgaaac cccagaagat  2460
ttagaattga tcacaaacca agtg                                         2484

SEQ ID NO: 82        moltype = AA  length = 828
FEATURE              Location/Qualifiers
source               1..828
                     mol_type = protein
                     organism = Bacillus thuringiensis
SEQUENCE: 82
MTTLSDLYSP IPYNVMVTPP LKEGKYWDQF KALIKELKGG WNEFEKTGYS KPYLSAIDEA   60
LKIYKGGDVD YTALVKSFLS IGSTLGEFIP GGTIIVPIFN GLVDLIFPHL FGSKEADNNT  120
KFFNMIIAEV AKMIDKSIQD LVIELDTNTI NGIGEAAKLL QTEIQTAIGA PAAVFGPKLD  180
AAALQLDSCS TSPCKTPTVD ALKKVENQFI ASTTTIATNI PSLLLKTGSD RNAQRQTVML  240
TLPMYVTGAT LHLSLIQGYI QFMQQWKDVY AANLSSAIST LQRYIQQYSN TVLNMYNDYN  300
KDVIPGINNK DILNKYIQYN RVMATQVFDM VSMWSSFFPA DYPSTFNTDQ TRIAFGNIAG  360
PTEDQPTLHF DLYDVYSKKL PNNDIFNYFY NGMQLNTFEL AGAHSADYNR VYTTGINARY  420
NTYNTTNSIA QYAYTGPYIK NFSEQDVLNL TNINILSVKT KYQDINKLIY NCQSYNPEAS  480
RGYQLNGCDY SAGYTPQVQP KNVYVSANVP FSNQKIQAIY PVASTDVWGG KDKRGYLYTL  540
VDYDLFPQNV IGQPNEDGLI SQMIQGFPAE KGFISNNIGT LQLVPEPINS AAAVNLKFQQ  600
ILSLPITNLT VQNYQIRVRY ANKSDNTIYF RVETPNGNLN SGPQTLKNAQ DTTNITIKGN  660
NGDYTLQTLA DKVFLPSGNL TVHFQNNSNS DLFLDRIEFV PLPLKQEVLK PTDINIFKGS  720
PDPIVWESQD KEAVSAVLNV REEFGMPVTN FVFDFYLNNV LQFSEDIIGG EKTYMHNGKT  780
FNKITGRNTN PVVISDTLII SGIINEEYSR SSNIFETPED LELITNQV               828

SEQ ID NO: 83        moltype = DNA  length = 1947
FEATURE              Location/Qualifiers
source               1..1947
                     mol_type = other DNA
                     organism = Bacillus thuringiensis
SEQUENCE: 83
atgaaaccaa ataaccagga taatcatgaa accttatcca acaaagtgac agtcgaaaaa   60
ccttttacag attcactaaa aaatgaaaca actaaaaata gtaattatga agattgtttg  120
aaaatgtcta gacatgaaag cgtagagccg tttgttagtg tatcaacaat tcaaacggga  180
attggtattg ctggtaaaat ccttggtagc ctaggcgttc cttttgctgg gcaagtagct  240
agcctttata gttttattct aggtgagctt tggcctaagg ggaaaagtca atgggaaatc  300
tttatggaag atgtagaaaa acttgttgat caaaaaatat cgatttacgc aagaaacaaa  360
gcacttgcag atttaaaagg attaggagat gctctggctg tctaccatga atcccttgaa  420
agttggattg aaaatcgtaa taacagaaga gctagaagtg ttgttaaaga ccaatatatc  480
gcttggaac ttatgttgt tcagagactt ccttcttttg cagtatctgg agaagaggtg  540
ccgctattac caatttatgc tcaagctgca aatttacact tattgctatt aagagatgca  600
tcaatttttg gagaagaatg gggtttttca acttcagaaa tttcaacatt ttataaccgc  660
caatctagtc ggacgataga atattctgac tattgctcag gatggtataa tacaggacta  720
aatcgcttga gaggtgcaaa tgctgaaagt tgggtacgat ataatcaatt ccgtagagac  780
atgactttaa tggtactaga tctagtagca ctattcccaa gctatgacac tcgcacttat  840
ccaattaaaa ctagtgccca acttacaaga gaagtctata cagatccaaa cggtattgta  900
gcaggaggca ataataattg gtttagaaat gggggcttcgt tttccactat agaaaacgca  960
attattcgac aacctcacct atatgatttt ctaacgaacc ttacaattta caattta cacgagaata 1020
agtcgagcaa accctgctta tatgaatttg tgggcagggc atagaattac ttctaataga 1080
ataggttcta gtaatagtag tgaattggtg tatgggggcta taactaatcc agttagtact 1140
actaacttat catttgtcaa tcgggatgtt taccgaactg aatcattagc tggtgggctt 1200
ggcactctga atggaatact ttatggttta actagagttg attttgatat gatatttcgt 1260
aaccgtcctg atatagtaac tggattattt tatcatccgg gacacgcggg cattgcaacc 1320
caagtaaaag attcagaaac agaattacca cctgaaacga cagaacagcc aaattatagaa 1380
gcatttagtc atctactaag tcatatttca atgggtccaa cgactcaaga cgtacctcca 1440
gtatattctt ggacacacca gagtgcagac cgttcaaata caatcgattc ggataggata 1500
acacaaatac cattggtaaa ggcgcatacc cttcaatcgg gtaccactgt agtaaaaggg 1560
ccaggggttta caggagggga tatcctccgt cgaacaagtg gaggaccatt tgcttttagt 1620
aatgttaatc tagatttttaa cttgtcacaa aggtatcgtg ctagaattcg ttatgcctct 1680
actactgact taagaattta cgtaacggtt gcaggcgaac gaatttatgc tggtaaattt 1740
aataaaacca tgaaaaaagg tgacccatta acattccaat catttagtta cgcaactatt 1800
aatacagctt ttacattccc agaaagatcg agcagcttga ctgtaggtgc tgatacgttc 1860
gattcaggta atgaagtttta tgtagataga tttgaattaa tcccgatac tgtaacattt 1920
gaggcagagt ctgatttaga aaaagcg                                      1947

SEQ ID NO: 84        moltype = AA  length = 649
FEATURE              Location/Qualifiers
source               1..649
```

```
                         mol_type = protein
                         organism = Bacillus thuringiensis
SEQUENCE: 84
MKPNNQDNHE TLSNKVTVEK PFTDSLKNET TKNSNYEDCL KMSRHESVEP FVSVSTIQTG    60
IGIAGKILGS LGVPFAGQVA SLYSFILGEL WPKGKSQWEI FMEDVEKLVD QKISIYARNK   120
ALADLKGLGD ALAVYHESLE SWIENRNNRR ARSVVKDQYI ALELMFVQRL PSFAVSGEEV   180
PLLPIYAQAA NLHLLLLRDA SIFGEEWGFS TSEISTFYNR QSSRTIEYSD YCSGWYNTGL   240
NRLRGANAES WVRYNQFRRD MTLMVLDLVA LFPSYDTRTY PIKTSAQLTR EVYTDPNGIV   300
AGGNNNWFRN GASFSTIENA IIRQPHLYDF LTNLTIYTRI SRANPAYMNL WAGHRITSNR   360
IGSSNSSELV YGAITNPVST TNLSFVNRDV YRTESLAGGL GTLNGILYGL TRVDFDMIFR   420
NRPDIVTGLF YHPGHAGIAT QVKDSETELP PETTEQPNYR AFSHLLSHIS MGPTTQDVPP   480
VYSWTHQSAD RSNTIDSDRI TQIPLVKAHT LQSGTTVVKG PGFTGGDILR RTSGGPFAFS   540
NVNLDFNLSQ RYRARIRYAS TTDLRIYVTV AGERIYAGKF NKTMKKGDPL TFQSFSYATI   600
NTAFTFPERS SSLTVGADTF DSGNEVYVDR FELIPDTVTF EAESDLEKA              649

SEQ ID NO: 85            moltype = DNA  length = 2130
FEATURE                  Location/Qualifiers
source                   1..2130
                         mol_type = other DNA
                         organism = Bacillus thuringiensis
SEQUENCE: 85
atgaattcaa ataatcaaaa tgaatatatt gcttcatcta ctacttctgt atccaatgat     60
tctaacagat acccttagc gaatgggcca acaaatgcgt tacaaaatat gaattataaa    120
gagtatttaa gaatgtccga gggctatgat agagaatatt ctgcttcacc tggagcactt    180
gttagtggga aagaagcaat taaggttgga atcgatattg tcggcaaaat attaggggga    240
ttagggattc catttgttcc tcagatagtt agttttataa attttattct cgatcagcta    300
tggccatcaa attctgtgag tgtatggaa cagattataa cgctagtgga agaacttgta    360
gatcaaaaaa taacagaata tgcaagaaat aaggcactcg ctgaattaaa agggctagga    420
gatgctttga atgtatatca gcaatcactt gaagcatggt tggaaaatcg caatgacaca    480
agagctagaa gtgttgtttc taatcaattt gcagtttgca atcttgattt tgttggggca    540
attccatcct ttgcagtatc cgggcaggaa gtaccattat tagcagtata tgcacaggct    600
gtgaacatgc acttattgtt actaagagac gcttctattt ttggagaaga gtggggattc    660
acatcatatg aaatttccac ttactacaac cgtcaagtac aactcacttc tcaatatact    720
gattattgcg taaagtggta caataccaggt ttagaaaaat taaaaggtac gcgcgctgag    780
aattggttgg agtatcatca attccgcaga gagatgactc tcatgtgtatt agatttggtt    840
gcattatttc caaactacaa tacacacacg tatccacttg aaacaaaggc tcaacttaca    900
cgagaagtat atacgaccc gatcgccttt aatcttctg gggcagcggg ttttgtaga     960
ccttggtcaa agtatactgg tatttccttt tcggagattg aaaatgctgt aattcgtccg   1020
cctcatttat ttaatgtact cagaagttta gaaattaata cagttgaggg gacaatttta   1080
ggtaatacta aagattacct aaactattgg tcaggtcatt ctctacgata taatttttata  1140
ggtgatacaa cagtaaggga aaataattat ggatatctta cttcagaaaa aactaggatt   1200
gaattagaca ctagagatat ttttgaaatt aattcaactg ccgctagctt agcgaattac   1260
tatcaagaga cttatggtgt gccagaatct tggctccata cagttgcaatg ggatagccta   1320
tattatacat catcttatct ttattctaaa acacatacaa ctggagaagg ttgtacacaa   1380
gtttatgaat caagtgagga aatacctgta gacggaacgg taccggtaaa tgaaggttat   1440
agtcacagac tatcttatgt cacctctctc tttttccaga aaattattaa tactttttat   1500
acaaatggaa ctctcacctgt cttttgtttgg acacatcgga gtcggattt caccaataca   1560
atttatccgg ataaaatcac gcaacttcca atagtaaaaa catacacttt accttcaggt   1620
acttccgtaa tacagggtcc tggatttaca ggaggaaata tattaaaaag aacaagcact   1680
ggcagaatag gaacttttcg aattaactta accggaccat tgacacaaag atatcgtgta   1740
agaattcgtt atgcttcttc tagtgatata aatttccgtg taacttcatgc gggtaagacg   1800
gttaatgact atttctttag taaaactatg aagcaaggag catctttaac atatgaaaca   1860
tttaaatttg ctagctttac tacgcctttc agatttgaaa atacttcagg tgaaataggg   1920
atagatgtgt ataattttct ctcaagtgga gaagtttatg tagaccgaat cgaagtcatc   1980
ccagtagatg cgacatatga agcggaacaa gatttagagg cggcaaagaa agcagtgaat   2040
gccttgttta cgaatacaaa agatggcctta cgaccaggcg taacggatta tgaagtgaat   2100
caggcggcaa acttagtgga atgcctatcg                                    2130

SEQ ID NO: 86            moltype = AA  length = 710
FEATURE                  Location/Qualifiers
source                   1..710
                         mol_type = protein
                         organism = Bacillus thuringiensis
SEQUENCE: 86
MNSNNQNEYN ASSTTSVSND SNRYPLANGP TNALQNMNYK EYLRMSEGYD REYSASPGAL    60
VSGKEAIKVG IDIVGKILGG LGIPFVPQIV SFYNFILDQL WPSNSVSVWE QIITLVEELV   120
DQKITEYARN KALAELKGLG DALNVYQQSL EAWLENRNDT RARSVVSNQF AALDLDFVGA   180
IPSFAVSGQE VPLLAVYAQA VNMHLLLLRD ASIFGEEWGF TSYEISTYYN RQVQLTSQYT   240
DYCVKWYNTG LEKLKGTRAE NWLEYHQFRR EMTLMVLDLV ALFPNYNTHT YPLETKAQLT   300
REVYTDPIAF NLSGAAGFCR PWSKYTGISF SEIENAVIRP PHLFNVLRSL EINTVRGTIL   360
GNTKDYLNYW SGHSLRYNFI GDTTVRENNY GYLTSEKTRI ELDTRDIFEI NSTAASLANY   420
YQETYGVPES WLHMVQWDSP YYTSSYLYSK THTTGEGCTQ VYESSEEIPV DGTVPVNEGY   480
SHRLSYVTSL FFQKIINTFY TNGTLPVFVW THRSADFTNT IYPDKITQLP IVKTYTLPSG   540
TSVIQGPGFT GGNILKRTST GRIGTFRINL TGPLTQRYRV RIRYASSSDI NFRVTHAGKT   600
VNDYFFSKTM KQGASLTYET FKFASFTTPF RFENTSGEIG IDVYNFLSSG EVYVDRIEVI   660
PVDATYEAEQ DLEAAKKAVN ALFTNTKDGL RPGVTDYEVN QAANLVECLS              710

SEQ ID NO: 87            moltype = DNA  length = 2268
FEATURE                  Location/Qualifiers
```

```
source                  1..2268
                        mol_type = other DNA
                        organism = Bacillus thuringiensis
SEQUENCE: 87
atgacaggag gaaaatccat gaaccaatac gatagaaatg atgaaatgga aattcttgat  60
ccaggaaggg gccaggtcag atatccgtat gcatatgagc caaattcaga gttacaatcg  120
atacattaca aagattggct agatatgtgt gaaaggaatg gcaacggtcc cacagggtta  180
cgaacgggta cattggtatc gtcacaagat attattaatg ttagcttaga tattgttggt  240
aacgttttag gacttatacc tgtagtaggt ggagctataa aagcaggagt ttcaatactt  300
aagtccatac ttggtctact ttggccaaag ccagaagaac caggaacaga tccaaatgca  360
atatggatcg agtttatgga aaaggtagaa gtactgattg atcaaaaaat ttctcaagaa  420
gcatttaatg cagcaattgg aaggttaaac ggcttaaaac gagctttaaa tttatatcaa  480
gtagcatttg aactttgggc tggcgatcaa gttgatgaag agctaaaaga ggatgtacga  540
actcgcttta cagcggccct ctttgaaatg gtggctacaa tagagacgtt tagatatgct  600
ggacaagagg taaatctact cacagtgttt gcacaagctg cagatcttca cttgttgcta  660
ttaagagaag ggattatgtt tggattacaa tggggtttg atcaaagaac agtagattct  720
ttttatacaa attctcaaaa agaagggcta aaggatttac ttcctatata cactgattat  780
tgtacctctt ggtataatga aggtttaaaa atcacctata cattgaagcc agatttatca  840
aatactgaaa gatatccatg ggctgcagac aaaccttcat ggaaccttcg agttcttgaa  900
gaattagaag gttggaatct atttaacgat tggcgaagag atgtgacgat tatggcatta  960
gatttggttg ccttgtggcc aacttatgac ctatattatt atgataattt gaagtatggt  1020
gtaaaaactg aacttacacg tccagtgtat tctcaagcgg ctggaaccag ctggggtagc  1080
atattaccac gggatcgcta tgaacaaggt atagtccgtt caccacattt agtgacatgg  1140
ttacattcaa ttgattttca tttaaaccct ggtccgttct ctgtgagtaa tagctataaa  1200
cattatacgg gtcttaaact gaaatattat tattccggtc gagattacac agtatatgaa  1260
tcgccactaa taggtactac gtcttctagt gggaaaacaa ttaatgtgga agctaaatat  1320
gggactgcta ttttccaatc agatattaag cataacgatg cagtatatac aatggatttc  1380
tttaaaaata acgggagtag tgacaaggtt ggatatctat atgagccaaa ctattctaca  1440
ctgtcatggc cacctgagac tggggtttcc aattatggtc atcaaatgac gtggataagt  1500
ggcccagtag aaagtggtac gataccggct ttcggtgcag aatgggtaca tgaaagttgc  1560
tctcctttta atgctatagc agacgacaca gtagaaaatc ctatcattac tcaaattcca  1620
gcagtgaagg gggcaagtat agcaggaaat gcaacggtga taaaaaatcc tggtcataca  1680
ggtggtgatc tcgtacaatt acctgcgaat tctggatcac aagctcaatt gttaataagt  1740
atggaaactc cttattcaaa ggtaggaaaa gcatatcaaa tacgagttcg ctatgcggct  1800
agttccaatg ctaccttaca agtggatcaa tgtgcttatc ttggaggaag ttgttataac  1860
agcgcatcta ttcctgttac agctacgtat tctaataatg tattatcgta tagtgcattt  1920
cagtatgcag atgtgttccc gataacgata caaagtgcgg acttttcctt acagtttttc  1980
aacagaagtg gtggacctat tatcctcgat aaaatcgagt ttattccaat agaaggttcc  2040
ttagaagagt atcaagcgaa acaagagtta gagaatgcga gaaaggccgt gaatgcctta  2100
tttacgaatg atacaaaaaa cgcattgcgt ttagaaatca cggattatga tgtggatcag  2160
gctgcaaata aagtcgcgtg tatgtctaat gatagatatg gaaaagaaaa aatgatctta  2220
ctcgatcttg taaaatacgc caaacactta agccaggaaa gaaatgta              2268

SEQ ID NO: 88           moltype = AA  length = 756
FEATURE                 Location/Qualifiers
source                  1..756
                        mol_type = protein
                        organism = Bacillus thuringiensis
SEQUENCE: 88
MTGGKSMNQY DRNDEMEILD PGRGQVRYPY AYEPNSELQS IHYKDWLDMC ERNGNGPTGL  60
RTGTLVSSQD IINVSLDIVG NVLGLIPVVG GAIKAGVSIL KSILGLLWPK PEEPGTDPNA  120
IWIEFMEKVE VLIDQKISQE AFNAAIGRLN GLKRALNLYQ VAFELWAGDQ VDEELKEDVR  180
TRFTAALFEM VATIETFRYA GQEVNLLTVF AQAADLHLLL LREGIMFGLQ WGFDQRTVDS  240
FYTNSQKEGL KDLLPIYTDY CTSWYNEGLK ITYTLKPDLS NTERYPWAAD KPSWNLRVLE  300
ELEGWNLFND WRRDVTIMAL DLVALWPTYD LYYYDNLKYG VKTELTRPVY SQAAGTSWGS  360
ILPRDRYEQG IVRSPHLVTW LHSIDFHLNP GPFSVSNSYK HYTGLKLKYY YSGRDYTVYE  420
SPLIGTTSSS GKTINVEAKY GTAIFQSDIK HNDAVYTMDF FKNNGSSDKV GYLYEPNYST  480
LSWPPETGVS NYGHQMTWIS GPVESGTIPA FGAEWVHESC SPFNAIADDT VENPIITQIP  540
AVKGASIAGN ATVIKNPGHT GGDLVQLPAN SGSQAQLLIS METPYSKVGK AYQIRVRYAA  600
SSNATLQVDQ CAYLGGSCYN SASIPVTATY SNNVLSYSAF QYADVFPITI QSADFSLQFF  660
NRSGGPIILD KIEFIPIEGS LEEYQAKQEL ENARKAVNAL FTNDTKNALR LEITDYDVDQ  720
AANKVACMSN DRYGKEKMIL LDLVKYAKHL SQERNV                            756

SEQ ID NO: 89           moltype = DNA  length = 588
FEATURE                 Location/Qualifiers
source                  1..588
                        mol_type = other DNA
                        organism = Bacillus thuringiensis
SEQUENCE: 89
atgaatttc agaacaaaag ggaggcgtat gtcatggaca acaagcatca aaaccacatc  60
caaagtgaat cacaagataa tccccttgca actaattttg aacctaacat acaacaacat  120
tcaaatgtaa aagaaaagaa tcatcgatta ccatttagta ttgtgttaaa tattccaaat  180
ggatttcaga tacaaaagga aaagaatcct aaagtgatgt atgatttaaa ccatctctct  240
atgataaaag aaacatgtaa aaaatccatt gacgtggata attgtggata cgttgatgtt  300
gacttacatg cgttaaagat aaagggatgt ctatcttttt tacttaatct atatattgaa  360
ccaatccatg atggtaaaat ctacgaaaaa aattctaagg atggttctat cgcgttatct  420
tataaagaaa cattacatgt tgaccacgta gtaaaatata gtgtggggca attaccttat  480
tatattattg atgatgaaca tgtccaaata cgccatttag aaatacaagt atttaatgaa  540
aattgtaata tagtaaaaat ttccggtgag ttttattttg agtatgaa              588
```

```
SEQ ID NO: 90             moltype = AA    length = 196
FEATURE                   Location/Qualifiers
source                    1..196
                          mol_type = protein
                          organism = Bacillus thuringiensis
SEQUENCE: 90
MNFQNKREAY VMDNKHQNHI QSESQDNPLA TNFEPNIQQH SNVKEKNHRL PFSIVLNIPN    60
GPQIQKEKNP KVMYDLNHLS MIKETCKKSI DVDNCGYQDV DLHALKIKGC LSFLLNLYIE   120
PIHDGKIYEK NSKDGSIALS YKETLHVDHV VKYSVGQLPY YIIDDEHVQI RHLEIQVFNE   180
NCNIVKISGE FYFEYE                                                  196

SEQ ID NO: 91             moltype = DNA   length = 2250
FEATURE                   Location/Qualifiers
source                    1..2250
                          mol_type = other DNA
                          organism = Bacillus thuringiensis
SEQUENCE: 91
atgaaggaaa gcaataataa cgaatatgaa gttttagata tgaattcttc atcttatcca    60
tctaactcac ctcaaacaaa caacaataat tttagatacc cttttcaaa taacgaaaat   120
gatatattac agtataatga ttggattaat aggaatcaag ttagtgattt agagaatttt   180
aatgcagata atttagccgc agttagtgca ggtattattg tagttggtac gatattatct   240
gttttagtg gtggagctat tccaggagcc gctatcattt cttttggaac attgatgcct   300
attctttggc caagtggcga acaagataga acagttgga ctcagttcat gacacacgga   360
tcaaatctta taaatcaacc tctaattgat actgttaaag aatcagcatt ggcaacttta   420
aatggtttta gacaagtact aggaaactat gcagatgggc ttgagtattg gcaaaaatta   480
aaacaacagc agattccagg aacaccaccg tcttcagaat gcgacaagc tgctcaaaca   540
gttaaaactc gatttgaaat tgttcataat gactttgtta gagatatgtc tgactttcaa   600
ttaccatctt ataaggtaat tctattaagc acatatgcac aagctgcaaa tttacattta   660
aatttattac aacaaggtgt tatatttgca gatcaatgaa atgcagatat ttaccctct   720
caagttgtac ctgatgtata tgcaggaacc tcacaagcat actatgaact tttacaaaaa   780
tatttagctg tttatagtaa ttattgtaca aatacctaca agaaggttt aaatattctt   840
aaaactcaat ctggtgtaaa gtggaatacg tataattcat atcgcagaga aatgactata   900
actgttttgg accttgtagc acttttcaa aattatgatg tgaaaagata tccaattgga   960
acccagtctc aacttactag ggagattat acagatgcat ttttatcaaa ctatgcaaat  1020
aataatttta gcttagatag aatagaaact gaattaacaa gaccacctca cttatttact  1080
tggttaaaca aaataaattt ttatacaaga acttataata ttgacatgag acaattaggt  1140
tttctgactg caaattccat aaactattca ttaacaaata gtgaaatgaa tactagtgta  1200
atatatggtt ctcacagaag tacagataaa ttaagctcaa tatctattcc atttggtagt  1260
tatatttaca atatttttagc cacttatcaa gtgaatttc ccgaccatat tcaaaaaatg  1320
aattttagtt taactaatca aaatacatta atttatgaac cggggtttta tttagaagac  1380
tatgaaaaaa ggaatacaat aatatcattt ccagactag ataaaacatt tccacctaaa  1440
tttaatagat acagccatat cctgtcttat atgaaaacat ggtatattgc gaatatgcct  1500
gtatatgaaa caggtagaaa tgttctttt gcatggacac attatagtgt tgattcgca   1560
aacactatta aagacaaatt aattacacaa ataccagcag ttaaatctag atttttacaa  1620
agtgctgatg ttgttcaggg tcctggtcat acaggaggag atttagtatc tatttcaaaa  1680
cctggttcgt ctgtagaact tcaatgtcat gtgcctaata cttacaaaa atataggtta  1740
cgtatccgat atgcattgta cgctccacag tctctctcta cggttactat tggggttcga  1800
ttaacaggat caaatcctac aattgcttac tatgatgagg aagtacgatt acctaaaact  1860
gtctcatcat ttgatggtgc ttcaaatcta aaatatgaag actttcaata tttcgattta  1920
ttctcaaatg ttcgattaga tatgggaagc acaatttctt tgagaatatc taagatcaa  1980
ataataggat ctggtacgat aattttagat aaagttgaat ttatcccttc aaatctatat  2040
gagataaaat catatgaaaa agaaaagcta gaaactacta caacgtgt taattcttta   2100
tttacaaata aacaaaaat taatttaaaa ttcgaaacta catcttatca tatcgatcaa  2160
actgcaattt tgcagaagc catttcgat gagttatatg cacaagaaaa aatgatacta  2220
ttagatgaaa ttaaatatgc gaaacgactg                                   2250

SEQ ID NO: 92             moltype = AA    length = 750
FEATURE                   Location/Qualifiers
source                    1..750
                          mol_type = protein
                          organism = Bacillus thuringiensis
SEQUENCE: 92
MKESNNNEYE VLDMNSSSYP SNSPQTNNNN FRYPFSNNEN DILQYNDWIN RNQVSDLENF    60
NADNLAAVSA GIIVVGTILS VFSGGAIPGA AIISFGTLMP ILWPSGEQDR TVWTQFMTHG   120
SNLINQPLID TVKESALATL NGFRQVLGNY ADGLEYWQKL KQQQIPGTPP SSELRQAAQT   180
VKTRFEIVHN DFVRDMSDFQ LPSYKVILLS TYAQAANLHL NLLQQGVIFA DQWNADIYPS   240
QVVPDVYAGT SQAYYELLQK YLAVYSNYCT NTYKEGLNIL KTQSGVKWNT YNSYRREMTI   300
TVLDLVALFQ NYDVKRYPIG TQSQLTREIY TDAFLSNYAN NNFSLDRIET ELTRPPHLFT   360
WLNKINFYTR TYNIDMRQLG FLTANSINYS LTNSEMNTSV IYGSHRSTDK LSSISIPFGS   420
YIYNILATYQ VNFPDHIQKM NFSLTNQNTL IYEPGFYLED YEKRNTIISF PDLDKTFPPK   480
FNRYSHILSY MKTWYIANMP VYETGRNVSF AWTHYSVDFA NTIKDKLITQ IPAVKSRFLQ   540
SADVVQGPGH TGGDLVSISK PGSSVELQCH VPNTLQKYRL RIRYALYAPQ SLSTVTIGVR   600
LTGSNPTIAY YDEEVRLPKT VSSFDGASNL KYEDFQYFDL FSNVRLDMGS TISLRISQDT   660
IIGSGTIILD KVEFIPSNLY EIKSYEKEKL ETTIQRVNSL FTNKQINLK FETTSYHIDQ   720
TAIFAEAISD ELYAQEKMIL LDEIKYAKRL                                   750

SEQ ID NO: 93             moltype = DNA   length = 2295
FEATURE                   Location/Qualifiers
```

```
source                  1..2295
                        mol_type = other DNA
                        organism = Bacillus thuringiensis
SEQUENCE: 93
atgaatgtta acgaaagcga tttatatgac attaccgatg cttcgacctg ccaatgcccg  60
acagataatt ttttaaaata ccctttggca aatgatcctt attcatccaa tttaaatctt  120
aattcttgtc aaaacagtaa cgttactaat tggataaata tattaggaag cgcagcgaga  180
gaagcagtat ctattagtag aacagtaata tcacttctca aagcacctac tatctctgga  240
ttagtttcat tagcatataa tcttataact agaatgcaag gaggtagcag tggaagatct  300
ttatcagagt tatctatatg tgacttatta gctattattg atttacgagt aaatcagagt  360
gttttaaacg acggaattgc agactttaat ggttctttaa gcatatatag aaactatttg  420
caggctttag agagttggaa caatagacca acatcagcta ctgctgaaga gctacgtact  480
cgttttagaa tagctgattc tgaatttgat cggattttaa caagggggtc tttaacgaat  540
ggcggttcgt tagctagaca aaatgctcaa ctattattat taccctcttt tgccaatgca  600
gcctattttc atttaatatt acttagagat gctataaagt atggatctag ttggggattg  660
tttagcacta cacctgttat attttatcga gagaaattag tagaacttat taaattatat  720
actaattatt gtatacattg gtataatcaa ggtcttaacg aacttagaca aggaggtact  780
aatgctaatg cttggttaga atttcataga taccgtaggg aaatgacatt aacggtgctg  840
gatatagttt cattatactc aaatattgat attaccaaat atccaataga aacaaattta  900
gaattgagca gggtcattta tacagatcca attggttttg taaatcgtgg tacttcaagt  960
agattaagct ggtttgattg gcaaaataga gctaattttt cagaattaga aagggcaata  1020
ccagatcccg tactttcgca atttttaaat agtattcgta tatatactgg tatactgtca  1080
ttacctgttt ctccaaatac cgttagagga cgggtatggt atgggaatca aaatcaggtt  1140
agtagtgcta attcacaaga tgttttcaat cagactttcg gccaagtaac aaatgataga  1200
caaaaccttt caggattaaa tatatttagg gttgattcgc aagcagctaa tctaaataat  1260
tctttgtatg gtgtaagtag agctgaattt ttccacgatg ctagccaagg gtctagaagg  1320
tccgtatatc aagggtatat tagaactagc gggctagata accctgtaac gcagactatt  1380
cgaacttttt taccaggaga gaattcggat acaccaactc cagaagatta tactcatgta  1440
ttaagtgctg caataaattt aactggcggc cttcgacaac cagtaactaa tcgtcgttct  1500
tctgtggtga tgtatggatg gacacatagg agcctaagtc gtgaaaatac aatattttca  1560
gatagaatca atcaatttcc ggcagttaaa gctgtgcaag gcggaggacg aacatttcca  1620
gttgtaagtg gtccaggttt tacgggagga gatttagctc aaatgcctag cacaggtgaa  1680
ggtttatggt tcaatggtag agtcgaacca gatgcgttaa ataaggcatt tcgtgtaaga  1740
gttcgttatg cggctaatcg tgaggataga ctagatttca atgtacatca aggaaatagt  1800
acaacactat ccattcaacg tactatgaca agtgaaatac cctcacgttt tgaagatttt  1860
tcctatgcta catttcctgg tatattcaca tttggaaatg ttaattctag ttggttttta  1920
cgtaggcaaa tgggtggtcc tgaaaataac agagtttata ttgataaaat tgaatttatc  1980
ccaatagatg aaacacgtga agcagaacaa gacctagaga aagcaaagaa agcagtgaat  2040
gccttgttta caaatagaaa agatgcctta caggcaggtg tgaccgacta tcaaatcaat  2100
caggctgcaa atttaataga atgtatatct aatgagttat atccaaatga aaaacggatg  2160
ttattagatg ctgtaaaaga agcaaaacgt ctgagtgggg cacgtaactt acttcaagat  2220
actgattttc agatggcgta tggggacgga gaaaacggat ggactacaag tacggggatt  2280
gaaatagtag aagga                                                  2295

SEQ ID NO: 94           moltype = AA  length = 765
FEATURE                 Location/Qualifiers
source                  1..765
                        mol_type = protein
                        organism = Bacillus thuringiensis
SEQUENCE: 94
MNVNESDLYD ITDASTCQCP TDNFLKYPLA NDPYSSNLNL NSCQNSNVTN WINILGSAAR  60
EAVSISRTVI SLLKAPTISG LVSLAYNLIT RMQGGSSGRS LSELSICDLL AIIDLRVNQS  120
VLNDGIADFN GSLSIYRNYL QALESWNNRP TSATAEELRT RFRIADSEFD RILTRGSLTN  180
GGSLARQNAQ LLLLPSFANA AYFHLILLRD AIKYGSSWGL FSTTPVIFYR EKLVELIKLY  240
TNYCIHWYNQ GLNELRQGGT NANAWLEFHR YRREMTLTVL DIVSLYSNID ITKYPIETNL  300
ELSRVIYTDP IGFVNRGTSS RLSWFDWQNR ANFSELERAI PDPVLSQFLN SIRIYTGILS  360
LPVSPNTVRG RVWYGNQNQV SSANSQDVFN QTFGQVTNDR QNLSGLNIFR VDSQAANLNN  420
SLYGVSRAEF FHDASQGSRR SVYQGYIRTS GLDNPVTQTI RTFLPGENSD TPTPEDYTHV  480
LSAAINLTGG LRQPVTNRRS SVVMYGWTHR SLSRENTIFS DRINQFPAVK AVQGGGRTFP  540
VVSGPGFTGG DLAQMPSTGE GLWFNGRVEP DALNKAFRVR VRYAANREDR LDFNVHQGNS  600
TTLSIQRTMT SEIPSRFEDF SYATFPGIFT FGNVNSSWFL RRQMGGPENN RVYIDKIEFI  660
PIDETREAEQ DLEKAKKAVN ALFTNRKDAL QAGVTDYQIN QAANLIECIS NELYPNEKRM  720
LLDAVKEAKR LSGARNLLQD TDFQMAYGDG ENGWTTSTGI EIVEG                 765

SEQ ID NO: 95           moltype = DNA  length = 2313
FEATURE                 Location/Qualifiers
source                  1..2313
                        mol_type = other DNA
                        organism = Bacillus thuringiensis
SEQUENCE: 95
atgaaccgaa ataatcaaaa tgattatgaa gttattgacg cttccaattg tggttgtgcg  60
tcaggtgatg ttgtgaaata tcctttgaca aatgatccga atgccggatt acaaaatatc  120
aattataaag agtacttaca aatgtcagat gagaactaca ctgattccta tataaatcct  180
agtttgtcta ttagtgggaa atctgtaata caagttggaa ttaacattgt agggaggttg  240
ttgagctttt ttggattccc atttgctaat caagtggtcg ctgtctatag ctacctttta  300
aacaccttat ggccaaataa tgatactgaa gtatgggaat cttttatggc acaagtagaa  360
gaacttgttg atcaaaaaat atcagaagcg gtagtaggga ccgcattgga tcatttatct  420
ggattaaact ataattatga attatatgta gaggctttgg aagagtggct ggaaagacca  480
aatgccgcaa gagccaacct agtttttaat agatttacta cactagatag tctatttacg  540
```

-continued

```
caatttatgc caagttttgg ctctggtcct gggagtaata ggtatgcaga ttcattactt   600
tcagtatatg cacaagcagc aaaccttcat ttgttattct taaaagatgc agacatttat   660
ggagctagat gggggctgaa tcaaactcaa atagatcaat accataatcg tcaacaaacc   720
cttactcgga attatacaaa tcattgtgtt actacgttta atgatggatt agagaaaata   780
agaaacacaa gcgctgagag ttggtttaaa tacaatcaat atcgtagaga gatgacatta   840
atggcaatgg atttagtggc attatttccg tattataatg tacgagaata ctcaatggca   900
gtaaatcctc aacttacacg agaggtgtat acagatccaa ttgcatttga tccatcagaa   960
caaccgaata ctcaattgtg tcgaaaatgg tatactgccc gctttgtaca gaataacgtt  1020
aattttttctc agttagaaaa tgcattcatt cgttcaccac atctcttcga aagattacat  1080
tctctggaaa ttaattttat aaatggagct aattggtggt ggcataaggt aaggaaccaa  1140
cttttaaata attcattaat actcgaaaga gattacggta catctactgt taattctcct  1200
acgactcaac ttaccgtgaa tacttcaaat gctgatatat accaagtacg ttctcgtgca  1260
gaaaatccga ctgcagctgc aggtacttac tattcagtta gaggtgttga gttttattta  1320
agctcaggcg ttaagaggga gttttctgga actacagtcg ctcctttggc ttgccaagaa  1380
ttgcgaaatt caattgatga gttaccaagt ttagaaccaa atgagcctat catcagaaat  1440
tatagtcata gattatctca tattacttgg taccaattta gtggccgcca aagtggaaat  1500
ccgactacta ataatgggga tatacctact tatgtctgga cacatcgcga tgtggacttt  1560
aataatacaa ttactcccaa tagaattact caaatacct ggataaaggc atctgaaata  1620
gctgcgaata ctactgtcgt aaaaggccca ggatttacag gagggatat acttcgaagc  1680
acgatccctg gtacagttgg aacgattagg gctaatgtta tggccccatt aacacaacaa  1740
tatcgtataa gattacgtta tgcgtcgaca caaaattttg ttgttaattt atttgttaac  1800
aattcagcta gtggttttac tctcccaagt acaatggtc aaaatgagtc tttaactac  1860
gaatcgttta ataccgaaga ggtgacaaga actattgat tttcacagtc agacactaca  1920
ctgagattgg gtatattttc gtttgaccct ggtcaagaag tgtatgtaga taaacttgaa  1980
atcgttccaa ttaatccagc tcgtgaggcg aagaggatt tagaagcagc gaaaaaagcg  2040
gtggcgagct tgtttacacg tactagagac ggattacaag taaatgctag agattaccaa  2100
gtcgatcaag cggcaaattt agtgtcgtgc ttatcagatg aacaatatgg gcatgataaa  2160
aagatgttat tggaagccgt acgcgcagca aaacgcctca gccgcgaacg caacttgctt  2220
caagatccag attttaatga aataaatagt acagaagaga atggctggaa ggcaagtagc  2280
ggcgttacta ttagcgaggg cggtccattc ttt                                2313

SEQ ID NO: 96          moltype = AA  length = 771
FEATURE                Location/Qualifiers
source                 1..771
                       mol_type = protein
                       organism = Bacillus thuringiensis
SEQUENCE: 96
MNRNNQNDYE VIDASNCGCA SGDVVKYPLT NDPNAGLQNI NYKEYLQMSD ENYTDSYINP    60
SLSISGKSVI QVGINIVGRL LSFFGFPFAN QVVAVYSYLL NTLWPNNDTE VWESFMAQVE   120
ELVDQKISEA VVGTALDHLS GLNYNYELYV EALEEWLERP NAARANLVFN RFTTLDSLFT   180
QFMPSFGSGP GSNRYADSLL SVYAQAANLH LLFLKDADIY GARWGLNQTQ IDQYHNRQQT   240
LTRNYTNHCV TTFNDGLEKI RNTSAESWFK YNQYRREMTL MAMDLVALFP YYNVREYSMA   300
VNPQLTREVY TDPIAFDPSE QPNTQLCRKW YTARFVQNNV NFSQLENAFI RSPHLFERLH   360
SLEINFINGA NWWWHKVRNQ LLNNSLILER DYGTSTVNSP TTQLTVNTSN ADIYQVRSRA   420
ENPTAAAGTY YSVRGVEFYL SSGVKREFSG TTVAPLACQE LRNSIDELPS LEPNEPIIRN   480
YSHRLSHITW YQFSGRQSGN PTTNNGDIPT YVWTHRDVDF NNTITPNRIT QIPWIKASEI   540
AANTTVVKGP GFTGGDILRS TIPGTVGTIR ANVMAPLTQQ YRIRLRYAST TNFVVNLFVN   600
NSASGFTLPS TMVQNESLTY ESFNTEEVTR TIRFSQSDTT LRLGIFSFDP GQEVYVDKLE   660
IVPINPAREA EEDLEAAKKA VASLFTRTRD GLQVNVTDYQ VDQAANLVSC LSDEQYGHDK   720
KMLLEAVRAA KRLSRERNLL QDPDFNEINS TEENGWKASS GVTISEGGPF F            771

SEQ ID NO: 97          moltype = DNA  length = 1155
FEATURE                Location/Qualifiers
source                 1..1155
                       mol_type = other DNA
                       organism = Bacillus thuringiensis
SEQUENCE: 97
atgacaattg tagatattga acaaggcgct attgattata cgagatggca tatagtaaat    60
tatggcttag catcgcctgg cacctcaccc aatatgcgtt ttttcccata cgaattgaga   120
gatgttacag ctacacctac cggtactctt tttaacgtat ttccaacacc aaaaataact   180
tccatccagg tactgaaaaa taatacgaac tcaactcaat ctcaatctgt caaattttcc   240
gaaaaagtaa tcgaatcgac tactactagt actactgaag gttacaaaat tggggctggg   300
ataaaatcaa caactaaatt caaaattaaa gtcggctttt tagtatcagg tgagttggag   360
cagtcagttg aagtttccct tacatcagaa tataatcata gttcaactca atcagtaacg   420
aggtcggaag aaagagattg ggaagtcaca caacccgtat ctgttcctcc ccgctcacgc   480
gtaattgcct ctcttgtcat aatgggagca gatgtaccaa tccctacgtt attatctgct   540
aaccttaggg gtactggtac ctcaggtgga gcaaatgcat ttttttctgc tactttccca   600
ggaactcaag acagactcg aagttttggg ggaccagctg cgttccttgc tgatagaaat   660
tggccttcta gacctgcagc tttcagatct tcaggttcag aatctagcct taatttagaa   720
ggttactcaa ctaccttagc aggcacagct ttatatagta ctgtcagatt tgaggaaact   780
ccattatcag ggtatagtgg accaagaaga gtttggtatt caaaccaaat acaattaaga   840
gatggcagtt ttataactct accatatctt aatccattaa caggaaagat agataattct   900
cagtattttc aagaatataa taattctcaa gaagactctt ataatattca aaaaacaagt   960
catgtctgta aggagccact tcattacatt caaaatttcta gtgataatca aattgattct  1020
tacaatatcc caaattatta gtaaccaaa gctgattctt ataatacctc aaattattat  1080
agtaaccaag ctaattctta taatacctca gattattata gtaataacca agctgattct  1140
tataatacct cagat                                                    1155

SEQ ID NO: 98          moltype = AA  length = 385
```

```
FEATURE                 Location/Qualifiers
source                  1..385
                        mol_type = protein
                        organism = Bacillus thuringiensis
SEQUENCE: 98
MTIVDIEQGA IDYTRWHIVN YGLASPGTSP NMRFFPYELR DVTATPTGTL FNVFPTPKIT     60
SIQVLENNTN STQSQSVKFS EKVIESTTTS TTEGYKIGAG IKSTTKFKIK VGFLVSGELE    120
QSVEVSLTSE YNHSSTQSVT RSEERLWEVT QPVSVPPRSR VIASLVIMGA DVPIPTLLSA    180
NLRGTGTSGG ANAFFSATFP GTSGQTRSFG GPAAFLADRN WPSRPAAFRS SGSESSLNLE    240
GYSTTLAGTA LYSTVRFEET PLSGYSGPRR VWYSNQIQLR DGSFITLPYL NPLTGKIDNS    300
QYFQEYNNSQ EDSYNIQKTS HVTQEPLHYI QNSSDNQVDS YNIPNYYSNQ ADSYNTSNYY    360
SNQANSYNTS DYYSNNQADS YNTSD                                         385

SEQ ID NO: 99           moltype = DNA   length = 2883
FEATURE                 Location/Qualifiers
source                  1..2883
                        mol_type = other DNA
                        organism = Bacillus thuringiensis
SEQUENCE: 99
atgaaactca aaaatttatt taaatgtctt acaattacag cgatattatc tcaaattgct     60
gtatcacccg taacatcttc tgctgaaaga agtaacgaaa aaaagtagc taataaaaca    120
aatatggaag agaaaaataa tatacaagga ctattgggat attatttaa agatgctcaa    180
tttcgggatt tagcttctat taaggttggt gaacaaagta ataaactaat agatgagaca    240
aaagtaatga agaataatca aattattcat gccgtacgtt ggatgggaag agtgaagcca    300
acccagaccg gagaatatat actttctaca tcatctgata aaacattat gttacaaatt    360
aatggggaaa ctattataaa ccaaggtaag atggaaaaac ctcttaaatt agagaaaggt    420
caggtatatg aattaaagat tgaatatcga aatgcagcga atactttgtc tgatttacaa    480
ttattttggt caatagatgg aaaagaaaaa gagcaaattt cacaaaaaaa tatttttatct   540
cccgatttt ccgaaaaaga aaaattatca agtgataaaa aaggattgtc gttattacct    600
aattttactc tatttgataa taaacccttt gaagcagaat taaaagacgc agatcaagat    660
ggaatccctg acgaatggga gatacaaggt tatacattta aagatcaaca aattgtaaaa    720
tgggatgatg catatcttgt acaagggtac aaaaaatatg tatcgaatcc aataaggct    780
cgaactgtcg ccgatccata tacagatttt gaaaaagtaa cagggtatat gcctgcagca    840
acaaaagatg aagctagaga tccttttagtt gctgcttatc cagctgtagg agtagggatg    900
gaaaaattac tatttctcaa gaatgaaaat gtaacagaag ggacttctgg gaccaagtcc    960
aaaagtgtaa cagatacaaa tacgaacaca aatactgtag agattggtgg aaatatagga  1020
tggagtgata agggttttc atttcaaatt tcaccaaagt actcacatac ttggaccaat   1080
agtacagcaa tccaaaattc agaaagtgaa tcttggtcaa atcaaatcgg aattaacacc  1140
gcagaatcg cctatttgaa tgcaaatgta cgttattata atgcaggaac agcacctatt  1200
tatgacttgc gtcctacttc gaactttgta tttcaaaact caggtacttc cattgcgacg  1260
ataacagctg gaccaaatca aatcggaaat agcttgggac ctagtgatac atatccaaca  1320
aggaatcaag cacctatctc tttagataag gcaaacgaat caggaacagc taaaatagct  1380
gtaaatgcag atcaattaga tgctcttcaa gatggcaggg aaacattaaa cttagaaacg  1440
acgcaaaaca aaggacaata tggtgttttt gatgctacag gtaatctagt tacgacgca   1500
tctaaacaat gggaccctat tcgaacaaat attgatgcag tctcaggttc cttagcgctg  1560
cattatggta ctagtaaaga aagtttagaa agaagggttg ccgcaaaaaa tgaaaatgac  1620
cctgaaacaa aaacacctga gattacgata ggagaagcga taaaaaaagc atttaatgcc  1680
aaagaaaaag atgggcgatt atactacacg gatcaaacag gaaaagatgt atgtctagat  1740
gagtcagcag taaatctcat tggggatgaa aaaaacacaaa aagaattga aaagcagcta  1800
gatcaaatgc aagataaaaa agtatataat gcgaagtgga acgagggtat gaatattact  1860
cttcacatgc caactgtttta ttatgattt gagaaagatg gtgatactga atggaacaat  1920
atttctcaaa ctaatatagg atatacaggt aaaaaaagtg gagaaattga tcagaatgga  1980
aatggatatg caaaaaaaga tcttgaattg aaaccatata caagttatac agctcgtgca  2040
tatgttagaa cagcatccca accaggtaaa aacaatgtaa tattctacgt agatagcaac  2100
acgaatggga atgaaaagg tgcaaaacaa agcgtaacaa ttgagggga taaatgggag  2160
ttgatagaat ttctttcaa cacaacaggg aatccagagt atttcaagaa attaggtctt  2220
aaaaataatg gaaatacaaa actgtatatt gatgatgtat ccgtaacaga atggaaacag  2280
ggcgaagaca ttcaaaaact tcatgtgttt gaaaaatgga atccaaatct taatggatat  2340
ggtggagtat cttcaattac attttctaaa gttccaaata caaagtttcg atatcaatgg  2400
ggagctatta actctctagg gaatgaagata tggtctgata ttatgcctgc cagagataca  2460
ggtgagaatg gtaaaggac tgtggatata ggattgtacc atgctggggc taagctatat  2520
gctgtagatc aatacaatga taatttgaaa gttgaaattg cacagtattt tccaatagga  2580
tatgaacatc atgtggataa aaattggaac aaagttaaac acaacaataa agaatatata  2640
aatggtataa cttttaaaaa ggtaacagat aaaaaagtta gataaggt agtagtaat   2700
tatacggaca ataaaggtat aaaacctgca tatgaaatag actctcaggg gaatagatat  2760
gtaaatttgt tagaatataa taatggaaaa ggaattccag cagatgtttc tctatagca   2820
gtttatgttg tagatgaaaa ggatgataat attttttgata agttgcagaa atatcatcct  2880
tgg                                                                 2883

SEQ ID NO: 100          moltype = AA    length = 961
FEATURE                 Location/Qualifiers
source                  1..961
                        mol_type = protein
                        organism = Bacillus thuringiensis
SEQUENCE: 100
MKLKNLFKCL TITAILSQIA VSPVTSSAER SNEKKVANKT NMEEKNNIQG LLGYYFKDAQ     60
FRDLASIKVG EQSNKLIDET KVMKNNQIIH AVRWMGRVKP TQTGEYILST SSDKNIMLQI   120
NGETIINQGK MEKPLKLEKG QVYELKIEYR NAANTLSDLQ LFWSIDGKEK EQISQKNILS   180
PDFSEKEKLS SDKKGLSLLP NFTLFDNKPF EAELKDADQD GIPDEWEIQG YTFKDQQIVK   240
```

-continued

```
WDDAYLVQGY KKYVSNPNKA RTVADPYTDF EKVTGYMPAA TKDEARDPLV AAYPAVGVGM  300
EKLLFSKNEN VTEGTSGTKS KSVTDTNTNT NTVEIGGNIG WSDKGFSFQI SPKYSHTWTN  360
STAIQNSESE SWSNQIGINT AESAYLNANV RYYNAGTAPI YDLRPTSNFV FQNSGTSIAT  420
ITAGPNQIGN SLGPSDTYPT RNQAPISLDK ANESGTAKIA VNADQLDALQ DGRETLNLET  480
TQNKGQYGVL DATGNLVTDA SKQWDPIRTN IDAVSGSLAL HYGTSKESLE RRVAAKNEND  540
PEDKTPEITI GEAIKKAFNA KEKDGRLYYT DQTGKDVCLD ESAVNLIGDE KTQKEIEKQL  600
DQMQDKKVYN AKWKRGMNIT LHMPTVYYDF EKDGDTEWNN ISQTNIGYTG KKSGEIDQNG  660
NGYAKKDLEL KPYTSYTARA YVRTASQPGK NNVIFYVDSN TNGNGKGAKQ SVTIEGDKWE  720
LIEFSFNTTG NPEYFKKLGL KNNGNTKLYI DDVSVTEWKQ GEDIQKLHVF EKWNPNLNGY  780
GGVSSITFSK VPNTKVRYQW GAINSLGNEI WSDIMPARDT GENGKRTVDI GLYHAGAKLY  840
AVDQYNDNLK VEIAQYFPIG YEHHVDKNWN KVKHNNKEYI NGITFKKVTD KKVRYKVVVN  900
YTDNKGIKPA YEIDSQGNRY VNLLEYNNGK GIPADVSSIA VYVVDEKDDN IFDKVAEYHP  960
W                                                                 961

SEQ ID NO: 101          moltype = DNA  length = 1998
FEATURE                 Location/Qualifiers
source                  1..1998
                        mol_type = other DNA
                        organism = Bacillus thuringiensis
SEQUENCE: 101
atgaattcat atcaaaatac aaatgaatat gaaatattgg aatcttcatc gaataacaca  60
aatatgccaa acagatatcc ttttgcaaat gatcgggata tgtctcctat gtcttggaat  120
gattgtcagg gaacctcatg gcaagatgtg tgggaatcaa gcacgagtat cgcaggtatt  180
gggatagatc ttataaattt tgtggcagaa cctagtttag gtggagttaa tttattattt  240
tcgataatag gaaaactaat tccacctaat cgtcaatcta tttcagcact ttctatatgt  300
gatttattat ctataattcg taaagaggta gccgagagtg tgttaaatgc cgcgattgca  360
gattttaacg gtaaattgaa aaattataga gagtattatc tttcttatct tgaggcttgg  420
cttaaagacg gtaaaccact caaaaagacg aataattccg acatcggaaa attagttgaa  480
tatttcgaac tttcagaaag ggaattcaat gaaattctag gagggtcatt agcaagaagt  540
aatgctcaaa tattgttatt acctactttt gcacaagctg caaatgtgca gttattacta  600
ttaagggatg cagttcaata taaagaacaa tggttcccat ttttgagtgc agagaatgta  660
aaatcggaat taaaatcacc taacagtggt tgtgatttta ctggcgatta ctatgagcga  720
ttaaaatgta aaacagcaga gtataccaat tattgtgtat attggtatca ggcaggttta  780
gatcagataa aacaggcggg tacaggtgct gacacctggt cgaaatttaa taaatttcgt  840
agagaaatga cgttagcggt attggatatt atcgctatat ttccaactta tgattttgag  900
aaatatccat tagcaacaga tgtagagtta actagagaaa tttatacaga tgcagtggga  960
tattcatcgg gaacttatag ctggttaaac tattggaccg gtgcttttaa tgcgttagaa  1020
gctaatggaa cacggggacc tggtttagtt acttggctta gcagtatagg tatatataat  1080
gagtatgttt cgagatattt tagcggctgg gtaggaactc gtcattatga agactacaca  1140
aagggtaacg gtacttttca gcgtatgtct ggaactacga gtaatgatct acgtaatgtg  1200
actttttccc ctttcgatat atttaaaatt agttcattag ccatcatgaa cctagcagga  1260
gagactaacc ctagaccaga gtatcgtgtt tcacgtacag aatttagtag tacgtcatta  1320
ccatctaaac acctgtatga tgcaaataat aatgggctaa gccgaatgac aattgaatct  1380
acgttaccag gtatttggaa tccgaaacct agttatacag attactctca cagattatca  1440
aatgcggcat gtgttgtata tggaaattcc agagttaacg tatatgggtg gacacataca  1500
agtatgtcaa aacataatcc aatttatcca gataaaattt cacaaatacc ggctgtgaaa  1560
gcatttgctt tagaatcagg cgcttatgtt agcgctggac ctggtcatac aggaggaaat  1620
gtagtatggt taccatattt agggcgttta aaaatacgtt taacttctgc gcccacgaat  1680
aaaaattacc gtgttagagt tcgctatgca ggtttgtact caggtcgttt aatggtacaa  1740
agatggtcgc tgagtgggtc tgcaactggt gattttcctt attcatctac gggttctaat  1800
aatacatttg gatatgtgga gaccttagtt actacattta atcaatcagg tgttgaaata  1860
attatacaaa atcaaacttc tccacaactt atcattgaca aaattgaatt tatcccagtt  1920
gatctaacaa atttagaata tgagggagaa caaaacctag aaaaaacaaa aaacgcggtg  1980
aacgatttat ttatcaat                                                1998

SEQ ID NO: 102          moltype = AA  length = 666
FEATURE                 Location/Qualifiers
source                  1..666
                        mol_type = protein
                        organism = Bacillus thuringiensis
SEQUENCE: 102
MNSYQNTNEY EILESSSNNT NMPNRYPFAN DRDMSPMSWN DCQGTSWQDV WESSTSIAGI  60
GIDLINFVAE PSLGGVNLLF SIIGKLIPPN RQSISALSIC DLLSIIRKEV AESVLNAAIA  120
DFNGKLKNYR EYYLSYLEAW LKDGKPLKKT NNSDIGKLVE YFELSEREFN EILGGSLARS  180
NAQILLLPTF AQAANVQLLL LRDAVQYKEQ WFPFLSAENV KSELKSPNSG CDFTGDYYER  240
LKCKTAEYTN YCVYWYQAGL DQIKQAGTGA DTWSKFNKFR REMTLAVLDI IAIFPTYDFE  300
KYPLATDVEL TREIYTDAVG YSSGTYSWLN YWTGAFNALE ANGTRGPGLV TWLSSIGIYN  360
EYVSRYFSGW VGTRHYEDYT KGNGTFQRMS GTTSNDLRNV TFSPFDIFKI SSLAIMNLAG  420
ETNPRPEYRV SRTEFSSTSL PSKHLYDANN NGLSRMTIES TLPGIWNPKP SYTDYSHRLS  480
NAACVVYGNS RVNVYGWTHT SMSKHNPIYP DKISQIPAVK AFALESGAYV SAGPGHTGGN  540
VVWLPYLGRL KIRLTSAPTN KNYRVRVRYA GLYSGRLMVQ RWSLSGSATG DFPYSSTGSN  600
NTFGYVETLV TTFNQSGVEI IIQNQTSPQL IIDKIEFIPV DLTNLEYEGE QNLEKTKNAV  660
NDLFIN                                                            666

SEQ ID NO: 103          moltype = DNA  length = 2157
FEATURE                 Location/Qualifiers
source                  1..2157
                        mol_type = other DNA
                        organism = Bacillus thuringiensis
```

```
SEQUENCE: 103
atgaaatcga agaatcaaaa tatgtatcaa agtttttgta gcaatgcgac agttgataaa    60
agttttacag atccactaga aaataacaca aatatggaat tacaaaactc taatcatgaa   120
gattgtttga aaatgtctga gtatgaaagt gtagagccgt tgttagtgt atcaacaatt    180
caaatgggaa ttggtattgc tggtaaaatc cttggtaacc taggcgttcc ctttgctggg   240
caagtagcta gcctctatag ttttatccta ggtgagcttt ggcccaaagg gaaaagccaa   300
tgggaaattt ttatggaaca tgtagaagag cttattaatc aaaaaatatc gacttacgca   360
agaaacaaag cacttgcaga tttaaacgga ttaggagatg cttttagctgt ctaccatgaa   420
tcgcttgaaa gttgggttga aaatcgtaat aacacacgag cgaggagtgt tgtcaaaaac   480
caatatatcg cattagaatt gatgtttgtt cagaaactgc cttcttttgc agtatctggt   540
gaggaagtac cattattacc gatatatacc caagctgcaa atttacattt gttactatta   600
agagatgcat ctgttttcgg aaaagaatgg gggctagcag attcagaaat ttcaacattt   660
tataaccgcc aagtcgaacg agcaagcgat tattccgacc attgtgtaaa atggtataat   720
acgggtataa ataacttgag gggtacaaat gctgaaagct gggttcgtta taatcaattt   780
cataaagata tgacattaat ggtattagat ttagtcgcgc tattcccaag ctatgataca   840
cttgtatatc ctattaaaac tactgctcaa cttacaagag aagtatatac agacgcaatt   900
gggacagtac atccgaatgc aagttttgca agtacgactt ggtataataa taatgcacct   960
tcgtttttcg ccatagagcc cgctgtttatc cgaagcccac atctacttga cttttctagaa  1020
aaagttacaa tttacagctt attaagtcgg tggagtaaca ctcagtatat gaatatgtgg  1080
ggagcacata gacttgaatt acgaacaata ggaggggcat taaatacctc aacacaaggt  1140
tctaccaata cttctattaa tcctgtaaca ttacagttta cgtctcgaga cgtatatagg  1200
actgaatcat gggcaggact gaatctattt ttaactcaac cagttaatgg agtacctaga  1260
gttgattttc attggagatt tcccacactt ccgattgcat ctgataattc ttattatcca  1320
gggcatgttg gagttgggac gcaattacaa gattcagaaa ctgaattacc accagaaaca  1380
acagaacgac caaattatga atcttacagt catagattat tcatataggactcatttca    1440
gcatcacatg tgaaagcatt ggtatattct tggacgcatc gtagtgcaaa tcgtacaaat  1500
actattgagc caaatagcat tacacaaata ccattagtaa aagcattcaa tcttccttca  1560
ggtgccactg ttgttagagg accaggattt acaggtgggg atatctttcg aagaacgaat  1620
acgggtacat tggggatat cgagtaaat attaatccac catttgcaca aaggtttcgc    1680
gtaaggattc gctatgcttc tactacagat ttacaattcc atacgtcaat taacggaaaa  1740
gctattaatc aaggtaattt ttcagcaact atgaatagag gagaggcctt agactataga  1800
acctttagga ctgtaggctt tactactcca tttagctttt cagatgcaca aagtacattc  1860
acaataggtc cttggagctt ctcttcaggt aacgaagttt atatagatag aattgaattt  1920
gttccgatag aagtaacata tgaggtagag tatgattttg aaaaagcgca agaggaggtt  1980
actgcattgt ttacatctac gaatccaaga gggttaaaaa caaatgtaac ggattatcat  2040
attgaccagg tatcaaattt agtagagtct ctatcagatg aattctacct cgatgaaaag  2100
agagaattat tcgagatagt taaatatgcg aagcaactcc atattgagcg taacatg     2157

SEQ ID NO: 104       moltype = AA   length = 719
FEATURE              Location/Qualifiers
source               1..719
                     mol_type = protein
                     organism = Bacillus thuringiensis
SEQUENCE: 104
MKSKNQNMYQ SFCSNATVDK SFTDPLENNT NMELQNSNHE DCLKMSEYES VEPFVSVSTI    60
QMGIGIAGKI LGNLGVPFAG QVASLYSFIL GELWPKGKSQ WEIFMEHVEE LINQKISTYA   120
RNKALADLNG LGDALAVYHE SLESWVENRN NTRARSVNKN QYIALELMFV QKLPSFAVSG   180
EEVPLLPIYT QAANLHLLLL RDASVFGKEW GLADSEISTF YNRQVERASD YSDHCVKWYN   240
TGINNLRGTN AESWVRYNQF HKDMTLMVLD LVALFPSYDT LVYPIKTTAQ LTREVYTDAI   300
GTVHPNASFA STTWYNNNAP SFSAIEAAVI RSPHLLDFLE KVTIYSLLSR WSNTQYMNMW   360
GAHRLELRTI GGALNTSTQG STNTSINPVT LQFTSRDVYR TESWAGLNLF LTQPVNGVPR   420
VDFHWRFPTL PIASDNSYYP GHVGVGTQLQ DSETELPPET TERPNYESYS HRLSHIGLIS   480
ASHVKALVYS WTHRSADRTN TIEPNSITQI PLVKAFNLPS GATVVRGPGF TGGDIFRRTN   540
TGTFGDIRVN INPPFAQRFR VRIRYASTTD LQFHTSINGK AINQGNFSAT MNRGEALDYR   600
TFRTVGFTTP FSFSDAQSTF TIGAWSFSSG NEVYIDRIEF VPIEVTYEVE YDFEKAQEEV   660
TALFTSTNPR GLKTNVTDYH IDQVSNLVES LSDEFYLDEK RELFEIVKYA KQLHIERNM   719

SEQ ID NO: 105       moltype = DNA   length = 2205
FEATURE              Location/Qualifiers
source               1..2205
                     mol_type = other DNA
                     organism = Bacillus thuringiensis
SEQUENCE: 105
atgaatccta ataataatga atacgaaatt atagattcaa acacttcacc ttatccttcg    60
aacagaagca ttaatcattt tagatatcct tacacaaata atccaaatca accattacaa   120
aacacgaatt acaagattg gcttgatttg tgtcaacaaa atcaacaata tagtggaaat   180
cttgaaacat ttgctagtgc tgatacaatt gctgcagtta gtgcaggtac tatttgtatcc   240
ggtactctgt tagccggtgt aggtgggctc actgctatat ccggacccat aggattaatc   300
ggtgctataa taatatcttt tgggtaccta ctgcctatct tttggccaca gggagaacaa   360
gacaaaacag tctggacaca attcattaga atgggagaaa ttcttgttga tacaacgttg   420
tcagaaactg taaagaaact aaagttagga acttagaag gaattagaca aatattaaaa   480
agctatgaag atggattaaa cgattggata agattaaaaa acaacaagc tcctggatta   540
ccaccatcat cacaattaca caagctgcc tctactgtta acaacgatt tgagaatgtt    600
cataattta tatacgaga aatacctggt tccaacttga aaacttataa aacgctatta   660
ttacctattt atacgcaagt tgctaatatg catttaaatt tgttacaaca aggtgttgaa   720
tttgctgatc aatggaatgc agatatacat ccttcacaaa ttgaacctaa tgctggaaca   780
tcaaatgact attataaact tttaaaagaa aatataccta aatatagtaa ctattgtgca   840
aatacctata aacaggact aaataatctt agaaacgaac ctgatataag atggagtata   900
tttaatgatt atcgaagata tatgactatt actgtattag ataccatctc tatatttcct  960
```

-continued

```
ttatatgata taaaaaaata tagagataca ataggaggaa tacaaggcat taactatgaa  1020
ctcacaagag aaatttatac aactgaaata aattttgacc gtattacttc ccctaaagtt  1080
caacccgatc tctataccat ggaatataat ttaacacgtt caaggcttag attattttca  1140
tttttagatg agcttatatt ttatacagca aatgaaacat acgggaatcg tttagttggt  1200
attgcgaatc ataatagata tacttatgct acaacaggaa ctgaaattat atatggaaaa  1260
agaacaggtc cacccacaac aaaaatttta agaccatttg aatcttataa agtttcaatt  1320
gtaactgata gacaagtaca acctactgcc ccttttaata acatatactt tataattaat  1380
caaattgaac tttatttaaa taattcacct agtaataaat taacatattc agctggggga  1440
aattatatcta atgataaaaa aacaactgat tttcaatttc ctgtaaaaaa agactgtaaa  1500
caaattactg atccaaattg tttaccaagc tataatagtt atagtcatat tttatcccag  1560
ttttctttat atacttattc ctatctaact ggattagcgg taactacatt atatacaggt  1620
gcattaggat ggacacacag tagtgttaat agaaataatg caatatcaga taaaataatt  1680
acaatgatcc cagcaatcaa aggtaacagt cttgatacaa actccaaggt aattgaagga  1740
cctggtcata caggaggaaa cttggtttat ttacaaagtc aaggacattt agagattaca  1800
tgtagaactc ctaattctac acaatcttat tacattagac ttcgatacgc tacaaatggt  1860
gctgaaata ctcttcctaa tatatctctt acaataccag gagtaacagg aatccaccct  1920
ctacgactca acaacacttt ttctagtaca aattataata atttcaata tgaaaacttt  1980
gagtatttcc aatttccagg tacaataaca ttaccttaa atcgaaacat acaatgtata  2040
tttaatcgtg cagatgtatc aaattcaatt ttaatcattg ataaaattga atttatacca  2100
attacttcct ctatacacca aaatagagaa aaacaaaaat tagaaactat ccaaacaaaa  2160
ataaatacat tttttacaaa tcatgagggt gttgcaaaac taaaa           2205

SEQ ID NO: 106         moltype = AA   length = 735
FEATURE                Location/Qualifiers
source                 1..735
                       mol_type = protein
                       organism = Bacillus thuringiensis
SEQUENCE: 106
MNPNNNEYEI IDSNTSPYPS NRSINHFRYP YTNNPNQPLQ NTNYKDWLDL CQQNQQYSGN   60
LETFASADTI AAVSAGTIVS GTLLAGVGGL TAISGPIGLI GAIIISFGTL LPIFWPQGEQ  120
DKTVWTQFIR MGEILVDTTL SETVKELKLG TLEGIRQILK SYEDGLNDWI RLKKQQAPGL  180
PPSSQLQQAA STVKQRFENV HNDFIREIPG FQLETYKTLL LPIYTQVANM HLNLLQQGVE  240
FADQWNADIH PSQIEPNAGT SNDYYKLLKE NIPKYSNYCA NTYRTGLNNL RNEPDIRWSI  300
FNDYRRYMTI TVLDTISIFS LYDIKKYRDT IGGIQGINYE LTREIYTTEI NPDRITSPKV  360
QPDLYTMEYN LTRSRLRLFS FLDELIFYTA NETYGNRLVG IANHNRYTYA TTGTEIIYGK  420
RTGPPTTKIL RPFESYKVSI VTDRQVQPTA PFNNIYFIIN QIELYLNNSP SNKLTYSAGG  480
NLSNDKKTTD FQFPVKKDCK QITDPNCLPS YNSYSHILSQ FSLYTYSYLT GLAVTTLYTG  540
ALGWTHSSVN RNNAISDKII TMIPAIKGNS LDTNSKVIEG PGHTGGNLVY LQSQGHLEIT  600
CRTPNSTQSY YIRLRYATNG AGNTLPNISL TIPGVTGIPP LRLNNTFSST NYNNLQYENF  660
EYFQFPGTIT LPLNRNIQCI FNRADVSNSI LIIDKIEFIP ITSSIHQNRE KQKLETIQTK  720
INTFFTNHEG VAKLK                                                  735

SEQ ID NO: 107         moltype = DNA   length = 2163
FEATURE                Location/Qualifiers
source                 1..2163
                       mol_type = other DNA
                       organism = Bacillus thuringiensis
SEQUENCE: 107
atgataggaa taaggggaa aaatatgaat tcatatcaga ataagaataa cgatgaaata    60
ctgagttctt cgtcaaacca gtctaacatg ttcaatgctt atccaaaata cccactagct   120
tcgatgcaga atacgaatta taaagagtgg atgaatcaga gtgaaaatat tactccttct   180
tcatttactg caatattcac tgcattaaga attgttaacg cgcaatttc ttttttggga    240
gtatcaagtg aattagaaac atcttttcaa gtaatttcac gttattgggg atttattaat   300
agaggaacag gaaatgattt attaactctt acagaacaac tcattaatca acattagca    360
acacagtata ggaatgcagc aacagggcg gtatatgcta tagctagggc atagaagac    420
tatttgaaat ggtttagaca atggcaagcg aatccaaccg cacaaaatgg tagtcaatta   480
gagactgaat ttggaacggt taatactta tgtattagtg ttttaactta tggcaataca   540
cttgctcgta ggggatttga aacactttta ttaccaaact atgcagtagc agcaaattt    600
catttgttat tattaagaga tgctgctctt tttagagata gctggacaga aacttctaat   660
ttgacaaaag acttaaatct tggaagatta agagattcca taagagaata tagcaatcat   720
tgtaaaaggt ggtatgaaga tggttaaac agactccgga atgcaaggcc gggcgatcct   780
tttggtccaa ggggagatga ttggattaga tttaatgctt atcgtagaga catgacgttg   840
gcggtattag atcttgttac aatatttcca acttatgacc ctagttatt tccaggttca   900
acaagtgttc aattatcaag gatatttat acagatccag tagctttagc cagcccccaa   960
gaatggtttt tcgtgactt ggaacatgct ttaactttcc gtggtacagt ttctttcttg   1020
aatgaaatgg atgtatatta ttggtactat tttagacctc ataatgtgga taggaattat   1080
tgggctggta atcgtaattt tttaagcaac aggacttcgg ttcttactgg ccaatctact   1140
tcggcgcgaa gaagattgga tatgaaaaat agggatattt tcagggtaga tatgtcgagt   1200
catgaaggtg gtgctttaa tgataactat agaggtattc agagggctaa tttcttaggt   1260
gtaaatatac aaacgaatca agcaacaat gtattatttc aagtgaattt taatgctaat   1320
gggtttaac acaataatca ttctagattt ttaccaggag aagaacgtga agtaccaaat   1380
gcaaatgatt atactcatag gttattccaa gtgctgaatg ctgtccatac tacacataat   1440
gtacgtacaa catttttttc acatgcatgg acgcataaaa gtttaacccg tcaaaataca   1500
ttagtgctg ataaaatttt acaaatacca gctgtaaaga cagtgacgaa tagtgctgaa   1560
cgtgctgtaa tatcaaatac tggagaaaat gtaataaaat tggataactt gactacaaat   1620
ttattatatc cattaacatc ggctgattta caatcatcaa atacacgttt tatttgtcgt   1680
attcgttatg ctagtatgag taataataga ttgaatcttc ttttaaatga tgctcaagta   1740
gcattactaa atgcggagcg tacagtgcgg agtgggggag cactgacaa tcttcaatat   1800
gaagattta aatatgctac atttgcaggt aaatttcaaga tgggttctca ttctatatta   1860
```

```
ggtatttta aagagacatc taatacagaa tttgtattag ataaaattga attaatccca 1920
gttggtactt ttgcaaatca actattagaa gaaacaatag attacaacaa agattgccac 1980
cagaattcta gtattatgta tgatcaaaac ttcaacactt atgaccagaa catgagaat  2040
acgtatgatc aaagctataa cacttatgac cagaacatgg agaatacgta tgatcaaagc 2100
tataactata atcataatcc tagctgtaca tgtaaccaag gttataacaa taccgtcct  2160
aaa                                                               2163

SEQ ID NO: 108         moltype = AA  length = 721
FEATURE                Location/Qualifiers
source                 1..721
                       mol_type = protein
                       organism = Bacillus thuringiensis
SEQUENCE: 108
MIGIRGKNMN SYQKNNDEI LSSSSNQSNM FNAYPKYPLA SMQNTNYKEW MNQSENITPS   60
SFTAIFTALR IVNGAISFLG VSSELETSFQ VISRLLGFIN RGTGNDLLTL TEQLINQTLA  120
TQYRNAATGA VYAIARAYED YLKWFRQWQA NPTAQNGSQL ETEFGTVNTL CISVLTYGNT  180
LARRGFETLL LPNYAVAANF HLLLLRDAAL FRDSWTETSN LTKDLNLGRL RDSIREYSNH  240
CKRWYEDGLN RLRNARPGDP FGPRGDDWIR FNAYRRDMTL AVLDLVTIFP TYDPSLFPGS  300
TSVQLSRIVY TDPVALAQPQ EWFFRDLEHA LTFRGTVSFL NEMDVYYWYY FRPHNVDRNY  360
WAGNRNFLSN RTSVLTGQST SARRRLDMKN RDIFRVDMSS HEGGAFNDNY RGIHRANFLG  420
VNIQTNQATN VLFQVNFNAN GFQHNNHSRF LPGEEREVPN ANDYTHRLFQ VLNAVHTTHN  480
VRTTFFSHAW THKSLTRQNT FSADKILQIP AVKTVSNSAE RAVISNTGEN VIKLDNLTTN  540
LLYPLTSADL QSSNTRFIVR IRYASMSNNR LNLLLNDAQV ALLNAERTVR SGGALDNLQY  600
EDFKYATFAG NFKMGSHSIL GIFKETSNTE FVLDKIELIP VGTFANQLLE ETIDYNKDCH  660
QNSSIMYDQN FNTYDQNMEN TYDQSYNTYD QNMENTYDQS YNYNHNPSCT CNQGYNNNRP  720
K                                                                 721

SEQ ID NO: 109         moltype = DNA  length = 1848
FEATURE                Location/Qualifiers
source                 1..1848
                       mol_type = other DNA
                       organism = Bacillus thuringiensis
SEQUENCE: 109
atgaaaaaaa gtatatttac gctatcaacc gcagcttttt tttccaccgg ggcggctaca   60
cttgttcatg cagctgaaca gcatgttgtt aaaccaggtg aaacattaga cagtattgct  120
aaacagtatg aaatggacgt cagcacattg aaggcattaa acaatttaga aaatgacgct  180
ctccaagtaa atcagacctt aacggtagct agccattctt ccggggcttc cgaaagcacg  240
cacattgttc aagctggcga gacgattcac gccattgccc agctgtacca gatgccagaa  300
acagaattaa agcaattgaa tcagctggaa aacaacacaa tttatgcagg acagaaacta  360
aaggtaagcg gaaataaggc tgtccatcag tctgctgccg ttcagcgtcc tctcccagaa  420
gcagaattac atacacaagc agccaagcca gctgtagaag cagaagttaa agagctgcct  480
gtgacaggaa catacatagt acagcgaggg gatacactgg gagctattgc aagagcttat  540
cagatggagc cagcccagct tcggcaatta aacggacttg aaaatgactc tatttatgct  600
gggcaaacat tgaagataag cagccagacg gttgctgaaa aggaaccgcc ggcgctgtct  660
gcaaggatcg cttctgccgg tacttataca ataaagagcg gagattcgct tggtgccatt  720
gcaaaagcgc ataatatgac agtggctgaa ctgcagaagc tgaatggact ggcgtcccac  780
atgatttatg caggccaaac gctcaaggtg aagggcaaag cggcggctgc gaagccctca  840
cagccaaaac cgaagccatc ggtgacgcca tcgccatctt ctgcggggta tacagtcaaa  900
agcggtgatt cgctaagtct tattgcgaaa aggcatcaaa tgagcgtgac ggaattaaag  960
cagcttaatc aattggcatc agaccttata tttattggcc aaaagctcaa ggtgagcggc 1020
aagccgacac cgtctcagcc gaaaccaaag ccgccggccg cgccacagcc atcttccggc 1080
agttatacgg tcaaaagcgg cgattcgtta agtctcattg cacaaaagca tcaaatgagc 1140
ttagcagagt taaagcagct caatcaatta acgtctgata tgatatttat tggccaaaat 1200
ctcaaggtga gcggcaagcc aggagcgaac aagccgacac cgtcccagcc gacaccgaag 1260
ccgccggtga cgccatctcc gtcctccggc aattatacgg tcaaaagcgg tgattcgcta 1320
agcctcatcg cccaaaagca tcaaatgagc ttagccgaat taaaaaggcg gaatcaatta 1380
acatctgata tgatatttgc cggccagatc ttaaagatca gcggcggagg gtcagggacg 1440
ggcacgcctc cttccagcaa gccaggctct tctggcggcg gggcgttttc cgtggcgtca 1500
ttgattgcag aggctaagaa gcatctcggc actccttatg atggggcgg cgttcagccc 1560
tccggctttg attgcagcgg cttcatttac tatgtattta ataaagccgg caagagcatc 1620
ccgcgcacca atacggaagg ctactacagc cgttcctact atgtcgataa gccgcaggta 1680
ggcgacttgg tattcttcgt aaatacgtat aaaaaaggca tttcccacat gggcatctat 1740
attggcggca accagttcat tcaggcgagc tcttcacaag gaattaccat cacgagtctg 1800
gataacagtt acttaagca gcggtttgac agctttaagc gcttttac              1848

SEQ ID NO: 110         moltype = AA  length = 616
FEATURE                Location/Qualifiers
source                 1..616
                       mol_type = protein
                       organism = Bacillus thuringiensis
SEQUENCE: 110
MKKSIFTLST AAFFSTGAAT LVHAAEQHVV KPGETLDSIA KQYEMDVSTL KALNNLENDA   60
LQVNQTLTVA SHSSGASEST HIVQAGETIH AIAQLYQMPE TELKQLNQLE NNTIYAGQKL  120
KVSGNKAVHQ SAAVQRPLPE AELHTQAAKP AVEAEVKELP VTGTYIVQRG DTLGAIARAY  180
QMEPAQLRQL NGLENDSIYA GQTLKISSQT VAEKEPPALS ARIASAGTYT IKSGDSLGAI  240
AKAHNMTVAE LQKLNGLASH MIYAGQTLKV KGKPAAAKPS QPKPKPSVTP SPSSGGYTVK  300
SGDSLSLIAK RHQMSVTELK QLNQLASDLI FIGQKLKVSG KPTPSQPKPK PPAPQPSSG   360
SYTVKSGDSL SLIAQKHQMS LAELKQLNQL TSDMIFIGQN LKVSGKPGAN KPTPSQPTPK  420
PPVTPSPSSG NYTVKSGDSL SLIAQKHQMS LAELKRLNQL TSDMIFAGQI LKISGGGSGT  480
```

```
GTPPSSKPGS SGGGAFSVAS LIAEAKKHLG TPYVWGGVQP SGFDCSGFIY YVFNKAGKSI    540
PRTNTEGYYS RSYYVDKPQV GDLVFFVNTY KKGISHMGIY IGGNQFIQAS SSQGITITSL    600
DNSYFKQRFD SFKRFY                                                   616

SEQ ID NO: 111           moltype = DNA   length = 177
FEATURE                  Location/Qualifiers
source                   1..177
                         mol_type = other DNA
                         organism = Bacillus thuringiensis
SEQUENCE: 111
atgaccttga ttatggaaaa aacacaattt tgtttgctaa gatgtatata tagcttaatt     60
attaaaaggc ccttagaaaa aacgtattta aatttaaagt taatgaattg taaggaaagg    120
cacttcatta tcacctcgtt atgtcataga agaattagaa tgtttcccag aaatagaa     177

SEQ ID NO: 112           moltype = AA   length = 59
FEATURE                  Location/Qualifiers
source                   1..59
                         mol_type = protein
                         organism = Bacillus thuringiensis
SEQUENCE: 112
MTLIMEKTQF CLLRCIYSLI IKRPLEKTYL NLKLMNCKER HFIITSLCHR RIRMFPRNR      59

SEQ ID NO: 113           moltype = DNA   length = 1677
FEATURE                  Location/Qualifiers
source                   1..1677
                         mol_type = other DNA
                         organism = Bacillus thuringiensis
SEQUENCE: 113
atgtttacaa gtggcgaaaa aaataggttg aaaatagtaa cgactgatta tgaaatagat     60
caagtggcaa attcgataga aaatatgtca aatgaacaac attcacaaga gaaagcgatg    120
ctatgggatg aagtgaaaca tgccaaatac ctcagtcagt ctcgtaattt actccaaaat    180
ggtgattttg aggattatt tagcagctgg actacaagta atcacatgtt cattcagaca    240
gataattcaa cttttaaagg aaattatctc aatatgtctg gagcaagaaa tatcgatgga    300
aatatatttc caacctatat ctatcaaaaa atagatgagt ctagattaga accatataca    360
cgttatcgag tacgagggt tgtggggagt agtaaaaatc tggaattaat ggtaacgcgt    420
tactggaaag aaattgatgc tattatggat gttccaaatg atttggccta tatgcagcct    480
agcccttcac gtggagatta ttactgcgaa tcatcgtccc agtatgtgag ccaagggtat    540
cctacacgag taacagatgg atatgcttct gataagtatg tatgccagcc aaatctaggt    600
aaaaaacatg tgaagtatca cgatcgtcat ccatttgatt ttcatattga cacaggacaa    660
ttagatacaa atacaaactt aggcgtttgg gtcttgttta aaatttccaa ttcagatgga    720
tatgctacat tagggaatct agaagtagtt gaagaaggac cactaacggg tgaatcattg    780
tcacatgtga acaaaagga aagaatggt catcaacaca tggagaaaaa acgtatggaa    840
acacagcaag cctacgatcc agcaaaacag gctattgatg cattatttac aaatgaacaa    900
gagttacact atcatattac tttagatcat attcaaaacg ctgatcgact gatacagtcg    960
attcccctata taccatgc ttggttaccg gatgctccag gtatgaacta tgatatgtat   1020
caagggctaa acgcaagtat catgcaagca cgctacttct atgatgcacg aaatagtata   1080
acaaatggtg actttacaca aggattaacg ggatggcacg caacaggaaa ggcaacggta   1140
caacaaatgg atggaacttc agtattattt ctatcaaatt ggagtgcggg ggtatctcag   1200
aacctgcatg cccaaaatca tcatggatat gtgctacgtg cgattgccaa aaaagaagga   1260
cctggaaaag ggtatgtaac attgatggat tgtaatggca agcaggaaac actgaagttc   1320
acttcttgtg aagaaggata tatgacaaaa acagtagagg tatttccaga aagtgatcgt   1380
gtacgaatag agattggaga aaccgaaggt acgttttata tagatagcat cgagttgatt   1440
tgtatgaaag gcaataataa cccgcacacg gataatatgt atgagcaaag ttataatgga   1500
aattataatc agaataagag cgatgtatat caccaaggat acaaacaa ctatcaccaa   1560
gactctagta atatgtataa tcaaaattat aatcaaaatt atactcacaa tgatgaccag   1620
cattccgatt gcacatgtaa ccaaggacat aactctggct gtacatgtag tcaaaga      1677

SEQ ID NO: 114           moltype = AA   length = 559
FEATURE                  Location/Qualifiers
source                   1..559
                         mol_type = protein
                         organism = Bacillus thuringiensis
SEQUENCE: 114
MFTSGEKNRL KIVTTDYEID QVANSIENMS NEQHSQEKAM LWDEVKHAKY LSQSRNLLQN     60
GDFEDLFSSW TTSNHMFIQT DNSTFKGNYL NMSGARNIDG NIFPTYIYQK IDESRLEPYT    120
RYRVRGFVGS SKNLELMVTR YWKEIDAIMD VPNDLAYMQP SPSRGDYYCE SSSQYVSQGY    180
PTRVTDGYAS DKYVCQPNLG KKHVKYHDRH PFDFHIDTGQ LDTNTNLGVW VLFKISNSDG    240
YATLGNLEVV EEGPLTGESL SHVKQKEKKW HQHMEKKRME TQQAYDPAKQ AIDALFTNEQ    300
ELHYHITLDH IQNADRLIQS IPYIYHAWLP DAPGMNYDMY QGLNASIMQA RYFYDARNSI    360
TNGDFTQGLT GWHATGKATV QQMDGTSVLF LSNWSAGVSQ NLHAQNHHGY VLRAIAKKEG    420
PGKGYVTLMD CNGKQETLKF TSCEEGYMTK TVEVFPESDR VRIEIGETEG TFYIDSIELI    480
CMKGNNNPHT DNMYEQSYNG NYNQNKSDVY HQGYTNNYHQ DSSNMYNQNY NQNYTHNDDQ    540
HSDCTCNQGH NSGCTCSQR                                                559

SEQ ID NO: 115           moltype = DNA   length = 2040
FEATURE                  Location/Qualifiers
source                   1..2040
                         mol_type = other DNA
                         organism = Bacillus thuringiensis
```

```
SEQUENCE: 115
atggcaaatg gaaacaataa caacacgtac aattctggaa atactgagaa caacggatat    60
atgaatgata atacttacaa tcctgaaagt gctaataaca acgaatacac taataaagat   120
ctatacacaa gtagctttat agattcaaat cccctgagtt gcgaggaccc aaatcttgat   180
acgtgtaaac aaaacatttg taaaggaaac aacggtcaaa ttggtcccac tgtagttcct   240
gttattgtcg caccgattgt attaacacct gcttttatag gatttggaaa gttttttattg   300
tcaagtgtaa aggattgggc attagaagaa ggattaaaac gcgtgaaaga gtggttattt   360
ccaagtaata acccaacgta tgaagaaatg gaaaagcac ttcaaaaatt agaagaccaa    420
tttaatagac aattaagctc tacagtagat tccttgctac agtcacgatt taatggtgcg   480
gtaggattaa ttaatcattt tttaactgct ctgaataatt tgaaagagat tgaaaatgcg   540
atgttaacgg ctccaaccga tgaaaataaa caattattag aagaaacaaa aagtgttgtg   600
tctgatagat ttagagaagt taatacgaat ttagcaggtg ttgtaccaca atttattgtg   660
caagggtatg aagaattaag tttaccttta tttgcgaaag tagcttcgat gcatcttgta   720
catttaaaag atggcatatt aaatgctact gcttggatta tcagggga gaattagcg     780
cagtataaaa cagatttttt tacacgtaga gcggattatg taaatacggg cactgcagcg   840
tctttacgtg cacggaatag aatattaaac gaacaagggg caggaggag tattcatttc   900
caatcaatca tgaaagtagc tctatatgat gaaatgtatt tatggacttt attacaatat   960
gagggaatta caccctacggt gtctcgtact attcatcatt acattggata tccaactaca  1020
ttaaaaccta gcgaaatgaa tactttaaat acactgatga caggagttcc caataaaaaa  1080
cttagaatta tttacggatt atattatatg acttctactg cagttccatg ggttatgaat  1140
ggtgtgaaag tgggatatag tggttggcga gatacgctga tagggcgtaa tttcttttac  1200
caagggtggg gggctcatat tggtgatcca aatacatcac cttcaagaaa cgtgacaggg  1260
tggttattaa atacaggtgg ttctcgttgg gaccttcgta ttgacgaatc ttttattgta  1320
ggaaataagt atctagatag ttcaaattcg aatcgaatta atatttcgta tgcagatact  1380
tcaaaaatag gagaagcaca ttatattcga tcagcggcct aaaaccagc tggtgatatc    1440
tctgggaaac agtattcgtt agctgacgat cttgaatata taaatccagg tgaaagtggt  1500
gatattataa acaacaatat gattatcggt tttgcaccag ataatacacg taattttatg  1560
tcaactggta agcataaatt agcatggcat acttcttata ccattccagc tttgcattat  1620
gattatattc ttttcaatcc tgaagattat tatatagact ggggttatgt agaggttaca  1680
ggaacagatg gttttctata taaaaaagca gacccccag cattgtatcc aattagttat    1740
aaattagacc tctcacaaat taatccaaat gaagaatatg tgtgtatcat acgaactgtt  1800
ttaggaagta catcatataa acttgagctt cctgatacta taacggtttt attaaaacta  1860
gaatttcctg gcgtactttt atttaatttt cataatcaac ttgatttaat ttcaacaccg  1920
tttaaatttc attcaacctc ttcaaatcaa acaatgaatt taataagtga atatcccgac  1980
aaagaagcta agttagtaag tataatgttt attccagcaa gtcgatataa aaaacatttt  2040

SEQ ID NO: 116           moltype = AA  length = 680
FEATURE                  Location/Qualifiers
source                   1..680
                         mol_type = protein
                         organism = Bacillus thuringiensis
SEQUENCE: 116
MANGNNNNTY NSGNTENNGY MNDNTYNPES ANNNEYTNKD LYTSSFIDSN PLSCEDPNLD    60
TCKQNICKGN NGQIGPTVVP VIVAPIVLTP AFIGFGKFLL SSVKDWALEE GLKRVKEWLF   120
PSNNPTYEEM EKALQKLEDQ FNRQLSSTVD SLLQSRFNGA VGLINHFLTA LNNLKEIENA   180
MLTAPTDENK QLLEETKSVV SDRFREVNTN LAGVVPQFIV QGYEELSLPL FAKVASMHLV   240
HLKDGILNAT AWGISEELA QYKTDFFTRR ADYVNTGTAA SLRARNRILN EQGAGGGIHF    300
QSIMKVALYD EMYLWTLLQY EGITPTVSRT IHHYIGYPTT LKPSEMNTLN TLMTGVPNKK   360
LRIIYGLYYM TSTAVPWVMN GVKVGYSGWR DTLIGRNFFY QGWGAHIGDP NTSPSRNVTG   420
WLLNTGGSRW DLRIDESFIV GNKYLDSSNS NRINISYADT SKIGEAHYIR SAALKPAGDI   480
SGKQYSLADD LEYINPRESG DIINNNMIIG FAPDNTRNFM STGKHKLAWH TSYTIPALHY   540
DYILFNPEDY YIDWGYVEVT GTDGFLYKKA RPHALYPISY KLDLSQINPN EEYVCIIRTV   600
LGSTSYKLEL PDTNNGLLKL EFPGRTLFNF HNQLDLISTP FKFHSTSSNQ TMNLISEYPD   660
KEAKLVSIMF IPASRYKKHF                                               680

SEQ ID NO: 117           moltype = DNA  length = 1560
FEATURE                  Location/Qualifiers
source                   1..1560
                         mol_type = other DNA
                         organism = Bacillus thuringiensis
SEQUENCE: 117
atgttaggtg ttatgggtga attgcaaaat atattataca aaaggagtgg gaaaatgaat    60
acacatggaa aaaatgaaga gtggaatcag catcacgatg gaacttgtgg ttgtcaacaa   120
aacaaaccgg attatggata tgaacaaata caagaacatg ataagcaaca atatgcattt   180
aatgaatatg aaaaccaaga gtatacatat cacaactctt gtggagaaat aggaacagat   240
cattacatta aatataatgg ggattttcaa tgtgatacca ttcgatatac tgcacccaat   300
ttacctgtag aaagtacgag gtttcagaaa attagaaatg taaatggtgg agatcgagta   360
gttgatgcaa ggaatacacc tgttggtctg gtcttcaac aaagagtagg tggttgtcca    420
tggcaaatag atgttgaaaa taccgtagta aatacagaac ctagtcctca gtatcaaaca   480
caagattta ttttctatgc aacagatagt ggagattttg ttattacgaa tcaaggaaat   540
ggtcgcgttc tagaaatggt agaatttccg gggagtgatc cgcagtggca tcaagtttta   600
atttctagtt tctatgagaa tagaagaaat caaatatta ctaaacgtga attaactaat     660
actgattttt tactaacgac aacaacagaa acgggtaatg tttttggcat aaataattgt   720
aataataatc caaatgtatg gcaaatctat acgactgtta atgaaaatga gtctgttgga    780
tttcggaata atacgtataa attccaagat gaacgccctc tctctttacc atctctacga   840
tctgggaaaa cgttaaatcc tttgccggca ttaagatatc tacaagattc aggtctaagt   900
ccctcagaag cgccaagggc agtaatagga agtgcattac ttccagctat atttgtagaa   960
gatgtattac cattacctgc aagaatgaca cagagtccgt attatgtact agaacataga  1020
caatattggc atagattatg gtcagatata ataccagctg tggtcaatc ttggtttaat   1080
```

-continued

```
gaaacaacag ggatgcttgg tggagggcct gcacaaacaa atatgaaaaa tacgataagc  1140
atgtctatcg ggcaagattt agggataaga ttcggaacgc aatcaatgcc atttagtatt  1200
aagattgcag aaaatttaag aagacaaaga tcgaatgcaa ctgcagatat aggcgaatct  1260
agtcaagaat ttcgatatca aaatcctcaa aatcaaccta caagatttgc aaggtttgca  1320
ttagcacatg aatatgcgtt actaaatatg aatggaagag tgatgaatag atggacagtg  1380
gtagatagaa atagtatgta tcttttatca tttccacaaa atgcattgtt aacaatgcat  1440
tgcaataaaa taatacgtac agataatagt tatgatttat cggtgtggaa aacaccgatg  1500
caaataaaaa gtgggcaagt gattaccaaa aatgaaaaga attcaaagcc ctacaatgca  1560

SEQ ID NO: 118         moltype = AA  length = 520
FEATURE                Location/Qualifiers
source                 1..520
                       mol_type = protein
                       organism = Bacillus thuringiensis
SEQUENCE: 118
MLGVMGELQN ILYKRSGKMN THGKNEEWNQ HHDGTCGCQQ NKPDYGYEQI QEHDKQQYAF  60
NEYENQEYTY HNSCGEIGTD HYIKYNGDFQ CDTIRYTAPN LPVESTRFQK IRNVNGGDRV  120
VDARNTPVGL GLQQRVGGCP WQIDVENTVV NTEASPQYQT QDFIFYATDS GDFVITNQGN  180
GRVLEMVEFP GSDPQWHQVL ISSFYENRRN QIFTKRELTN TDFLLTTTTE TGNVFGINNC  240
NNNPNVWQIY TTVNENESVG FRNNTYKFQD ERPLSLPSLR SGETLNPLPA LRYLQDSGLS  300
PSEAPRAVIG SALLPAIFVE DVLPLPARMT QSPYYVLEHR QYWHRLWSDI IPAGGQSWFN  360
ETTGMLGGGP AQTNMKNTIS MSIGQDLGIR FGTQSMPFSI KIAENLRRQR SNATADIGES  420
SQEFRYQNPQ NQPTRFARFA LAHEYALLNM NGRVMNRWTV VDRNSMYLLS FPQNALLTMH  480
CNKIIRTDNS YDLSVWKTPM QIKSGQVITK NEKNSKPYNA                        520

SEQ ID NO: 119         moltype = DNA  length = 2253
FEATURE                Location/Qualifiers
source                 1..2253
                       mol_type = other DNA
                       organism = Bacillus thuringiensis
SEQUENCE: 119
atgggaggaa taaatatgag ttcaaattat tcaaatgaag acggaatcat aaatgcttca  60
ccaagtactt ctcaaagata tcctttagta aaagatccaa ctgcacaatt gaaagatata  120
aattacaaag agtatttaca aaggataagt gaaaatgaga ttggtattag acctacatca  180
gttggttcag gagcaggttt taatgctgca gcagctattg tggctacatt attaggtgtt  240
gcaggccatc caggtagttc tgcgattgtc accactctta atataattat tggtttgtta  300
tggcctaaag gtgagacgga tactattata tgggatgatc tcttaaaaat agcagaagaa  360
attgttgatc aggcagtatc ggaggcagta ttagaagcag caaatactgc gttagaagaa  420
atgtatagag ttgcagagga ttatcagcgt acgttagagg attgggtatc aggaagacgt  480
gtagagcaag catatatgag aggtaaattt gaaaatgcga aagatatatt aaatagtaag  540
atagcgaatt ttaagaaacc aggctatgaa ttaccactat taacaatgta tgcacaagcc  600
gcaaacttgt atttatatat aacgaaagat attacagttt tcggaaaaga atgggggtat  660
cttcccgagg gtgatccaga agttagtgga cagggaacta ttgattatat ttatgagaaa  720
gaatttttat atcacatgtc tgaacattct gaatattgcg ttaaatggta taacgaaggg  780
ttaaatcgtt taccacgttc ttcatttatt gattggattg attataatcg ttaccgtaga  840
gaaatgacat tacttgtact agatattatt tcgttatttc caagttacga tgcatttgta  900
tatccaatgt tgacaaatcc agagattaca agagaagttt atacagatcc tttagttatg  960
ggtagtgatt atggtcaagt tggttttgct tttgctttcg gaaatataga ggaactgact  1020
cggaagccac atctgtttga ttggttaaat tcactaacaa tatatacaca agaaatacac  1080
gctgctgatg acgtatggaa ctgttttata aaaggtacta aatcaaaatt atcttataca  1140
aatagttcgg gtacttttga gttgggaggt acgatgagtt ccacttatga agatacttat  1200
gacgtaaaat caaaagatat ctatcaaact ctattgaata taggttcgga ttatgaaggg  1260
acttcttcag agagtagtat gataatagga tgcgttgggg gtgattttaa ttatatatcg  1320
gaaagtggtt caacagggag ttttcaccac ggacattgcg gattaggtag tatggtaacg  1380
gtagattctt tattacaatt acctttagaa gacgaatccg atgtatcttc ttatactcat  1440
agactctcct atatgaattt tgcttatgat gattattttg aaagtttcag aaaagatcgt  1500
tcagattatc gttctgtagg tatacaaggt tggacacata caagtgtatc tcctgaaaat  1560
tacattcaca gggataaaat tacacaatta tatggtgtta aaggaaacca tctttctaat  1620
gcttctgttg aagtagggcc tggatttta ggaggaaata taattaaatg taatactgat  1680
ggtggctctt atggcggaag tgtggatttt acaattagat tggatggtcc agacagtgca  1740
ttccgtatta gaattcctta tgctgctgaa acagatggcg tatttagtat tactattcga  1800
gacgagttga gcccttatac tatagagcag ggttttgtag caacaatgga ccccggagat  1860
cctttatctt atgaaaaaat taaatatttt gaattcgata aaacgctaaa tatgggtgag  1920
cgtcatggtg cttttttcgt taaggtaaaa gatttaatag atagaagtgc taatgtatat  1980
tggcataaag ttgagattgt cccagtagat gaaaattacg atgagagagt aacactagaa  2040
aaagcacaga aagccgtgaa tgcattgttt acagcgggaa gaaacgcact accaaaagat  2100
gtgacagatt ttaaagtgga tcaggtttcc atattagtag attgtgtgtc aggggagtta  2160
tatccaaatg aaaaacgcga actactaagt ttagtcaaat atacaaaacg tttgagctat  2220
tctcgtaatt tactcctaga tccaacattt gat                               2253

SEQ ID NO: 120         moltype = AA  length = 751
FEATURE                Location/Qualifiers
source                 1..751
                       mol_type = protein
                       organism = Bacillus thuringiensis
SEQUENCE: 120
MGGINMSSNY SNEDGIINAS PSTSQRYPLV KDPTAQLKDI NYKEYLQRIS ENEIGIRPTS  60
VGSGAGFNAA AAIVATLLGV AGHPGSSAIV TTLNIIIGLL WPKGETDTII WDDLLKIAEE  120
IVDQAVSEAV LEAANTALEE MYRVAEDYQR TLEDWVSGRR VEQAYMRGKF ENAKDILNSK  180
```

```
IANFKKPGYE LPLLTMYAQA ANLYLYITKD ITVFGKEWGY LPEGDPEVSG QGTIDYIYEK   240
EFLYHMSEHS EYCVKWYNEG LNRLPRSSFI DWIDYNRYRR EMTLLVLDII SLFPSYDAFV   300
YPMLTNPEIT REVYTDPLVM GSDYGQVGFA FAFGNIEELT RKPHLFDWLN SLTIYTQEIH   360
AADDVWNCFI KGTKSKLSYT NSSGTFELGG TMSSTYEDTY DVKSKDIYQT LLNIGSDYEG   420
TSSESSMIIG CVGGDPNYIS ESGSTGSFHH GHCGLGSMVT VDSLLQLPLE DESDVSSYTH   480
RLSYMNFAYD DYFESFRKDR SDYRSVGIQG WTHTSVSPEN YIHRDKITQL YGVKGNHLSN   540
ASVEVGPGFL GGNIIKCNTD GGSYGGSVDF TIRLDGPDSA FRIRIPYAAE TDGVFSITIR   600
DELSPYTIEQ GFVATMDPGD PLSYEKIKYF EFDKTLNMGE RHGAFFVKVK DLIDRSANVY   660
WHKVEIVPVD ENYDERVTLE KAQKAVNALF TAGRNALPKD VTDFKVDQVS ILVDCVSGEL   720
YPNEKRELLS LVKYTKRLSY SRNLLLDPTF D                                  751

SEQ ID NO: 121          moltype = DNA   length = 2145
FEATURE                 Location/Qualifiers
source                  1..2145
                        mol_type = other DNA
                        organism = Bacillus thuringiensis
SEQUENCE: 121
atgaaactaa agaatcaaga taagcatcaa agttattcta gcaatgagaa ggtagataaa    60
atctctacaa ataaaacaga tatagaatta aaaaatatgg ataatgaaga ttatttgaga   120
gtgtctgagc acgagagcat taatccattt gttagtgcat caacaattca aacgggtatt   180
ggaattgctg gaaaaatcct tggtactcta ggtgttcctt ttgctggaca aatagcaagc   240
ctttatagtt ttatcttggg cgagcttttgg cctaaaggga aaagccaatg ggaaatcttt   300
atggaacatg tagaagagat tattaatcaa aaaatatcaa cttatgcaag aaataaagca   360
cttacagact tgaaaggatt aggagatgct ttagctgtct accatgaatc gcttgaaagt   420
tgggttgaaa accgtaataa cacacgagcg aggagtgtag tcaagggcca atacatcgca   480
ttagaactga tgtttgttca gaaacttcct tcttttgtga tatctggtga ggaagtacca   540
ttattaccga tatatgtaca agcggcaaat ttgcattttgt tgctattgag agatgcatct   600
atttttggaa agaatggggg attgtcacct tcggaaattt caacttttta taaccgtcaa   660
gtcgatcgaa caagagatta ttccgaccat tgtgtaaaat ggtataatac aggcctaaat   720
aatttgagag gtacaaatgc cgaaagctgg gttcgttata atcaatttcg taaagatatg   780
acattaatgg tattagattt aattgcgcta ttcccaagct atgatacaat tgtttatcct   840
attaaaacca cttcacaact tacaagagaa gtatatacag acgcaattgg gacagtacat   900
ccgcatccaa gttttacaag tacgacttgg tataataata atgcaccttc gttctctgcc   960
atagaggctg ctgttatccg aagcccacac ctacttgatt ttctagaaaa agttacaatt  1020
tatagtttat taagtcggtg gagtaatact cagtatatga atatgtgggg aggacataga  1080
cttgaatccc gcccaatagg aggggcatta aatatctcaa cacaaggatc taccaatact  1140
tctattaatc cagtaacatt acagttcacg tctcgtgacg tctataggac agaatcatgg  1200
gcagggctga atttattttt aactcaacct gttaatggag tacctagagt tgatttccat  1260
tggaaatacc ccacacttcc aatagcatct gataattttt attactagg gtatgctgga  1320
gttgggacac aattcaagat ttcagaaaat gaattaccac ctgaaacaac aggacagcca  1380
aattatgaat catatagtca tagattatct catataggac tcatttcagc atcccacgtg  1440
aaaagcattag tatattcttg gacgcatagt agtgcaaatc gtacaaatac aattgaggca  1500
aacagcatta cacaaatacc attagtaaaa gcattcaatc ttccttcggg tgctactgtt  1560
gttagagggc aggatttac aggagggat atccttcgaa gaacgaatac gggtacattt  1620
ggagatatac gagtaactat taatccgcca tttgcacaaa ggtatcgcgt aaggattcgt  1680
tatgcttcta acagagattt acaattccat acatcaatta tggaagagc tattaatcaa  1740
gggaattttt cagcaactat gaataggaa gataacttaa actatagaac ctttagaact  1800
gcgggattta cgactccatt tagcttttca gatacacaaa gtacattcac aataggtgct  1860
tggagcttct cttcaggtaa cgaagtttat atagatagaa ttgaatttgt tccggtagaa  1920
gtagcgcatg aggaaaatta tgattttgaa aaagtgcaag aggaggttac agcactgttt  1980
acacctacta atcctagagg attaaaaaca aatgtaacgt attatgatat tgaccaggta  2040
ttaaatctag tagagtctct atcagatgaa ttctacgtcg atgaaaagag agaattactc  2100
gaaattgtta aatatgcgaa gcaacttaat attgaccgta acatg              2145

SEQ ID NO: 122          moltype = AA   length = 715
FEATURE                 Location/Qualifiers
source                  1..715
                        mol_type = protein
                        organism = Bacillus thuringiensis
SEQUENCE: 122
MKLKNQDKHQ SYSSNEKVDK ISTNKTDIEL KNMDNEDYLR VSEHESINPF VSASTIQTGI    60
GIAGKILGTL GVPFAGQIAS LYSFILGELW PKGKSQWEIF MEHVEEIINQ KISTYARNKA   120
LTDLKGLGDA LAVYHESLES WVENRNNTRA RSVVKGQYIA LELMFVQKLP SFAVSGEEVP   180
LLPIYVQAAN LHLLLLRDAS IFGKEWGLSP SEISTFYNRQ VDRTRDYSDH CVKWYNTGLN   240
NLRGTNAESW VRYNQFRKDM TLMVLDLIAL FPSYDTIVYP IKTTSQLTRE VYTDAIGTVH   300
PHPSFTSTTW YNNNAPSFSA IEAAVIRSPH LLDFLEKVTI YSLLSRWSNT QYMNMWGGHR   360
LESRPIGGAL NISTQGSTNT SINPVTLQFT SRDVYRTESW AGLNLFLTQP VNGVPRVDFH   420
WKYPTLPIAS DNFYYLGYAG VGTQLQDSEN ELPPETTGQP NYESYSHRLS HIGLISASHV   480
KALVYSWTHS SANRTNTIEA NSITQIPLVK AFNLPSGATV VRGPGFTGGD ILRRTNTGTF   540
GDIRVTINPP FAQRYRVRIR YASTTDLQFH TSINGRAINQ GNFSATMNRE DNLNYRTFRT   600
AGFTTPFSFS DTQSTFTIGA WSFSSGNEVY IDRIEFVPVE VAHEENYDFE KVQEEVTALF   660
TPTNPRGLKT NVTDYDIDQV LNLVESLSDE FYVDEKRELL EIVKYAKQLN IDRNM        715

SEQ ID NO: 123          moltype = DNA   length = 1971
FEATURE                 Location/Qualifiers
source                  1..1971
                        mol_type = other DNA
                        organism = Bacillus thuringiensis
SEQUENCE: 123
```

-continued

```
atgaattcat atcaaaataa aaatgaatat gagatattgg atacttcacc aaacagctct  60
actatgtcta ctcgttatcc tagttaccca ctagcaaaaa atccacaaat atccatgcaa  120
aatacgaatt ataaagactg gctaaatatg tgtacaaata ataacgggat tcctatagaa  180
cctgtagacc ttacctggca aaatgctctt gttgcagtct tcggtatcgc ttcagctgtt  240
gcaggattgt tagcatctcc aattactggc ggaacatcta tagcagctgg agcggctata  300
atagctaata tattaccatt aacctttccc gctaatgctg agagtgttcc gaataagcta  360
atggatgcca cacaagaatt acttggccct ctagaagaat acactagaaa tagagcaaat  420
tcggagctac tcagtttgag ttcacagtta gaagcattta aaggtctatt tgattattgg  480
ctcgctgacc gccaaaatcc aaatgcaact aattcagtta gtgctcgttt tactgcaatt  540
cataataatt ttataggggc aatggctctt tttaaaatac cgggttatga agccttactg  600
ttaccggtat atgctcaggc tgcacgttta catttgcttc atttaagaga cggtatcacg  660
tacgctgatc aatggcagtt agctgatcca actaatgcag cttatgcggg agaataccac  720
tatagtgaat ttaagaaata ttctgcgcaa tatgcagatc attgtgaagt agtagttaat  780
aatcaactaa ataagataaa aaatacaaac ggtaaaacat ggaaagacta caacgaatat  840
cgtcgaaaga tgatattatc tgttttcgat attgttgctg aattttcaac ctttgatcca  900
attttatata aaggagcgat aaatagagaa attttaacaa ggaaaatata tacagaccca  960
gttaatttca cacctggttc ttcaattgct aatgatgaaa acaaatatac aatctatcct  1020
accgctgtta gacaattggt cgcctcaaca ctatttacta acgtggtatc tgctcagtat  1080
gctggattta ttggaaataa aaatcgttat ttaagtttat caggtggaga gccatttgac  1140
ggccctctaa tcggaaacga tgtattcgaa aaggttttag caggtgtacc gacagatgaa  1200
tcgatttatg aagttggtgt aaatggttac ccgaatgatt atccacgtaa tataggtttg  1260
agatggggtt cgttaactgg atttcaaaat tattatgctg gaggtacgac taatttaggg  1320
gggatgacta cggtctctgt gccacctaaa aataatgccc caataaataa tactaatttt  1380
actcatcgat tatcagatat aattcttcct ggaaatagtg gctcatcttt tgcatggact  1440
catgttgaaa tcaatcctac aggaaactat ctatcaacag atcaaattaa tttaatatct  1500
gctacaaaaa cttcatccta ttcaaatttt aactttatag aaggaccgag atttacagga  1560
ggatatttaa tcagaaattt gtcaagtaca aggtgccaat catcttatcc gttgaattta  1620
aaacccggtg gtagctcaac aagttttaga gttcgtatac gttatggatc taatattgct  1680
gggaaagtat attttagatt taatggtaaa gattcttcac ctacttcttt tcctagtact  1740
aacttcagta ctgcttataa atatgatacg tttagagtcg tagagctgct tagtacttta  1800
caaaatttca caggaggtga attgattatt attatagagc tagatagtat tacgtctttc  1860
tttgtactag aaagattgga attaattcct atgacaggga tgccaacaga atacactgaa  1920
ccacaaaaat tggaaacagc acagaaagca gtaaacgatt tatttaccaa t          1971

SEQ ID NO: 124          moltype = AA  length = 657
FEATURE                 Location/Qualifiers
source                  1..657
                        mol_type = protein
                        organism = Bacillus thuringiensis
SEQUENCE: 124
MNSYQNKNEY EILDTSPNSS TMSTRYPSYP LAKNPQISMQ NTNYKDWLNM CTNNNGIPIE  60
PVDLTWQNAL VAVFGIASAV AGLLASPITG GTSIAAGAAI IANILPLTFP ANAESVPNKL  120
MDATQELLGP LEEYTRNRAN SELLSLSSQL EAFKGLFDYW LADRQNPNAT NSVSARFTAI  180
HNNFIGAMAL FKIPGYEALL LPVYAQAARL HLLHLRDGIT YADQWQLADP TNAAYAGEYH  240
YSEFKKYSAQ YADHCEVVVN NQLNKIKNTN GKTWKDYNEY RRKMILSVFD IVAEFSTFDP  300
ILYKGAINRE ILTRKIYTDP VNFTPGSSIA NDENKYTIYP TAVRQLVAST LFTNVVSAQY  360
AGFIGNKNRY LSLSGGEPFD GPLIGNDVFE KVLAGVPTDE SIYEVGVNGY PNDYPRNIGL  420
RWGSLTGFQN YYAGGTTNLG GMTTVSVPPK NNAPINNTNF THRLSDIILP GNSGSSFAWT  480
HVEINPTGNY LSTDQINLIS ATKTSSYSNF NFIEGPRFTG GYLIRNLSST RCQSSYPLNL  540
KPGGSSTSFR VRIRYGSNIA GKVYFRFNGK DSSPTSFPST NFSTAYKYDT FRVVELLSTL  600
QNFTGGELII IIELDSITSF FVLERLELIP MTGMPTEYTE PQKLETAQKA VNDLFTN     657

SEQ ID NO: 125          moltype = DNA  length = 2040
FEATURE                 Location/Qualifiers
source                  1..2040
                        mol_type = other DNA
                        organism = Bacillus thuringiensis
SEQUENCE: 125
atgaaaccaa ataaccagga taatcatgaa accttatcca acaaagtgac agtcgaaaaa  60
ccttttacag attcactaaa aaatgaaaca actaaaaata gtaattatga agattgtttg  120
aaaatgtcta gacatgaaag cgtagagccg tttgttagtg tatcaacaat tcaaacggga  180
attggtattg ctggtaaaat ccttggtagc ctaggcgttc cttttgctgg gcaagtagct  240
agcctttata gttttattct aggtgagctt tggcctaagg ggaaaagtca atgggaaatc  300
tttatggaag atgtagaaaa gctagttgat caaaaaatat cgatttacgc aagaaacaaa  360
gcacttgcag atttaaaagg attaggagat gctctggctg tctaccatga atcccttgaa  420
agttggattg aaaatcgtaa taacagaaga gctagaagtg ttgttaaaga ccaatatatc  480
gctttggaac ttatgtttgt tcagagactt ccttcttttg cagtatctgg agaagaggtg  540
ccgctattac caatttatgc tcaagctgca aatttacact tattgctatt aagagatgca  600
tcaatttttg gagaagaatg gggtttttca acttcagaaa tttcaacatt ttataaccgc  660
caatctagtc ggacgataga atattctgac tattgctcag gatggtataa tacaggacta  720
aatcgcttga gaggtgcaaa tgctgaaagt tgggtacgat ataatcaatt ccgtagagac  780
atgactttaa tggtactaga tctagtagca ctattcccaa gctatgacac tcgcacttat  840
ccaattaaaa caagtgccca acttacaaga gaagtctata cagatccaaa cggtattgta  900
gcaggaggca ataataattg gtttagaaat ggggcttcgt tttccactat agaaaacgca  960
attattcgac aacctcacct atatgatttt ctaacgaacc ttacaattta cacgagaata  1020
agtcgagcaa accctgctta tatgaatttg tgggcagggc atagaattac ttctaataga  1080
ataggttcta gtaatagtag tgaattggtg tatggggcta taactaatcc agttagtact  1140
actaacttat catttgtcaa tcgggatgtt taccgaactg aatcattagc tggtgggctt  1200
ggcactctga atggaatact ttatggttta actagagttg attttgatat gatatttcgt  1260
```

-continued

```
aaccgtcctg atatagtaac tggattattt tatcatccgg acacgcgggg cattgcaacc   1320
caagtaaaag attcagaaac agaattacca cctgaaacga cagaacagcc aaattataga   1380
gcatttagtc atctactaag tcatatttca atgggtccaa cgactcaaga cgtacctcca   1440
gtatattctt ggacacacca gagtgcgagc cgttcaaata caatcgattc ggataggata   1500
acacaaatac cattggtaaa ggcattcaac cttcattcag gcgccactgt tgttagagga   1560
ccaggattta caggtggtga tatcttacga agaactaatc ctggtacatt tgcagatatg   1620
agagtgaata ttactggatc ttattcccaa agatatcgtg taaggattca tttatgcttct  1680
actacaaatt tacaattcca tacatcaatt aacggaagag ctattaatca agggaatttt   1740
tcagcaacta tgaatagtgg ggggaattta cagtcaggta gctttaggac tgcaggtttt   1800
actactccat ttagcttttc agatgcacaa agcacattta caatagtgac ctggagcttc   1860
tcttcaggta acgaagttta tatagatcga attgaatttg ttccggcaga agtaacattt   1920
gaagcagaat atgatctaga aagagcgcag aaggcggtga atgccctgtt tacttctaca   1980
aatccaagag gattaaaaac agatgtaacg gattatcata tcgaccaagt atccaatcta   2040

SEQ ID NO: 126        moltype = AA  length = 680
FEATURE               Location/Qualifiers
source                1..680
                      mol_type = protein
                      organism = Bacillus thuringiensis
SEQUENCE: 126
MKPNNQDNHE TLSNKVTVEK PFTDSLKNET TKNSNYEDCL KMSRHESVEP FVSVSTIQTG    60
IGIAGKILGS LGVPFAGQVA SLYSFILGEL WPKGKSQWEI FMEDVEKLVD QKISIYARNK   120
ALADLKGLGD ALAVYHESLE SWIENRNNRR ARSVVKDQYI ALELMFVQRL PSFAVSGEEV   180
PLLPIYAQAA NLHLLLLRDA SIFGEEWGFS TSEISTFYNR QSSRTIEYSD YCSGWYNTGL   240
NRLRGANAES WVRYNQFRRD MTLMVLDLVA LFPSYDTRTY PIKTSAQLTR EVYTDPNGIV   300
AGGNNNWFRN GASFSTIENA IIRQPHLYDF LTNLTIYTRI SRANPAYMNL WAGHRITSNR   360
IGSSNSSELV YGAITNPVST TNLSFVNRDV YRTESLAGGL GTLNGILYGL TRVDFDMIFR   420
NRPDIVTGLF YHPGHAGIAT QVKDSETELP PETTEQPNYR AFSHLLSHIS MGPTTQDVPP   480
VYSWTHQSAD RSNTIDSDRI TQIPLVKAFN LHSGATVVRG PGFTGGDILR RTNPGTFADM   540
RVNITGSYSQ RYRVRIHYAS TTNLQFHTSI NGRAINQGNF SATMNSGGNL QSGSFRTAGF   600
TTPFSFSDAQ STFTISAWSF SSGNEVYIDR IEFVPAEVTF EAEYDLERAQ KAVNALFTST   660
NPRGLKTDVT DYHIDQVSNL                                              680

SEQ ID NO: 127        moltype = DNA  length = 1065
FEATURE               Location/Qualifiers
source                1..1065
                      mol_type = other DNA
                      organism = Bacillus thuringiensis
SEQUENCE: 127
atggtgaaaa gagatatttc agctagggat cttggcggta aggaggattc tcctttttta    60
ttaaaaaaag aagaatggat taaaattcaa aatacacag gtgatggtgc atatttacct   120
gtaaatgtta ctgagatgcg caaagtttta gcattggaaa actcagcaac actacctgat   180
tttcaagaat tgtatactgt taatacgaat attaaagcc attgtaaaaa ttggacagat   240
aatacctaca gagaagttct tactgttgcg aatgagattg ttaattatgc aagaagagca   300
agtgtttatt atgcacccct tacttgaata ttaccggata ttttaaatgg tgatactgag   360
gccttagaaa agttcaagaa atttgtggt aagttagcga atgaagcgaa ggatttttagt   420
gaccatgcta aaactttagc tgatgacgtt ggaaagttca tgcagatac ctcaactgat   480
tacacaaact tagtaacagt taaagcaaaa tatgataagt tgtatggcga acagagcgaa   540
gatgtaaaac tacttagggc tgaagtagag cagttgcgga agatttaga ggaatatatg   600
gaagattatg aggaatatca atctcaatct tggttgtctt tgttacttgg tcctgttttt   660
ggttttgtgt taaagggaat tctcgacagt acgaaaggga aatgttaca agctaaaatt   720
gaagctacaa aacaaaaaat cgaagcaat gatgaaataa acagcgaaaa tgtttactta   780
atggctttac tcgataaagc agataaagga acagacaaga ctcaaaaaca aattgaggat   840
gcgcttcctg tgattcaaaa aatccaaggt atttggaatt ctcttcacag tgacctttg   900
gaactttcga taattacgat ggaagatatt caaaatgatc cggaattgc cgatcttgga   960
atcgaattag caattttaca gtgggaagct gtaggcaaac aagcagatga tttccgagtt   1020
aatgcagatg ttggatttat agttgatcaa tattttgcat cagca                  1065

SEQ ID NO: 128        moltype = AA  length = 355
FEATURE               Location/Qualifiers
source                1..355
                      mol_type = protein
                      organism = Bacillus thuringiensis
SEQUENCE: 128
MVKRDISARD LGGKEDSPFL LKKEEWIKIQ KYTGDGAYLP VNVTEMRKVL ALENSATLPD    60
FQELYTVNTN IKGHCKNWTD NTYREVLTVA NEIVNYARRA SVYYAPLLEY LPDILNGDTE   120
ALEKFKKICG KLANEAKDFS DHAKTLADDV GKFATDTSTD YTNLVTVKAK YDKLYGEQSE   180
DVKLLRAEVE QLRKDLEEYM EDYEEYQSQS WLSLLLGPVF GFVLKGILDS TKGKMLQAKI   240
EATKQKIEAN DEIIQRNVYL MALLDKADKG TDKTQKQIED ALPVIQKIQG IWNSLHSDLL   300
ELSIITMEDI QNDPEFADLG IELAILQWEA VGKQADDFRV NADVGFIVDQ YFASA        355

SEQ ID NO: 129        moltype = DNA  length = 2520
FEATURE               Location/Qualifiers
source                1..2520
                      mol_type = other DNA
                      organism = Bacillus thuringiensis
SEQUENCE: 129
atgaatacag atcaaaatag aaatgaatat gaaatactgg atgcttcaac ccatcatgag    60
tacatatcaa acagatatcc tttcgcaaag aatcccaacg ttatgcaagg taccaattat   120
```

```
aaagattggt tcaatgagta tcaagatatt gctccttctt ctcttgtaag tactctagtc    180
accatgttta atctctttaa acaattcatt actttcattg agacgcctaa cgtttccta    240
agggagatta taggcgcatt gcggagtcgt caagtaataa atcttactat aaatgatgta    300
caacgactta ttgatacagc attaaaaatc acatcagaat tgaggcaagt caaaaatttg    360
atagtataca attataatca atatctttcc aataaaagta actatataaa taatccatcg    420
aatcctaacc gaaacctatt tgtaaatagt cttattttaa atgagcgtga tttgagaata    480
gcactagatg ttcatttagc aatattaaaa gatgctgtaa tatttagggg accagactta    540
atagcgcctg cgattattga aacacctgag aatcctttt tgaatcgacc tcctagtaat    600
tcttatgaat tggcgctttt aactagcata cgtatgtatt ctaattattg cgtaagacac    660
tataatgaag gtttaaatcg cataagaaac aggggtacat ttagtaatgt ttggttggat    720
ttccataatt atcgcagaga aatgacatta atagtattag attttgtcgc attgttctca    780
cttttgaca caactaaata tccaatatta ggaagttcta caccgccagt agtttctcaa    840
ttaagtaggg taatttatac cgatccggta ggtgctataa gaaccgatgg tcgggggtgg    900
tttgatccac ccgtaggaac tgatagatt agagtcaatt ggcatcaat agaaaatgaa    960
caaaccggcc ctactacttc tcggcattta tcggaattaa caatttcttc agggccgctt   1020
ggttttggca taaatccaag taggacacat tcgtggcagg gtaatcgaaa tgttaatata   1080
tccgctccta cggatgtttc tggagtaatt tctaatcgga cgcaaactat tcctgctaga   1140
aatattttca gagtgaattc acgtgtttat actcttgatt ggaggttgta tggagtttat   1200
agagctgaat ttttcagga tgctagtcaa aattctcaaa tacgtgtatt tgcagaaaat   1260
cctccaacag gtgctggtgc ccaaagcgca aataacttcc gatttttacc tggagaaaat   1320
tcggatacac caactccgca ggattatacc catttattaa gtgagtagt aaatgcaact   1380
gtaggactta caccggcaac aggaaatcaa cgtaattctg tattgatatt tggttggaaa   1440
cataagagtt taacctctga aaatatatat agaatcaacg aaattacgca agtagctgct   1500
gtgaatacaa gaaataattt gggtattcgg gtaatttcag gacctggatt tacaggtgga   1560
gatttagtaa aatggattc taacggtagc gtaagttaca attttacacc cgctaatcag   1620
caagccttgc aatcaagtgt tgcaattcgt ttacgttatg ctggtcaagg ggaagcatca   1680
ttaagaataa catttggtaa tggttctagc caagtaattc cacttgtctc tacaacttca   1740
tcactaaatg atcttcaata tgaaagtttt cgtttcgcta atgttccaaa taacgttagt   1800
tttcaaacat tcggaacttc aatgactatt caaaatataa gtgcgaattc taacgtagtt   1860
ctagataggg ttgaacttt ttccaacata cctatacca ttctcgaaga tacttataac   1920
ctaggctcaa atagccagta tagccaacac tataatgatt cttataacca cagcacgaac   1980
agcccgtata accaaattta tgatgattct tataaccaca gcacgcatag cccgtataac   2040
caagactatg atgattctta taccaaaac acgcataacc agtatagtca agactatgat   2100
gattcttata accacagcac gcatagcccg tataacacta gttcttataac   2160
caaaacacgc ataaccagta tagtcaagac tatgatgatt cttataacca aaacgcgcat   2220
agtcagtata gtcaagacta tgatgattct tataaccaca gcacgcatag cccgtataac   2280
caagactatg atgattctta taccaaaac acgcataacc agtatagtca agactatgat   2340
gattcttata accacagcac gcatagcccg tataaccaaa tttatgatga ttcttataac   2400
caaagtacgc ataaccggta tagccaacac tataataata atttaaatca caatagtccg   2460
tgtgatccta gctttaatca ttattacaat caaaatgttc ataaaaactg taattgtaaa   2520
```

SEQ ID NO: 130        moltype = AA  length = 840
FEATURE                   Location/Qualifiers
source                    1..840
                           mol_type = protein
                           organism = Bacillus thuringiensis
SEQUENCE: 130

```
MNTDQNRNEY EILDASTHHE YISNRYPFAK NPNVMQGTNY KDWFNEYQDI APSSLVSTLV     60
TMFNLFKQFI TFIETPNVSL REIIGALRSR QVINLTINDV QRLIDTALKI TSELRQVKNL    120
IVYNYNQYLS NKSNYINNPS NPNRNLFVNS LILNERDLRI ALDVHLAILK DAVIFRGPDL    180
IAPAIIETPE NPFLNRPPSN SYELALLTSI RMYSNYCVRH YNEGLNRIRN RGTFSNVWLD    240
FHNYRREMTL IVLDFVALFS LFDTTKYPIL GSSTPPVVSQ LSRVIYTDPV GAIRTDGRGW    300
FDPPVGTDRI RVNFASIENE QTGPTTSRHL SELTISSGPL GFGINPSRTH SWQGNRNVNI    360
SAPTDVSGVI SNRTQIPAR NIFRVNSRVY TLDWRLYGVY RAEFFQDASQ NSQIRVFAEN    420
PPTGAGAQSA NNFRFLPGEN SDTPTPQDYT HLLSRVVNAT VGLTPATGNQ RNSVLIFGWK    480
HKSLTSENIY RINEITQVAA VNTRNNLGIR VISGPGFTGG DLVRMDSNGS VSYNFTPANQ    540
QALQSSVAIR LRYACQGEAS LRITFGNGSS QVIPLVSTTS SLNDLQYESF RPANVPNNVS    600
FQTFGTSMTI QNISANSNVV LDRVELFSNI PIPILEDTYN LGSNSQYSQH YNDSYNHSTN    660
SPYNQIYDDS YNHSTHSPYN QDYDDSYNQN THNQYSQPYD DSYNHSTHSP YNQDYDDSYN    720
QNTHNQYSQD YDDSYNQNAH SQYSQDYDDS YNHSTHSPYN QDYDDSYNQN THNQYSQDYD    780
DSYNHSTHSP YNQIYDDSYN QSTHNRYSQH YNNNLNHNSP CDPSFNHYYN QNVHKNCNCK    840
```

SEQ ID NO: 131        moltype = DNA  length = 2238
FEATURE                   Location/Qualifiers
source                      1..2238
                           mol_type = other DNA
                           organism = Bacillus thuringiensis
SEQUENCE: 131

```
atggcaactt taaatgagct ttatcctgtg ccttataatg ttttatcttc gagcacgtt     60
aattcctggc ctaatactgt ttcaaaagct caagacacac ttatgatta tgaacaattg    120
ctaaataatt ttgggaaaag tatacaagat ggaagctatg aaaaagaaat tgtttccatc    180
tttcaagcag ttatagatca aaaaataaac tatcaaacct ttattcttct ggactgcaa    240
actgtttcac tagcagttcc tgaaatcggt gtcttaactc catttgtcag tttatttttt    300
tcagcaatca ataaacacaa tgacgacgtt ccgccccaa cccctaaaag cattttgag    360
gctattaaac ctgcaattga gaaatgatt gagcgagcac tattgacgca agaacagact    420
tatttagaaa atctaattaa gggattagag agtttgatgc aaaagtatca caatcagatg    480
aacaatattc aagaaatcgg aggttttccc aaagcaactg cgggacaaat taaacttttc    540
gaggatgatc taaccgcttt agataactat tttacaacaa tgttgcctca atttacaaat    600
tcaagggacc ctgtgaatgg agagtacaat gctgaattta ctctgattgg tcttcctat    660
```

```
tattgtattt tggcttgtat gcatctcatg ttgtatagag atattatttc taatggtaaa  720
aattggattc cgagtaagta cgatgaaggt tctattcgcg acatacaaaa ggaactacaa  780
acgaatatta aaaactattc taacacagtt cggacagttt ttaataacgt gctgaattcg  840
cctaaatata ataacggcga tttagcacct acagataaaa ctactttttc aaagcaaaaa  900
gcattcattg aaggaatgac aataaattgt tttgatttcg ctatgctatt ccccacattt  960
gacagatctg tctattcaca agaaacaacg ttagaaaaaa caaggttaat aatatctcca  1020
atactagatg tgactgggtt atctatcccc ttagattttt caaactggcc tgatttcaa  1080
aatggactta tgccctacaa aggtagagag atgacacaaa tagatgtata tggtaatttt  1140
aaacattctt cgtttgagat gattagtaat atgacgatag ctgacaatta cgaaactaga  1200
agttatggcg accaagcatt aagttcagat gatcatacaa aggtttcaat atcttcagat  1260
gatccattgg tatactttaa ttcaaatgca aacttaggtc ctcttccaga ttatggtgga  1320
tcttttgggt ttcaatctgg aaaaatggta tcttatggag ctgatcggga aacaactgat  1380
ggccaatacg ctgctcctag taatcataaa atttcatata tttatccatt tcttaatact  1440
aatcttaatg ctgcgagatt ttcatattac gcagttgtaa gtatgccaaa ggatttatct  1500
ttaacaaaca taataggaga cattgattct gataccaaac aaccatctac acaaatcaaa  1560
ggatttccat ttgaaaaata ttctacgttt actgatcaat ttagtaatcc ttataatatc  1620
gtcgttcgta aggaatggat aaatggggct aatgctatac aagttgatgg tcaacaagct  1680
atcgcaatga atgtaactaa tattacaccg caaaagtata aaattcgttt acgctacaca  1740
acacagaatg gtgcgaatgc ggacatttgg ttccatatca taaattcttt taatcaagac  1800
atcacaaatg gagtggctaa tttgatacct ataggctcag cagttcctat aaaaggggaa  1860
atgggagatt acgtgttaag agaaatagac ggagaatttg ctttatctgc cggtacaaat  1920
aaaataatag ttcaaaatag ggattctgat catctgctct tttagaccg tattgaattc  1980
atgcccatag tttctgataa tggtggcaat ggtggcaatg gtggcaatgg cggtaatggt  2040
ggcaatggcg gtaatggtgg caatggcggt aatggtggca atggcggtga tggtggcaat  2100
ggcggtgatg gcggtgattt ctgtccattt ggacaaatag gaatttgctt tactgaacaa  2160
agtgatttac aaaacatcac aacgcaagtc aatgccctat tcgcttccag cgcacaagat  2220
gctctcgcga caagtgtc                                                2238
```

```
SEQ ID NO: 132          moltype = AA  length = 746
FEATURE                 Location/Qualifiers
source                  1..746
                        mol_type = protein
                        organism = Bacillus thuringiensis
SEQUENCE: 132
MATLNELYPV PYNVLSSRHV NSWPNTVSKA QDTPYDYEQL LNNFGKSIQD GSYEKEIVSI  60
FQAVIDQKIN YQTFILLGLQ TVSLAVPEIG VLTPFVSLFF SAINKHNDDV PPLTPKSIFE  120
AIKPAIEEMI ERALLTQEQT YLENLIKGLE SLMQKYHNQM NNIQEIGGFS KATAGQIKLF  180
EDDLTALDNY FTTMLPQFTN SRDPVNGEYN AEFTLIGLPY YCILACMHLM LYRDIISNGK  240
NWIPSKYDEG SIRDIQKELQ TNIKNYSNTV RTVFNNVLNS PKYNNGDLAP TDKTTFSKQK  300
AFIEGMTINC FDFAMLFPTF DRSVYSQETT LEKTRLIISP ILDVTGLSIP LDFSNWPDFQ  360
NGLMPYKGRE MTQIDVYGNF KHSSFEMISN MTIADNYETR SYGDQALSSD DHTKVSISSD  420
DPLVYFNSNA NLGPLPDYGG SFGFQSGKMV SYGADRETTD GQYAAPSNHK ISYIYPFLNT  480
NLNAARFSYY AVVSMPKDLS LTNIIGDIDS DTKQPSTQIK GFPFEKYSTF TDQFSNPYNI  540
VVRKEWINGA NAIQVDGQQA IAMNVTNITP QKYKIRLRYT TQNGANADIW FHIINSFNQD  600
ITNGVANLIP IGSAVPIKGE MGDYVLREID GEFALSAGTN KIIVQNRDSD HLLFLDRIEF  660
MPIVSDNGGN GGNGGNGGNG GNGGNGGNGG NGGNGGDGGN GGDGGDFCPF GQIGICFTEQ  720
SDLQNITTQV NALFASSAQD ALATSV                                      746
```

```
SEQ ID NO: 133          moltype = DNA  length = 2088
FEATURE                 Location/Qualifiers
source                  1..2088
                        mol_type = other DNA
                        organism = Bacillus thuringiensis
SEQUENCE: 133
atgaatactg tattgaataa cggaagaaat actacttgtc atgcacataa tgtagttgct  60
catgatccat ttagttttga acataaatca ttaaatacca tagaaaaaga atggaaagaa  120
tggaaaagaa ctgatcatag tttatatgta gcccctattg tgggaactgt gggtagtttt  180
ctattaaaga aagtagggag tcttgttgga aaaaggatac tgagtgagtt acagaattta  240
atttttccta gtggtagtat agatttaatg caagagattt taagagcgac agaacaattc  300
ataaatcaaa ggcttaatgc agacaccctt ggtcgtgtaa atgcagaatt ggcaggtctt  360
caagcgaatg tggcagagtt taatcgacaa gtagataatt ttttaaaccc taatcaaaac  420
cctgttcctt tagcaataat tgattcagtt aatacattgc agcaattatt tctaagtaga  480
ttaccacagt tccagataca aggctatcaa ctgttattat tacgtttatt tgcggaattg  540
gcagggctgc aagcaaatgt agaagagttt aatcgacaag tagataattt tttgaaccct  600
aaccgaaacg ctgttccttt atcaataact tcttcagtta atacaatgca acaattattt  660
ctaaatagat taccccagtt ccagatgcaa ggataccaac tgttattatt acctttattt  720
gcacaggcag ccaatttaca tctttctttt attagagatg ttattcttaa tgcagatgaa  780
tggggcattt cagcagcaac attacgtacg tatcgagatt acttgagaaa ttttacaaga  840
gattactcta attattgtat aaatacgtat caaagtgcgt ttagaggttt aaacactcgt  900
ttacacgata tgttagaatt tagaacatat atgtttttaa atgtatttga atatgtatct  960
atctggtcgt tgtttaaata tcaaagtctt ctagtatctt ccggtgctaa tttatatgca  1020
agtggtagtg gaccacagca gacccaatca tttacttcac aagactggcc atttttatat  1080
tctcttttcc aagttaattc aaattatgtg ttaaatggat ttagtggtgc taggcttttct  1140
aataccttcc ctaatatagt tggtttacct ggttctacta caactcacgc attgcttgct  1200
gcaagggtta attacagtgg aggaatttcg tctggtgata taggtgcatc tccgtttaat  1260
caaaatttta attgtagcac atttctcccc ccattgttaa cgccatttgt taggagttgg  1320
ctagattcag gttcagatcg ggagggcgtt gccaccgtta caaattggca aacagaatcc  1380
tttgagacaa ctttagggtt aaggagtggt gcttttacag ctcgcggtat ttcaaactat  1440
ttcccagatt attttattcg taatatttct ggagttcctt tagttgttag aaatgaagat  1500
```

```
ttaagaagac cgttacacta taatgaaata agaaatatag caagtccttc aggaacacct  1560
ggtggagcac gagcttatat ggtatctgtg cataacagaa aaaataatat ccatgccgtt  1620
catgaaaatg gttctatgat tcatttagcg ccaaatgact atacaggatt tactatttcg  1680
ccgatacatg caactcaagt gaataatcaa acacgaacta ttatttctga aaaatttgga  1740
aatcaaggtg attccttaag gtttgaacaa aataacacga aagctcgtta tacgcttaga  1800
gggaatggaa atagttacaa tcttttattta agagtttctt caataggaaa ttccactatt  1860
cgagttacta taaacggtag ggtatatact gctacaaatg ttaatactac tacaaataac  1920
gatggagtta atgataacgg agctcgtttt tcagatatta atatcggtaa tgtagtagca  1980
agtagtaatt ctgatgtacc attagatata aatgtaacat taaactccgg tactcaattt  2040
gatcttatga atattatgct tgtaccaact aatatttcac cactttat            2088

SEQ ID NO: 134          moltype = AA  length = 696
FEATURE                 Location/Qualifiers
source                  1..696
                        mol_type = protein
                        organism = Bacillus thuringiensis
SEQUENCE: 134
MNTVLNNGRN TTCHAHNVVA HDPFSFEHKS LNTIEKEWKE WKRTDHSLYV APIVGTVGSF   60
LLKKVGSLVG KRILSELQNL IFPSGSIDLM QEILRATEQF INQRLNADTL GRVNAELAGL  120
QANVAEFNRQ VDNFLNPNQN PVPLAIIDSV NTLQQLFLSR LPQFQIQGYQ LLLLRLFAEL  180
AGLQANVEEF NRQVDNFLNP NRNAVPLSIT SSVNTMQQLF LNRLPQFMQ GYQLLLLPLF   240
AQAANLHLSF IRDVILNADE WGISAATLRT YRDYLRNFTR DYSNYCINTY QSAFRGLNTR  300
LHDMLEFRTY MFLNVFEYVS IWSLFKYQSL LVSSGANLYA SGSGPQQTQS FTSQDWPFLY  360
SLFQVNSNYV LNGFSGARLS NTFPNIVGLP GSTTTHALLA ARVNYSGGIS SGDIGASPFN  420
QNFNCSTFLP PLLTPFVRSW LDSGSDREGV ATVTNWQTES FETTLGLRSG AFTARGISNY  480
FPDYFIRNIS GVPLVVRNED LRRPLHYNEI RNIASPSGTP GDGARAYMVSV HNRKNNIHAV  540
HENGSMIHLA PNDYTGFTIS PIHATQVNNQ TRTFISEKFG NQGDSLRFEQ NNTTARYTLR  600
GNGNSYNLYL RVSSIGNSTI RVTINGRVYT ATNVNTTTNN DGVNDNGARF SDINIGNVVA  660
SSNSDVPLDI NVTLNSGTQF DLMNIMLVPT NISPLY                           696

SEQ ID NO: 135          moltype = DNA  length = 2013
FEATURE                 Location/Qualifiers
source                  1..2013
                        mol_type = other DNA
                        organism = Bacillus thuringiensis
SEQUENCE: 135
atggagatta ataatcagaa ccaatgtgtc cctataatt gtttgaataa tcctgaaagc    60
gagatattaa acgttgcaat ttttagtagc gaacaggtag cagaaattca cttaaagatc   120
acgcgcttaa tttagagaa ttttttacca ggtgggagtt ttgcattcgg cttatttgat   180
ttaatatggg ggattttaa tgaagatcaa tggagcgcat tcttccggca ggtagaagaa   240
ttaattaatc aaaggataac ggaattcgca agagggcaag caattcagag acttgtaggg   300
tttggaagga gttatgatga atatatttta gcactaaaag aatgggaaaa cgatcctgat   360
aacccagctt caaaggaaag agtgcgcact cgatttcgga caactgatga tgccttgcta   420
accggtgttc ctcttatggc aattccaggt tttgaattag ctactttatc tgtttatgct   480
caatcagcca atctacattt agccctatta agagatgctg tatttttgg ggagagatgg    540
ggattgacac aaacaaatat aaatgattta tatagtagat taaaaaactc cattcgtgat   600
tatacaaaatc attgtgttcg tttttataat ataggtttga ggaatttaaa tgttataaga   660
ccagagtatt accgtttcca agagaatta acaatatctg tcttagatct tgtagctctt   720
tttccaaatt acgatatccg aacatatcca atacccaact aaaagtcaatt aacaagagaa   780
atttatacag atccgattat ttcacctggt gcacaggcag ttatactct tcaagatgtt   840
ttgagagaac cacaccttat ggacttttta aaccgactta ttatttatac tggtgagtat   900
cgcggaattc gtcactgggc aggacatgaa gtagaatcta gtagaacagg tatgatgact   960
aatataagat ttcctttgta tgaacagcc gcaacagcag aaccaacacg atttataact   1020
cctagtactt ttcctggtct taatttattt tatagaacat tatcagctcc tattttaga   1080
gatgaaccgg gagctaatat tattatttaga tatagaacga gtttggtgga aggagtagga  1140
tttattcaac caaataacgg tgaacagctt tacagagtga gaggacatt agattctctt   1200
gatcaattac cacttgaggg tgagagtagt ctaactgaat atagtcatcg attatgccat   1260
gttagatttg cgcaatcatt gaggaatgca gaacctttag attatgcaag ggttccgatg   1320
ttttcttgga cacatcgtag tgcaaccct acaaataca ttgatccaga tgtcatcacc    1380
caaataccgt tagtaaaggc tttcaatctt cattcaggtg ccacggttgt tagaggacca   1440
ggatttacag gtggggatat ccttcgaaga acgaatactg gtacatttgg ggatatacga   1500
gtaaatatta atccaccatt tgcacaaaga tatcgcgtga ggattcgcta tgcttctact   1560
acagatttac aattccatac gtcaattaac ggtaaagcta ttaatcaagg taattttca    1620
gcaactatga atagaggaga ggactttagac tataaaacct ttagaactgt aggcttttacc   1680
actccattta gcttttcaga tgtacaaagt acattcacaa taggtgcttg gaacttctct   1740
tcaggtaacg aagtttatat agatcgaatt gaatttgttc cggtagaagt aacttatgag   1800
gcagaatatg attttgaaaa agcgcaagag aaggttactg cactgtttac atctacgaat   1860
ccaagaggat taaaaacaga tgtaaaggat tatcatattg ccaggatc aaatttagta     1920
gagtctctat cagatgaatt ctatcttgat gaaaagagaa attattcga gatagttaaa   1980
tacgcgaagc aaatccatat tgagcgtaac atg                                2013

SEQ ID NO: 136          moltype = AA  length = 671
FEATURE                 Location/Qualifiers
source                  1..671
                        mol_type = protein
                        organism = Bacillus thuringiensis
SEQUENCE: 136
MEINNQNQCV PYNCLNNPES EILNVAIFSS EQVAEIHLKI TRLILENFLP GGSFAFGLFD   60
LIWGIFNEDQ WSAFLRQVEE LINQRITEFA RGQAIQRLVG FGRSYDEYIL ALKEWENDPD  120
```

```
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAFNL HSGATVVRGP  480
GFTGGDILRR TNTGTFGDIR VNINPPFAQR YRVRIRYAST TDLQFHTSIN GKAINQGNFS  540
ATMNRGEDLD YKTFRTVGFT TPFSFSDVQS TFTIGAWNFS SGNEVYIDRI EFVPVEVTYE  600
AEYDFEKAQE KVTALFTSTN PRGLKTDVKD YHIDQVSNLV ESLSDEFYLD EKRELFEIVK  660
YAKQIHIERN M                                                      671

SEQ ID NO: 137          moltype = DNA  length = 378
FEATURE                 Location/Qualifiers
source                  1..378
                        mol_type = other DNA
                        organism = Bacillus thuringiensis
SEQUENCE: 137
atgacagtat ataatgcaac tttcaacatt aatttctata atgaagggga atgggggggg  60
ccggaacctt atggttatat aaaagcatat cttacaaatc cagatcatga ttttgaagtt  120
tggaaacaag atgattgggg ggaaagtaca cctgaaagaa attcttatac gcaaaccatt  180
aaaataagta gcgatactgg ttcccctata acccaaatgt gtttttatgg tgatgtgaaa  240
gaatacgatg tcggaaatgc agatgatatt cttgcttatc caagtcaaaa agtatgcagt  300
acacctggtg taacagtacg acttgatgga gatgagaaag gttcttatgt aacaattaaa  360
tattccttga ctccagca                                                378

SEQ ID NO: 138          moltype = AA  length = 126
FEATURE                 Location/Qualifiers
source                  1..126
                        mol_type = protein
                        organism = Bacillus thuringiensis
SEQUENCE: 138
MTVYNATFNI NFYNEGEWGG PEPYGYIKAY LTNPDHDFEV WKQDDWGEST PERNSYTQTI  60
KISSDTGSPI TQMCFYGDVK EYDVGNADDI LAYPSQKVCS TPGVTVRLDG DEKGSYVTIK  120
YSLTPA                                                            126

SEQ ID NO: 139          moltype = DNA  length = 1638
FEATURE                 Location/Qualifiers
source                  1..1638
                        mol_type = other DNA
                        organism = Bacillus thuringiensis
SEQUENCE: 139
atgactaaaa ggaaaaaata catgagattt ggcttgttca tattcagttg ttcagttgtt  60
ttgttcgtca gcggctgtaa aacacaacaa acagaagatc catcaacagc tggccctact  120
tcaagcaaaa tgaaacaggc aatcagcatg gagacaccag aggagagcta tttcaaaaaa  180
gaaaacaatt cttctcattt gtttgagttt gcttctcaat ttagaaaacc actggatctt  240
cccacggaag caatgatcaa ggatgaaacc aatcagctga gaatcgctta ccttgaagcc  300
acaacagtct ctcaaaatcg ggaaaataca gaatcaagaa gcaatctcac gaatcgcttc  360
gaagaaaacg aacaaaaagg tactctatcc aatatttcag caattccaga gagcgataat  420
cattggcaag gtccttacgt ccatgcaaat gctccattgc agatcttacc aagaggaaca  480
gcaattgatc cctttaccta ttttactgtt gttcaaggaa gtgatcccgt tccagtgatc  540
cattatacgc ccgtcgatcc taatgaatct ggctaccaag tgatgcagat cacagcaatt  600
gattcaaaag ggaaagtgag tgttgcgaca gtcacctttc tgtttaatca ctctccgatc  660
attcagcaag taagacaaag tcaccacatc acgattggtt caagtattga cttattagcg  720
ggcatttctg ctcatgatga agaagatggt gaattgacct cagaagttca agtacaaacc  780
acactccaaa cagaacaaga aggcagttat gaagtgattt attctgtgac tgatcaattt  840
ggagcaagta ccaagctgat aagtaatatg aggatcacca atgaagcacc aataatcgcg  900
gggccgaacc agctcgtttt acctgttgat caatcattct ctttatttga ttatttctcc  960
gcaaatgatc aagaagatgg tgcgatcaac cttacttcag acaatatctt ggcatccgat  1020
cttgtccctt atgtaccagg aaactacttc gtaagaattg ggaatgtcgt tgatcggtat  1080
ggcaaaagag cggcagagcg tacgatccgt gttcacttaa caaatgaagc gccgacgatt  1140
acaaatacgc acatgactct tcctgtattt agtgaactga ataaagaaag ctatctagca  1200
aaacttgttc ttgcagatcg tgaagatccg gttgagcaat tacatgtggc aatcgatctg  1260
cctttttggg agaaaatcga cacttcccga ttaaatacct atcgttttcc tcttcaagtc  1320
caagatacac atggagagat caccaaaacc tttgggagca tccaagtaat caatgaacca  1380
cctgtatttt ctgggataga ggataagaga atcattgtag gcgaagaaaa gccagattta  1440
ttagcaggga tctccgtttc ggatcgtgaa gagagtattg gaatagaaga tgttgagatc  1500
atagaagaaa tcgcttggga tacacctgga agctatcctg tttatttgac ggtcaaagat  1560
acatttacag aaacgacagt atcttttcat gtcattattc aagacaacaa tccagaaatg  1620
ccagagaaat tgagcgaa                                                1638

SEQ ID NO: 140          moltype = AA  length = 546
FEATURE                 Location/Qualifiers
source                  1..546
                        mol_type = protein
                        organism = Bacillus thuringiensis
SEQUENCE: 140
MTKRKKYMRF GLFIFSCSVV LFVSGCKTQQ TEDPSTAGPT SSKMKQAISM ETPEESYFKK  60
ENNSSHLFEF ASQFRKPLDL PTEAMIKDET NQLRIAYLEA TTVSQNRENT ESRSNLTNRF  120
EENEQKGTLS NISAIPESDN HWQGPYVHAN APLQILPRGT AIDPFTYFTV VQGSDPVPVI  180
```

```
HYTPVDPNES GYQVMQITAI DSKGKVSVAT VTFLFNHSPI IQQVRQSHHI TIGSSIDLLA    240
GISAHDEEDG ELTSEVQVQT TLQTEQEGSY EVIYSVTDQF GASTKLISNM RITNEAPIIA    300
GPNQLVLPVD QSFSLFDYFS ANDQEDGAIN LTSDNILASD LVPYVPGNYF VRIGNVVDRY    360
GKRAAERTIR VHLTNEAPTI TNTHMTLPVF SELNKESYLA KLVLADREDP VEQLHVAIDL    420
PFWEKIDTSR LNTYRFPLQV QDTHGEITKT FGSIQVINEP PVFSGIEDKR IIVGEEKPDL    480
LAGISVSDRE ESIGIEDVEI IEEIAWDTPG SYPVYLTVKD TFTETTVSFH VIIQDNNPEM    540
PEKLSE                                                              546

SEQ ID NO: 141          moltype = DNA  length = 1710
FEATURE                 Location/Qualifiers
source                  1..1710
                        mol_type = other DNA
                        organism = Bacillus thuringiensis
SEQUENCE: 141
atgtttacaa gtagtacgaa aaattcgttg aaaatagaaa cgacagatta tgaaatagat      60
caagtagcca attcgataga atttatgcca gatgaacaaa attccccaaa aaaaatgatg     120
ttatgggatg aagtaaaaca ggcaaaacaa cttagtcagt ctcgtaattt actccaaaat    180
ggagactttg gaggtttaac tggaaataat tggatactta aaaatgatat tatcatagaa    240
tccaatgatc ctatttttaa agggaagttt cttcagatgc gtggagcacg agacatatat    300
ggaaccatat ttccaactta tatctatcaa aaaatagagg aatccaaatt aagaccctat    360
acacgttatc gagtaagagg gtttgtggga agtagtaaag gtttgaaatt aatggtaaca    420
cgttactgga agaaattgaa taccattatg gatgttccca atgatttggc ctatatgtgg    480
cttatccctt catgtggaga ttatcgctgt gaatcatcat cccagtatat gggccaaggg    540
tattctaaac cagcaacaga tggatatact tctgataggt atgcttgccc gtcaaattca    600
ggtgaaaaac atgttatgtg tcacgatcgt catccatttg attttcgtat tgacactgga    660
gaattagata caaatacaaa cgtaggaatt gatgttttat ttaaaatatc taatccagat    720
ggatacgcta cattagggaa tttagaagtc attgaagaag gaccactaac agacgaagca    780
ttggcacatg tgaaacataa ggaaaagaaa tggaatcaac acctggagaa aaagcgaatg    840
gaaacacaac aggcctatga tccagcaaaa caagcattag gtgcattatt cacaaatgca    900
caaggtgaag agttacacta tcatactact ttaaatcaca ttcaaaacgc tgatcggctg    960
gtacagtcga ttcctatgt ataccatgat tggttaccgg atgctccagg tatgaactat   1020
gatttatata acaattcaaa gtcacgtata gaacaagcac gctatttata tgatgcacga   1080
aatgtcatca aaatggtga ctttacacaa ggactaacgg gatggcacgc aacaggaaag   1140
gcaacggtac aaaaactgga tggagcttct gtattagttc tgtcaaactg gagtgctggg   1200
gtatctcaga atctccatgc ccaagatcat catgggatata tgttacgtgt gattgccaaa   1260
aaagaaggac ctggaaaagg gtatgtaacg atgatggatt gtaacggcaa tcaggaaacg   1320
ctgaagttca cttcttgtga agaaggatat atgacaaaaa cagtagaggt attcccagaa   1380
ggcgaccgtg tacggattga aatggggaga accgaaggta catttatat acaaagcatt   1440
gagttgcttt gtatgaaagg gtatactagc aataataatc cgcacacggg taatatgtat   1500
gagcaaagtt ataatggaaa ttataatcaa aatactagcg atgtgtatca ccaagggtat   1560
acaaacaact ataacaaga ctctagtaat atgtataatc aaaattatac taacaatgat   1620
aacctgcatt ccggttgtac gtgtaaccaa ggtcataaca ataatgataa ccaaaactct   1680
ggctgtacat gtaatcaagg atataaccgt                                   1710

SEQ ID NO: 142          moltype = AA  length = 570
FEATURE                 Location/Qualifiers
source                  1..570
                        mol_type = protein
                        organism = Bacillus thuringiensis
SEQUENCE: 142
MFTSSTKNSL KIETTDYEID QVANSIEFMP DEQNSPKKMM LWDEVKQAKQ LSQSRNLLQN     60
GDFGGLTGNN WILKNDIIIE SNDPIFKGKF LQMRGARDIY GTIFPTYIYQ KIEESKLRPY    120
TRYRVRGFVG SSKGLKLMVT RYWKEIDTIM DVPNDLAYMQ LIPSCGDYRC ESSSQYMGQG    180
YSKPATDGYT SDRYACPSNS GEKHVMCHDR HPFDFRIDTG ELDTNTNVGI DVLFKISNPD    240
GYATLGNLEV IEEGPLTDEA LAHVKHKEKK WNQHLEKKRM ETQQAYDPAK QALGALFTNA    300
QGEELHYHTT LNHIQNADRL VQSIPYVYHD WLPDAPGMNY DLYNNSKSRI EQARYLYDAR    360
NVITNGDFTQ GLTGWHATGK ATVQKLDGAS VLVLSNWSAG VSQNLHAQDH HGYMLRVIAK    420
KEGPGKGYVT MMDCNGNQET LKFTSCEEGY MTKTVEVFPE GDRVRIEMGE TEGTFYIQSI    480
ELLCMKGYTS NNNPHTGNMY EQSYNGNYNQ NTSDVYHQGY TNNYKQDSSN MYNQNYTNND    540
NLHSGCTCNQ GHNNNDNQNS GCTCNQGYNR                                    570

SEQ ID NO: 143          moltype = DNA  length = 1737
FEATURE                 Location/Qualifiers
source                  1..1737
                        mol_type = other DNA
                        organism = Bacillus thuringiensis
SEQUENCE: 143
atgtatgcat tatgtttga aaaacagata aaacacctat taaaaaatta tcaagtaaga      60
attcgttatg cttcaaaagg cataaattca ttaatagtac gggggattg gctttcttat     120
gctaaacaat ctacagaaga tacatttcaa gatactcaac tttctaattt aacatacgaa    180
aatttccaat atataaatat aaataccaga ataaatataa atgatataac aacaagggat    240
tttcattata tattttaga aatcaaaacc ttaactccta ataatatgct tattattgat    300
aaaatcgaaa ttattccaat aactcaacaa tacctagaaa caagtgaaaa agaaaaagta    360
gaaacagttc aaaaaagcat caacaattta tttattaatc aacaaaaaca atatttaaaa    420
acagaaacga cggattatga aatagatcaa gtggcaattt ctataaaatg tatgtcagat    480
aaacagcaat atacccaaga aaatatgctt tggtgggatg aagtgaaaca tgccaaatat    540
ctcagtcatt ctcgtaatct acttcaaaat ggtgattttg aagatgtatt taatggctgg    600
actacaagta aaaatatatt cattcacaca gataattcaa cttttaaagg aaaatatcta    660
cacatgtatg gagcgcggga tattgacgga actttattcc caacatatat ataccagaaa    720
```

```
attgacgaat caaaattaaa accgtataca cgttatcaaa taagaggatt tgtgggaagt    780
agtaaggagc taaaattaat ggtaattcgt tatggaaaag aaatagatac catcatgaat    840
gtaccaaatg atataccata cgtaccttct atgctttctt gtaatgaatt atacaacagt    900
gaacaatcac tgtaccagaa gagaaatgtt gactattaca atcagatgcc agagtataca    960
tttaacactt atcagtgtat accagaccaa aaacaagcaa tctgtcatga ttctcatcaa   1020
ttcaagtttc atattgatat aggtgaagtg gattacaata caaatttagg aatgttagtt   1080
ttatttaaaa tttcttcacc tgatggttac gcaacattag gaatctaga agttattgaa    1140
gaaggaccta taacaggaga agcattagta cttgtaaaac aaaaggaaaa gaaatggaat   1200
caacacatgg agaaaaagcg aatggacaca aagcaagcct atgaccgac aaaggaggcg    1260
gtagatgcat tatttacagg agaagagtta aactataatg ttacattgtc tcagattaag   1320
aacgctgatc agttggttca gtcgattccg tatatacaca acatacaagg attacaagga    1380
tggcacgcag aagggaaagt agaaatacag caaatgaata gaatgtctgt attagtctta   1440
tccaattgga gttctggagt atctcaaaac ctgcatgtgc aacatcaaca tggatatgtg   1500
ttacgtgtga gtgcgaaaaa agaaggacct ggaaaaggat atgttacgat gatgggttgt   1560
aatggaaggc aggaaacact tatgtttacg ccctgtgacg gaggatatat gacaaaaact   1620
ttagaggtat tcctagatac ggatcgtata cgaatagaaa ttggagaaac cgaaggttcg   1680
ttttatatag aaagtataga gttgaattgt gtgaaaggct ataacaatga atacaat      1737

SEQ ID NO: 144           moltype = AA  length = 579
FEATURE                  Location/Qualifiers
source                   1..579
                         mol_type = protein
                         organism = Bacillus thuringiensis
SEQUENCE: 144
MYALCFEKQI KHLLKNYQVR IRYASKGINS LIVRGDWLSY AKQSTEDTFQ DTQLSNLTYE     60
NPQYININTR ININDITTRD FHYIFLENQT LTPNNMLIID KIEIIPITQQ YLETSEKEKV    120
ETVQKSINNL FINQQKQYLK TETTDYEIDQ VAISIKCMSD KQQYTQENML WWDEVKHAKY    180
LSHSRNLLQN GDFEDVFNGW TTSKNIFIHT DNSTFKGKYL HMYGARDIDG TLFPTYIYQK    240
IDESKLKPYT RYQIRGFVGS SKELKLMVIR YGKEIDTIMN VPNDIPYVPS MLSCNELYNS    300
EQSLYQKRNV DYYNQMPEYT FNTYQCIPDQ KQAICHDSHQ FKPHIDIGEV DYNTNLGMLV    360
LFKISSPDGY ATLGNLEVIE EGPITGEALV LVKQKEKKWN QHMEKKRMDT KQAYDRAKEA    420
VDALFTGEEL NYNVTLSQIK NADQLVQSIP YIHNIQGLQG WHAEGKVEIQ QMNRMSVLVL    480
SNWSSGVSQN LHVQHQGYV LRVSAKKEGP GKGYVTMMGC NGRQETLMFT PCDGGYMTKT    540
LEVFLDTDRI RIEIGETEGS FYIESIELNC VKGYNNEYN                          579

SEQ ID NO: 145           moltype = DNA  length = 2091
FEATURE                  Location/Qualifiers
source                   1..2091
                         mol_type = other DNA
                         organism = Bacillus thuringiensis
SEQUENCE: 145
atgaatggag gagagaatat gaatcaaaat aatcaaaatg aaatgcaaat aatagattct     60
tcatccaatg attttagtca atcaaacagg tatccaagat accattagc taaagagtca    120
aattataaag attggctagc tagttgtgat gaatcaaatg tagatacgct atcagctaca    180
agtgatgtaa agggttcagt ctccaggggtt ttgggtattg tgaatcagat tttgggttt    240
ctgggtcttg gatttattgg aacaggtctt ggtatactag gtgattatt taattcattt    300
tggccatcca ataatatgc ggtttgggag gcttttctac gtagtgttga agaactaatt    360
gatgaacgaa tacgtgaagc tgagaggtcc cgtatcgtac ccgaatttaa tggtttaaga    420
aacgttatgt tcaattataa tggtgctctt gaggattggg atagaaatcg tgaggatacc    480
gcacttcaaa gtgaagtaaa aagccgcttc gataatgcag atgatttttt tgcaaatcgt    540
attcctgtat ttgcaataga agggtttgaa gtacaatcgc tagctgtata tgcacaggct    600
gcaactcttc atttattatt ttaagggat gggttctta atgggctgct atggggacag    660
aatgccgata cggttaaccg taattataac aaattggtag aaaagagtgg tcaatataca    720
gatcattgta catcctttta taggcagggt ttgcaggagt taggaacag agggaattgg    780
aatgcattca atacttatcg cagaaacatg actcttcaag tattagatgt cattttttta    840
ttttcaaatt atgaccctcg catatataga aataatacaa acacacaact tacaagagaa    900
atatatactg aaccacttgc tgttcctgga tggcttaatt ctcattccaa tccaactcaa    960
ttccaacaaa tagaaaatga tcttattcgc tcaccttcag tgtttttctaa tctccagact  1020
cttttatgg aagctggtttt tgcattcttc caagccggta tagctaggca aacagtgtta  1080
agaacacgta cgtctagttt aaatacgggg cgtactgctg tcatcgtaac tccttggcaa  1140
ggtgcacctc atcctaatgt ttcacaacaa ctgcaggtgc aatttgaaaa taggaatgtt  1200
tttaatatca actcagtagt aggtagggaa atttctagtc aaaccggctt attatttggg  1260
gtccaacaag ccattttttaa ctttgtgtac gaaggcggaa acgcagcttc gacaacacaa  1320
ttcaatctac cgatttctgg acattcaaat tctataacat ctaatatacc aggaacaaca  1380
tcaacaactc caaccgcttc agattatact catagactat cttcgataac ttcaacttca  1440
gtaggaactt ggcagagaga taggacgaat attatggctt atggatggac acatgttagt  1500
gcagagcgta ctaataggat tataccgaat agaattacac aaattccggc tgtaaaagga  1560
tcactgttta gtgataatcc accaaacaca ttacgaacac gtgtagaaag tggccctggt  1620
catactgggg gcggactcgt tgttatgggc ggaggaacaa gtgtattaca gatgagaatc  1680
acttcttcag cacggcaaag gtatgatatg cgtttacgtt atctagctct tgctccagct  1740
gctgttgaag taagaattcc ggaattaggg gtgcatgtta ggtttcagat gccacagact  1800
gcaacgatgt tgcctgcgcc tctaccatac agccatttgc gatatgtgga tatcccgctg  1860
aggtttgaga cacccaatgg tgaaaatact tggacgtttg aactacggac tacgaatgca  1920
gcagttacaa ttgacagggt cgaattcata ccagttaatg ttacagctct agaatatgaa  1980
ggaaaacgac atctagaaaa agcaaagaaa gccgtgggtg atctgtttat caataatgaa  2040
aaagaggctt taaagtagag tacgacggat tatgatgtga atcaagctgc a            2091

SEQ ID NO: 146           moltype = AA  length = 697
FEATURE                  Location/Qualifiers
```

```
source                  1..697
                        mol_type = protein
                        organism = Bacillus thuringiensis
SEQUENCE: 146
MNGGENMNQN NQNEMQIIDS SSNDFSQSNR YPRYPLAKES NYKDWLASCD ESNVDTLSAT    60
SDVKGSVSRV LGIVNQILGF LGLGFIGTGL GILGDLFNSF WPSNNNAVWE AFLRSVEELI   120
DERIREAERS RIVAEFNGLR NVMFNYNGAL EDWDRNREDT ALQSEVKSRF DNADDFFANR   180
IPVFAIEGFE VQSLAVYAQA ATLHLLLLRD GVLNGLLWGQ NADTVNRNYN KLVEKSGQYT   240
DHCTSFYRQG LQELRNRGNW NAFNTYRRNM TLQVLDVISL FSNYDPRIYR NNTNTQLTRE   300
IYTEPLAVPG WLNSHSNPTQ FQQIENDLIR SPSVFSNLQT LFMEAGFAFF QAGIARQTVL   360
RTRTSSLNTG RTAVIVTPWQ GAPHPNVSQQ LQVQFENRNV FNINSVVGRE ISSQTGLLFG   420
VQQAIFNFVY EGGNAASTTQ FNLPISGHSN SITSNIPGTN STTPTASDYT HRLSSITSTS   480
VGTWQRDRTN IMAYGWTHVS AERTNRIIPN RITQIPAVKG SLFSDNPPNT LRTRVESGPG   540
HTGGGLVVMG GGTSVLQMRI TSSARQRYDM RLRYLALAPA AVEVRIPELG VHVRFQMPQT   600
ATMLPAPLPY SHLRYVDIPL RFETPNGENT WTFELRTTNA AVTIDRVEFI PVNATALEYE   660
GKRHLEKAKK AVGDLFINNG KEALKVDTTD YDVNQAA                            697

SEQ ID NO: 147          moltype = DNA  length = 915
FEATURE                 Location/Qualifiers
source                  1..915
                        mol_type = other DNA
                        organism = Bacillus thuringiensis
SEQUENCE: 147
atgacagtgg ttgattttaa tcaattaatt acagcgtacg ctcaaagtat ggcgagctcc    60
cccggtaatc aaggggttac atttacaggg caatatggat atatagaggt aggcgatcct   120
agtggggctc caccctttat agttagtaat gtcgtggcca atccagatac aaccacatat   180
aattttttcac ctggaagtag tgtattctca tcctctcaag ttgttcaaaa cagctccggat   240
gttccgataa cacaaagttt ggccttaggt caagccgtgc aagatagtaa ctctacgtca   300
acaacaaatg gccttagtac taattattct atcactacta aaagtacctt tacaattaaa   360
tttggtgtca cagatgggaa ctcgatttca gaagagattg atgctacatt cggtcaaaca   420
tttaattttta gtaccacaga ctccaataca caaacagagt cccaaaattg gaccgaaacg   480
acatccttta cggttcctcc ctactctcaa atgactgtat tatacactgt gttaggaggg   540
acttatagta tcaatacaac tttaacgtgt gagttacaag gatgcatttg gtttacctta   600
aattatccag gcataggtga tgtaaaagaa atagtgatta tctatttttgt cattgaaaat   660
gcgggtttaa atggcagtta tccaccacca ggtgatacgg gaacaccatt tagtatatca   720
gagcctggag aggttgcatt ttttggagga acgggtgaat ttacggggac acaaggcata   780
cagtcaattg ttacagcaac ttcatctccc ctacctggtt acccaggaca aacaaccaca   840
agtactacgc cattaacttc aattaattct gatggtactg tcaccccagc aagctcgcct   900
atccctattt atagt                                                    915

SEQ ID NO: 148          moltype = AA  length = 305
FEATURE                 Location/Qualifiers
source                  1..305
                        mol_type = protein
                        organism = Bacillus thuringiensis
SEQUENCE: 148
MTVVDFNQLI TAYAQSMASS PGNQGVTFTG QYGYIEVGDP SGAPPFIVSN VVANPDTTTY    60
NFSPGSSVFS SSQVVQNSSD VPITQSLALG QAVQDSNSTS TTNGLSTNYS ITTKSTFTIK   120
FGVTDGNSIS EEIDATFGQT FNFSTTDSNT QTESQNWTET TSFTVPPYSQ MTVLYTVLGG   180
TYSINTTLTC ELQGCIWFTL NYPGIGDVKE IVDIYFVIEN AGLNGSYPPP GDTGTPFSIS   240
EPGEVAFFGG TGEFTGTQGI QSIVTATSSP LPGYPGQTTT STTPLTSINS DGTVTPASSP   300
IPIYS                                                               305

SEQ ID NO: 149          moltype = DNA  length = 2373
FEATURE                 Location/Qualifiers
source                  1..2373
                        mol_type = other DNA
                        organism = Bacillus thuringiensis
SEQUENCE: 149
atgaacatga acaagaataa tactaaatta agcgcaagag ccttaccaag ttttattgat    60
tattttaatg gcatttatgg atttgcgatg ggtatcaaag acattatgaa catgattttt   120
aaaacggata caggtggtga tctaacccta gacgaaattt taagaatca gcagttacta   180
aatgatattt ctggtaaatt ggatggggtg aatggtagct taaatgatct tatcgcacag   240
ggaaacttaa atacagaatt atctaaggaa atattaaata ttgcaaatga acaaaatcaa   300
gttttaaatg atgttaataa caactcgat gcgataaaata cgatgctgca tatatatcta   360
cctaaaatta cctctatgtt aagtgatgta atgaaacaaa attatgcgct aagtgtgcaa   420
atagaatacc taagcaaaca attgcaagaa atttctgata agctggatat tattaacgta   480
aatgtactta ttaactctac acttactgaa attacacctg cgtatcaacg gattaaatat   540
gtgaacgaaa aatttgagga attaactttt gctacagaaa ctaatttaaa agtaaaaaag   600
gatggctctc ctgcagatat tcttgatgag ttaactgagt taactgaact agcgaaaagt   660
gtaacaaaaa atgatgtgga tggttttgaa ttttacctta atacattcca cgatgtaatg   720
gtaggaaata atttattcgg acgttcagct ttaaaaactg catcggaatt aattactaaa   780
gaaaatgtga aaacaagtgg cagtgaggtc ggaaatgttt taatttctt aattgtatta   840
acagctcgc aagcaaaagc atttcttact ttaacaacgt gccgaaaatt attaggctta   900
gcagatattg attatacttc tattatgaat gaacatttaa ataaggaaaa agaggaattt   960
agagtaaaca tccttcctac actttctaat acttttctta atcctaatta tgcaaaagtt  1020
aaaggaagtg atgaagatgc aaagatgatt gtggaagcta aaccaggaca tgcattggtt  1080
gggttttgaa ttagtaatga ttcaatcaca gtattaaaag tgtatgaggc taagctaaaa  1140
caaaattatc aagttgataa ggattcctta tctgaagtta tttatggtga tatggataaa  1200
```

-continued

```
ttattgtgtc cagatcaatc tgaacaagta tattatacaa ataacatagt atttccaaat    1260
gaatatgtaa ttactaaaat tgattttact aaaaaaatga aaactttaag atatgaggta    1320
acagcgaatt tttatgattc ttctacaggg aaaattgact aaataagac aaaagtagaa     1380
tcaagtgaag cggagtatag aacgttaagt gctaaagatg atggagtgta tatgccgtta    1440
ggtgtcatca gtgaaacatt tttgactccg attaatgggt ttggccttca agctgatgaa    1500
aattcaagat taattacttt aacatgtaaa tcatatttaa gagaggtatt attagcaaca    1560
gacttaagta ataaagaaac taaattaatt gtccctccta ttagttttat tagtaatatt    1620
gtagaaaatg ggaacttaga gggagaaaac ttagagccgt ggatagcaaa taacaaaaat    1680
gcgtatgttg atcatgcagg cggagtaaat ggaactaaag ttttatatgt tcataaggat    1740
ggtgagtttt cacaatttat tggaggtaag ttaaaatcga aaacagaata tgtaattcaa    1800
tatattgtaa aaggaaaagc atctatttat ttaaaagata aaaaaaatga gaattccatt    1860
tatgaagaaa aaaataatga tttagaagat tttcaaactg ttactaaacg ttttattaca    1920
ggagcggatt catcaggagt ttatttaata tttagcagtc aaaatggtga ggaagcattt    1980
gggggggaact ttattatttc agaaattaag tcatccgaaa agttattaag tccagagttg    2040
ataaaatcgg atgcttgggt tggatctcag ggaacttgga tctcaggaaa ttctctcaca    2100
atttatacta atacaaatgg aacttttcga caaaaccttc cgttagaaag ttattcaact    2160
tatagtatga actttaatgt aaatggatttt ggcaaggtga caataagaaa ttctcgtgaa    2220
gtattatttg aaaaaaacta tatgcagctt tcgcctaaag attttctga aaaattcaca    2280
actacagcca gcaataccgg attgtatgta gagctttcac gaggaacatc gagtggtaat    2340
ataaatttcc gagatttttc aattaagaat aga                                2373

SEQ ID NO: 150           moltype = AA   length = 791
FEATURE                  Location/Qualifiers
source                   1..791
                         mol_type = protein
                         organism = Bacillus thuringiensis
SEQUENCE: 150
MNMNKNNTKL SARALPSFID YFNGIYGFAM GIKDIMNMIF KTDTGGDLTL DEILKNQQLL     60
NDISGKLDGV NGSLNDLIAQ GNLNTELSKE ILKIANEQNQ VLNDVNNKLD AINTMLHIYL    120
PKITSMLSDV MKQNYALSVQ IEYLSKQLQE ISDKLDIINV NVLINSTLTE ITPAYQRIKY    180
VNEKFEELTF ATETNLKVKK DGSPADILDE LTELTELAKS VTKNDVDGFE FYLNTFHDVM    240
VGNNLFGRSA LKTASELITK ENVKTSGSEV GNVYNFLIVL TALQAKAFLT LTTCRKLLGL    300
ADIDYTSIMN EHLNKEKEEF RVNILPTLSN TFSNPNYAKV KGSDEDAKMI VEAKPGHALV    360
GFEISNDSIT VLKVYEAKLK QNYQVDKDSL SEVIYGDMDK LLCPDQSEQV YYTNNIVFPN    420
EYVITKIDFT KKMKTLRYEV TANFYDSSTG KIDLNKTKVE SSEAEYRTLS AKDDGVYMPL    480
GVISETFLTP INGFGLQADE NSRLITLTCK SYLREVLLAT DLSNKETKLI VPPISFISNI    540
VENGNLEGEN LEPWIANNKN AYVDHAGGIN GTKVLYVHKD GEFSQFIGGK LKSKTEYVIQ    600
YIVKGKASIY LKDKKNENSI YEEKNNDLED FQTVTKRFIT GADSSGVYLI FSSQNGEEAF    660
GGNFIISEIK SSEELLSPEL IKSDAWVGSQ GTWISGNSLT IYTNTNGTFR QNLPLESYST    720
YSMNFNVNGF GKVTIRNSRE VLFEKNYMQL SPKDFSEKFT TTASNTGLYV ELSRGTSSGN    780
INFRDFSIKN R                                                         791

SEQ ID NO: 151           moltype = DNA   length = 2364
FEATURE                  Location/Qualifiers
source                   1..2364
                         mol_type = other DNA
                         organism = Bacillus thuringiensis
SEQUENCE: 151
atgaacatga acaagaataa tactaaatta agcgcaagag ccttaccaag ttttattgat      60
tattttaatg gaatttatgg atttgccact ggcatcaaag acattatgaa catgattttt     120
aaaacggata caggtggtga tctaaccta gacgaaattt taaagaatca gcagttacta     180
aatgatattt ctggtaaatt ggatggggtg aatggtagct aaatgatct tatcgcacag     240
ggaaacttaa atacagaatt atctaaggaa atattaaaaa ttgcaaatga acaaaatcaa     300
gttttaaatg atgttaataa caaactcgat gcgataaata cgatgcttca tatatatcta     360
cctaaaatta catctatgtt aagcgatgta atgaagcaaa atatcgcaa agcctgcaa      420
atagaatacc taagtaaaca actgcaagaa atttctgata agctggatat tattaacgta     480
aatgtactta ttaactctac acttactgaa attcacacctg cgtatcaacg gattaaatat     540
gtgaacgaaa aatttgagga attaactttt gctacagaaa ctaatttaaa agtaaaaaag     600
gatggctctc ctgcagatat tcttgatgag ttaactgagt taactgaact agcgaaaagt     660
gtaacaaaaa atgatgtgga tggttttgaa ttttaccta atacattcca cgatgtaatg     720
gtaggaaata atttattcgg gcgttcagct ttaaaactg catcggaatt aattactaaa     780
gaaaatgtaa aacaagtgg cagtgaggtc ggaaatgttt ataacttctt aattgtatta     840
acagctctgc aagcaaaagc atttcttact ttaacaacat gccgaaaatt attaggctta     900
gcagatattg attatacttc tattatgaat gaacattaa ataaggaaaa agaggaattt     960
agagtaaaca tccttcctac acttttctaat acttttttcta atcctaatta tgcaaaagtt    1020
aaaggaagtg atgaagatgc aaagatgatt gtggaagcta aaccaggaca tgcattggtt    1080
gggtttgaaa ttagtaatga ttcaatgaca gtattaaaag tatatgaggc taagctaaaa    1140
caaaattatc aagttgataa ggattccta tcggaagtta tttatggtga tatggataaa    1200
ttattgtgcc caggtcaatc tgaacaaatt tattatacaa ataatagt atttccaaat      1260
gaatatgtaa ttactaaaat tgattttact aagaaaatga aactttaag atatgaggta     1320
acagctaatt cttatgattc ttctacagga gaaattgact aaataagaa gaaagtagca    1380
tcaagtgaag cggagtatag gacgttaagt gctaatgatg atggagtgta tatgccgtta    1440
ggtgtcataa gtgaaacatt tttgactccg attaatgggt ttggcctcca agctgatgaa    1500
aattcaagat taattacttt aacatgtaaa tcatatttaa gagaactact gctagcaaca    1560
gatttaagca ataaggaaac taattgatc gtcccaccaa atggtttat tagcaatatt     1620
gtagagaacg ggtccataga agaggacaat ttagagccgt ggaaagcaaa taataagaat    1680
gcttatgtag atcatacagg cggagtgaat ggaactaaag cattatatgt tcataaggac    1740
ggaggatttt cacaatttat tggagataag ttaaaccga aactgagta tgtaatccaa     1800
tatactgtta aaggaaaaacc ttctattcat ttaaaagatg aaaatactgg atatattcat    1860
```

-continued

```
tatgaagata caaataataa tttagaagat tatcaaacta ttactaaacg ttttactaca  1920
ggaactgatt taaagggagt gtatttaatt ttaaaaagtc aaaatggcaa tgaagttttt  1980
ggagataact ttattatctc agaaattagg cctttagaag agttattaag tccagaatta  2040
ataaaatcgg atgcttggat tcgatctcag ggtacttcgg gtagtggaaa ctctctcttt  2100
attagtaata atgcaaatgg aacctttaga caaaatctgt cgttagaaaa ctattcaact  2160
tatagtatga actttaatgt gaatgggttt ggcaaggtga cagtaagaaa ttatcgcgaa  2220
gtagtatttg aaaaaacata tcctcagtta acacctagag atatttcgga aaagttcaca  2280
acaaccaata atactggatt atatgtagaa ctttctcgtg gcacgggacc tgggtctata  2340
aatttccgtg acttttcaat taaa                                          2364

SEQ ID NO: 152          moltype = AA  length = 788
FEATURE                 Location/Qualifiers
source                  1..788
                        mol_type = protein
                        organism = Bacillus thuringiensis
SEQUENCE: 152
MNMNKNNTKL SARALPSFID YFNGIYGFAT GIKDIMNMIF KTDTGGDLTL DEILKNQQLL  60
NDISGKLDGV NGSLNDLIAQ GNLNTELSKE ILKIANEQNQ VLNDVNNKLD AINTMLHIYL  120
PKITSMLSDV MKQNYALSLQ IEYLSKQLQE ISDKLDIINV NVLINSTLTE ITPAYQRIKY  180
VNEKFEELTF ATETNLKVKK DGSPADILDE LTELTELAKS VTKNDVDGFE FYLNTFHDVM  240
VGNNLFGRSA LKTASELITK ENVKTSGSEV GNVYNFLIVL TALQAKAFLT LTTCRKLLGL  300
ADIDYTSIMN EHLNKEKEEF RVNILPTLSN TFSNPNYAKV KGSDEDAKMI VEAKPGHALV  360
GFEISNDSMT VLKVYEAKLK QNYQVDKDSL SEVIYGDMDK LLCPGQSEQI YYTNNIVFSN  420
EYVITKIDFT KKMKTLRYEV TANSYDSSTG EIDLNKKKVA SSEAEYRTLS ANDDGVYMPL  480
GVISETFLTP INGFGLQADE NSRLITLTCK SYLRELLLAT DLSNKETKLI VPPNGFISNI  540
VENGSIEEDN LEPWKANNKN AYVDHTGGVN GTKALYVHKD GGFSQFIGDK LKPKTEYVIQ  600
YTVKGKPSIH LKDENTGYIH YEDTNNNLED YQTITKRFTT GTDLKGVYLI LKSQNGNEVF  660
GDNFIISEIR PLEELLSPEL IKSDAWIRSQ GTSGSGNSLF ISNNANGTFR QNLSLENYST  720
YSMNFNVNGF GKVTVRNYRE VVFEKTYPQL TPRDISEKFT TTNNTGLYVE LSRGTGPGSI  780
NFRDFSIK                                                            788

SEQ ID NO: 153          moltype = DNA  length = 1869
FEATURE                 Location/Qualifiers
source                  1..1869
                        mol_type = other DNA
                        organism = Bacillus thuringiensis
SEQUENCE: 153
atgaataata tattgaataa cgaaagaact actatttgtg atgcgcataa tgtagtggct  60
catgatccat ttagttttga acataaatca gtagatacca tccaaaaaga atggacggaa  120
tggaagagaa ctgatcatag tttatacgta gctcctattg ttgggaccgt tgctagtttg  180
ctgctaaaga aagtggggag tcttattgga aaaaggatat tgagtgagtt atggggttta  240
atatttccta gtggtagtac aaatctaatg caagatattt taagagcgac agaacaattc  300
ataaatcaaa gacttaatgc agacactctc gctcgtataa atgcagaatt ggtagggctt  360
caatccaatg taagggagtt taatcaacaa gtagataatt ttttaaaccc tactcaaaac  420
cctgttcctt tatcaataac ttcttcagtt aatacaatgc agcaattatt tctaaataga  480
ttaccccagt tccagataca aggatacgag ctgttattat tacctttatt cgcacaagca  540
gccaatatgc atctttcttt tattagagat gttattctta atgcagatga atggggcatt  600
tcaccagcaa tgttacgtac atatcgagat tacctaaaaa gatatacaaa cgaatattcc  660
aattattgta taaatacgta tcgaactgaa tttgaagggt taaatgttcc tttaaaagat  720
atgttagaat ttagaaccta tatgttttta aatgtatttg aatatgtatc gatatggtcg  780
ctatttaaat accagagcct tctggtaact tctggcgcta acttgtatgt ttctggtaca  840
actgtaggtg caaatcaatc ttttactgca agaaattggc cgtttttaaa tactcttttc  900
caagttaatt caaattatat attgactgga tttagtggag ctagatttca atcaaccgta  960
ctcaattcat ttgttatcac attattggct gcacgtattc attacatggg aggagtctca  1020
tctggtaatt taggtccagc agctaactat aatgttggtt gtaatttatc atcccctata  1080
caattgccat atcgaacatc ttatttagac tcatttatat taagagatgg aaatcgaaca  1140
aatgaatatt ttacgggcgc ttttcttgca ttgatactac cttgtggtgt tactggacct  1200
actctgggtg cagctaactc tttcccaaat tattctatac ggaatatttc tggggctgtt  1260
ggctggttta gaaatgaaga tttaggaaga cctttacatt ttaatgaaat aagaaatata  1320
gaaggtcaac cgggagtagg tggtggaagt agaatctcta gtttagtatc tgtgcataac  1380
agaaaaaata atatcgtcgc tcatgaaaat ggtactatga ttcatttagc gccagatgat  1440
tatacaggat tcactatatc accgatacat gcaactcaag tgaataatca aacgcgaaca  1500
attatttctg aaaaatttgg aaatcaaggt gattccttaa ggtttgaaca aagcaacacg  1560
acagctcgtt atacgctag agggaatgga aatagttaca atctttattt aagagtatct  1620
tcaataggaa attccactat tcgggttact ataaacggta gagtttatac tgctacaaat  1680
gttaatacta ctacaaataa cgatggagta cttgataatg gagctcgttt ttcagatatt  1740
aatatcggta atgtagtggc aagtgctaat actaatgtac cattagatat aaatgtgaca  1800
tttaacgcca atacaccatt tgatcttatg aatattatgt ttgtaccaac taatcttcca  1860
ccagtttat                                                           1869

SEQ ID NO: 154          moltype = AA  length = 623
FEATURE                 Location/Qualifiers
source                  1..623
                        mol_type = protein
                        organism = Bacillus thuringiensis
SEQUENCE: 154
MNNILNNERT TICDAHNVVA HDPFSFEHKS VDTIQKEWTE WKRTDHSLYV APIVGTVASL  60
LLKKVGSLIG KRILSELWGL IFPSGSTNLM QDILRATEQF INQRLNADTL ARINAELVGL  120
QSNVREFNQQ VDNFLNPTQN PVPLSITSSV NTMQQLFLNR LPQFQIQGYE LLLLPLFAQA  180
```

```
ANMHLSFIRD VILNADEWGI SPAMLRTYRD YLKRYTNEYS NYCINTYRTE PEGLNVPLKD    240
MLEFRTYMFL NVFEYVSIWS LFKYQSLLVT SGANLYVSGT TVGANQSFTA RNWPFLNTLF    300
QVNSNYILTG FSGARFQSTV LNSFVITLLA ARIHYMGGVS SGNLGPAANY NVGCNLSSPI    360
QLPYRTSYLD SFILRDGNRT NEYFTGAFLA LILPCGVTGP TLGAANSFPN YSIRNISGAV    420
GWFRNEDLGR PLHFNEIRNI EGQPGVGGGS RISSLVSVHN RKNNIVAHEN GTMIHLAPDD    480
YTGFTISPIH ATQVNNQTRT IISEKFGNQG DSLRFEQSNT TARYTLRGNG NSYNLYLRVS    540
SIGNSTIRVT INGRVYTATN VNTTTNNDGV LDNGARFSDI NIGNVVASAN TNVPLDINVT    600
FNANTPFDLM NIMFVPTNLP PVY                                           623

SEQ ID NO: 155           moltype = DNA  length = 1941
FEATURE                  Location/Qualifiers
source                   1..1941
                         mol_type = other DNA
                         organism = Bacillus thuringiensis
SEQUENCE: 155
atgaattcga ataataaaac taaccctaat gtaataggca cttcatctga ccaatcttta     60
ttaaccaact ctgtaaaaaa accttcggca acgatcaaa gcaatccatt acaacatagg    120
gattctaatg attgtttgag tgtgtctgag ggaaataga attctctgaa ttatgatgtg    180
tttattagtg ccccaggtct agttgatact acagctaata ttacaagtgt tatactgagt    240
gctttaggtg ttccgatgtt agggactgtt gttaaattat atagtaaatt atttggtttt    300
ttatggggat caacgccagg acaagatcct tggaaagagc tgatggatcg agtggaaata    360
ctcattgatc agaaattaac agaatacgca agaagtaaga cattagcaga attggaagga    420
ttgcaaaatg ttatgaagtc ttatgtggat gcacttgaat catggcaaaa taattctcgg    480
aattcacaaa caagattatt agtacaacag agattggttg ttgcagattc gcaatttaaa    540
caggcaatgc cttcctttgc aattaaagat tatgaagttt cattattacc ggtatatgca    600
caagctgcaa atcttcattt acttttatta agagatagtc agatttttcgg aaaagattgg    660
ggaatgcctc aacatgaaat tgatctttt tataaagaac acttagagtg catgaaaaa    720
tattctgacc attgtgtgga atggtatcat actggcttaa ataaacttaa aggttcaact    780
gctaaggatt gggttgacta caatcgtttc cgaagagaaa tgacagtggc agttttagat    840
atcattgctt tacttcctaa tgatgta cacatgtatc caatgccaat acatgcagaa    900
cttacacggg aaattatac aaatccagtt gggagttatt tgccctacaa aggtaatttc    960
aaggatgtta tgtcttggta tgaaatgaaa agatatcgcc agcctacatt tcacgattta   1020
gaaagtttaa tccgaaagcc tagtcggttt acttggctaa agatcttaa gatgtataca   1080
aggaaaagac aaaattggga aatgagtat tataatatt gggtaggaca tcagttagag   1140
aaagcgttaa ttggtgaaa ataccctaaga gaaacaacaa ttagtggtga aattacaagt   1200
gaagaagata catttacttt tgaagattat gatattcata gggttttatg caattatata   1260
gggagatacg ataatagttt ggtggggta aaccaagtgg agtttcatta tctcgataac   1320
aatacacctc ggaagaagga atataaaaaa gatatttggg ttacgagtca atcacaaaaa   1380
ataattgact cagaagagga attacatagt catagattaa gttatgttga atcttttgat   1440
ttatattgga atcataacaa tgagaaagga gggacaatac ccgtatttgg ttggacacat   1500
catagtgtag cccctaaaaa tataattcat gaggataaga ttcagtaat ctcagctact   1560
aaagctaatg gttatttcac ttctgaagtt atacaaggtc ctggatattc aggagggat   1620
ttaataaaag gatctaatag catgggaaac attcaattaa ctccacctcg tgatgcactc   1680
aacaaaaagt atcgtttgag aattcgctat gccgctgatt cagatgattt acttacaatg   1740
acttttacct ctggtattgg accagttaaa tatcaaacgc tctataagc aacaatgaaa   1800
aaaggggatt ctttcaaata taattccttt caatatgtag aaaaagtagt acatatttcg   1860
tctggtataa acgcataaa attcagtaca ggaagtggtt ttacttgga taaggttgaa   1920
tttattccag tgaatgaaaa t                                             1941

SEQ ID NO: 156           moltype = AA  length = 647
FEATURE                  Location/Qualifiers
source                   1..647
                         mol_type = protein
                         organism = Bacillus thuringiensis
SEQUENCE: 156
MNSNNKTNPN VIGTSSDQSL LTNSVKKPSA NDQSNPLQHR DSNDCLSVSE GNRDSLNYDV     60
FISAPGLVDT TANITSVILS ALGVPMLGTV VKLYSKLFGF LWGSTPGQDP WKELMDRVEI    120
LIDQKLTEYA RSKALAELEG LQNVMKSYVD ALESWQNNSR NSQTRLLVQQ RLVVADSQFK    180
QAMPSFAIKD YEVSLLPVYA QAANLHLLLL RDSQIFGKDW GMPQHEIDLF YKEHLECIEK    240
YSDHCVEWYH TGLNKLKGST AKDWVDYNRF RREMTVAVLD IIALLPNYDV HMYPMPIHAE    300
LTREIYTNPV GSYLPYKGNF KDVMSWYEMK RYRQPTFHDL ESLIRKPSRF TWLKDLKMYT    360
RKRQNGKYEY YNYWVGHQLE KALIGEKYLR ETTISGEITS EEDTFTFEDY DIHRVLCNYI    420
GRYDNSLVGV NQVEPHYLDN NTPRKKEYKK DIWVTSQSQK IIDSEEELHS HRLSYVESFD    480
LYWNHNNEKG GTIPVFGWTH HSVAPKNIIH EDKITVISAT KANGYFTSEV IQGPGYSGGD    540
LIKGSNSMGN IQLTPPRDAL NKKYRLRIRY AADSDDLLTM TFTSGIGPVK YQTLYQATMK    600
KGDSFKYNSF QYVEKVVHIS SGINGIKFST GSGFYLDKVE FIPVNEN                 647

SEQ ID NO: 157           moltype = DNA  length = 1914
FEATURE                  Location/Qualifiers
source                   1..1914
                         mol_type = other DNA
                         organism = Bacillus thuringiensis
SEQUENCE: 157
atgaataatg tattgaatag cggaaaatct agtagttgtg atccttataa cgtagtggtt     60
catgatccat ttagttttca acataaatca ttagatacca tacaaaaaga atggacggag    120
tggaaaagaa cagatcatag tttatatgta gcccctattg tgggaactgt ggctagtttt    180
ctgttaaaga aagtagggag ccttgttgga aaaggataa tgagtgagtt acagaattta    240
atatttccta tggtgatgt aaattagtg gaagagattt taagaacgac agaacaattc    300
ctaaatcaaa gacttagtac agacaccttt gaacgtgtaa aagcagaatt ggaaggtctt    360
```

-continued

```
caaaggaatg tggaagagtt taatcgacaa gtagataatt ttttaaaccc taatcaaacc  420
cctgttcctt tagcgataat tgattcagtt aatacattgc agcaattatt tctaggtaga  480
ataccccagt ttcgactatc aggctacgag ctgttattat tacctttata tgcacaggtg  540
gctaacttac atctttcttt tattagagat gtcatcctta atgcagatga atggggaatt  600
acatctgaag caacattacg tacgtatcga ggttacctga aagattatac aaaagagtac  660
tctaatcatt gtataactac gtatcaaaat gcgtttagag gtttaaacac cagtttacac  720
gatatgttag aatttagaac ctatatgttt ttaaatgtat ttgaatatgt ctctatctgg  780
tcgttgttta aatatcaaag tcttctagta tcttccggcg ctaatttata tgcaagtggt  840
agttcaattg gtagtgtacc agagcggacc caaacatata cttcacaaga ctggccattt  900
ttaaattccc ttttccaagt taattcaaat tatatattat ctggttatag tggttttagg  960
ctttttgctg gtacccctaa tcctggtctt cctccaggct ctactacaat tcaagcattg  1020
cttggtgcaa gggttaatta tagtggaggg atttcgtctg gtgatatagg tacatctcca  1080
tttaatcaga attttaattg taacacatct ttgttaacac cttatgttag gagttggcta  1140
gattcaggtt cagatcggca gggccttaat acctctacaa attggcaaac agaatccttt  1200
gggacaactg caggctcatg gtgtggtgct tttacacctc gcggtaattc aaactatttc  1260
cctgattatt ttatccgtaa tatttctggc gttcctttag ttgttagaaa tgaagattta  1320
agaagaccgt tacactataa tgaaagaaga aatatatcaa gtcctccagg aacacctgtt  1380
ggaggaagag catatatggt atctgtgcat aacagaaaaa ataatatcta tgatactcat  1440
gaaaacggta ctatgattca tttggcgccg gaagattata caggatttac tatatcaccg  1500
atacatgcaa ctcaagtgaa tagtcaagct aatcaagcgc gaacatttat ttctgaaaaa  1560
tttggaaatc agggtgattc cttaagggtt gaacaaagca cctcaacggt tcaatacaca  1620
tttagaggga atggaaatag ttacaatctt tatttaagag tatcttcaat aggaagttcc  1680
actattcgag tttcaataaa cggtagagtt tatactgttc aaaatgttaa tactactaca  1740
aataatgatg gagtacttga taatggagct cgtttttcag atatttatat cggtaatgta  1800
gtggcaagtg ctaatactaa tgtaccatta aatataacac ctacatttaa caccggtaca  1860
caatttgagc ttatgaatat tatgtttgtg ccaactaata tcccaccact atat        1914

SEQ ID NO: 158          moltype = AA  length = 638
FEATURE                 Location/Qualifiers
source                  1..638
                        mol_type = protein
                        organism = Bacillus thuringiensis
SEQUENCE: 158
MNNVLNSGKS SSCDPYNVVV HDPFSFQHKS LDTIQKEWTE WKRTDHSLYV APIVGTVASF  60
LLKKVGSLVG KRIMSELQNL IFPNGDVNLV EEILRTTEQF LNQRLSTDTF ERVKAELEGL  120
QRNVEEFNRQ VDNFLNPNQT PVPLAIIDSV NTLQQLFLGR IPQFRLSGYE LLLLPLYAQV  180
ANLHLSFIRD VILNADEWGI TSEATLRTYR GYLKDYTKEY SNHCITTYQN AFRGLNTSLH  240
DMLEFRTYMF LNVFEYVSIW SLFKYQSLLV SSGANLYASG SSIGSVPERT QTYTSQDWPF  300
LNSLFQVNSN YILSGYSGFR LFAGTPNPGL PPGSTTIQAL LGARVNYSGG ISSGDIGTSP  360
FNQNFNCNTS LLTPYVRSWL DSGSDRQGLN TSTNWQTESF GTTAGSWCGA FTPRGNSNYF  420
PDYFIRNISG VPLVVRNEDL RRPLHYNERR NISSPPGTPV GGRAYMVSVH NRKNNIYDTH  480
ENGTMIHLAP EDYTGFTISP IHATQVNSQA NQARTFISEK FGNQGDSLRV EQSTSTVQYT  540
FRGNGNSYNL YLRVSSIGSS TIRVSINGRV YTVQNVNTTT NNDGVLDNGA RFSDIYIGNV  600
VASANTNVPL NITPTFNTGT QFELMNIMFV PTNIPPLY                          638

SEQ ID NO: 159          moltype = DNA  length = 2124
FEATURE                 Location/Qualifiers
source                  1..2124
                        mol_type = other DNA
                        organism = Bacillus thuringiensis
SEQUENCE: 159
atgaatcgaa ataatcaaaa tgaatatgaa gttattgatg ccccccattg tgggtgtccg  60
tcagaggatg ttgtaaaata tcctttgaca gatgattcga atgctggatt gcaaaatatg  120
aattataaag agtatttgaa tatgtctgag ggagattatg ctgattcaat tagatatcct  180
ttagccaata atccatattc atctgcttta aatttaaatt cttgtcaaaa tagtagtatt  240
ctcaactgga ttaacatatt aggaaatgca gcaaaagaag ccatatctat tgggacaaca  300
ataatctcta ttattacaac accttctctc actggattaa tttcaataac ttatgatctt  360
ataagtaaag tgctaggagg tagtagtggc ccatccatat cagatttgtc tatatgtgac  420
ttattatcta ttattgattt acggataagt caaagtgttt tgaatgatgg gattgctgat  480
tttaacggtt ctataatcat atataggaac tatttggaag cattagatag ctggaataag  540
aataatactc ctgctgctgc tgaagaggtc cgtgctcgtt ttagagccgc tgacacagaa  600
tttgatagaa ttttaacacg agggtcttta acaaatggtg gctcgttagc tagacaagat  660
ggccaaatat tattattacc ttcttttgca agtgctgcat atttccattt atcactattg  720
agagatgctg ctaggtatgg ggctaattgg gggctattca atgctacacc tcttataaat  780
tatcagtcaa aattagtaga acttattgaa tcatatacta attattgtgt acattggtat  840
aatcaaggtc ttaaccaact aaggcaacga ggtaatagtg ctacagcttg gttagaattt  900
catagatatc gtagagagat gacattgatg gtattagata tagtagcatc attttcaagt  960
cttgatatta ctagatatcc gatagaaaca gattttcagt tgagtagggt catttataca  1020
gatccaatcg gttttgtaaa tcgtggtaat cttaggctgg aaagctggtt cagctctgtt  1080
aataacgcta ctttttcagg gctagaaagt gcaataccta atcctagcca gtcttggttt  1140
ttaaatagta tgattatatc tactggttca cttacattgc cagttagccc aaatactgat  1200
agagcgaggg tgtggtatgg ggggcgagat cgagtttctc ctgctagttc acaatttatt  1260
actgaacaaa tgtctgggca acagacggct gatacccaaa atattttagg gcgaaatata  1320
tttagaatag attctcaagc atgtaattta aataatacca cttatggagt taatagggct  1380
ttattttatc atgatgctag tcagggttct caaagatctt tatatgaagg ttttattaga  1440
acaacaggga tagataatcc tgttgttcag aatattaaca cttatttccc tggagaaaat  1500
tcagatatcc caactccaca agactatact catatattaa gtagaacaat aaatttaaca  1560
gggggactta gacaagtagc atctggtcgt cgttcttctc tagtaatgta tggttggaca  1620
cataagagcc tgactcttaa caataccatt aatccagata gaattacaca gataccgttg  1680
```

-continued

```
acaaagctag atagccgggg ttcaaatatt tcttatgtga acgatccagg atttataggc    1740
ggaaatctac tcagaatgac ggccaatggt acacttggaa cattaagggc aaatttccca    1800
cttaacatta gatcacattt tcgcattaga gtccgttatg ctgctacaag aaatattcga    1860
ttgagtgtaa atggaagttt cggtactatt tctcaggaat ttcctagtac aatgagattg    1920
ggagaggatt taagatacgg ttcctttgct ataagaagat ttagtacatc tgttagaccg    1980
actgcaagtc ctgacgtaat ccgattgaca gtagagccaa ttttctctgg gcaacagatt    2040
tatgtagaca gaattgagtt cgtcccagtt attcccacaa gagaagcgga agagaattta    2100
gacgcagcga agaaagcggt ggcg                                           2124

SEQ ID NO: 160          moltype = AA  length = 708
FEATURE                 Location/Qualifiers
source                  1..708
                        mol_type = protein
                        organism = Bacillus thuringiensis
SEQUENCE: 160
MNRNNQNEYE VIDAPHCGCP SEDVVKYPLT DDSNAGLQNM NYKEYLNMSE GDYADSIRYP    60
LANNPYSSAL NLNSCQNSSI LNWINILGNA AKEAISIGTT IISIITTPSL TGLISITYDL    120
ISKVLGGSSG PSISDLSICD LLSIIDLRIS QSVLNDGIAD FNGSIIIYRN YLEALDSWNK    180
NNTPAAAEEV RARFRAADTE FDRILTRGSL TNGGSLARQD GQILLLPSFA SAAYFHLSLL    240
RDAARYGANW GLFNATPLIN YQSKLVELIE SYTNYCVHWY NQGLNQLRQR GNSATAWLEF    300
HRYRREMTLM VLDIVASFSS LDITRYPIET DFQLSRVIYT DPIGFVNRGN LRLESWFSSV    360
NNATFSGLES AIPNPSQSWF LNSMIISTGS LTLPVSPNTD RARVWYGGRD RVSPASSQFI    420
TEQMSGQQTA DTQNILGRNI FRIDSQACNL NNTTYGVNRA LFYHDASQGS QRSLYEGFIR    480
TTGIDNPVVQ NINTYFPGEN SDIPTPQDYT HILSRTINLT GGLRQVASGR RSSLVMYGWT    540
HKSLTLNNTI NPDRITQIPL TKLDSRGSNI SYVNDPGFIG GNLLRMTANG TLGTLRANFP    600
LNIRSHFRIR VRYAATRNIR LSVNGSFGTI SQEFPSTMRL GEDLRYGSFA IREFSTSVRP    660
TASPDVIRLT VEPIFSGQQI YVDRIEFVPV IPTREAEENL DAAKKAVA                708

SEQ ID NO: 161          moltype = DNA  length = 1656
FEATURE                 Location/Qualifiers
source                  1..1656
                        mol_type = other DNA
                        organism = Bacillus thuringiensis
SEQUENCE: 161
atgaattcta atctatcat cgaaaaagag gtacaagaga atcaatatat tgatattcgt     60
aacatttgta gcataaatgg ttctgctaaa tttgatccta atactaacat tacaaccttg    120
acagaagcta taaatactca agcaggtgcg attgctggaa aaactgcctt agatatgaga    180
cgtgatttta ctctcgtagc agatatatac ctagggtcta aaggcagtgg ggctgatggt    240
attgctataa cgtttcatag aggatcaatt ggtttttatcg gtactatggg cggaggatta    300
ggaattctag gagcacccaa cgggatagga tttgaaatag atacgtattg gaaagcatct    360
tcagatgaag caggggattc catttgggcat ggtcaaatga atggaccaca tgcaggtttt    420
gtgagtacaa atcgaaatgc aagctattta acagcctag ctcctatgaa aagaatagct    480
ccacctaatg gtcaatggag ggtgttaact attaagtggg atgcgcgtaa caacaaacta    540
acagcaagtc ttcaagagaa aagcaacgat gatcctacta gatctgctac accaagatat    600
caaacatggg agttattaaa tcctgcattt gatttaaatc agaaatatac ttttgttatt    660
ggctcagcta caggggctgc taataacaag catcagatcg gagttacttt gtttgaagca    720
cactttacaa aaccaactat agaggcaaac cctgttgata ttgaactagg tacagcgttt    780
gatccattaa actatgagcc aattggactc aaggcaacag atgaagtaga tggagatata    840
acaaaggaca tcacggtaga atttaatgac gtagatacat ccaaaccagg tgcataccgt    900
gtaacatata agtaataaa tagttatgga aaagtgatg agaaaacaat aggagtcgta    960
gtatacgaa aaccaactat aactgcacat gatgtcgcga ttaagaaaga cttagcattt    1020
gatccattaa aatatgaacc aattggactc aaagcaacag atccaattga tggagatata    1080
acagataaaa ttactgtaaa atttaataat gtcgatacct cgaaaccagg taataccat    1140
gtaacatata agtgataaa tagttatgaa aaaattgatg aaaaacaat gccgttacg    1200
gtacctgtta ttgatgatgg gtgggagaat ggcgatccga caggatggaa attcttctct    1260
ggtgaaacca ttactctaga agaagatgaa gagaatgctc ttaatgaaa atgggtattt    1320
tatgctgata acatgtagc aatatacaaa caagtagagt tgaagaataa tacccttat    1380
caaattacag tatatgttaa accagaagat gaaggaactg tggcacacca tattgttaaa    1440
gtatcttca aatcggattc tgctggtcaa gaaagtgaag agattctaaa tgaaagatta    1500
attgatgcag aacagataca aaaaggatac agaaagttaa caagtattcc atttacacca    1560
acaacaattg ttcccaacaa aaaaccagtg ataattgttg aaaactttt accaggatgg    1620
ataggtggag ttagaatcat tgtagagcct acaaag                              1656

SEQ ID NO: 162          moltype = AA  length = 552
FEATURE                 Location/Qualifiers
source                  1..552
                        mol_type = protein
                        organism = Bacillus thuringiensis
SEQUENCE: 162
MNSKSIIEKE VQENQYIDIR NICSINGSAK FDPNTNITTL TEAINTQAGA IAGKTALDMR    60
RDFTLVADIY LGSKGSGADG IAIAFHRGSI GFIGTMGGGL GILGAPNGIG FEIDTYWKAS    120
SDEAGDSFGH GQMNGPHAGF VSTNRNASYL TALAPMKRIA PPNGQWRVLT IKWDARNNKL    180
TASLQEKSND DPTRSATPRY QTWELLNPAF DLNQKYTFVI GSATGAANNK HQIGVTLFEA    240
HFTKPTIEAN PVDIELGTAF DPLNYEPIGL KATDEVDGDI TKDITVEFND VDTSKPGAYR    300
VTYKVINSYG ESDEKTIGVV VYTKPTITAH DVAIKKDLAF DPLKYEPIGL KATDPIDGDI    360
TDKITVKFNN VDTSKPGKYH VTYKVINSYE KIDEKTIAVT VPVIDDGWEN GDPTGWKFFS    420
GETITLEEDE ENALNGKWVF YADKHVAIYK QVELKNNTPY QITVYVKPED EGTVAHHIVK    480
VSFKSDSAGQ ESEEILNERL IDAEQIQKGY RKLTSIPFTP TTIVPNKKPV IIVENFLPGW    540
IGGVRIIVEP TK                                                         552
```

| SEQ ID NO: 163 | moltype = DNA  length = 1902 |
|---|---|
| FEATURE | Location/Qualifiers |
| source | 1..1902 |
| | mol_type = other DNA |
| | organism = Bacillus thuringiensis |

SEQUENCE: 163

```
atgaatagtg tattgaatag cggaagaact accactcgtg atgcgtataa tgtagtggct   60
catgatccat ttagttttca acacaaatca ttagatacca tacaaaaaga atggacggag  120
tggaaaaaaa ataatcatag tttatatgta gatcctattg ttggaactgt ggctagtttt  180
ctgttaaaga aagtgggaag tcttattgga aaaaggatac taagtgagtt acggaattta  240
atatttccta gtggcagtac aaatctaatg caagatattt taagagagac agaaaaattc  300
ctgaatcaaa gacttaatac agacactctt gcccgtgtaa atgcggaatt gacagggatg  360
caagcaaatg tagaagagtt taatcgacaa gtagataatt ttttgaaccc taaccgaaca  420
gctgttcctt tatcaataac ttcttcagtt aatacaatgc agcaattatt tctaaaatga  480
ttaccccagt tccagatgca aggataccaa ctgttattat tacctttatt tgcacaggca  540
gccaatttac atctttcttt tattagagat gttattctta atgcagatga atggggaatt  600
tcagcagcaa cattacgtac gtatcgagat tacctgaaaa attatacaag agattactct  660
aactattgta taaatacgta tcaaagtgcg tttagaggtt taaacaccag tttacacgat  720
atgttagaat ttagaaccta tatgttttta aatgtatttg aatatgtctc tatctggtcg  780
ttgtttaaat atcaaagtct tctagtatct tccggcgcta atttatatgc aagtggtagt  840
tcaattggta gtgtaccaga gcggacccaa acatatactt cacaagactg gccatttta   900
aattccctt  tccaagttaa ttcaaattat gtattatctg gttatagtgg tgctagaatt  960
tttattacta gccctaatat tggtctacct cctggcacta ctacaactca agcattgctt 1020
ggtgcaaggg ttaattatag tggagggatt cgtctggtg atataggtac atctccattt 1080
aatcagaatt ttaattgtaa cacatctttg ttaaccactt atgttaggag ttggctagat 1140
tcaggttcag atcggcaggg ccttaatacc tctacaaatt ggcaaacaga atcctttggg 1200
acaactgcag gctcatggtg tggtgctttt acacctcgcg gtaattcaaa ctattttccct 1260
gattatttta tccgtaatat ttctggcgtt cctttagttg ttagaaatga agagttaaga 1320
agaccgttac actataatga aagaagaaat atatcaagtc cttcaggaac acctgttgga 1380
gcacgagctt atatggtatc tgtgcataac agaaaaaata tatttatac cgttcatgaa 1440
aatggtacta tgattcattt agcgccagat gattatacag gattcactat atcaccgata 1500
catgcaagtc aagtgaataa tcaaacgcga acatttattt ctgaaaagtt tggaaatcaa 1560
ggtgattcgt taaggtttga acaaagcaac acgacagctc gttatacgct tagagggaat 1620
ggaaatagtt acaatcttta tttaagagta tcttcaatag gaaattccac tattcgagtt 1680
actataaacg gtagagttta tactgcttta aatgttaata ctactacaaa taacgatgga 1740
gttaatgata atggagctcg ttttttcgat attaatatcg gtaatgtagt agcaagtagt 1800
aatactgatg taccattaga tgtaaatata acattaaact ccggcactca atttgatctt 1860
atgaatatta tgtttgtgcc aactaatatt tcaccacttt at                    1902
```

| SEQ ID NO: 164 | moltype = AA  length = 634 |
|---|---|
| FEATURE | Location/Qualifiers |
| source | 1..634 |
| | mol_type = protein |
| | organism = Bacillus thuringiensis |

SEQUENCE: 164

```
MNSVLNSGRT TTRDAYNVVA HDPFSFQHKS LDTIQKEWTE WKKNNHSLYV DPIVGTVASF   60
LLKKVGSLIG KRILSELRNL IFPSGSTNLM QDILRETEKF LNQRLNTDTL ARVNAELTGM  120
QANVEEFNRQ VDNFLNPNRN AVPLSITSSV NTMQQLFLNR LPQFQMQGYQ LLLLPLFAQA  180
ANLHLSFIRD VILNADEWGI SAATLRTYRD YLKNYTRDYS NYCINTYQSA FRGLNTSLHD  240
MLEFRTYMFL NVFEYVSIWS LFKYQSLLVS SGANLYASGS SIGSVPERTQ TYTSQDWPFL  300
NSLFQVNSNY VLSGYSGARI FITSPNIGLP PGTTTTQALL GARVNYSGGI SSGDIGTSPF  360
NQNFNCNTSL LTPYVRSWLD SGSDRQGLNT STNWQTESFG TTAGSWCGAF TPRGNSYFP   420
DYFIRNISGV PLVVRNEELR RPLHYNERRN ISSPSGTPVG ARAYMVSVHN RKNNIYTVHE  480
NGTMIHLAPD DYTGFTISPI HASQVNNQTR TFISEKFGNQ GDSLRFEQSN TTARYTLRGN  540
GNSYNLYLRV SSIGNSTIRV TINGRVYTAL NVNTTTNNDG VNDNGARFSD INIGNVVASS  600
NTDVPLDVNI TLNSGTQFDL MNIMFVPTNI SPLY                              634
```

| SEQ ID NO: 165 | moltype = DNA  length = 1914 |
|---|---|
| FEATURE | Location/Qualifiers |
| source | 1..1914 |
| | mol_type = other DNA |
| | organism = Bacillus thuringiensis |

SEQUENCE: 165

```
atgaataatg tattgaatag cggaaaatct agtagttgtg atccttataa cgtagtggtt   60
catgatccat ttagttttca acataaatca ttagatacca tacaaaaaga atggacggag  120
tggaaaagaa cagatcatag tttatatgta gcccctattg tgggaactgt ggctagtttt  180
ctgttaaaga aagtagggag ccttgttgga aaaaggataa tgagtgagtt acagaattta  240
atatttccta atggtgatgt aaatttagtg gaacgatcta taagacgac agaacaattc  300
ctaaatcaaa gacttagtac agacaccttt gaacgtgtaa aagcagaatt ggaaggtctt  360
caaaggaatg tggaagagtt taatcgacaa gtagataatt tttaaaaccc taatcaaacc  420
cctgttcctt tagcgataat tgattcagtt aatacattgc agcaattatt tctaggtaga  480
atacccagt ttcgactatc aggctacgag ctgttattat tacctttata tgcacaggtg  540
gctaacttac atctttcttt tattagagat gtcatcctta atgcagatga atggggaatt  600
acatctgaag caacattacg tacgtatcga ggttacctga agattatac aaaagagtac  660
tctaatcatt gtaaactac gtatcaaaat gcgtttagag gtttaaacac cagtttacac  720
gatatgttaa aatttagaac ctatatgttt ttaaatgtat tgaatatgt ctctatctgg  780
tcgttgttta aatatcaaag tcttctagta tcttccggcg ctaatttata tgcaagtggt  840
agttcaattg gtagtgtacc agagcggacc caaacatata cttcacaaga ctggccatttt 900
```

```
ttaaattccc ttttccaagt taattcaaat tatatattat ctggttatag tggttttagg  960
ctttttgctg gtacccctaa tcctggtctt cctccaggct ctactacaat tcaagcattg  1020
cttggtgcaa gggttaatta tagtggaggg atttcgtctg gtgatatagg tacatctcca  1080
tttaatcaga attttaattg taacacatct ttgttaacac cttatgttag gagttggcta  1140
gattcaggtt cagatcggca gggcgctaat acctctacaa attggcaaac ggaagcattt  1200
cagacaactg atggccggag ttgtggtgct tttggagctc gtggtaattc gaactttttc  1260
cctgattatt ttatccgtaa tatttctggc gttcctttag ttgttagaaa tgaagattta  1320
agaagaccgt tacactataa tgaaagaaga aatatatcaa gtcctccagg aacacctgtt  1380
ggaggaagag catatatggt atctgtgcat aacagaaaaa ataatatcta tgatactcat  1440
gaaaacggta ctatgattca tttggcgccg gaagattata caggatttac tatatcaccg  1500
atacatgcaa ctcaagtgaa tagtcaagct aatcaagcgc gaacatttat ttctgaaaaa  1560
tttggaaatc agggtgattc cttaagggtt gaacaaagca cctcaacggt tcaatacaca  1620
tttagaggga atggaaatag ttacaatctt tatttaagag tatcttcaat aggaagttcc  1680
actattcgag tttcaataaa cggtagagtt tatactgttc aaaatgttaa tactactaca  1740
aataatgatg gagtacttga taatggagct cgtttttcag atatttatat cggtaatgta  1800
gtggcaagtg ctaatactaa tgtaccatta aatataacac ctacatttaa caccggtaca  1860
caatttgagc ttatgaatat tatgtttgtg ccaactaata tcccaccact atat        1914

SEQ ID NO: 166          moltype = AA  length = 638
FEATURE                 Location/Qualifiers
source                  1..638
                        mol_type = protein
                        organism = Bacillus thuringiensis
SEQUENCE: 166
MNNVLNSGKS SSCDPYNVVV HDPFSFQHKS LDTIQKEWTE WKRTDHSLYV APIVGTVASF  60
LLKKVGSLVG KRIMSELQNL IFPNGDVNLV EEILRTTEQF LNQRLSTDTF ERVKAELEGL  120
QRNVEEFNRQ VDNFLNPNQT PVPLAIIDSV NTLQQLFLGR IPQFRLSGYE LLLLPLYAQV  180
ANLHLSFIRD VILNADEWGI TSEATLRTYR GYLKDYTKEY SNHCITTYQN APRGLNTSLH  240
DMLEFRTYMF LNVFEYVSIW SLFKYQSLLV SSGANLYASG SSIGSVPERT QTYTSQDWPF  300
LNSLFQVNSN YILSGYSGFR LFAGTPNPGL PPGSTTIQAL LGARVNYSGG ISSGDIGTSP  360
FNQNFNCNTS LLTPYVRSWL DSGSDRQGAN TSTNWQTEAF QTTDGRSCGA FGARGNSNFF  420
PDYFIRNISG VPLVVRNEDL RRPLHYNERR NISSPPGTPV GGRAYMVSVH NRKNNIYDTH  480
ENGTMIHLAP EDYTGFTISP IHATQVNSQA NQARTFISEK FGNQGDSLRV EQSTSTVQYT  540
FRGNGNSYNL YLRVSSIGSS TIRVSINGRV YTVQNVNTTT NNDGVLDNGA RFSDIYIGNV  600
VASANTNVPL NITPTFNTGT QFELMNIMFV PTNIPPLY                          638

SEQ ID NO: 167          moltype = DNA  length = 1902
FEATURE                 Location/Qualifiers
source                  1..1902
                        mol_type = other DNA
                        organism = Bacillus thuringiensis
SEQUENCE: 167
atgaatagtg tattgaatag cggaagaact accactcgtg atgcgtataa tgtagtggct  60
catgatccat ttagttttca acacaaatca ttagatacca tacaaaaaga atggacggag  120
tggaaaaaaa ataatcatag tttatatgta gatcctattg ttggaactgt ggctagtttt  180
ctgttaaaga aagtgggaag tcttattgga aaaaggatac taagtgagtt acggaattta  240
atatttccta gtggcagtac aaatctaatg caagatattt taagagagac agaaaaattc  300
ctgaatcaaa gacttaatac agacactctt gcccgtgtaa atgcggaatt gacagggatg  360
caagcaaatg tagaagagtt taatcgacaa gtagataatt ttttgaaccc taaccgaaac  420
gctgttcctt tatcaataac ttcttcagtt aatacaatgc agcaattatt tctaaataga  480
ttaccccagt tccagatgca aggataccaa ctgttattat taccttttatt tgcacaggca  540
gccaatttac atctttcttt tattagagat gttattctta atgcagatga atggggaatt  600
tcagcagcaa cattacgtac gtatcgagat tacctgaaaa attatacaag agattactct  660
aactattgta taaatacgta tcaaagtgcg tttagaggtt taaacaccag tttacacgat  720
atgttagaat ttagaaccta tatgttttta aatgtatttg aatatgtctc tatctggtcg  780
ttgtttaaat atcaaagtct tctagtatct tccggcgcta atttatatgc aagtggtagt  840
tcaattggta gtgtaccaga gcggacccaa acatatactt cacaagactg gccattttta  900
aattcccttt tccaagttaa ttcaaattat atattatctg gttatagtgg ttttaggctt  960
tttgctggta cccctaatcc tggtcttcct ccaggctcta ctacaattca agcattgctt  1020
ggtgcaaggg ttaattatag tggagggatt tcgtctggtg atataggtac atctccattt  1080
aatcagaatt ttaattgtaa cacatctttg ttaacacctt atgttaggag ttggctagat  1140
tcaggttcag atcggcaggg ccttaatacc tctacaaatt ggcaaacaga atcctttggg  1200
acaactgcag gctcatggtg tggtgctttt acacctcgcg gtaattcaaa ctatttccct  1260
gattatttta tccgtaatat ttctggcgtt cctttagttg ttagaaatga agagttaaga  1320
agaccgttac actataatga aagaagaaat atatcaagtc cttcaggaac acctgttgga  1380
gcacgagctt atatggtatc tgtgcataac agaaaaaata atatttatac cgttcatgaa  1440
aatggtacta tgattcattt agcgccagat gattatacag gattcactat atcaccgata  1500
catgcaagtc aagtgaataa tcaaacgcga acatttattt ctgaaaagtt tggaaatcaa  1560
ggtgattcgt taaggtttga acaaagcaac acgacagctc gttatacgct tagagggaat  1620
ggaaatagtt acaatcttta tttaagagta tcttcaatag gaaattccac tattcgagtt  1680
actataaacg gtagagttta tactgcttta aatgttaata ctactacaaa taacgatgga  1740
gttaatgata atggagctcg tttttcagat attaatatcg gtaatgtagt agcaagtagt  1800
aatactgatg taccattaga tgtaaatata acattaaact ccggcactca atttgatctt  1860
atgaatatta tgtttgtgcc aactaatatt tcaccacttt at                    1902

SEQ ID NO: 168          moltype = AA  length = 634
FEATURE                 Location/Qualifiers
source                  1..634
                        mol_type = protein
```

```
                        organism = Bacillus thuringiensis
SEQUENCE: 168
MNSVLNSGRT TTRDAYNVVA HDPFSFQHKS LDTIQKEWTE WKKNNHSLYV DPIVGTVASF  60
LLKKVGSLIG KRILSELRNL IFPSGSTNLM QDILRETEKF LNQRLNTDTL ARVNAELTGM  120
QANVEEFNRQ VDNFLNPNRN AVPLSITSSV NTMQQLFLNR LPQFQMQGYQ LLLLPLFAQA  180
ANLHLSFIRD VILNADEWGI SAATLRTYRD YLKNYTRDYS NYCINTYQSA FRGLNTSLHD  240
MLEFRTYMFL NVFEYVSIWS LFKYQSLLVS SGANLYASGS SIGSVPERTQ TYTSQDWPFL  300
NSLFQVNSNY ILSGYSGFRL FAGTPNPGLP PGSTTIQALL GARVNYSGGI SSGDIGTSPF  360
NQNFNCNTSL LTPYVRSWLD SGSDRQGLNT STNWQTESFG TTAGSWCGAF TPRGNSNYFP  420
DYFIRNISGV PLVVRNEELR RPLHYNERRN ISSPSGTPVG ARAYMVSVHN RKNNIYTVHE  480
NGTMIHLAPD DYTGFTISPI HASQVNNQTR TFISEKFGNQ GDSLRFEQSN TTARYTLRGN  540
GNSYNLYLRV SSIGNSTIRV TINGRVYTAL NVNTTTNNDG VNDNGARFSD INIGNVVASS  600
NTDVPLDVNI TLNSGTQFDL MNIMFVPTNI SPLY                             634

SEQ ID NO: 169          moltype = DNA  length = 1803
FEATURE                 Location/Qualifiers
source                  1..1803
                        mol_type = other DNA
                        organism = Bacillus thuringiensis
SEQUENCE: 169
atgaataaaa aaatgggtaa aagcatagta ctttcagaat ggatgcggaa aatacctgat  60
tcatggacat tagcccaaat gtctatccca ggaacccatg atagcggtac ttttaagtta  120
aaagatccta taaaagtaac atgggcaaag acacaagacc gtgaatttga tcaacaaatg  180
caaatgggtg tgagattttt tgatattaga gggcgtgtaa ctgatgacaa tacaattgtt  240
ctacaccacg gttcaatata tctttatgta acccttcatc aatttattaa tactgctaaa  300
agatttttaa aagatcatcc aagtgaaacg attattatgt cactaaaaga agaatataaa  360
gcaatgccag gagcgaaaga tacattcgta gatacgtttg aaaatagata ctttaaagac  420
tctatctttt taaaaaagga gggaaatata acaatgggag atgctcgcgg gaaaattgta  480
ctactaagaa gatacgcggg cggtaagatg acagggggtt ataggaattt tggatgggct  540
gataacaaaa catttacttc tactacaaat ggaaatataa aagtaactgt gcaagaccaa  600
tacgatgtta aaaaagatgt aaagaaagat gcaattaaca acatgttaat tgctacagca  660
gccaatgatc ttgatcctaa tcacatccat attaacttta caagtttatc ttctggtggt  720
acagcatgga gtagtccctt ttattttgcc tctcatttaa atagttggac tgcggaaatt  780
gtgaagaaat caggaagaaa agcaggctgg gttattatgg attatgttgg agatgagtgg  840
aatccgaagc tatattggga cgtaatagat actaacttta acctcccaaa tagatataaa  900
ataaaaacag ccttaaacgg tacaagcggt gttgatgttt cagtcaatcg agatcaatat  960
ggtaatagga aagtacattt gtataatgat aatttaacta aaagacatca atgggatctt  1020
cagcatgata gcaattataa agcatttcaa atacatagtg ttgaggaacc tactaaagtt  1080
ttggcctgga atggtaatat ggattcaaaa aatgtattta ttacaaaaaa tgagtataaa  1140
gaagaatact attggacatt agaagatgta ggaaatggtt actatattat aaaaaacttc  1200
aaaaatccta atcttgtatt ggatgttaaa ggcggtaaaa caaataacga taccccctatt  1260
caagtgtatg aaagaaatga aacaaatgct caaaagttca aactaagcca agtaatcata  1320
caaggtgtat ataaaataaa aacagcttta aatggtacaa gtggtgttga tgtttctagc  1380
gctggagata aaaatgtaca tttgtatcgg gacaattctg ttacaagatc tcactggaag  1440
tttcattata ataaaaataa agacgcctat cagatcgtca acatatactt tgaaaacgaa  1500
gtaatggcct ggaatgatta taagggaaca aaaaatgtat ttgttacaaa aaatcagcat  1560
aaagatgaac attattggag attagaggat gtagggaatg gttattatgt tataaaaaat  1620
ttaaaagatt cagaatttgt gttggatatt gaatggagta atacaaatga ctttacaaat  1680
attcaggtgc ataaaaggaa tgaaacagat gctcaaaagt ttaaattagt taaagtagat  1740
gtagatttag caacattata tcatcagcaa aatccattag agcaagaatt tgaaaataaa  1800
tta                                                                1803

SEQ ID NO: 170          moltype = AA  length = 601
FEATURE                 Location/Qualifiers
source                  1..601
                        mol_type = protein
                        organism = Bacillus thuringiensis
SEQUENCE: 170
MNKKMGKSIV LSEWMRKIPD SWTLAQMSIP GTHDSGTFKL KDPIKVTWAK TQDREFDQQM  60
QMGVRFFDIR GRVTDDNTIV LHHGSIYLYV TLHQFINTAK RFLKDHPSET IIMSLKEEYK  120
AMPGAKDTFV DTFENRYFKD SIFLKKEGNI TMGDARGKIV LLRRYAGGKM TGGYRNFGWA  180
DNKTFTSTTN GNIKVTVQDQ YDVKKDVKKD AINNMLIATA ANDLDPNHIH INFTSLSSGG  240
TAWSSPFYFA SHLNSWTAEI VKKSGRKAGW VIMDYVGDEW NPKLYWDVID TNFNLPNRYK  300
IKTALNGTSG VDVSVNRDQY GNRKVHLYND NLTKRHQWDL QHDSNYKAFQ IHSVEEPTKV  360
LAWNGNMDSK NVFITKNEYK EEYYWTLEDV GNGYYIIKNF KNPNLVLDVK GGKTNNDTPI  420
QVYERNETNA QKFKLSQVII QGVYKIKTAL NGTSGVDVSS AGDKNVHLYR DNSVTRSHWK  480
FHYNKNKDAY QIVNIYFENE VMAWNDYKGT KNVFVTKNQH KDEHYWRLED VGNGYYVIKN  540
LKDSEFVLDI EWSNTNDFTN IQVHKRNETD AQKFKLVKVD VDLATLYHQQ NPLEQEFENK  600
L                                                                  601

SEQ ID NO: 171          moltype = DNA  length = 999
FEATURE                 Location/Qualifiers
source                  1..999
                        mol_type = other DNA
                        organism = Bacillus thuringiensis
SEQUENCE: 171
atgtaccaaa tgaaaaataa taaaaaatta ggaaaaaaat tattagctct tagtgcaatc  60
gcatctatgg gagtaacgta tgctactata tctccagaat tggcaagtgc tgctcaactt  120
gatacaattc aaaaaacttc gcccattaat gaattcatag gtgaaacaaa agcaatacaa  180
```

```
                    gactggcaaa ctcctttgac tgaagctgaa cttgtttatg gaaagcattt agatagtcag    240
                    cgaaaatata aattttcgaa cggcgatgct aatcataata tgagggatat taagtttcat    300
                    agtaatgcag tatcaccaga tggtccacct aactttactg atgtagggga tgtatttgta    360
                    ggacacgcaa ctttaaacaa cgatcttgat gaaaaatag atttaaaaac agatagtttc     420
                    tcaagaacgc ttacagattc tgttactact tctaccacac atgggtttaa gattggagag    480
                    aaaacaagtg gtaaaatatc ttttcccata ggagaaatgt cgcaggaaat ctctctagaa    540
                    tataattttt ctactacgga tagtcaaaca aatacagata gtaggactta tacaattcct    600
                    tcacaaacta ttcctgtcaa accccattct tctgttgaag taattgtcat gttaaaagga    660
                    agtaaggcta cagggaatgt aaatctctta actaaaatgt caggaagagt tgtaaattgg    720
                    aatcacagtt attatccttt acctggtgaa cagtatggta aggcttatgt acatagtggt    780
                    tctatcgcta gtatggttaa gtatgcaaaa aacttcgaga aacttccaaa tttatctgtg    840
                    aacttagatg atacaatcaa tttaattggt aaaggtactt atgaagctga atttggtaca    900
                    gaatattcgg taactgtaaa accaattgat aaaaagggaa aatatacggg ggaagattac    960
                    acatataccg ttaagccaga agttacaaaa gcagaagcg                           999

SEQ ID NO: 172          moltype = AA  length = 333
FEATURE                 Location/Qualifiers
source                  1..333
                        mol_type = protein
                        organism = Bacillus thuringiensis
SEQUENCE: 172
MYQMKNNKKL GKKLLALSAI ASMGVTYATI SPELASAAQL DTIQKTSPIN EFIGETKAIQ     60
DWQTPLTEAE LVYGKHLDSQ RKYKFSNGDA NHNMRDIKFH SNAVSPDGPP NFTDVGDVFV    120
GHATLNNDLD EKIDLKTDSF SRTLTDSVTT STTHGFKIGE KTSGKISFPI GEMSQEISLE    180
YNFSTTDSQT NTDSRTYTIP SQTIPVKPHS SVEVIVMLKR SKATGNVNLL TKMSGRVVNW    240
NHSYYPLPGE QYGKAYVHSG SIASMVKYAK NFEKLPNLSV NLDDTINLIG KGTYEAEFGT    300
EYSVTVKPID KKGKYTGEDY TYTVKPEVTK AEA                                 333

SEQ ID NO: 173          moltype = DNA  length = 2172
FEATURE                 Location/Qualifiers
source                  1..2172
                        mol_type = other DNA
                        organism = Bacillus thuringiensis
SEQUENCE: 173
atgaattcaa ataatcaaaa tgaatataat gcttcatcta ctacttctgt atccaatgat     60
tctaacagat acccttttgc gaatgagccc acaaatgcgt tacaaaatat gaattataag    120
gattatttaa gaatatctga gggttatgat agtgaatatt tgggtacacc tgaagtgctt    180
attagtgagc aagatgcggt taagaaagca atcagtctgt taggtacaat attgaggagt    240
ttaggggtcc cattcgtggg accgattgtg agcctatata gtacacttat tgatgtttta    300
tggccaggtg gaaagagtca atgggaaatt tttatggaac aagtagaagc actcattaat    360
caaaaaatag cagaacacgt aaggaataga gcgctagcag atttagaggg tttagggaat    420
aactaccaat tatatttaac agcacttgaa gaatggcagg aaaatccaag cagtacaaga    480
gtcttacgag atgttcggaa tcgatttgaa atccttagaa gtttatttac acaatttatg    540
cctttctttc gggaaaagga ttatgaagta ccattactta cagtatatgc gcaggcagct    600
aaccttcatt tactgttatt aaaggatgct tcgattttg gagaagaatg gggattctct    660
acaaccgcta ttaataacta ttataatcgt caaatgagtc ttatcgcgca atattctgat    720
cattgtgtac aatggtatag aactgggtta gatcgattaa aaggatcgaa cgctaaacaa    780
tgggttgcat ataaccgctt ccgaagagaa atgacattaa cggtgttaga tattatgacg    840
ttatttccaa tgtatgacac acgcacgtac ccaatcgaaa cgaaagcaca actaacaagg    900
gaagtatata cagatccaat tggtgcaata ggaccgcaag catcttggta tgactcagca    960
ccttcgttca atactctgga aagtactttt ataagaggaa agcatctatt tgattttata   1020
actagactaa atatatatac agggagaagt ttatgggatg ctagtcatta cttaaaaaaa   1080
tggatagggc atcaaaatatc ctctcaacct ataggcggca gtatacaaac tcaaacctat   1140
ggcactacga gtggcagttc tgttattgct acgcagcaaa ttggctttac aggttatgac   1200
gtttataaga ctttatcaac agcggggggtt ctgtttgctt atacttcgaa atattatgc   1260
gtatctaaag ttgttttga tgcgatatat cctgacaaca agtataaaac aacattcact   1320
tataatcctg gatctgaagg tattgcagcg caagaaaagg attcagaagt tgaattgcca   1380
ccagaaacat tagatcaacc caattatgag gcgtatagcc ataagttgaa ttatgttaca   1440
tttattgaaa atccaggtgt accagtattt tcttggacac accggagtgc ggatcgtacg   1500
aatacagttt attcagataa aatcactcaa ataccagttg taaaggccag tgacggccct   1560
aaaccttccg ctaacgaagt tggacactat cttggtggag atccaatatc atttaactct   1620
tctggtagca ctggagtgat aaggttaaat ataaattcac cattatccca aaaataccgt   1680
gtgagaattc gctattgctc ttcagttgat tttgacttat atgtagttcg tggagacact   1740
actgtaaata atggtagatt taacaaaagc gcgcctaagtc tcggatggga aagtttgaag   1800
tatgaaaatt ttaaatttgc tagcttttct cacaccttta catttaatca agctcaagat   1860
acattaaaaa taagtgtagg gaattttagt tcaatcgtag ggggcagcac agtttatata   1920
gaccgaatcg agctcatccc agtaaatgca acttatgagg cagaacaaga tttagattcg   1980
gcaaagaaag cagtgaatac cttgtttacg aatacaaaag atggtttacg accaggggta   2040
acagattatg aagtgaatca agcggcaaac ttagtggaat gccatcggaa tgatttgtat   2100
ccaaatgaaa aacgcttgtt atttgatgca gtcagagagg caaaacgact cattcaggta   2160
cgcaactcgc tt                                                        2172

SEQ ID NO: 174          moltype = AA  length = 724
FEATURE                 Location/Qualifiers
source                  1..724
                        mol_type = protein
                        organism = Bacillus thuringiensis
SEQUENCE: 174
MNSNNQNEYN ASSTTSVSND SNRYPFANEP TNALQNMNYK DYLRISEGYD SEYLGTPEVL     60
```

```
ISEQDAVKKA ISLLGTILGG LGVPFVGPIV SLYSTLIDVL WPGGKSQWEI FMEQVEALIN    120
QKIAEHVRNR ALADLEGLGN NYQLYLTALE EWQENPSSTR VLRDVRNRFE ILDSLFTQFM    180
PSFREKDYEV PLLTVYAQAA NLHLLLLKDA SIFGEEWGFS TTAINNYYNR QMSLIAQYSD    240
HCVQWYRTGL DRLKGSNAKQ WVAYNRFRRE MTLTVLDIMT LFPMYDTRTY PIETKAQLTR    300
EVYTDPIGAI GPQASWYDSA PSFNTLESTF IRGKHLFDFI TRLNIYTGRS LWDASHYLKK    360
WIGHQISSQP IGGSIQTQTY GTTSGSSVIA TQQIGFTGYD VYKTLSTAGV LFAYTSKYYG    420
VSKVVFDAIY PDNKYKTTFT YNPGSEGIAA QEKDSEVELP PETLDQPNYE AYSHKLNYVT    480
FIENPGVPVF SWTHRSADRT NTVYSDKITQ IPVVKASDGP KPSANEVGHY LGGDPISFNS    540
SGSTGVIRLN INSPLSQKYR VRIRYCSSVD FDLYVVRGDT TVNNGRFNKS APSVGWQSLK    600
YENFKFASFS TPFTFNQAQD TLKISVGNFS SIVGGSTVYI DRIELIPVNA TYEAEQDLDS    660
AKKAVNTLFT NTKDGLRPGV TDYEVNQAAN LVECLSDDLY PNEKRLLFDA VREAKRLIQV    720
RNSL                                                                724

SEQ ID NO: 175           moltype = DNA  length = 2037
FEATURE                  Location/Qualifiers
source                   1..2037
                         mol_type = other DNA
                         organism = Bacillus thuringiensis
SEQUENCE: 175
atgaattcat atcaaaatac aaatgaatat gagatattgg atgcttcacc aagctattct     60
aacatgacga atagttatcc aaggtaccca ctagcaaata tcgacaagg ttcaatgaaa    120
aatacgaact ataaagattg gttagctatg tgtgaaggaa atgcggaagg attttttttta   180
actgatgaac aaatggtttc tattgttggg gctgcgattt caaaacttct tggatttgtc    240
cctgtagttg gagatatttt aagtttcttg gcggatacgt attggccaaa aattgcagga    300
caagagccca atacaagagt ttgggcagga ttgataagac atacagcaaa tctaatagat    360
aataggaaag ctgatagagt aataggcaa gcaactgcta atttaatgtc actctacgga    420
gctttaggtg tatataacag atttcttgag caatggaaat cgcctgtaaa gccgtatgcc    480
ggccttgctg atgaagtacg agcacagatg agtactcttc acattctatt tacgacaaaa    540
attattagtg atttcacgat acagggttat gaatccatat tactaccttc atacgcaagt    600
gccgcgaatc tgcacttact actattgcgc gatattgcaa tttatgggaa aagtttaggt    660
tttgatccac aggttctgca agcatatcat aatgaacaag tgaaatttac aacagattat    720
acggctcatt gtataaagac gtacaattta actttaaatg cacaaaaatc aaaaggttgg    780
gtagctttca atcaatatcg tagggatatg actttgacag tactagattt aattgcatta    840
tttccaagtt atgatacgca tagatatcct gtagatgaaa aaaatgtaaa aaaactatca    900
aaaacagaac ttacaagaga aatttataca gcactaacga aatcttatcc tagtaaaaca    960
gtagaagaaa tggaaaaatc tcttacaaga gattctcatt tattcacttg gccaaagaga   1020
ttagatttct ggaccttaa ttataatatg tacccagata caagatactt atctgctaat   1080
agaattggtt tttcatatac aaattcttct aaaataggag atagtggaat ttatggaagc   1140
actacttttg gcacagtact tactcgtcaa attccgctta attctaatgt ttatagaact   1200
tctatcacag atactacatt agtccctaat caagttacaa aaatggatt ctacaaaatt   1260
gatggcacta tgaatcctta taattcaaat ataacgccag ttcctgttaa tttaagaacc   1320
acatttttg gattctcatc agatgcgagc agaccccta atcaaccaac tgtacaagat   1380
tataataata ttttaagtta tataaaact gatttttag gaggtcacca gggaagggtt   1440
tcatttgctt ggacacatag aggtgttgac cctaagaatc aaatactcac agataatgtc   1500
acacaagttc cagctgtaaa atctagttta ttaaatgcac cagctaaagt aattaaaggt   1560
ccgggtcata caggaggaga tttagttgct cttctaaaca atggtactca agccggtaca   1620
atgcaaatcc aatgtaacac aggtagcttt actgaaactt ccagacgtta tggtatacgg   1680
atgcgttatg ctgcaaataa tgcatttaca gtgagtctat catatacatt acaggggggg   1740
aatccaatag gtacaacatt tgttacagaa cgtacatttt caagaactaa taatataata   1800
ccaacagatt taaaatacga ggagtttaaa tataaagagt ataatcaaat tattacaatg   1860
acttcacctc aaaatacaat agtaactata aatattcgac aactaaatcc gtcttcaaat   1920
gatcaattaa ttattgacag aattgaattt attccgataa ctcaatcggt attagattat   1980
actgtgaaac aaaatttaga aaccgcacag gaagtggtag acaatctatt cataaat      2037

SEQ ID NO: 176           moltype = AA  length = 679
FEATURE                  Location/Qualifiers
source                   1..679
                         mol_type = protein
                         organism = Bacillus thuringiensis
SEQUENCE: 176
MNSYQNTNEY EILDASPSYS NMTNSYPRYP LANNRQGSMK NTNYKDWLAM CEGNAEGFFL     60
TDEQMVSIVG AAISKLLGFV PVVGDILSFL ADTYWPKIAG QEPDTRVWAG LIRHTANLID    120
NREADRVIGQ ATANLMSLYG ALGVYNRFLE QWKSPVKPYA GLADEVRAQM STLHILFTTK    180
IISDFTIQGY ESILLPSYAS AANLHLLLLR DIAIYGKSLG FDPQVLQAYH NEQVKFTTDY    240
TAHCIKTYNL TLNAQKSKGW VAFNQYRRDM TLTVLDLIAL FPSYDTHRYP VDEKNVKKLS    300
KTELTREIYT ALTESYPSKT VEEMEKSLTR DSHLFTWPKR LDFWTFNYNM YPDTRYLSAN    360
RIGFSYTNSS KIEDSGIYGS TTFGTVLTRQ IPLNSNVYRT SITDTTLVPN QVTKMDFYKI    420
DGTNESYNSN ITPVPVNLRT TFFGFSSDAS RPPNQPTVQD YNNILSYIKT DPIGGHQGRV    480
SFAWTHRGVD PKNQILTDNV TQVPAVKSSL LNAPAKVIKG PGHTGGDLVA LLNNGTQAGT    540
MQIQCNTGSF TETSRRYGIR MRYAANNAFT VSLSYTLQGG NPIGTTFVTE RTFSRTNNII    600
PTDLKYEEFK YKEYNQIITM TSPQNTIVTI NIRQLNPSSN DQLIIDRIEF IPITQSVLDY    660
TVEQNLETAQ EVVDNLFIN                                                 679

SEQ ID NO: 177           moltype = DNA  length = 1137
FEATURE                  Location/Qualifiers
source                   1..1137
                         mol_type = other DNA
                         organism = Bacillus thuringiensis
SEQUENCE: 177
```

```
atgaaattac tatcaaagaa aatcctgaca gggttactcg taggagcaac gagtctatct    60
atctgggctc ctgcaagtga agcggctcca gagaataatc gatattattc tattaatttg   120
aaagctaatc aaaacttagt ttgggatgga tggcaattta gtaatggtgc tcagattctt   180
ttatatggtg caaaccaggg tgacaatcaa caatttgtat tttttccact tgatggagga   240
ttatatgcaa ttgtaagtaa agagagtgga agacctgtat catttggaga tactaatgat   300
tacaatgcta atgacatatt gatggaatat ggttggactg gtaacgctcg tcaaaaatgg   360
tatttacgag acaagggaag taattattat gaaattgtaa accaagaaaa tgggaaagtt   420
gcatcttatg cgcggagggg gctagggcca gccgggacgg agtatgtaga tttagatcaa   480
ccaaatgcgt ctgatccaga taaggtattt tacattgcta attctcgaag tggtttctca   540
ttaccaactt taccagctat aggaactaga ccaaatgctc cagagtataa tcctactgga   600
ggtattgatc aacaattacc tcaaatttca aattctgttg ttgtgggggc atctttaata   660
ccttgtatta tggtaaagga taatcaagca agtgattata caaaaatca caattccaca    720
tattatacttt tggaaaaaga agaatattgg gataaaacat tttcagcggt tattccagct   780
ggtttgactc gtaattatac atttaaaaca ggtatttctt ctgtgatca acaaaagatg    840
actgatacgc tttctatgaa gattggagca gatttgggat tgaaatttgg agaaacaact   900
gcagcactta aaacagagat tacaaaaaca ctacaaactg aaattagtac aactaatacg   960
gaagcaacgg aagaaacaat ttcaagtact gttacaagcg aacctggtaa aacaacagga  1020
tttacagaat atcagctggc aacaaaatat acgttaaaga gagcagatgg tacagttgtt  1080
tcagatcctt ggattgtaaa aaacaacaag ataacagtag caagaaaaaa acaaata     1137

SEQ ID NO: 178          moltype = AA  length = 379
FEATURE                 Location/Qualifiers
source                  1..379
                        mol_type = protein
                        organism = Bacillus thuringiensis
SEQUENCE: 178
MKLLSKKILT GLLVGATSLS IWAPASEAAP ENNRYYSINL KANQNLVWDG WQFSNGAQIL    60
LYGANQGDNQ QFVFFPLDGG LYAIVSKESG RPVAFGDTND YNANDILMEY GWTGNARQKW   120
YLRDKGSNYY EIVNQENGKV ASYARRGLGP AGTEYVDLDQ PNASDPDKVF YIANSRSGFS   180
LPTLPAIGTR PNAPEYNPTG GIDQQLPQIS NSVVVGASLI PCIMVKDNQA SDYTKIHNSP   240
YYTLEKEEYW DKTFSAVIPA GLTRNYTFKT GISSVDQQKM TDTLSMKIGA DLGLKFGETT   300
AALKTEITKT LQTEISTTNT EATEETISST VTSEPGKTTG FTEYQLATKY TLKRADGTVV   360
SDPWIVKNNK ITVARKKQI                                                379

SEQ ID NO: 179          moltype = DNA  length = 1143
FEATURE                 Location/Qualifiers
source                  1..1143
                        mol_type = other DNA
                        organism = Bacillus thuringiensis
SEQUENCE: 179
atgacattag ctgtttcgga tattgctgct gaattttcaa tcattgatcc aattttatat     60
aaaggaggga taaataggga aattttaacg aggaaaatat atacagaccc agttatttc    120
tcgcctggcc cttcaattgc agatgatgaa aatagatata cagtcccacc atcacctgtt   180
agaaaacttg tcggctcaac attatttagt tctcagacgc ctgctaatcc tgatgaggag   240
ggtgagttta ttggaaatcg aaaccgttat ttaagtttag caggtggaga atcatttgat   300
ggtcctctaa tcggaaactc gacaaaccgt tcgatacaag caggaatccc gacaactgaa   360
tcggtttatg aagttggtgt aatggtcgt agtgggtctc caaggatttt aggttttgaga  420
tggggttcgt taactgactt tcaaaagttt agtgctggag agaagtgta taatttagtt    480
atgaataggg tctctgtgcc aaataaaaaa aatgagccaa taataatac taattttact    540
catcgattat cagatataat tcttcctgga ataggggct catcttttgc atggactcat   600
gttgaggtcg atcctacagg aaactattta tcaacaaatc agattaattt aatatctgct   660
acaaaaatat ctaacccacc acttttcatta caaataagac agggaccagg atttacaggg  720
ggagatttag tcagatttcc aaataatatc ggagtttctt ataagtttaa gttcaaatcc   780
gatagctcag ctaattttag aattcgtata cgttatgcag gtgcaggttc aggtgctagt   840
ggtggtggac gggtatattt taaattaggg aattatagat ctccagatac tccttgggc    900
catactggat ttacctattc caatgtgaag tataatcaat taaattatt agagctttt     960
ggaactgcag aaaatattac aggcaacgac ttggagatta tagtattgac aggaggctca  1020
ggtgcttctg attttatct agatagattg gaattaatcc caatgacggg gataccaaca   1080
gaatacaatg aaccacaaaa attggaaaca gccaaaaag cagtgaccga tttgtttacc   1140
aat                                                                 1143

SEQ ID NO: 180          moltype = AA  length = 381
FEATURE                 Location/Qualifiers
source                  1..381
                        mol_type = protein
                        organism = Bacillus thuringiensis
SEQUENCE: 180
MTLAVSDIAA EFSIIDPILY KGGINREILT RKIYTDPVIF SPGPSIADDE NRYTVPPSPV    60
RKLVGSTLFS SQTPANPDEE GEFIGNRNRY LSLAGGESFD GPLIGNSTNR SIQAGIPTTE   120
SVYEVGVMGR SGSPRILGLR WGSLTDFQKF SAGGEVYNLV MNRVSVPNKK NEPINNTNFT   180
HRLSDIILPG NRGSSFAWTH VEVDPTGNYL STNQINLISA TKISNPPLSL QISKGPGFTG   240
GDLVRFPNNI GVSYKFKFKS DSSANFRIRI RYAGAGSGAS GGGRVYFKLG NYRSPDTPWG   300
HTGFTYSNVK YNQFKLLELF GTAENITGND LEIIVLTGGS GASDFYLDRL ELIPMTGIPT   360
EYNEPQKLET AKKAVTDLFT N                                             381

SEQ ID NO: 181          moltype = DNA  length = 2112
FEATURE                 Location/Qualifiers
source                  1..2112
                        mol_type = other DNA
```

```
                         organism = Bacillus thuringiensis
SEQUENCE: 181
atgagactta catcaaagtt aaagggagtg gtgtttacaa tgcgacgtca attaaaaaat  60
gttagaaata taggaggaat aactatgggt acagatcaaa atagaaatga atatgaaata  120
ctggattctt taccttatca tgagtacaca tcaaacagat atccgttcgc aaaaaatcca  180
aacattatga aaaacaccaa ttataaagat tggttcaatg agggtcaaga gactgaacct  240
tctgcacttg taagtacact gggcatcatg ttcagtctct ttagacaatt cacatctttc  300
cttaggacgc cttccgtgtc tggtggagta gaaatactac gagagataat aagtacaata  360
caggatcgtt cagtaataaa tcttactata aatgatgtcc aacaacttat tgatcaagca  420
ttagaaaatc atatcagaaa tgaggcaaat caaagattta atagtataca agccaatttt  480
aatcaatatc tttccaataa aaatctctat ttaaataatc cttcggattc aacccgaagg  540
ctgtttgtaa atagccttag tgcaaatgag cgtgaattga ggatagcact agatgttact  600
tttagcttgg caaatcgaga ggtattatta ttgcccaatt ttacgcaaat cgcaatgtta  660
catttaacaa cattaaaaga tgctgtaata tttagtggtc cagacttaat agcacctacg  720
gttagtgaaa caactgggaa ttcttttttg aatcgacctc ctagtaattc gtatgaagag  780
gcacttttaa ctagcatacg tatgtattct aattattgca taagattcta taatgaaggt  840
ttaaatcgca taagaaacag gggtacatct agtaatgttt ggctggcttt ccataattat  900
cgcagggaaa tgacattaat agtattagat tttgtcgcat tgttttcact tttgatacca  960
actaaatatc cagcatcaag aaattttaca ccaccagtag tttctcagtt aagtagggtg  1020
atctatacgg acccagtagg tgctataaga accgatggtc gtgggtggtt tgatccgccc  1080
gtaggaactg atgggactag ggttaatttt gcatcaatag aaaatgaaat accagcccct  1140
actacttctc ggcatttatc ggaattaaca atttcttcag gtcctcttgg ttttggcgta  1200
aatccaagta ggacacactc gtggcaaggt aatcgaaatg ttaatatatc cgctcctact  1260
gatgtttctg gagtaatttc taatcggacg caaactattc ctgctagaaa tattttcaga  1320
gtggattcac gtgtttatac tcttgattgg agattgtatg gagtttatag agctgaattt  1380
tttcaggatg ctagtcaaaa ttctcaaagg cgtgtatttg cagaaaatcc tccaacaggt  1440
gctggtgccc aaagcgcaaa taactttcga tttttacctg gagaaaattc ggatacacca  1500
actccgcagg attatactca tttattaagt agagtagtaa atgcaactgt aggacttaca  1560
ccggcaacag gaaatcaacg taattctgta ttgatatttg gttggacaca taaaagttta  1620
acctctgaaa atatatatag aatcaacgaa attacgcaag tagctgctgt gaatacaaga  1680
agtaattcgg gtattcaggt aatttcagga cctggattta caggtggaga tttagtaaga  1740
atggacccta atggtagcgt aagttacaat tttacacccg ctaaacagca agcaggacaa  1800
tcaaatctag caatacgtct acgttatgct tgtcaaggga ccgcttcatt aagaataacg  1860
tttggcaatg gttctagcca agtgattcca cttgatgcta caacttcatc aataaaaaat  1920
cttcaatatg aagggcttcg ctttgttgat gttccaaata atgttagttc tctaccgact  1980
ggtacttcaa tgaccattca aaatataagt acaaactcta acgtagtgct agatagagtt  2040
gaactttttt ccgacatacc tattcccatt tccgaagaac caattattat tccagggaat  2100
tatcaaattg ta                                                     2112

SEQ ID NO: 182           moltype = AA  length = 704
FEATURE                  Location/Qualifiers
source                   1..704
                         mol_type = protein
                         organism = Bacillus thuringiensis
SEQUENCE: 182
MRLTSKLKGV VFTMRRQLKN VRNIGGITMG TDQNRNEYEI LDSLPYHEYT SNRYPFAKNP  60
NIMKNTNYKD WFNEGQETEP SALVSTLGIM FSLFRQFTSF LRTPSVSGGV EILREIISTI  120
QDRSVINLTI NDVQQLIDQA LENHIRNEAN QRFNSIQANF NQYLSNKNLY LNNPSDSTRR  180
LFVNSLSANE RELRIALDVT FSLANREVLL LPNFTQIAML HLTTLKDAVI FSGPDLIAPT  240
VSETTGNSFL NRPPSNSYEE ALLTSIRMYS NYCIRFYNEG LNRIRNRGTS SNVWLAFHNY  300
RREMTLIVLD FVALFSLFDT TKYPASRNFT PPVVSQLSRV IYTDPVGAIR TDGRGWFDPP  360
VGTDGTRVNF ASIENEIPAP TTSRHLSELT ISSGPLGFGV NPSRTHSWQG NRNVNISAPT  420
DVSGVISNRT QTIPARNIFR VDSRVYTLDW RLYGVYRAEF FQDASQNSQR RVFAENPPTG  480
AGAQSANNFR FLPGENSDTP TPQDYTHLLS RVVNATVGLT PATGNQRNSV LIFGWTHKSL  540
TSENIYRINE ITQVAAVNTR SNSGIQVISG PGFTGGDLVR MDPNGSVSYN FTPAKQQAGQ  600
SNLAIRLRYA CQGTASLRIT FGNGSSQVIP LDATTSSIKN LQYEGLRFVD VPNNVSSLPT  660
GTSMTIQNIS TNSNVVLDRV ELFSDIPIPI SEEPIIIPGN YQIV                  704

SEQ ID NO: 183           moltype = DNA  length = 2043
FEATURE                  Location/Qualifiers
source                   1..2043
                         mol_type = other DNA
                         organism = Bacillus thuringiensis
SEQUENCE: 183
atgtgggtgt tattttataa aaatatatat aaatttatcc caagttattt atatataggg  60
ggaatagata tggacccaaa tgctaaatat gaaatcacga atactaaata taatctatca  120
cataagggca ataggtattc aagatttcct ttagacaata ctcagtatag aaaattgcaa  180
aatatgaatt acgaagatat gttgacagct tatcaaaaaa atgggaattt tgcagagctt  240
ccaagtgtaa caagtgttga ttggtcagct gcatcttctg caatgataat tgtagctggt  300
actcttctta gcttatcgtc tgctggtgtc ggtgccggta ttatatcaat cggaacattg  360
ctgcctttgt tttggtctga tattgttggg aaaccaggag aaaatacatg gcaaagttta  420
attgcacaag gtgatagctt atacgccgat caaaatttaa cacccgcttt tttgcttaca  480
gtcaataacg aaataagcag ggtacagggg tatttgagtt tatttaatga tatttttaat  540
tattgggaaa ctaacgataa ccctaatacc agagattcag tacgtagggc atttgagaat  600
gctaatgcag ctattgtagg aagtatcaac ataatttcaa atgcgacggg ctataatatc  660
atatctcttt cttcctatac aaatctcgcg cttttccatt taaccctact tcgtcaagga  720
gttttgaatg cagataagtg gggggttaatt cgagaggaag gagagtttta caagcaactg  780
ttaaaacagc gaatagacat gtatgttaat tattgtcaat ccacgtatca aacaggtttg  840
gatcgcctca aaactggaac gtttcttggt gcatggatct cttttaatac ttatcggaga  900
```

-continued

```
gaatacacta tttctgtact gaatattgct gcaacattta gtagttttga cctagacatg   960
tatccctcta atttcgcgac tactactcaa attacagaaa aaatccatgt accaacacgt  1020
aatagtactg atacatttta tgcgggtttt ccaaacctga aaacactgga agagaagctg  1080
atacctacat taagtctatt taaagggtta acgagattga attttatac atccagtcta   1140
actggaataa aattcttgaa tcaaattaca aattattaca attatatagg aggaagatct  1200
gctggtactt taactaccac agggagtgat atttcctcac ttccggatgg tactgttgaa  1260
aatccttggg tgcacaaatg cgaatacgat cagatttgga gccccgtgcc ccctttcagt  1320
ccggattatg ggatcaacaa acttacattt acttcgggaa atctaccacc taatgacgtt  1380
tataatgcac atgtacccct tgtaaataca aagacgacc ctgtactacc acctatacca   1440
cctctgccgc cttctctacc accaaacgtg gtcccaatta atatatatatt atctgatatg  1500
actacaattg atttaagacc gaatagcatg aatcttttat ataattttag ttggacggtt  1560
gcaagtgcta atgctgataa tgtgataaaa ggagggggatt atattacaca aatcccagca  1620
gtaaaaggcg atacacttag caatggtgct aaagttagag aaggacctgg ccatacaggt  1680
ggaccaatag tcgaattcgg tccacatgta ccggcaccc ctcccgcagt aaacataaag   1740
tgtaacgtat caactgaagc tgccaataaa aaccttgtta tgaggattcg ctatgcctca  1800
agttcaaaaa atgccacgct cctaaactta aatatagggg gggaggttca taatagtata  1860
gtatgtacag ggaccggggc ggatataaaa aaaattgata taaagtacaa tgagtttaat  1920
actactgacg aaatttcaat agtaaatcct aaaagtgctg gatctatgga tgtatatata  1980
gagaaagcta gtaacatcaa tgagcacctt cttattgaca aaattgaatt ttatataaaa  2040
agt                                                                2043

SEQ ID NO: 184       moltype = AA  length = 681
FEATURE              Location/Qualifiers
source               1..681
                     mol_type = protein
                     organism = Bacillus thuringiensis
SEQUENCE: 184
MWVLFYKNIY KFIPSYLYIG GIDMDPNAKY EITNTKYNLS HKGNRYSRFP LDNTQYRKLQ   60
NMNYEDMLTA YQKNGNFAEL PSVTSVDWSA ASSAMIIVAG TLLSLSSAGV GAGIISIGTL  120
LPLFWSDIVG KPGENTWQSL IAQGDSLYAD QNLTPAFLLT VNNEISRVQG YLSLFNDIFN  180
YWETNDNPNT RDSVRRAFEN ANAAIVGSIN IISNATGYNI ISLSSYTNLA LFHLTLLRQG  240
VLNADKWGLI REEGEFYKQL LKQRIDMYVN YCQSTYQTGL DRLKTGTFLG AWISFNTYRR  300
EYTISVLNIA ATFSSFDLDM YPSNFATTTQ ITEKIHVPTR NSTDTFYAGF PNLKTLEEKL  360
IPTLSLFKGL TRLNFYTSSL TGIKFLNQIT NYYNYIGGRS AGTLTTTGSD ISSLPDGTVE  420
NPWVHKCEYD QIWSPVPPFS PDYGINKLTF TSGNLPPNDV YNAHVPLVNT KTVTVLPPIP  480
PLPPSLPPNV VPIKYILSDM TTIDLRPNSM NLLYNFSWTV ASANADNVIK GGDYITQIPA  540
VKGDTLSNGA KVREGPGHTG GPIVEFGPHV PATPPAVNIK CNVSTEAANK NLVMRIRYAS  600
SSKNATLLNL NIGGEVHNSI VCTGTGADIK KIDIKYNEFN TTDEISIVNP KSAGSMDVYI  660
EKASNINETL LIDKIEFYIK S                                            681

SEQ ID NO: 185       moltype = DNA  length = 2103
FEATURE              Location/Qualifiers
source               1..2103
                     mol_type = other DNA
                     organism = Bacillus thuringiensis
SEQUENCE: 185
atgaattcaa ataataataa tgaatacgaa attattgatt caaacacttg cccttatcca    60
cctaacagaa agaatgagta tactaaatat ccttatgcga ataatccaga gcaatatttg   120
ccaaacatcc ctcttgaaaa atggctcagt gatcctcaaa ctagaataac aacaactctt   180
tctataaatg gcgctattac tgaattaatg atagcttcat attttggtcc gggtgtattt   240
atagtagctg ggacagctat tatgtcagac ttaatacctc ttatttggga taatttacaa   300
gaaaatcttc ctagtggact tataaatgtc acacaagaaa tgcttaatac acaactagac   360
gaatatactt tacccaagc aatatatcga tataaaggtt taatagatgg ttttaaccaa   420
ttcaagctat attttaacgc gtggaaaaat aaccctaatg attttaacaa aatatcagat   480
gtatcaggtt attttagaac tttaaatggt acatttaata ctacaatggc tacatttcaa   540
caacaaggtt atgaacacat actattacca gtttatgcac aagctgcaca agcacattta   600
cttcatttac gtgatggtat ttcatatgct gataaatgga atctaggaag agcaaattat   660
gattcaggag atactcatta tcaagaattc atagatgctt gtaaaagata cacaaaatat   720
tgtacagagt ggtattataa aagtttagac atttttaaaa gtaaaaattc aaactggttt   780
gactataatc tttaccgtag attttttaaca attactgtgt tagatattat ttctatgttt   840
tcatcttacg atgcacgttt tactctatc ccatcaaaag tagaaattct tacaagaaaa    900
atatatgcag atccaattaa ttattctcaa ggtaattctc tagcagaaga tgaaaaaaat   960
catacggtag ataacctaag attatttact caattaaata aactagaaat tagtagtgat  1020
atacaaaatg gttttaacgg ggttactaat ttttataagt tttatcacc cggcaacagt   1080
tcaatatcac attttctggg aacaccattt caatatataa gtacagtacc ttacactttt  1140
tatcctacta tgaaacatc tttttataaa attaaaacat ttaatattaa ccaacctagt  1200
gctacattag atgcaataga tataatgtat ttttatatgt gggatggaaa acaagagcac  1260
atacaaagaa tacttgcaag tacatctggt aacgaaacaa atgcaaaata cgtttatata  1320
gctggaaaaa aagatttaaa atagtgaaaa aatagttaca gaccaaatga ttttaattca  1380
ttaaattatc ataattctac tcatgtctta tcagatatga ttgtaaatac agccaataaa  1440
aatgcaatta gttactcttt tgcatttaca aataaatcta tttcttttag caatacaata  1500
aaaaaagatg taattacctt catcccggca gtaaaatgtt tcaaatgag ttctaatgta    1560
aaagttgtgg aaggacctgg tcatacagga gggaatttaa taagattgca aggcaatatg  1620
atgttcggta ttacatttgc tgatgatttg aatcaacttt acagaatacg tattcgttat  1680
gccagcgaca cgaacttgag gctttcactc ggtatgatat ctacccaagc tatcaatatt  1740
ggtagaactt ttttcaattt aagttctaat aatttacagt atgaacattt tgaatatgct  1800
acatttcaaa cagtaattgt accttcacct ggggcaaatc aattagtact tttagaaggt  1860
tttaacgata gcaatattaa tttatatata gacagaattg aatttattcc agtaacgcaa  1920
caatacttag aaacaagtga aagagaaaaa gtagaaacga ttcaacaaaa aatgaattgat  1980
```

```
gtgtttttag atcctcaaca tcaattttta caaacaaaaa caacagatta tgagattgat    2040
caaatcgcaa gtgacataga acaatatca gaagaatggt atccacaaga aaaaatgatg    2100
tta                                                                  2103

SEQ ID NO: 186          moltype = AA  length = 701
FEATURE                 Location/Qualifiers
source                  1..701
                        mol_type = protein
                        organism = Bacillus thuringiensis
SEQUENCE: 186
MNSNNNNEYE IIDSNTCPYP PNRKNEYTKY PYANNPEQYL PNIPLEKWLS DPQTRITTTL    60
SIIGAITELM IASYFGPGVF IVAGTAIMSD LIPLIWDNLQ ENLPSGLINV TQEMLNTQLD    120
EYTYTQAIYR YKGLIDGFNQ FKLYFNAWKN NPNDFNKISD VSGYFRTLNG TFNTTMATFQ    180
QQGYEHILLP VYAQAAQAHL LHLRDGISYA DKWNLGRANY DSGDTHYQEF IDACKRYTKY    240
CTEWYYKSLD IFKSKNSNWS DYNLYRRFLT ITVLDIISMF SSYDARLYSI PSKVEILTRK    300
IYADPINYSQ GNSLAEDEKN HTVDNLRLFT QLNKLEISSD IQNGFNGVTN FYRFLSPGNS    360
SISHFSGTPF QYISTVPYTF YPTNETSFYK IKTFNINQPS ATLDAIDIMY FYMWDGKQEH    420
IQRILASTSG NETNAKYVYI AGKKDLKDEK NSYRPNDFNS LNYHNSTHVL SDMIVNTANK    480
NAISYSFAFT NKSISFSNTI KKDVITFIPA VKCFQMSSNV KVVEGPGHTG GNLIRLQGNM    540
MFGITFADDL NQLYRIRIRY ASDTNLRLSL GMISTQAINI GRTFFNLSSN NLQYEHFEYA    600
TFQTVIVPSP GANQLVLLEG FNDSNINLYI DRIEFIPVTQ QYLETSEREK VETIQQKMND    660
VFLDPQHQFL QTKTTDYEID QIASDIETIS EEWYPQEKMM L                        701

SEQ ID NO: 187          moltype = DNA  length = 2052
FEATURE                 Location/Qualifiers
source                  1..2052
                        mol_type = other DNA
                        organism = Bacillus thuringiensis
SEQUENCE: 187
atggacccaa atgatcataa tgaatatgaa gtcatggata ctggcagcat gggctatcag    60
ccaaggtatc ctcttgcgaa tgcacctggt gctgaattgc aacagatgca ttacaaagat    120
tggatggata tgtgtgaaga tggagagtca ggagaaacgt ttgcagacct tacagttcag    180
gagggagtca ctatagctgt aagtattgca gcggccgttc ttagtgtatc atttccagta    240
acatcagcgg gattaagtat tatctctgta ctcattccat actggtggcc ggagacagca    300
ggaactcccg gtactccctc tgcgcaagtt acatgggaaa aatttatgag tgctgcggaa    360
attctcagta ataaacaaat tgtagcgagt aaacgatcag atgccattgc tagatggcaa    420
ggtatacaaa cccttggaag agattatttt caagcacaat gtgactggct acaagatcaa    480
aataatgaac tcaaaaaaag taaattacgg gatgcatttg atgacgtcga agattattta    540
aaagtgtcaa tgccattctt tggtgcgcaa ggctttgaaa ttcccatgtt agctatgtat    600
gcacaagctg cgaatatgca cttaattttg ctacgagatg ttgtccagaa tggtttgaat    660
tgggggttcc agcaatacca agttgaccga tattattcca atacagaccc ttttttaggg    720
aaccctggac tattacaact aatagaagga tatacggaat attgtgtaca atggtataat    780
acaggtttac gacaacaata tgaaaataat agatacgatt gggtgcatt caatgatttc    840
cgtagagata tgaccataat ggtattagat attgtagctt tatggccaac ttatgatccg    900
aagcgctatc ccctacctac aaaatcacaa cttacgcgaa ctgtgtatac cgatttaata    960
ggttattctg gagatttcga ataccaacaa atagctattg aacgtgcaga acgagagcta    1020
gtccagaggc ctggtctatt tacctcagctc cgtgagataa ttttcaagct gctattaccg    1080
accgtaaata attctttagc aggaagagaa atggtcttca attataccgc aagtcccgat    1140
gggtatgaag agaacaaggg gaatcccgga caaactagag agactcttgt tattccagca    1200
ccggatgtaa aagatgacat ctggaggatt ggcactcaaa tttactacca tcctttatat    1260
aatgttaata ccgttgaggg ctggagtttt tctttactc gatcattaga tcaaaaaata    1320
cattggatgt caaatccttc atatagaaca gtgatgcaag gattgtcttg tcacggacct    1380
tctatggatt cttgtaacct ttgtagcagt aatagtccat gtagaagtat tactcctaac    1440
tatagcctcc cttgtaatga caaggaggtc tatagtcacc gattttcata tttaggggcc    1500
ggacttaaat ccgacttaac aacgttgact tattttagct acggatggac acatcagc    1560
gcagacttca acaatctgat agatgctgaa aaaatcaccc aaattccagc agtcaaggca    1620
tcttcaataa gtggcaatgc tagggtaata cgaggacctg gaagtacggg aggagatttg    1680
gtggaatttt ctaccgaaac tacaggaggg acactgaaca tacgttacac accgccggaa    1740
gggacaagca gatatcagtt aagattgcgt tatgcaagta atgtagacaa cactaccatc    1800
acagttgacg ggagaggacg tacttatgcg gatattacta caaccgacat tacaaatctt    1860
acgtatgata aatttggcta tgtaaatatc aactatattc tgggtcatac tgatcggcca    1920
tcagacgctc tatcgtggtt ttccctcgga gtttcgggta ctggttcagg aacattcctt    1980
ctcgacaaaa tcgaattcat tccaatagaa ggatcggtgg aagaatttga agcgaaccaa    2040
gcattagaaa aa                                                        2052

SEQ ID NO: 188          moltype = AA  length = 684
FEATURE                 Location/Qualifiers
source                  1..684
                        mol_type = protein
                        organism = Bacillus thuringiensis
SEQUENCE: 188
MDPNDHNEYE VMDTGSMGYQ PRYPLANAPG AELQQMHYKD WMDMCEDGES GETFADLTVQ    60
EGVTIAVSIA AAVLSVSFPV TSAGLSIISV LIPYWWPETA GTPGTPSAQV TWEKFMSAAE    120
ILSNKQIVAS KRSDAIARWQ GIQTLGRDYF QAQCDWLQDQ NNELKKSKLR DAFDDVEDYL    180
KVSMPFFGAQ GFEIPMLAMY AQAANMHLIL LRDVVQNGLN WGFQQYQVDR YYSNTDPFLG    240
NPGLLQLIEG YTEYCVQWYN TGLRQQYENN RYNWDAFNDF RRDMTIMVLD IVALWPTYDP    300
KRYPLPTKSQ LTRTVYTDLI GYSGDFEYQQ IAIERAEREL VQRPGLFTWL REIIFKLLLP    360
TVNNSLAGRE MVFNYTASPD GYEENKGNPG QTRETLVIPA PDVKDDIWRI GTQIYYHPLY    420
NVNTVEGWSF SFTRSLDQKI HWMSNPSYRT VMQGLSCHGP SMDSCNLCSS NSPCRSITPN    480
```

-continued

```
YSLPCNDKEV YSHRFSYLGA GLKSDLTTLT YFSYGWTHIS ADFNNLIDAE KITQIPAVKA  540
SSISGNARVI RGPGSTGGDL VEFSTETTGG TLNIRYTPPE GTSRYQLRLR YASNVDNTTI  600
TVDGRGRTYA DITTTDITNL TYDKFGYVNI NYILGHTDRP SDALSWFSLG VSGTGSGTFL  660
LDKIEFIPIE GSVEEFEANQ ALEK                                          684

SEQ ID NO: 189          moltype = DNA  length = 1110
FEATURE                 Location/Qualifiers
source                  1..1110
                        mol_type = other DNA
                        organism = Bacillus thuringiensis
SEQUENCE: 189
atgaatggga gcaagatcaa ttttatgaaa tttatagtcc ccattagaca aaaaatagta  60
attcgtaatg ctgacacaaa aaatggtact gatgttattc aatataacag tggagaagat  120
aatgcaagat ttattttata taaagttgat ggtgataatt atcttattgt aaataaaaac  180
agtgggaaat tagtagtagt ttataattct gatcctggta atgatgttgg tatcaagcaa  240
tgggatagtg aaagtggaaa tggaagatgg catttgtga aaaatggtgg gaattcttat  300
ttaattcgta gtaatatgag tgggaaatta gcagtaattg aaaacggtag taaaaataat  360
gctgctttaa ttgttcaata tgatcaacaa agcgtaggaa acggagaatg ggaatttcat  420
ccggttgaga gctttactat gcccacttta cctgaactta aaccacagcc atcttctcct  480
gtatattcag aatcaggtgg tgaaggtcaa gcaatgcctg atacttcgga aaaagctgtt  540
gtagccgcta ctctttttcc tgctgttatg gttagaaata acagttggag tttatcaaca  600
caaatgagat atagcccgta ttatatttta gaaaaacaac aatattggaa aaaagttgtg  660
aatttatcat ttgctccagg ggaatcaaaa acaactacgt ataaatatgg aatgagagaa  720
accgatcaaa caactatgca taatacaatc agtatgactg ttggcatgga ttctggtgtg  780
aatattgaag gtgttacgga atctatgaaa ggagagatta caaattcgtt agaaataaca  840
gaaagtcata ctactgaatt aatgaaagat tatgatgaaa caattaccat aagtaatcca  900
tttcaaaaac aatctatgca atatgcaaaa tatatcctta ctactgaatt tgttttgaaa  960
cgtacagatg gttctgttgc agattcatgg tctatgactg ataataatac agttcatacg  1020
acttcatatc caagaatgtc agaagataca agatttacaa tagaatcaca atctaattct  1080
caatcttgta ataattcaaa accgtgcaaa                                    1110

SEQ ID NO: 190          moltype = AA  length = 370
FEATURE                 Location/Qualifiers
source                  1..370
                        mol_type = protein
                        organism = Bacillus thuringiensis
SEQUENCE: 190
MNGSKINFMK FIVPIRQKIV IRNADTKNGT DVIQYNSGED NARFILYKVD GDNYLIVNKN  60
SGKLVVVYNS DPGNDVGIKQ WDSESGNGRW HFVKNGGNSY LIRSNMSGKL AVIENGSKNN  120
AALIVQYDQQ SVGNGEWEFH PVESFTMPTL PELKPQPSSP VYSESGGEGQ AMPDTSEKAV  180
VAATLFPAVM VRNNSWSLST QMRYSPYYIL EKQQYWKKVV NLSFAPGESK TTTYKYGMRE  240
TDQTTMHNTI SMTVGMDSGV NIEGVTESMK GEITNSLEIT ESHTTELMKD YDETITISNP  300
FQKQSMQYAK YILTTEFVLK RTDGSVADSW SMTDNNTVHT TSYPRMSEDT RFTIESQSNS  360
QSCNNSKPCK                                                          370

SEQ ID NO: 191          moltype = DNA  length = 1974
FEATURE                 Location/Qualifiers
source                  1..1974
                        mol_type = other DNA
                        organism = Bacillus thuringiensis
SEQUENCE: 191
atgaattcat atcaaaatca atatgaaata ttggagtctt catcgaataa cacaaatatg  60
ccaaacagat atcctttttgc aaatgatcca aatatattcc ctattaacct ggacgcttgt  120
cagggaaggc catggcaaga tacgtgggaa tcagtctcgg atatagtaac tattgggaca  180
taccttatac aattcttgct agaacctggt ataggtggaa ttcctgtaat attgtcaata  240
ataaacaaac tcattccatc ttctggtcaa tctgtggcaa cactttctat atgtgattta  300
ttatctataa ttcgtaaaga gatagatgtg aatactttaa atcgtagagc tgcagatttt  360
aacggtgcat tggctgtcca tagaaagtat tatcttgctt ctcttcagga gtggcttgat  420
gcaggccaac caaaggaccc agcaaatcag aaacttaaga atgtagttag ggatttcata  480
gatgcggaca aagcattcat tgcacttata gaaggggggc tatcagaaag taaagctcaa  540
atattattat tgcctattta tgcacaagct gcaaatgtgc atttattact attaagagat  600
gcagttcaat ataaagaaaa atggggagga ttattggggg cggagaaagt aggagaggaa  660
ttaatatcac ctactatgga ttataacaag cgattaaaag atgcgataga acagtatacc  720
aattattgtg tagagtggta taacaagggt ttagatcaga taaaacaggc aggtacaagt  780
actgaaacct ggttgaaatt taataaattt cgtagagaaa tgactttggc ggtattggat  840
gttattgcta tatttccaac ttatgatttt gaaaaatatc ccttagcaac aaatgtagag  900
ttgactaggg aaatttatac agatccagtg gggtattcag gaagcagtat tcgttgggaa  960
cggacttttc ccaatgcttt taatacgcta gaagctaatg gaacacgggg accgggttta  1020
gttacttggc ttagcagtat aagtatatat agtcagtatt ttacggttta ttttagcggt  1080
tgggtaggaa ctcttcatgc tgaagattac acaaggggta acggtacttt ctatcgttta  1140
tctggaacta ctacgagtaa tgatccacgt aatttgcttt ttagcccttc cgatatattt  1200
aaaattgttt cattaggtat ctatgaaaca agagcagagc ttggatacac acggcaacgg  1260
ttttgtgttt cacgtgcaga atttagtacg tcaacaccat ataaatacct gtatgatgaa  1320
aataataatg gacaaggccg aatgacaatt gaatctacgt taccaggtat tgagaatcta  1380
gaacctagtt atacaaatta ctctcataga ttatcaaatg cggcatgtgt tcaatttaac  1440
gactccagag ttaacgtata tggttggaca catataagta tgaaaaaaag taatactatt  1500
tatccagata aaatttcaca aataccggct gtgaaagcat ttgctttaga atcaggcgct  1560
tatgttagcg ctggacctgg tcatacagga ggaaatgtag tatggttacc atatttaggg  1620
cgtttaaaaa tacgtttaac ttctgcgccc acgaataaaa attaccgtgt tagagttcgc  1680
```

```
tatgcaggtt tgtactcagg tcgtttaatg gtacaaagat ggtcgctgag tgggtctgca  1740
actggtgatt ttccttattc atctacgggt tctaataata catttggata tgtggagacc  1800
ttagttacta catttaatca atcaggtgtt gaaataatta tacaaaatca aacttctcca  1860
caacttatca ttgacaaaat tgaatttatc ccaattgatc taacaacttt agaatatgag  1920
ggagaacagg gcctagaaaa aacaaaaaac gcggtgaacg atttgtttat caat         1974

SEQ ID NO: 192          moltype = AA   length = 658
FEATURE                 Location/Qualifiers
source                  1..658
                        mol_type = protein
                        organism = Bacillus thuringiensis
SEQUENCE: 192
MNSYQNQYEI LESSSNNTNM PNRYPFANDP NIFPINLDAC QGRPWQDTWE SVSDIVTIGT  60
YLIQFLLEPG IGGIPVILSI INKLIPSSGQ SVATLSICDL LSIIRKEIDV NTLNRRAADF  120
NGALAVHRKY YLASLQEWLD AGQPKDPANQ KLKNVVRDFI DADKAFIALI EGGLSESKAQ  180
ILLLPIYAQA ANVHLLLLRD AVQYKEKWGG LLGAEKVGEE LISPTMDYNK RLKDAIEQYT  240
NYCVEWYNKG LDQIKQAGTS TETWLKFNKF RREMTLAVLD VIAIFPTYDF EKYPLATNVE  300
LTREIYTDPV GYSGSSIRWE RTFPNAFNTL EANGTRGPGL VTWLSSISIY SQYFTVYFSG  360
WVGTLHAEDY TRGNGTFYRL SGTTTSNDPR NLLFSPSDIF KIVSLGIYET RAELGYTRQR  420
FCVSRAEFST STPYKYLYDE NNNGQGRMTI ESTLPGIENL EPSYTNYSHR LSNAACVQFN  480
DSRVNVYGWT HISMKKSNTI YPDKISQIPA VKAFALESGA YVSAGPGHTG GNVVWLPYLG  540
RLKIRLTSAP TNKNYRVRVR YAGLYSGRLM VQRWSLSGSA TGDFPYSSTG SNNTFGYVET  600
LVTTFNQSGV EIIIQNQTSP QLIIDKIEFI PIDLTTLEYE GEQGLEKTKN AVNDLFIN    658

SEQ ID NO: 193          moltype = DNA   length = 2085
FEATURE                 Location/Qualifiers
source                  1..2085
                        mol_type = other DNA
                        organism = Bacillus thuringiensis
SEQUENCE: 193
atgggaggaa catatatgaa tccatataac aatgatggct atgagattat tgattcaaag  60
acttcacctt atcctgctaa cagaaataat tcatattcga attctagata tccttacatt  120
aataatccta atcaacctat gtcaacact aatcacaaaa attggatgaa tctatgtgaa  180
gaaaatgaag catatgatct aagtcctgaa acaattgctg caattggtgc aggaattatt  240
gtagttggta ctatgatagg tgcttttgct gctcctgtcg cagctggtgc tattatatca  300
tatggaactt tattgccaat tctttggcca tcaccaaacg accaaaccat ctggcaacaa  360
cttgtaaaaa ttgggaatag gccttctaat tcagaaatag atcaagcaat aataaaccat  420
ttacttactg tagtaaatgg tttaaaagct caatttacag actatcaaag ttactttgat  480
atatggaaag caaaccttc ttcaataaat gctgatgcgg taagaaataa atttctttca  540
ttagatagtg atataataag agagataaa actttaaaag gaaataatag tataatactc  600
ctcccttctt atacacaagt agctaatttg catttaattc tattacgaca agcagcattc  660
tattatgatg attgggttaa attcttacca catactaata tttcttctga cttctacgct  720
ggaaaactaa atgacaaaat agcggaaat actgattatt gtttcagaac ataccgtgaa  780
ggactgtatt caattgaaca gaactctcaa acaacatgga acttatataa cacttatcgt  840
aatgaaatga ccctcacagt attagattta gttgcacttt ttcctaattt taatcgtaat  900
aaatataatt taccgactaa atctcaatta actcgagaaa tttacactaa tactaattta  960
gaaataaata aatctatagt agaaaccgaa cgaggattaa ctagaaaccc tacattattc  1020
actagaatac aatcagctga ctttttcagt agaaagtatg atatcgttgg cgattattcg  1080
acaatgctta caggcaacca ggtaagtttt aactatataa acagtaacaa agcacctata  1140
aattcctcta tttatggaga tgttaaccaa ggcaattcca gtaaaacagt cacatttaac  1200
caacctattg atatggttaa actagaacac aatcaaaatt tcgaggata tatattgaga  1260
attatatttt tttcaaataa catagaggta gctcgatatt cttctgggtc cacattacca  1320
tctgaaagaa taaaaactat cgtttataca attccgagaa aagaacttaa taccaatgaa  1380
tattatcata ccttatctta tcaaaaact gataataata cagcacctca tgatggaaaa  1440
tacagaagtg ttgcatttgc ttggacccat agtagtgttg attctaataa tacaattttc  1500
ccaaatgaaa ttacccaaat ccctgctgta aaagcatttc aaattagtaa tgattcaaaa  1560
gttgtaagag gtcctggttt tacaggtgga gattagtag ttctaaaaca cagtattgat  1620
tttaaactta ggacacctac aagtaatcct tcttcttatc aagtacgtgt tcgttatgct  1680
tctaatgaca gtacacaaat aattatgtca ttaacaaccg ataacatacc cgtaacattt  1740
ccaagaactg taactcattc aattgttggt aatttacaat acaaagattt tcaacatgtc  1800
acattcccaa aaccattgtt aataaataga aacccaggag aagacatatt attgagctta  1860
ctaggtatac aaaatgatcc atttaacatc tggatagata aatcgaatt tattccggta  1920
acgcaacaat atttagaaac aagtgaaaaa gaaaaaatag aaacgattca acaaaaaatg  1980
aatgatgtgt ttttagatcc tcaacatcaa ttttacaaa caaaagcgac agattatgag  2040
attgaccaaa tcgcaaataa catagaaaca atatcagaag aatgg                  2085

SEQ ID NO: 194          moltype = AA   length = 695
FEATURE                 Location/Qualifiers
source                  1..695
                        mol_type = protein
                        organism = Bacillus thuringiensis
SEQUENCE: 194
MGGTYMNPYN NDGYEIIDSK TSPYPANRNN SYSNSRYPYI NNPNQPMSNT NHKNWMNLCE  60
ENEAYDLSPE TIAAIGAGII VVGTMIGAFA APVAAGAIIS YGTLLPILWP SPNDQTIWQQ  120
LVKIGNRPSN SEIDQAIINH LLTVVNGLKA QFTDYQSYFD IWKANPSSIN ADAVRNKFLS  180
LDSDIIREIE TLKGNNSIIL LPSYTQVANL HLILLRQAAF YYDDWVKFLP HTNISSDFYA  240
GKLNDKIAEY TDYCFRTYRE GLYSIEQNSQ TTWNLYNTYR NEMTLTVLDL VALFPNFNRN  300
KYNLPTKSQL TREIYTNTNL EINKSIVETE RGLTRNPTLF TRIQSADFFS RKYDIVGDYS  360
TMLTGNQVSF NYINSNKAPI NSSIYGDVNQ GNSSKTVTFN QPIDMVKLEH NQNFRGYILR  420
```

```
IIFFSNNIEV ARYSSGSTLP SERIKTIVYT IPRKELNTNE YYHTLSYIKT DNNTAPHDGK    480
YRSVAFAWTH SSVDSNNTIF PNEITQIPAV KAFQISNDSK VVRGPGFTGG DLVVLKHSID    540
FKLRTPTSNP SSYQVRVRYA SNASTQIIMS LTTGNIPVTF PRTVTHSIVG NLQYKDFQHV    600
TFPKPLLINR NPGEDILLSL LGIQNDPFNI WIDKIEFIPV TQQYLETSEK EKIETIQQKM    660
NDVFLDPQHQ FLQTKATDYE IDQIANNIET ISEEW                               695

SEQ ID NO: 195          moltype = DNA   length = 930
FEATURE                 Location/Qualifiers
source                  1..930
                        mol_type = other DNA
                        organism = Bacillus thuringiensis
SEQUENCE: 195
atgattacaa acatagagca gtcaacgata aattatatga aatggtatgc aataaaattat     60
ctaaatgcag aacctacaac ttttttaca gaagggatat atccatacga ggttcaaaat    120
attagtatca acccaaaatt aaataatttt tttgtaaata cctttccaaa agaagaatac    180
tttcaagtaa ttgaaaataa tacagataca aatcaacttc aaaacatcaa attttctgaa    240
aaatctatcg aaactattac taatactact actttagggt atacacttta taaggaata    300
aagttatcta ctacatttaa tattctagtc aattttatga ttcaggtag tattgaacaa    360
tctcttgaaa ttccatttaa ttccgaatttt aaatgttatt ctactgaaac aacaaagaaa    420
acatttaata aactttggga atttacccaa cctgtaattg tacctcccca tacgcgaatt    480
actgcaactc ttataattat gggagcgacc ataaaaattc ctactcaatt atcagctaat    540
attaacggag ctcatatgta taacaacaaa gagaattgat tctcttcaat ttcatttcga    600
caatttaatg gttcaaaggt caagacatta tttgctgcaa gtaatttaag ccaaaattct    660
tggcctaaaa aaccatcaat ctttgcttct ccaggaccac atggttcact aaatttaaga    720
ggcgaatcaa ttattactgt tgaaccaggt ttatatactg ttgctaaatt tgttgaatca    780
ccattagatg gattttcaaa tgaaagaaaa acttggtata cagataaagt aatattacga    840
gatggaagaa tgattcaact accaaattta aatccgttaa ctggaaaatc aagtttttatt    900
gatactgaaa taattcttat tgaggataaa                                     930

SEQ ID NO: 196          moltype = AA    length = 310
FEATURE                 Location/Qualifiers
source                  1..310
                        mol_type = protein
                        organism = Bacillus thuringiensis
SEQUENCE: 196
MITNIEQSTI NYMKWYAINY LNAEPTTFFT EGIYPYEVQN ISINPKLNNF FVNTFPKEEY     60
FQVIENNTDT NQLQNIKFSE KSIETITNTT TLGYTLYKGI KLSTTFNILV NFMISGSIEQ    120
SLEIPFNSEF KCYSTETTKK TFNKLWEFTQ PVIVPPHTRI TATLIIMGAT IKIPTQLSAN    180
INGAHMYNNK ENWFSSISFR QFNGSKVKTL FAASNLSQNS WPKKPSIFAS PGPHGSLNLR    240
GESIITVEPG LYTVAKFVES PLDGFSNERK TWYTDKVILR DGRMIQLPNL NPLTGKSSFI    300
DTEIILIEDK                                                           310

SEQ ID NO: 197          moltype = DNA   length = 2136
FEATURE                 Location/Qualifiers
source                  1..2136
                        mol_type = other DNA
                        organism = Bacillus thuringiensis
SEQUENCE: 197
atgaatccaa attataacaa gaatgaattt gaaatattaa atagtagtag cctgatcaca     60
gggcgaagat atcccttgc gaaggcacca gattctgaat acaacagat gaattacaaa    120
tattggatga ataagtgtgc aaatataacg caaccgatgt ctctagtccc tcgggcgga    180
ctagttctta aagaaggtgc gactttagta acggggatag tggctattat gctagccact    240
acgtttccgt tgactgcggc cgcatttgga cttatttctg tactattagc atttctgtgg    300
ccgttgctcg aagaacctga agctcccgac tcgcaaatat catgggaagt acttatggct    360
gctgcagaag aacttatgaa tgacaaaatt gcagatcttc aaaaaacgag agctctttct    420
caattacgga ttgtacagtc aaggctaaat gactataacc aggccctctg taatttagaa    480
ttagatccca ataatgaatc gaataaagcg gaagtaagag atgcatttga tgatgccgat    540
gatgcattga aaagtgctat gataatcttt agcgaaaaac cctacgaaaa gctcatgtta    600
accagttacg tgcagggtgc caatctgcat ttacttttat tacggggatgt tgtgaaattc    660
gggagaaagct ggggatttac accaattcgc gttcaacaat actattctaa cgtgaatgta    720
ggaaaccctg gtatgctaca actattagaa aaatatacag atcattgtat ggatacttac    780
catgcgacag ctccccccagc tcccctatc aacacggaca gtgagtacta tgagtatcgt    840
acgaatatga ttattatgct gttagatgtt gtagcattat ggccaacata tgacccgaaa    900
ttatatccat attatgtaac atcacaattg acgcgagaaa tgtatcacag tccaataggg    960
tactcttata actatcatcg attagaaaca tgggatcgtc caccttcttt atttcagtgg   1020
ttgcgtgata taacatttta tactcaaccg acaaagtggg tacccgggtac ccctgcaact   1080
tattatgtta cgcagtatac tggtttgcaa ttaacgtatc accacaccct gaatgatgca   1140
ttaattgaac ctccactagt gggatggtgg agtgatagtt tgaattctat taaatgggat   1200
gttaaaatta atcccgatca ggatatgtat atggttagga atcacttcca gggagggttt   1260
aggggtgacc tggagcagtc acctataaca caattcttct ttcatactag tccttacaac   1320
gaaattacaa cggtcggaaa atctttggat gtagatactc ctccagagtt ttcatatgga   1380
ctatcttgtc taaatagtcc taatgaatct tgtggtattt gtactcctg tgaattgagt   1440
aatgtcaatc gagaaattcc ttgtgagggc cctagtcttt atagtcatcg attgtcgtgg   1500
attagtacgg tagaagacg tgattataat ttgtgggttt ctttcccggg ctcagtaata   1560
agcgcgtttg cttacggctg gacacatgta agtgcggata aaaacaatat gctagaccttt   1620
gaaaaaatca cccaaatccc agcagtcaag gctaaagatt tattaggcga tgcgagggta   1680
atcaagggac ctggtagtac aggaggagat ttaatacagc tagtgtctca gggatttggc   1740
gatccggtac cgaatggtgg aagttttgtt attcaggtac agataccaat aaaaaaagcg   1800
tataaaaatac gatttcgtta ttcagctcca ctatatacca atataagagt taccgggtat   1860
```

-continued

```
gatgcgaaga acacagtaat atacgtagat tatgcgaatg ttgattccac atattatatt  1920
gaaggaacag cattgacata caagaatttt tcttatattg acctgaatgc gccgttagat  1980
tctctttcca cggatgtaac attggaattc ggcttcgact ctggggctca acctggtgaa  2040
tctatcatca ttgataaaat cgaattcatt ccaattgaag gttccctaga agcatatgaa  2100
gcagatcaag cattagacaa agcatggaag gcagtg                            2136

SEQ ID NO: 198          moltype = AA   length = 712
FEATURE                 Location/Qualifiers
source                  1..712
                        mol_type = protein
                        organism = Bacillus thuringiensis
SEQUENCE: 198
MNPNYNKNEF EILNSSSLIT GRRYPLAKAP DSELQQMNYK YWMNKCANIT QPMSLVPSGG   60
LVLKEGATLV TGIVAIMLAT TFPLTAAAFG LISVLLAFLW PLLEEPEAPD SQISWEVLMA  120
AAEELMNDKI ADLQKTRALS QLRIVQSRLN DYNQALCNLE LDPNNESNKA EVRDAFDDAD  180
DALKSAMIIF SEKPYEKLML TSYVQGANLH LLLLRDVVKF GESWGFTPIR VQQYYSNVNV  240
GNPGMLQLLE KYTDHCMDTY HATAPPAPPI NTDSEYYEYR TNMIIMLLDV VALWPTYDPK  300
LYPYYVTSQL TREVYTRPIG YSYNYHRLET WDRPPSLFQW LRDITFYTQP TKWVPGTPAT  360
YYVTQYTGLQ LTYHHTLNDA LIEPPLVGWW SDSLNSIKWD VKINPDQDMY MVRNHFQGGF  420
RGDLEQSPIT QFFFHTSPYN EITTVGKSLD VDTPPEFSYG LSCLNSPNES CGICTPCELS  480
NVNREIPCEG PSLYSHRLSW ISTVEERDYN YGFSFPGSVI SAFAYGWTHV SADKNNMLDL  540
EKITQIPAVK AKDLLGDARV IKGPGSTGGD LIQLVSQGFG DPVPNGGSFV IQVQIPIKKA  600
YKIRFRYSAP LYTNIRVTGY DAKNTVIYVD YANVDSTYYI EGTALTYKNF SYIDLNAPLD  660
SLSTDVTLEF GFDSGAQPGE SIIIDKIEFI PIEGSLEAYE ADQALDKAWK AV          712

SEQ ID NO: 199          moltype = DNA   length = 2124
FEATURE                 Location/Qualifiers
source                  1..2124
                        mol_type = other DNA
                        organism = Bacillus thuringiensis
SEQUENCE: 199
atgaatcaaa attatgagaa ctatggaaat aatgaaatga aaatattgga ttctggtatg   60
agaaggtcca gatatccgta tacgaatgca ccaagtgctg atttacaaaa catgaattat  120
aaagaatggg cggaaatgtg tggaaggaat gataacgttg ctgtcccatt gggatcagaa  180
actagagctt catctgaagc tctatcgatt gtcctaggta ttacaggaga tttgatcggt  240
aatgcctttc ctacagctgg attgatgatc gggataatgg gacatctttg gccaaaacaa  300
gaggcagata tgcaagaggt ctgggaaacc cttatgaatg cggtggaaga tctcattgat  360
gcaaaaattg acgagttggt acgatcagaa gcaatcgctg aattaagagc cttacaaagt  420
aatctcaatg tatataatgc ggcgttagac gcttggctca caacaggtga tgataataac  480
agacaatggg tcattgctga acatgacaat tgtgatcaac aatttcgaaa cgcattaaat  540
caattagcat taccaggttg ggagttacta ttattaccat cttttgcaga agctaccacc  600
ctgtatcatt tttttctatcg agattttatg ctgtactggc aagcctgggg catgtcccaa  660
gaggaattta actttaaaaa tagtgaacga aaacgtctat tccaagaaag taccgactat  720
tgcgttagaa tatataatga aggtttaccg gaatcaaaaa caccagacgt gaatatagag  780
gatgctgtcc gttatccatg ggcaaataga gaccaaccag atcattgtaa ttcagaatat  840
cgtgatgccg agggcgaata cctgtctact gaaacttgga atgcatacaa tgcttaccgg  900
agaaatatga cagtttatgg gttagacctt gtggcgatat ggccactata tgatatagat  960
ctctatccaa tagcgctaga agtgagaacg gagcttacgc gagaagtgta tacagatata 1020
gcaggatcaa cctggcgaac agattctagt caaaatacga tagacgcaat agaaaatcgt 1080
atgttaggaa atcgattagg gcctggctta tttacctggt aacagaact gaagttttat 1140
ctaaagaatg taactggtga ttatagaaca accggcaagc taatggtggt gttagaaaaa 1200
acagtaaaga acacccgttc tagtgagtat aaaattccat tagaaggaca gaacacggat 1260
tacacttcta tcgtcaatcc taaagtggat tattctccat attattgggc gatggttaat 1320
acacaacaat ggtttgaaac ccgatggctt cggatatcga ataatgtggg tagttatgct 1380
acaggcgagg taggatcgat aacagaatct tatcccccta ctgccagtac ggggtgtttt 1440
gataatgctg aaataaaagg gatatataat gaaggttctc gatttactag ttaacctat 1500
catcgattat cctggctcaa attcgatcca gtagtggatg gaacaatgc atggcctcag 1560
tataaacaat taagcgctct cttatgtggt tggacacaca ccagtgtaga ttacaataac 1620
acgctatcgc ttgataaaat taaccaaatt ccggcgtgta aagcatattc tctagattac 1680
ggtgctgttg ttattaaagg gcctggtagc acaggtggaa atttagtgca attacctcct 1740
ggtggaaggg taaagataaa attatggaag gaaactatag ttcccaactt atataacttc 1800
agaattcgtt atgcaactgc tgcgaataat gctaacataa cttttgggct agttcctgat 1860
gagtatgaaa cactcccat accatttgac ctacccgcta cgtattctgg aggagaattg 1920
acatataata cctttaaata taggctatt gatacgttga aatttcgag cgagaacgtg 1980
gaaatattta tcacgaatag tagtagtagt gcaggaactg ttatcatcga caaaatcgaa 2040
ttcgaaccac ttcaagcaag tatacctta gaagaatatg tagcggaaca agatctagaa 2100
aaagcatgga aggctgtgaa tgcc                                        2124

SEQ ID NO: 200          moltype = AA   length = 708
FEATURE                 Location/Qualifiers
source                  1..708
                        mol_type = protein
                        organism = Bacillus thuringiensis
SEQUENCE: 200
MNQNYENYGN NEMKILDSGM RRSRYPYTNA PSADLQNMNY KEWAEMCGRN DNVAVPLGSE   60
TRASSEALSI VLGITGDLIG NAFPTAGLMI GIMGHLWPKQ EADMQEVWET LMNAVEDLID  120
AKIDELVRSE AIAELRALQS NLNVYNAALD AWLTTGDDNN RQWVIAEHDN CDQQFRNALN  180
QLALPGWELL LLPSFAEATT LYHFFYRDFM LYWQAWGMSQ EEFNFKNSER KRLFQESTDY  240
CVRIYNEGLP ESKTPDVNIE DAVRYPWANR DQPDHCNSEY RDAEGEYLST ETWNAYNAYR  300
```

```
RNMTVMVLDL VAIWPLYDID LYPIALEVRT ELTREVYTDI AGSTWRTDSS QNTIDAIENR    360
MLGNRLGPGL FTWLTELKFY LKNVTGDYRT TGNLMVGLEK TVKNTRSSEY KIPLEGQNTD    420
YTSIVNPKVD YSPYYWAMVN TQQWFETRWL RISNNVGSYA TGEVGSITES YPPTASTGCF    480
DNAEIKGIYN EGSRFTSLPY HRLSWLKFDP VVDGNNAWPQ YKQLSALLCG WTHTSVDYNN    540
TLSLDKINQI PAVKAYSLDY GAVVIKGPGS TGGNLVQLPP GGRVKIKLWK ETIVPNLYNF    600
RIRYATAANN ANITFGLVPD EYENTPIPFD LPATYSGGEL TYNTFKYKAI DTLQISSENV    660
EIFITNSSSS AGTVIIDKIE FEPLQASIPL EEYVAEQDLE KAWKAVNA                708

SEQ ID NO: 201          moltype = DNA   length = 1167
FEATURE                 Location/Qualifiers
source                  1..1167
                        mol_type = other DNA
                        organism = Bacillus thuringiensis
SEQUENCE: 201
atgaaaaaaa cgttagtcgc agggttatta gttacagcag tatctacaag ttgcttctta     60
cctgtaaata cttttgcaga aaataaaaca acttattcac aactaacaag tagtcaaaat    120
caacttgcta tgaataggtt atcagattcg attaagacat taggatcaca gacaccatta    180
attcaaggat acgggctaat catagtaaag caaccaaacc ttgaagtaaa tgctatacct    240
ggaataacaa ctgatcaagg tactgcaaga accatgttaa agaatggctg gatacatat    300
aatccaaaac tattcaatgt aaatcaagac ctgcaggatt ttgggacaag atttacaaat    360
tattatgata tattggttga actagctgga aaagtgaatg atgattcgca aacaaaagaa    420
gactttgtaa gtatttttaa tgaacttcaa gatcaaatgc aagcaattca gtatgatatg    480
aaaggaactt cagtagactt aaacaattat aagaagact tggttgaaga gtaagagc     540
ttttctagta aagttagcag agcgattgaa ctttataagg gatcaggcgg agacattgaa    600
aaattcagaa cggaaattaa acaacttgat gaaaacattc aagatgatta caaaaacatt    660
ctagctctac caaaagaaaa tataaaaggt tctataaata ttggaaagac agttattgat    720
atttcgatag acgcaggtaa ggatcaaact ttagacacgt ctaatttgga agtgatttat    780
aaccaatttg gacaagtcca aaatgatgaa gtaacaagac tgaataatga tgttcgtaag    840
aagcaacaac aaaaaattct attgctacaa aaattatcga acattgaagt gcaagcaact    900
caaatgacac ttattgatct acagttaaat aactttacaa gagtagttaa aaagcaaatt    960
gagagttttg acaagctaat aagtggttgg gacatcttta ataacacaat gattcaaata   1020
aataagagtc ttagtactga tacgagaata gattctcatg cattacaagc acaattacaa   1080
gaactcaaaa agtttacgga tgaattgaat aaacaaacag cggaatatga aaatagtgtt   1140
acaaacataa agtaacagga ggaaaaaa                                      1167

SEQ ID NO: 202          moltype = AA   length = 389
FEATURE                 Location/Qualifiers
source                  1..389
                        mol_type = protein
                        organism = Bacillus thuringiensis
SEQUENCE: 202
MKKTLVAGLL VTAVSTSCFL PVNTFAENKT TYSQLTSSQN QLAMNRLSDS IKTLGSQTPL     60
IQGYGLIIVK QPNLEVNAIP GITTDQGTAR NHVKEWLDTY NPKLFNVNQD LQDFGTRFTN    120
YYDILVELAG KVNDDSQTKE DFVSIFNELQ DQMQAIQYDM KGTSVDLNNY KEDLVEDSKS    180
FSSKVSRAIE LYKGSGGDIE KFRTEIKQLD ENIQDDYTKL LALPKENIKG SINIGKTVID    240
ISIDAGKDQT LDTSNLEVIY NQFGQVQNDE VTRLNNDVRK KQQQKILLLQ KLSNIEVQAT    300
QMTLIDLQLN NFTRVVKKQI ESFDKLISGW DIFNNTMIQI NKSLSTDTRI DSHALQAQLQ    360
ELKKFTDELN KQTAEYENSV TNIKVTEEK                                     389

SEQ ID NO: 203          moltype = DNA   length = 2073
FEATURE                 Location/Qualifiers
source                  1..2073
                        mol_type = other DNA
                        organism = Bacillus thuringiensis
SEQUENCE: 203
atgagccaaa attacaacaa caatgaatat gaaatcatgg acactggtgg caagggctat     60
cagacaaggt accccctggt gcaggcacca ggttctgaat tcagcaaat gaattataaa     120
gattggatga atatatgtac aaatgaagag tcaggagaat tatttgcaga tttaaacact    180
gctgtgaaga atggggtcat tacaggaaca gctattgtat cgtatatcct cagtgtatca    240
tttcctgttg cttcagcagc agtcggtatt cttagtgtac tattgccaat attgtggcca    300
gaggaggctg aaaatcctca atcgcagttt acgtgggatc agctgatgac ggctgtagca    360
gaactcatta taatgctat tgctgcgaa gcaaaaaggg atgctattga tgcactccaa    420
aaattacaga tatccgtaga tcgttatcag agagcagtct gtaatcttaa agttaaccca    480
gatatggaca tttataaggc caatgtacga tcagcatttg tagaggttga tggagaagca    540
cgcagagcta ttgccaccat ggatgataat cctaccacac atgcagtcca attcttagct    600
agttatgcag aagctgccaa tgtacactta ctttattac gagatgttgt ccaacacgga    660
gaaagtgggg gtttacaccc acttgaagtt caacaatttt atgattatcc ttctggtgga    720
ccaggaaccc gcggtatgaa acagcctatg gcacattata cggactattg tgtacgatgg    780
tataatatcg gtttgcagca acaatacgac actgttgagt ggataaaatt caatgatttc    840
cgtagaaata tgaccatcat ggtaatggat attgtgtcat tatggccaac atatgatcca    900
agactttatg cactgcctac aaaatccaca cttacaagaa ctgtgtatca aggtcggatt    960
ggatataatt gggggctgac gcattctatt gagaacatag aacaggggc cactgttcct   1020
ccacgtctat ttgcatggtt gcaaggaata gatgcctatg ttggacaggt tactgtagat   1080
aatgaacaa tacctgagga gattaatggt tttacagaaa cctttcagaa cacttttgca   1140
aacttcttat ggacaacacc actgatggga ccgctgttgg cagaatcca aaccattaca   1200
attccgccgg tagaatctaa cgatgatgtc tggagaatta aagtggaac atttatgct   1260
gggcacccct ttggggata cgcccttaac gagatgcaat ttctctttaac taaatcagaa   1320
gatcaacaga tcggaactca gcttcctagt gaaagacaag aattgagcgg ttatctcgt   1380
aatcctgttg ctttcagtcc ttgtaatcct tgtgattcta taactcttg tgaacatgga   1440
```

```
                                  -continued
attcttgata cgagtgatcc ttgtaatgac aaactccttt atagtcatag attttcaaat    1500
ctaggactcg gagatgcaag ttacaatgga gtatatgcag gggttgtcta cggctggacc    1560
catgtaagcg cagatgtaaa caatctgata gatgctgaaa agattaccca aattccagct    1620
gtgaaggctt ccagaatgga ggggaatgca caagtaatca aagggcctgg tagcacagga    1680
ggtgatttga tagccataat cggcccccttc gctgcttcgc ggtaacatt gaacctgacg    1740
tttccactat tcaatgaaga acgatactat cgtatgcgtg ttcgttatgc ctgtaaatca    1800
cagggcgatt tagtaattta ttcaaattgg tttaatgata taacattcc atatgtaact    1860
cttcctttga atgctactta ttcttcggat tcattaacat ataattcttt tgattatgta    1920
gaagtgaatg aggtgatacc ggtatacgct tgggcgacta acccaaacgc taagtttagc    1980
ttggacactt catcaagttc gacaatcatc atcgataaaa tcgaattcat accaattgaa    2040
ggatctttgg aggagtatca agcgagtcaa gca                                 2073

SEQ ID NO: 204         moltype = AA  length = 691
FEATURE                Location/Qualifiers
source                 1..691
                       mol_type = protein
                       organism = Bacillus thuringiensis
SEQUENCE: 204
MSQNYNNNEY EIMDTGGKGY QTRYPLVQAP GSEFQQMNYK DWMNICTNEE SGELFADLNT     60
AVKNGVITGT AIVSYILSVS FPVASAAVGI LSVLLPILWP EEAENPQSQF TWDQLMTAVA    120
ELINNAIAAE AKRDAIDALQ KLQISVDRYQ RAVCNLKVNP DMDIYKANVR SAFVEVDGEA    180
RRAIATMDDN PTTHAVQFLA SYAEAANVHL LLLRDVVQHG ESWGFTPLEV QQFYDYPSGG    240
PGTRGMKQLL AHYTDYCVRW YNIGLQQQYD TGEWDKFNDF RRNMTIMVMD IVSLWPTYDP    300
RLYALPTKSQ LTRTVYQGRI GYNWGLTHSI ENIEQGATVP PRLFAWLQGI DAYVGQVTVD    360
NGTIPEKING FTQTFQNTLA NFLWTTPLMG PAVGRIQTIT IPPVESNDDV WRIKSGTFYA    420
GHPFWGYALN EMQFSLTKSE DQQIGTQLPS ERQELSGLSC NPVAFSPCNP CDSNNSCEHG    480
ILDTSDPCND KLLYSHRFSN LGLGDASYNG VYAGVVYGWT HVSADVNNLI DAEKITQIPA    540
VKASRMEGNA QVIKGPGSTG GDLIAIIGPF AASRVTLNLT FPLFNEERYY RMRVRYACKS    600
QGDLVIYSNW FNDINIPYVT LPLNATYSSD SLTYNSFDYV EVNEVIPVYA WATNPNAKFS    660
LDTSSSSTII IDKIEFIPIE GSLEEYQASQ A                                   691

SEQ ID NO: 205         moltype = DNA  length = 747
FEATURE                Location/Qualifiers
source                 1..747
                       mol_type = other DNA
                       organism = Bacillus thuringiensis
SEQUENCE: 205
atgattatac aagaaaaatt atcttttttca gatctagatt cattagattc aactacagat     60
tccataatgg acgcgtttaa agatctttat ggaatactcc ctgatgagat cgcagtaaat    120
aatgagacat ttcccattcg taataagcct gctattactg aaagttatgg tcacgcttgt    180
tataaaacgc ttggaccctt tatatttcga gaaattgaag agccttcaaa gaataaagta    240
agcctaggag aacaatttgt atttaatcct agtaatgaag aagcagaaat tgtagtctca    300
ataaaggagc aatgggctaa tattcaatct tggaattcaa aatcaactac aggtttaact    360
ttaacatcag atttttatcat gacaggtgaa tttcgatctg gaaataaatt taatatctca    420
actttttatgg gagaaaagtaa ttcaaaatca atcattgcct ctccttccat tgagcgttct    480
attaaagtac ctccaaatag taagataaaa ataacaacaa tcggaacatt aattacagaa    540
attctacatt ttcaatcaat tatatcggta cacggtatgt ttggtgcatg ttttccacga    600
atggttcgtg ggcattacgt tggattcaaa agtgccggtc acatcctaaa taaaactttt    660
ggttccataa aaggaccat ttataataca gcaattcagg atattcaaat aaaaactgga    720
gaggcagaac ggttctggtg cacaaaa                                        747

SEQ ID NO: 206         moltype = AA  length = 249
FEATURE                Location/Qualifiers
source                 1..249
                       mol_type = protein
                       organism = Bacillus thuringiensis
SEQUENCE: 206
MIIQEKLSFS DLDSLDSTTD SIMDAFKDLY GILPDEIAVN NETFPIRNKP AITESYGHAC     60
YKTLGPFIFR EIEEPSKNKV SLGEQFVFNP SNEEAEIVVS IKEQWANIQS WNSESTTGLT    120
LTSDFIMTGE FRSGNKFNIS TFMGESNSKS IIASPSIERS IKVPPNSKIK ITIGTLITE    180
ILHFQSIISV HGMFGACFPR MVRGHYVGFK SAGHILNKTF GSIKGTIYNT AIQDIQIKTG    240
EAERFWCTK                                                             249

SEQ ID NO: 207         moltype = DNA  length = 1944
FEATURE                Location/Qualifiers
source                 1..1944
                       mol_type = other DNA
                       organism = Bacillus thuringiensis
SEQUENCE: 207
atggataaca taaatcaaaa tgattttgaa atactagatg catcagcaga atatgcaaat     60
cctccaatca ttttagatga tacaagagat gcacaagaaa cccttacaac ggcactaacg    120
ataacagggg aaattcttag ttttgcgggg gtacccatttg ggacccat tattggtttt    180
actaatcgct tgatcaattt attatggccg caaaagacta cagatgtctg ggaagaattc    240
atgcagcgtg tagaggagct aataaacgag aaaattgcaa atatgcacg aagtaaagca    300
ttaacgaat tacaaggact acaaaatgtc tatcagttgt atcttgaggc actaagagaa    360
tgggaacaaa ccccagataa tccaagtgta caagaacgag taagaacgac atttcgtgat    420
gcaaatgctg cctttaatta tgcaatgcct caatttgcag ttagtggata tgaaattccc    480
ttattaacag tctatgcaca agcagcaaat ctgcatatag ttcttttaag agatgcagat    540
ttatttggaa gtgggtgggg ttttacagaa acaaatgtca acgaccgtta caatgaacaa    600
```

```
gtaagggtaa cagatgccta ttcaaatcat tgcgtaaaat ggtataataa agggttagag    660
aagttaaaaa atcatcaaag tggtggagat tggaagaaat ataatcaatt tcgtagagaa    720
atgacattga tggtactaga tattgtagcg ttattcatta accacgatac acgtaaaatat   780
cctatgaaaa cagcggcaca acttacaaga gatgtgtata cggaaccaat tgcatatacg    840
ggaagcggga attttcaga accttggtat actaaagtgg gattttctac aattgagagt    900
aaagtaatac gatcaccaca tattttgat atactagatt cagtagaaat cagtacagga     960
ttttagagt ttctacaggc ttcaggttat atgtattttt ggtctggaca tactttaact    1020
agctcacttg ctaataataa tacagtaaaa ataacaacca cctatggtgg tcttacaaat   1080
agtaaagaaa agtttagtat aattggaaaa gatttatata aaattaagtc ggttgcattg   1140
ggtcttttcta atgtaaatat agatatgtat ggagtgaacc ccgtagattt ctttatggta  1200
gataaaaaca cttcaaatgt ttcagaatat cactatagta aagcaagtaa tgtgttaagt   1260
gaaaataaag aaactatata ttcagaaaag gaactacctc cagaaacaga gatgaaccaa   1320
gattacaaag tattcagcca tcggttatct catatcacta tgcttgttgt agagccgaca   1380
accactcgtg cagcatatgt gtatttagca ggggttccaa cctatgtttg gacacacaag  1440
agtgcaacac ctacgaatac aatatattca gatcagatta cgcaaattcc agcggtaaaa  1500
atgtatgaat taggaagctc agcggttgtt gtaaagggac ctggatttac aggcggagat  1560
gtagttaaga gagcgggtaa tggtgctctg ggattttttta atattaatgt agagtcccca  1620
ggtgctcagc ggtatcgttt gagaattcgt tatcgttcag atgttagtgg cgtatttcat  1680
atgcaaatta acgacgtaga aactattcag ggaaattta gtagtactgt tgattcgcca   1740
agtactacgt caagcgcatc atataatcat agagaataca gcaccaccct ccgatttcca   1800
acgaatacga caagataaa ggtatcttta ggtgctattg tggtcaagg agactttat    1860
ttagatagaa ttgaattcat tccagtagat gaaaattacg atgaaagagt aacactagaa  1920
aaagcacaga aagccgtgaa tgcc                                          1944

SEQ ID NO: 208          moltype = AA  length = 648
FEATURE                 Location/Qualifiers
source                  1..648
                        mol_type = protein
                        organism = Bacillus thuringiensis
SEQUENCE: 208
MDNINQNDFE ILDASAEYAN PPIILDDTRD AQETLTTALT ITGEILSFAG VPFVGPIIGF    60
TNRLINLLWP QKTTDVWEEF MQRVEELINE KIAEYARSKA LTELQGLQNV YQLYLEALRE   120
WEQTPDNPSV QERVRTTFRD ANAAFNYAMP QFAVSGYEIP LLTVYAQAAN LHIVLLRDAD   180
LFGSGWGFTE TNVNDRYNEQ VRVTDAYSNH CVKWYNKGLE KLKNHQSGGD WKKYNQFRRE   240
MTLMVLDIVA LFINHDTRKY PMKTAAQLTR DVYTEPIAYT GSGNFSEPWY TKVGFSTIES   300
KVIRSPHIFD ILDSVEISTG FLEFLQASGY MYFWSGHTLT SSLANNNTVK ITTTYGGLTN   360
SKEKFSIIGK DLYKIKSVAL GLSNVNIDMY GVNPVDFFMV DKNTSNVSEY HYSKASNVLS   420
ENKETIYSEK ELPPETEDEP DYKVFSHRLS HITMLVVEPT TTRAAYVYLA GVPTYVWTHK   480
SATPTNTIYS DQITQIPAVK MYELGSSAVV VKGPGFTGGD VVKRAGNGAL GFFNINVESP   540
GAQRYRLRIR YRSDVSGVFH MQINDVETIQ GNFSSTVDSP STTSSASYNH REYSTTFRFP   600
TNTTKIKVSL GAIGGQGDFY LDRIEFIPVD ENYDERVTLE KAQKAVNA               648

SEQ ID NO: 209          moltype = DNA  length = 2124
FEATURE                 Location/Qualifiers
source                  1..2124
                        mol_type = other DNA
                        organism = Bacillus thuringiensis
SEQUENCE: 209
atggagggaa caaagatgaa tccatatcag aataaaaatg aatatgaaat agtagatggt    60
ccgcaaaatt atgatactat ttccaatagg tatcttacg cgaataatca ggatattgtg    120
atttccaacg aaatttcccc ctctattata ggaggacttg cgactttatt aagcctttt    180
ttggattaca atctttact tggaagtcct tctatatcag ggggaatcgg ttttctacaa    240
tctattatag gtataataac tgatactaac gtagcaactg ttactataga tgatgtgcaa   300
cgattgatta atcaatcgct agatacgtat acgagacaac aggcagagac taaaatggaa   360
tccataacga gtgaatttac tcaatatctt ctaaatttac gcgattatat agatggacga   420
gcaagtcgaa gtgattttgt acaaagtctt cgaaataatg aacagagact aagaaatgaa   480
ttggattctt ttttttagtttt gcaggggcga gaattgttgt tattaccgaa ctttgtgcaa   540
gtttcgttat tacatttagc aatattaagg gatgctgtgg tttatggagg aactgattta   600
gaaagaccac ttgtcagtga aacagctcaa ataccttttt aactcgacc tcctagtagt   660
tcttatcatg aagcaatttt aactagccta cgtgtatatt ccaattattg tacgcaacaa   720
tacaatatag gtttaaacaa tatgagaaat agaggtactt caggtagaga ttggttaaac   780
tttcatgcat atcggagaga cctaactttaa tccgtgttag atttttgtggc aatttttccca  840
tttttcgatc cattacaata tattacaacg agaaatgtat cgctaccagt aaattctcaa   900
ttaagtaggg ttatatatac agatcctgca ggtattatat ctatcaatgg acaaaccggc   960
tggtttaatc ctggtgctac tcagagtgtt gttaggccta cttttgcatc aatagaaaat  1020
gacatgccgg ctcctacaac ttcgcgattt ttagagaata tagaaatttt tcaggtcca   1080
cttggtgtag gtgtaaatcc aagtagaaca catgcgtggc agggaaatga aaatcgaaat  1140
tcaaataata cagtagatct tttttggaatg agaactaaaa aaggacaaa tctttctggt   1200
caaaatattt tcagggtggt ttcaaatgtt catactctgg attctcggtt gtttggagtt   1260
tatgagcgg atttcttca tgccaatggt caaatatctc gatatcaagc accacaaagc    1320
cctccatcag ctatcggtgt tgcacgacag actcattttt aatttttgcc aggaacaaca    1380
tccaatatac caaatacaaa taattatact catttattaa gtagggtagc aaatataact   1440
ggaggacttc agcaacaat agcggaacaa cgtaattctg tggtaataca tggttggaca   1500
catagaagtt taactcgtga aaatattatt gcaccttgata gcattacaga aatccctgta  1560
gtgaaaacaa gttttctccc gaattgtact gtaattccag gaccaggttt tactggaggt   1620
gatttagtaa gattagatgc taatggcaga tttgatatac aagttcaatt accaacaaca   1680
caaagaagtt atcgaattcg cttacgctat gcttctgcat cgacaggttc aataaatatt   1740
gtctttagtg gcactagtca tccaagtaca ctaccttcta cgacttcatc actcaacaat   1800
ctacaatatg agaattttcg ttattttgat gttattggta cttttttatc tttcattggg   1860
```

-continued

```
aatgggttaa gtatttcgaa tttaactatg aattctaatg ttgtaataga caaaattgaa  1920
ttcattccag ttggtacttt tacaaatcaa tcatttagag aaacacaagg gtataacaat  1980
aattacaatc agaatactag tagtacatat gacaatacgt cctaccaaaa taacaatgat  2040
atatataacc aagactatca caatacttac aaccaggact gtagatgtaa ttgtaatcaa  2100
ggttataata ataactatcc caag                                        2124

SEQ ID NO: 210           moltype = AA   length = 708
FEATURE                  Location/Qualifiers
source                   1..708
                         mol_type = protein
                         organism = Bacillus thuringiensis
SEQUENCE: 210
MEGTKMNPYQ NKNEYEIVDG PQNYDTISNR YLYANNQDIV ISNEISPSII GGLSTLLSLF   60
LDYKSLLGSP SISGGIGFLQ SIIGIITDTN VATVTIDDVQ RLINQSLDTY TRQQAETKME  120
SITSDYTQYL LNLRDYIDGR ASRSDFVQSL RNNEQRLRNE LDSFFSLQGR ELLLLPNFVQ  180
VSLLHLAILR DAVVYGGTDL ERPLVSETAQ IPFLTRPPSS SYHEAILTSL RVYSNYCTQQ  240
YNIGLNNMRN RGTSGRDWLN FHAYRRDLTL SVLDFVAIFP FFDPLQYITT RNVSLPVNSQ  300
LSRVIYTDPA GIISINGQTG WFNPGATQSV VRPTFASIEN DMPAPTTSRF LENIEIFSGP  360
LGVGVNPSRT HAWQGNENRN SNNTVDLFGM RTNQRTNLSG QNIFRVVSNV HTLDSRLFGV  420
YGADFLHANG QISRYQAPQS PPSAIGVARQ THFQFLPGTT SNIPNTNNYT HLLSRVANIT  480
GGLQPTIAEQ RNSVVIHGWT HRSLTRENII APDSITQIPA VKTSFSPNCT VIPGPGFTGG  540
DLVRLDANGR FDIQVQLPTT QRSYRIRLRY ASASTGSINI VFSGTSHPST LPSTTSSLNN  600
LQYENFRYFD VIGTFLSSLG NGLSISNLTM NSNVVIDKIE FIPVGTFTNQ SFRETQGYNN  660
NYNQNTSSTY DNTSYQNNND IYNQDYHNTY NQDCRCNCNQ GYNNNYPK              708

SEQ ID NO: 211           moltype = DNA   length = 2013
FEATURE                  Location/Qualifiers
source                   1..2013
                         mol_type = other DNA
                         organism = Bacillus thuringiensis
SEQUENCE: 211
atgagtccaa ataatcaaaa tgaatatgaa attatagatg cgacaccttc tacttctgta   60
tccaatgatt ctaacagata ccctttttgcg aatgagccaa caaatgcgct acaaaatatg  120
gattataaag attatttaaa aatgtctgcg ggaaatgcta gtgaatacccc tggttcacct  180
gaagtacttg ttagcggaca agatgcagct aaggccgcaa ttgatatagt aggtaaatta  240
ctatcaggtt taggggtccc atttgttggg ccgatagtga gtctttatac tcaacttatt  300
gatattctgt ggccttcagg ggaaaagagt caatgggaaa ttttttatgga acaagtagaa  360
gaactcatta atcaaaaaat agcagaatat gcaaggaata aagcgctttc ggaattagaa  420
ggattaggta ataattacca attatatcta actgcgcttg aagaatggga agaaaatcca  480
aatggttcaa gagcccttacg agatgtgcga aatcgatttg aaatcctgga tagtttattt  540
acgcaatata tgccatcttt tagagtgaca aattttgaag taccattcct tactgtatat  600
gcaatggcag ccaaccttca tttactgtta ttaaaggacg cgtcaatttt tggagaagaa  660
tgggatggt caacaactac tattaataac tattatgatc gtcaaatgaa acttactgca  720
gaatattctg atcactgtgt aaagtggtat gaaactggtt tagcaaaatt aaaaggcacg  780
agcgctaaac aatgggttga ctataaccaa ttccgtagag aaatgacact ggcgttttta  840
gatgttgttg cattattccc aaaattatgac acacgcacgt acccaatgga aacgaaagca  900
caactaacaa gggaagtata tacagatcca ctggggcgcg taaacgtgtc ttcaattggt  960
tcctggtatg acaaagcacc ttctttcgga gtgatagaat catccgttat tcgaccaccc 1020
catgtatttg attatataac gggactcaca gtgtatacac aatcaagaag catttcttcc 1080
gctcgctata taagacattg ggctggtcat caaaataagct accatcgtgt cagtaggggt 1140
agtaatcttc aacaaatgta tggaactaat caaaatctac acagcactag taccttttga 1200
tttacgaatt atgatattta caagactcta tcaaaggatg cagtactcct tgatattgtt 1260
tacccctggtt atacgtatat attttttgga atgccagaag tcgagttttt catggtaaac 1320
caattgaata ataccagaaa gacgttaaag tataatccag tttccaaaga tattatagcg 1380
agtacaagag attcggaatt agaattacct ccagaaactt cagatcaacc aaattatgag 1440
tcatatagcc atagattatg tcatatcaca gtattcccg cgacgggtaa cactaccgga 1500
ttagtacctg tatttcttg gacacatcga agtgcagaat taataatat aattgcatcg 1560
gatagtatta ctcaaatccc tgcagtgaag ggaaactttc tttttaatgg ttctgtaatt 1620
tcaggaccag gatttactgg tggggactta gttagattaa atagtagtgg aaataacatt 1680
cagaatagag ggtatattga agttccaatt cacttcccat cgacatctac cagatatcga 1740
gttcgtgtac ggtatgcttc tgtaaccccg attcacctca acgttaattg gggtaattca 1800
tccattttt ccaatacagt accagctaca gctacgtcat tagataatct acaatcaagt 1860
gattttggtt attttgaaag tgccaatgct tttacatctt cattaggtaa tatagtaggt 1920
gttagaaatt ttagtgggac tgcaggagtg ataatagaca gatttgaatt tattccagtt 1980
actgcaacac tcgaagctga atataatctg gaa                             2013

SEQ ID NO: 212           moltype = AA   length = 671
FEATURE                  Location/Qualifiers
source                   1..671
                         mol_type = protein
                         organism = Bacillus thuringiensis
SEQUENCE: 212
MSPNNQNEYE IIDATPSTSV SNDSNRYPFA NEPTNALQNM DYKDYLKMSA GNASEYPGSP   60
EVLVSGQDAA KAAIDIVGKL LSGLGVPFVG PIVSLYTQLI DILWPSGEKS QWEIFMEQVE  120
ELINQKIAEY ARNKALSELE GLGNNYQLYL TALEEWEENP NGSRALRDVR NRFEILDSLF  180
TQYMPSFRVT NFEVPPLTVY AMAANLHLLL LKDASIFGEE WGWSTTTINN YYDRQMKLTA  240
EYSDHCVKWY ETGLAKLKGT SAKQWVDYNQ FRREMTLAVL DVVALFPNYD TRTYPMETKA  300
QLTREVYTDP LGAVNVSSIG SWYDKAPSFG VIESSVIRPP HVFDYITGLT VYTQSRSISS  360
ARYIRHWAGH QISYHRVSRG SNLQQMYGTN QNLHSTSTFD FTNYDIYKTL SKDAVLLDIV  420
```

```
YPGYTYIFFG MPEVEFFMVN QLNNTRKTLK YNPVSKDIIA STRDSELELP PETSDQPNYE    480
SYSHRLCHIT SIPATGNTTG LVPVFSWTHR SAEFNNIIAS DSITQIPAVK GNFLFNGSVI    540
SGPGFTGGDL VRLNSSGNNI QNRGYIEVPI HFPSTSTRYR VRVRYASVTP IHLNVNWGNS    600
SIFSNTVPAT ATSLDNLQSS DFGYFESANA FTSSLGNIVG VRNFSGTAGV IIDRFEFIPV    660
TATLEAEYNL E                                                       671

SEQ ID NO: 213          moltype = DNA   length = 2010
FEATURE                 Location/Qualifiers
source                  1..2010
                        mol_type = other DNA
                        organism = Bacillus thuringiensis
SEQUENCE: 213
atgaaccaaa ataatcaaaa tgaatatgaa gttattgatg ctccccattg tgggtgtccg     60
tcagatgatg atgttaggta tcccttggca agtgaccga atgcagcgtt acaaaatatg    120
aactataaag agtatttaca aacgtatggt ggagactata cagattctct tatcaatcct    180
aatttatcta ttaatcctag agatgtgctg gaaattggaa ttcgttgt gggaagaata     240
ttaggattta taggttttcc cttctctgga gcaataacaa gttttata c gtttctctta    300
aatcaactgt ggccaactaa taataatgca gtatgggaag catttatggc gcaaatagaa    360
gagctgatcg atcaaagaat atcggctcaa gtactaaggg atgcacttaa tgccttaact    420
ggaatacacg attattataa cgaatattta gcggcattgg aagagtggct ggaaagaccg    480
agcggcgcaa gagctaactt agttacacag aggtttgaaa atctgcatca atcctttgta    540
actcagatgc ctagctttgg tagtggtcct ggtagcaaa gatgcggt agcattgttg      600
acggtatatg cacaagcagc gaatctccat ttgttattat aaaagatgc agaaatttat    660
ggggcaagat ggggacttca acaaggtcag attaacttat atttcaatgc gcaacaagag    720
cgtactcaag tttataccaa tcattgtgtg gaaacatata tagaggatt agaagatgta    780
agaggaacaa atactgaaag ctggttaaat taccatcgtt tccgtagaga gatgacatta    840
atggcaatgg atttagtcgc attattccca tattataacg tacgacgata tgcaaatggg    900
gcaaatccac agcttacacg tgagatatat acagatccga ttatatttaa tccccaggct    960
aatgtaggat tatgtagacg ttggggcaat aacccatata tacatttc ggaacttgaa    1020
aatgctttta ttcgtccacc acatcttttt gatagattaa atagcttatc aattaatcgg   1080
tctcgatatc caatttctaa taattttatt gaatattggt caggacatgt tgtacgccgt   1140
agttttcga atgactcgac tgtatatgaa aatagttacg gtgcaacaaa taatttaaca   1200
actatactca atatggggc tactggagtt agccgaattg attcaacagc agtagatttt   1260
cgtagcacta tagctggggt atatgtcgtt tctagagctc gttttggaaa tgtaggtcg   1320
tttattaatg tgtcacagcc ggtaatggg ggatgcaggc aagagtatga cacaatagat   1380
gaattaccac aagatgaaag taatgggatg ttcgaccata aattatctca tgtgaccttt   1440
ttaagttttc agactacgca ggcgggaacc cttgctcatg gaggtttcgt tcctacgtat   1500
gtttggaccc atcgcgatgt agatttaat aacacaatta cttcaaatag aactactcaa   1560
ctaccattag taaagtcatt tcaaatagat gggatacta ctgtcgtaag aggaccagga   1620
tttacaggag gagatgtact tcgaagaaca agtcctggtg cattaggaac aattagagta   1680
aatgttaatt caccattaac acaaagatat cgtgttagat tcggtatgc atcaacaaca   1740
gatttttaatt tctttgtaat acgtggaggt actactgtaa ataattttac attcccaaga   1800
acaatgaaca gcggacagga atcagatac gaatcctatg tcacaagaga gttttctacg   1860
cctttttaatt tcttacaggt acaagataca cttagattgg cggtgcaatc gtttagctct   1920
gggcaacaag tgtatgtcga tagaattgaa atcatccctg tgaatccgac aagagaagcg   1980
gaagaggatt tagaagcggc ggaagaaagcg                                    2010

SEQ ID NO: 214          moltype = AA   length = 670
FEATURE                 Location/Qualifiers
source                  1..670
                        mol_type = protein
                        organism = Bacillus thuringiensis
SEQUENCE: 214
MNQNNQNEYE VIDAPHCGCP SDDDVRYPLA SDPNAALQNM NYKEYLQTYG GDYTDSLINP     60
NLSINPRDVL EIGITVVGRI LGFIGFPFSG AITSFYTFLL NQLWPTNNNA VWEAFMAQIE    120
ELIDQRISAQ VLRDALNALT GIHDYYNEYL AALEEWLERP SGARANLVTQ RFENLHQSFV    180
TQMPSFGSGP GSQRDAVALL TVYAQAANLH LLLLKDAEIY GARWGLQQGQ INLYFNAQQE    240
RTQVYTNHCV ETYNRGLEDV RGTNTESWLN YHRFRREMTL MAMDLVALFP YYNVRRYANG    300
ANPQLTREIY TDPIIFNPPA NVGLCRRWGN NPYNTFSELE NAFIRPPHLF DRLNSLSINR    360
SRYPISNNFI EYWSGHVVRR SFSNDSTVYE NSYGATNNLT TILNMGATGV SRIDSTAVDF    420
RSTIAGVYVV SRARFGNVGS FINVSQPVNG GCRQEYDTID ELPQDESNGM FDHKLSHVTF    480
LSFQTTQAGT LAHGGFVPTY VWTHRDVDFN NTITSNRTTQ LPLVKSFQID GGTTVVRGPG    540
FTGGDVLRRT SPGALGTIRV NVNSPLTQRY RVRFRYASTT DFNFFVIRGG TTVNNFTFPR    600
TMNSGQESRY ESYVTREFST PFNFLQVQDT LRLAVQSFSS GQQVYVDRIE IIPVNPTREA    660
EEDLEAAKKA                                                          670

SEQ ID NO: 215          moltype = DNA   length = 2217
FEATURE                 Location/Qualifiers
source                  1..2217
                        mol_type = other DNA
                        organism = Bacillus thuringiensis
SEQUENCE: 215
atggaggaaa ataatcagaa tcaatgcgtc ccttataatt gtttgaataa tcctgcaatc     60
gaaatattag aaggagacag aatatcagtt ggtaacactc caatcgatat ttctctatca    120
cttgtggaac ttcttattag tgaatttgtc ccaggcggtg gaataataac aggattgttg    180
aacatagtat ggggatttgt agggccttcc caatgggacg catttcttgc tcaagtggaa    240
cagttaatta accaaaggat atcagaagct gtaagaaata cagcaattca ggaattagag    300
ggaatggcgc gggtttatag aacctatgct actgcttttg ctgagtggga aagagatcct    360
aataacacag atctaagaga agtagtacgg acacagttta cagcaactga gacttatatc    420
```

```
agtggaagaa tatctgtttt aaaaattcaa aattttgaag tgcagctgtt atcggtgttt    480
gcccaagctg ccaatttaca tttatcttta ttaagagacg ttgtgttttt tgggcaaaga    540
tgggggtttt caacgacaac cgtaaataat tactacaatg atttaacaga agagattagt    600
acctatacag attatgcagt acgctggtac aatacgggat tagagcgtgt atggggaccg    660
gattctagag attgggtaag gtataatcaa tttagaaggc agctaacact tactgtatta    720
gatatcgttg ctctattccc aaattatgat agtcgaaggt atccaattcg aacagtttcc    780
caattaacaa gagaaattta tacgaaccca gtattagaaa attttgatgg tagttttcga    840
ggaatggctc agagaataga acagaatatt aggcaaccac atcttatgga tatccttaat    900
agtataacca tttatactga tgtgcataga ggctttaatt attggtcagg gcatcaaata    960
acagcttctc ctgtaggatt ttcaggacca gaattctcat tccctttatt tgggaatatg   1020
ggaaatgcag ctccacccat acttgtctca ttaactggtt tggggatttt tagaacatta   1080
tcttcacctt tatatagaag aattatactt ggttcaggcc caaataatca ggaactgttt   1140
gtccttgatg gaacggagtt ttcttttgcc tccctaacga ccaacttgcc ttccactata   1200
tatagacaaa ggggtacagt cgattcacta gatgtaatac ccacagga taatagtgta   1260
ccacctcgtg cgggatttag ccatcgattg agtcatgtta caatgctgag ccaagcagct   1320
ggagcagttt acaccttgag agctccaacg ttttcttggc agcatcgcag tgctacgaca   1380
actaatataa ttgcagcgga tagtattact caaattcctg ctgttaaagg acgttctatt   1440
attaataatg gcacggtaat ttcaggacca gggtttaccg gaggcgattt ggttagatta   1500
tacaatgctg attttaatat taataataga gcataccttg aagttccgat attcttccaa   1560
tcaccctcta caaattatcg tgttcgtgtt cgttatgctt ctacatcttc actccctgta   1620
gatgtagttt tcgaaatat tagtcatcct actacattcc cagccactgc cagatcatta   1680
gataatctac aatccaatga ttttggatat attgatattg ctggaacttt cttaccttca   1740
ctagggccta gtataggtat cagacccatg ttatctacta ttaatttgat agtagataga   1800
tttgaattta ttccagtaac tgcaacctttg aagcagaat cggatttaga aagagcacaa   1860
aaggcggtga atgcgctgtt tacttctaca aaccaactag gataaaaac agatgtgacg   1920
gattatcata ttgatcaagt gtccaatcta gttgagtgtt tatcggatga attttgtctg   1980
gatgaaaagc aagaattatc cgagaaagtc aaacatgcga agcgactcag tgatgagcga   2040
aatttacttc aagatccaaa cttcaggggc atcaatagac aaccagatcg tggctggaga   2100
ggaagtacgg atattaccat ccaaggagga gatgacgtat caaagagaa ttacgtcaca   2160
ctaccaggta cctttgatga gtgctatcca acgtatttat atcaaaaaat agatgag     2217

SEQ ID NO: 216           moltype = AA  length = 739
FEATURE                  Location/Qualifiers
source                   1..739
                         mol_type = protein
                         organism = Bacillus thuringiensis
SEQUENCE: 216
MEENNQNQCV PYNCLNNPAI EILEGDRISV GNTPIDISLS LVELLISEFV PGGGIITGLL     60
NIVWGFVGPS QWDAFLAQVE QLINQRISEA VRNTAIQELE GMARVYRTYA TAFAEWERDP    120
NNTDLREVVR TQFTATETYI SGRISVLKIQ NFEVQLLSVF AQAANLHLSL LRDVVFFGQR    180
WGFSTTTVNN YYNDLTEEIS TYTDYAVRWY NTGLERVWGP DSRDWVRYNQ FRRELTLTVL    240
DIVALFPNYD SRRYPIRTVS QLTREIYTNP VLENFDGSFR GMAQRIEQNI RQPHLMDILN    300
SITIYTDVHR GFNYWSGHQI TASPVGFSGP EFSFPLFGNM GNAAPPILVS LTGLGIFRTL    360
SSPLYRRIIL GSGPNNQELF VLDGTEFSFA SLTTNLPSTI YRQRGTVDSL DVIPPQDNSV    420
PPRAGFSHRL SHVTMLSQAA GAVYTLRAPT FSWQHRSATT TNIIAADSIT QIPAVKGRSI    480
INNGTVISGP GFTGGDLVRL YNADFNINNR AYLEVPIFFQ SPSTNYRVRV RYASTSSLPV    540
DVVFGNISHP TTFPATARSL DNLQSNDFGY IDIAGTFLPS LGPSIGIRPM LSTINLIVDR    600
FEFIPVTATF EAESDLERAQ KAVNALFTST NQLGIKTDVT DYHIDQVSNL VECLSDEFCL    660
DEKQELSEKV KHAKRLSDER NLLQDPNFRG INRQPDRGWR GSTDITIQGG DDVFKENYVT    720
LPGTFDECYP TYLYQKIDE                                                 739

SEQ ID NO: 217           moltype = DNA  length = 1884
FEATURE                  Location/Qualifiers
source                   1..1884
                         mol_type = other DNA
                         organism = Bacillus thuringiensis
SEQUENCE: 217
atggagaata atattcaaaa tcaatgcgta ccttacaatt gtttaagtaa tcctgaggag     60
atactttag atggagaaag aatatctact ggtaattcat caattgatat ttctctgtca    120
cttgttcagc ttctggtatc aaactttgta ccaggggag gatttttagt tggattacta    180
gattttgtat ggggaatagt aggccccttct ccatgggatg catttttagt gcaaattgaa    240
caattaatta atgaaagaat agctgcatat gctaggatg ctgctattgc taatttagaa    300
ggtttaggaa acaatttcaa tatatatgtg gaagcattta agaatgggaa ggaaatcct    360
aatgattcag cagcaaggac cagagtaatt gatcgcttca gtactttga tgggctactt    420
gaaagggata ttccttcgtt tcgaattcct ggatttgaag taccccttttt atccgttat    480
gctcaagcgg ccaatctgca tctagctata ttaagagatt ctataatttt tggagaaata    540
tgggattgat caacgacaaa tgtcaatgaa actataata gactaattag gcatattgat    600
gaatatgctg atcactgtgc aaatacgtat aatcgggat taaataatt accgaaatct    660
acgtatcaag attggataac atataatcga ttacggagag acttaacatt gactgtatta    720
gatatcgccg ctttcttcc aaactatgac aataggagat atccaattca aacagttggt    780
caactatcaa gggaagttta tacggaccca ttaattaatt ttaatcccca gttacagtct    840
gtagctcaat tacctacttt taacgttatg gagagcagcg caattagaaa tcctcattta    900
tttgatatat taaaatcct tacaatcttt acggattggt ttagtgttgg acgcaacttt    960
ggggag gaagcgact aatatctaac cgtataggag gaggtaacat aacatctcat   1020
atatatggaa gagaggcgaa ccaggaacct ccaagatcct ttactttaa tggaccggta   1080
tttaggactt tatcaaatcc tactttcga ttattacagc aacctggcc ggcgccacca   1140
tttaattac gtggtgtga aggagtagaa ttttctacac ctacaaatag ctttacgtat   1200
cgaggaagag gtacgttga ttctttaact gaattaccgc tgaggataa tagtgtgcca   1260
cctcgcgaag gatatagcca tcgtttatgt catgcaactt ttgtccaaag atctggaaca   1320
```

```
cctttttta caactggtgt agtattttct tggacgcatc gtagtgctac tgatcgaaat   1380
ataatctacc cggatgtaat tactcaaatt cctgctgtta aaggtaactt tcttttaat   1440
gcagctgtaa acccagggcc aggatttact gggggagata cagttagatt aaacaatagt   1500
ggaaataata ttcaaaatag aggctacctt gagattccaa ttcaattcac atcgacagct   1560
atcagatatc gagttcgtgt acgttatgct tctgtaaacc caattctcct cagtgttaat   1620
tttgggaata caaacatttt ttctaacaca gtaccagcta cagctgcgtc attagataac   1680
ctaaaatcag gggatttggg ttatttagaa agcaccagtg cttttacatc tgtagcaagt   1740
aatgtagtag gtattagaaa ttttagtgag aatgcaggag tgataataga cagatttgaa   1800
tttattccag ttactgcaac atttgaggca gaatatgatt tagaaagagc gcaaaaggcg   1860
gtgaatgccc tgtttacgtc taca                                         1884

SEQ ID NO: 218           moltype = AA  length = 628
FEATURE                  Location/Qualifiers
source                   1..628
                         mol_type = protein
                         organism = Bacillus thuringiensis
SEQUENCE: 218
MENNIQNQCV PYNCLSNPEE ILLDGERIST GNSSIDISLS LVQLLVSNFV PGGGFLVGLL   60
DFVWGIVGPS PWDAFLVQIE QLINERIAAY ARDAAIANLE GLGNNFNIYV EAFKEWEGNP   120
NDSAARTRVI DRFRILDGLL ERDIPSFRIS GFEVPLLSVY AQAANLHLAI LRDSIIFGEI   180
WGLTTTNVNE NYNRLIRHID EYADHCANTY NRGLNNLPKS TYQDWITYNR LRRDLTLTVL   240
DIAAFFPNYD NRRYPIQTVG QLSREVYTDP LINFNPQLQS VAQLPTFNVM ESSAIRNPHL   300
FDILNNLTIF TDWFSVGRNF YWGGHRVISN RIGGGNITSP IYGREANQEP PRSFTFNGPV   360
FRTLSNPTLR LLQQPWPAPP FNLRGVEGVE FSTPTNSFTY RGRGTVDSLT ELPPEDNSVP   420
PREGYSHRLC HATFVQRSGT PFLTTGVVFS WTHRSATDRN IIYPDVITQI PAVKGNFLFN   480
AAVNPGPGFT GGDTVRLNNS GNNIQNRGYL EIPIQFTSTA IRYRVRVRYA SVTPILLSVN   540
FGNTNIFSNT VPATAASLDN LKSGDFGYLE STSAFTSVAS NVVGIRNFSE NAGVIIDRFE   600
FIPVTATFEA EYDLERAQKA VNALFTST                                     628

SEQ ID NO: 219           moltype = DNA  length = 978
FEATURE                  Location/Qualifiers
source                   1..978
                         mol_type = other DNA
                         organism = Bacillus thuringiensis
SEQUENCE: 219
atgaagaaga aaataataa aaagacaaaa caaattcttt ctcttgctat gcttggagct   60
attggaacat cattagcatt tacatctcca ggttcagtaa gtgctgctga attagttct   120
attcaaagtg ctgcgcaaga acaaggaagt gtatctatat cagattggcg tgagcctttc   180
agaaatgcat acaagattgc taacaagaat gatccttaca cttattttgg cgaggatgca   240
acagagtata cactcggtaa tgtttaccaa tcgtcggtgg aagcggatgg ttcccctact   300
attactaatt cacgtagttt atttgtaggg agagcaattt taaagaatga tttagatgaa   360
gagcaaacgc ttactacaga tcaatttca aagacattcg aaaattctgt cactaattcc   420
actacaaatg gatttaactt aggggtaagt gcctcttcat ttggtatcc cacttatt   480
ggagagacaa gtgttgaaat atctactgaa tataattttt caagtacaga ggaaaaaacg   540
aagagtgaaa gttatactta taccgctagt ccacaaaaca tcaaagttcc tgcacattca   600
tctgtagaag ttattgtaaa tttaaatacg gctaaaataa gcggtaaagt aaaacttctt   660
tctaaaattg atggtacatt tactcatgct tctggaggag atggtagctt cactgctacg   720
agaggtcttt gggcattaga gtacgatgct tctatgtatg agaaactag tgatttaaaa   780
tctgctagag taggagcaga agcatatggg ccggtatatt tgataggaag tggtaaatat   840
tcagctgaat atggaacaga gtttgctgta actgtaaggc cagttgaaaa acctaacgga   900
tttaaatcta tgattgctga aaatagcaaa tcaactaatg aaggttatac ttataaggta   960
aaaccagaaa ttaaaaaa                                                978

SEQ ID NO: 220           moltype = AA  length = 326
FEATURE                  Location/Qualifiers
source                   1..326
                         mol_type = protein
                         organism = Bacillus thuringiensis
SEQUENCE: 220
MKKKNNKKTK QILSLAMLGA IGTSLAFTSP GSVSAAEISS IQSAAQEQGS VSISDWREPF   60
RNAYKIANKN DPYTYFGEDA TEYTLGNVYQ SSVEADGSPT ITNSRSLFVG RAILKNDLDE   120
EQTLTTDQFS KTFENSVTNS TTNGFNLGVS ASSSFGIPLI GETSVEISTE YNFSSTEEKT   180
KSESESYTYAS PQNIKVPAHS SVEVIVNLNT AKISGKVKLL SKIDGTFTHA SGGDGSFTAT   240
RGLWALEYDA SMYEKLSDLK SARVGAEAYG PVYLIGSGKY SAEYGTEFAV TVRPVEKPNG   300
FKSMIAENSK STNEGYTYKV KPEIKK                                       326

SEQ ID NO: 221           moltype = DNA  length = 2139
FEATURE                  Location/Qualifiers
source                   1..2139
                         mol_type = other DNA
                         organism = Bacillus thuringiensis
SEQUENCE: 221
atgtttagag tccttatat caaaaatttt gagcatacgg agggaataaa atgaatact    60
tatcaatata aaaatgaata tgaaatattg gatgcttatc caaattattc gaacacggta   120
aatacttatt caaggtatcc gttagcaaat aattcacaag ctccttaca aaacacaaat   180
tataaagatt ggcttaatat gtgtccaaat aataatatat tgtgtactcc tagagatatt   240
gatattaatt ctgtctctgc cactataggg gcagtaggta ctatattatc tcttattcct   300
ggtccaggag aagcaatagg atttgtttta gcaactttca catcactaat accttatctt   360
tggccaagtg acacaaaaac aatatgggga gatttcacaa aacaaggatt gcaacttttt   420
```

```
agaccggagc taggcagaga tgcaatagaa attataggca acaacgtaca atcaggatac    480
aatacgttaa aagacatgat gcagaacttt gagactaggt ttgcaacttg gaaaatccat    540
agaactagag ctaatgcaac attggtcata tctgcatttg acaatgttag tgatcaaatt    600
ctccgactta aaaatgactt cttaataaat cccgaaaata aacccgcatt tctaaatctc    660
tatgcacaaa ctgccaattt tgatttaatt ttatatcaaa gaggggccgt atatggagat    720
gattgggtaa aagatataaa taatagatcc atattttctt ctggttcagc agcctattat    780
gaatgtttga aactgaaaat agtagagtat actaacaatt gtgcagaaac atatagaaac    840
agtttaaata tactcaaaaa caagtctaat atctcatggg atacgtataa taaataccgt    900
agagaggtga ctttaggtgc attagattta gttgcgttat tcccaaatta cgatatatgt    960
atttatccaa tacaaacaaa aacagaactt actagaaaaa tttatatgcc atcattctat   1020
ttacaagcac ttggacaaag cggaaatcta gaatcattgg aaaaccaact tacacatccc   1080
ccatcattat ttacttggtt aaacgaatta aacctttata caataagtga aaatttcaat   1140
ccggctttaa gggtatcttc attgtcaggt cttcaagcta aatatcgtta tacccaaaat   1200
ccggctatac ttcctaatcc ggctcaagga atcacaaatg gcacaccgat accaataggg   1260
ctaaataact tgtttattta taaattatca atgtcacaat atcatgatcc aaatgattgt   1320
tatccaaatag ctggaatttc cgatatgacc ttttataaaa gtgactataa tggtaatgcg   1380
tccacaactc aaacttatcg agcaggtaga aactcaaata atgtcataga tacatttatg   1440
aatggcccac aaaatgcatc aagctcaaat aatatttcaa ttaaacaaac aaaccatata   1500
ctatctgata ttaaaatgaa ctactctcga attggcggaa tatacccatc atatactttt   1560
ggatattcat ttgcttggac acatactagt gtagatcctg acaatctgat tgttccaaac   1620
agaattacac aaattcctgc tgttaaagct gattctctga cttcaccagc tagagtaatt   1680
gcaggccctg gtcatacagg aggcgattta gttgctcttc taaacgatgg cactcaagct   1740
ggcagaatgc aaatccgatg taaaacaggt aactttactg gagcttccag acgttatggt   1800
ttacgcatgc gttacgctgc aaataatgaa tttacagtga atctatcata tagcttacag   1860
ggtggtaatc catccggtac atcatttgtt acagaacgta cattttcaag aactaataat   1920
ataataccaa cagatttaaa ttacagggag cttaaatata agaatatta tcaaattatt   1980
acaatgactt tacctgcaaa tacagtaata actatatcta ttcaacaagc aaatgggttt   2040
ttaaataatc aattgattat tgacagaatt gaatttttatc caacggatca aggtatagta   2100
gcttgcgaac tggatcaaaa tgcaataagt tgtaaaatt                           2139

SEQ ID NO: 222        moltype = AA  length = 713
FEATURE               Location/Qualifiers
source                1..713
                      mol_type = protein
                      organism = Bacillus thuringiensis
SEQUENCE: 222
MFRVLYIKNF EHTEGIKMNT YQYKNEYEIL DALPNYSNTV NTYSRYPLAN NSQAPLQNTN     60
YKDWLNMCPN NNILCTPRDI DINSVSATIG AVGTILSLIP GPGEAIGFVL ATFTSLIPYL    120
WPSDTKTIWG DFTKQGLQLF RPELGRDAIE IIGNNVQSGY NTLKDMMQNF ETRFATWKIH    180
RTRANATLVI SAFDNVSDQI LRLKNDFLIN PENKPAFLNL YAQTANFDLI LYQRGAVYGD    240
DWVKDINNRS IFSSGSAAYY ECLKLKIVEY TNNCAETYRN SLNILKNKSN ISWDTYNKYR    300
REVTLGALDL VALFPNYDIC IYPIQTKTEL TRKIYMPSFY LQALGQSGNL ESLENQLTHP    360
PSLFTWLNEL NLYTISENFN PALRVSSLSG LQAKYRYTQN PAILPNPAQG ITNGTPIPIG    420
LNNLFIYKLS MSQYHDPNDC YPIAGISDMT FYKSDYNGNA STTQTYRAGR NSNNVIDTFM    480
NGPQNASSSN NISIKQTNHI LSDIKMNYSR IGGIYPSYTF GYSFAWTHTS VDPDNLIVPN    540
RITQIPAVKA DSLTSPARVI AGPGHTGGDL VALLNDGTQA GRMQIRCKTG NFTGASRRYG    600
LRMRYAANNE FTVNLSYSLQ GGNPSGTSFV TERTFSRTNN IIPTDLNYRE LKYKEYYQII    660
TMTLPANTVI TISIQQANGF LNNQLIIDRI EFYPTDQGIV ACELDQNAIS CKI           713

SEQ ID NO: 223        moltype = DNA  length = 981
FEATURE               Location/Qualifiers
source                1..981
                      mol_type = other DNA
                      organism = Bacillus thuringiensis
SEQUENCE: 223
atgaaaaata gtaaaaaatt aaaaagaaaa atattagctt gtggagcaat cgcatctatt     60
gggaccacac ttgtatcgtc atcaccaatt ttagctagtg cagagcaaat taatacttca    120
gaattagaaa gagatcaaaa ggctgaagct atattagaat ggaagaaacc acttttcaag    180
gctacggaag tttatggaaa aaacatagtt gttccaagtg gatatgaata tcgttccact    240
tggtcggacg ggtatcatac ttcctataaa aatttagaat atcacaatt ttcagtagca    300
gcagatggtc tgcctaacat tactaattta aacactgtat ttgttggaaa gaccacccta    360
actaataata caaaccaaga acaaacgtta tctactaata gttttttcgaa agcgattaca    420
aattcagtta ctcattcaac tacacatggt tttaaatttg gaaccaaagc atcttcgaaa    480
tttaaaattc ctattgtagg agaaacaaca gttgaattat ctgcagaata caattttcca    540
gatacatcta gtcaaacaag ctctgaaagt tacacttata tttctacacc acagaatata    600
aaagttcctg cccattcatc tgtagaagtt tttgtaactt taaatacagt aaagcaaaa    660
gggaatgtaa aacttcttgc taaatgtctt ggtgaggata gaggtagctt tatttataac    720
tctacaacag gaggtcctgg taaagatgta gtttataata aaacatttaa ttcaatagtt    780
tcatatgctt cgaaaattga aaaacttcaa aatatctcag ctaatcctaa tggcaaaaca    840
gtaaatatta taggttcagg tatttatgaa gctgaatatg gaactgagtt tgatgtaact    900
gtaacaccta ttgataaaaa tggaaagtcg gtagataagg ttatacgta taaggtgaaa    960
ccggagatta caaagaaaaa a                                              981

SEQ ID NO: 224        moltype = AA  length = 327
FEATURE               Location/Qualifiers
source                1..327
                      mol_type = protein
                      organism = Bacillus thuringiensis
SEQUENCE: 224
```

```
MKNSKKLKRK ILACGAIASI GTTLVSSSPI LASAEQINTS ELERDQKAEA ILEWKEPLFK   60
ATEVYGKNIV VPSGYEYRST WSDGYHTSYK NLEYHQFSVA ADGLPNITNL NTVFVGKTTL  120
TNNTNQEQTL STNSFSKAIT NSVTHSTTHG FKFGTKASSK FKIPIVGETT VELSAEYNFS  180
DTSSQTSSES YTYISTPQNI KVPAHSSVEV FVTLNTVKAK GNVKLLAKMS GEDRGSFIYN  240
STTGGPGKEY VYNKTFNSIV SYASKIEKLQ NISANPDGKT VNIIGSGIYE AEYGTEFDVT  300
VTPIDKNGKS VDKGYTYKVK PEITKEK                                     327

SEQ ID NO: 225          moltype = DNA   length = 2202
FEATURE                 Location/Qualifiers
source                  1..2202
                        mol_type = other DNA
                        organism = Bacillus thuringiensis
SEQUENCE: 225
atgaatcaga attacaataa caatgaatat gaaatcaaag atgttggcgt catggactat   60
cagccaaggt atcctcttgc gcaggcacct agtgccgaat gcaacaaat gagttataag  120
gattggatgg ataggtgtga acgaggatcg ctggcaatca catttaaatc cgttattaca  180
accgctttag atattacgtc tgcaatcctc ggtgcggcaa aatctccaaa agctaaagta  240
gcaagagctg cggttcaagt ccttaatagc gttattaaat tgctgtggcc tgaaccagaa  300
aaaccttctg aaccagcata cgatatagat ttcatatgga aagaactgat aaagagagtc  360
gagatactga ttgaagaaaa aattgatcga gaacgtatata acgccgcaat ggaagatta  420
tcaggattaa agagagcttt aaatttatat caaatagcgt tttgggattg gctcaaagat  480
gaaaatgacc ctgagttaca ggcagagtta cgaactcggt ttacggctgc actgtttgaa  540
cttgtgacta caattgaaac atttaaatac aatggacaag agttaaattt gctgacaatt  600
tttgtacaag ctgcagattt tcacttaatg ttattacaac aagggataat gtatggagtt  660
cggtggggat cgatcagag acggtagat tctctttatc aaaatgacag tggagaaggt  720
ttgaaaaatt tgctaccgaa gtattctgat tatgccactt attggtatgg ccaaggtttg  780
aatagagcaa aaaacttgaa ggcaaattta tcagatacag taagatatacc ttgggccgca  840
aacttagaag atacgagtgt attacaagag ctagaggatt ggaacctata taacgattat  900
cgaagagaca tgacaatctt agtattagac ttggttgctg tatggccaac atatgacctc  960
cattattacg ataatggaaa ctatgggta cagtctgaac tcacacgatc tatatactct 1020
caagcagtag gaaatgtaat gggaactgta tttacaaaag agcaatacga ggttagcttc 1080
gttcgcccac cacacttagt tacatggtta gaaaaaatgt ttgttcatat aagagacaag 1140
gaacagggcg cacctaacga tgcagaaatg gctggtataa gtctagatta ttcttattca 1200
ggttgggata atacggttta tgacatactt caaggtatac cagcgactgg gggtagtcaa 1260
attcgtgtgc ttgcaaaaag taacgtgatc gttcaagatc aagagaaaaa tcgagcgatt 1320
tacaatacag atctccaaca tgataaatta gtagatcgat ttgttttta tcaaaatagt 1380
ggagaagtta actatgctgg tagagataat ccgtcaagct ataaacatt tgcatgggat 1440
actgatgtta ccaactatag tagtcaaatg acatggaata atggaccagt aaatgaaggc 1500
catttttggtt atattcaggc ttatgcgccg aatgtgattc ctgcaagttg tgaaccgttt 1560
aatactatcg tggatgcaga agatgtaatt actcaaatac cggcagtgaa agctcgagaa 1620
ttaaaatatg gtgcacgtgt tataaagggt ctgggctata caggtggaga tctagtgtct 1680
attgcaccca atggtttgtg tgagttgtac gtgtcatttc caaatgtagc ccgaagatat 1740
caggttcgag tacattatgc atgtcaggat tcgaccaaaa taaaactacg tataggggat 1800
tcaagtcatg atattaaact tcaatctacg tattctggag gggcattaac atacgattca 1860
tttggttatg caacaagtga atacagttat ctattttatc ctgattttta tgatgagaaa 1920
cagatagtac gtttgggaaa tgattttgat ataacacagc aagatatcat cattgataag 1980
attgaattta ttcctgttga tatcttctat gcagaggaac agcattaaa acaagcaaga 2040
aaggccgtga atgccttgtt tacaggtgct gcaaaagatg tcctgaaatt gaatgtgacg 2100
gattatgcag tcgatcaagc tgccaatctt gtcgaatgtg tatcggatga attccatgct 2160
caagaaaaaa tgatcctact ggatcaagtg aaattcgcca aa                    2202

SEQ ID NO: 226          moltype = AA    length = 734
FEATURE                 Location/Qualifiers
source                  1..734
                        mol_type = protein
                        organism = Bacillus thuringiensis
SEQUENCE: 226
MNQNYNNNEY EIKDVGVMDY QPRYPLAQAP SAELQQMSYK DWMDRCERGS LAITFKSVIT   60
TALDITSAIL GAAKSPKAKV ARAAVQVLNS VIKLLWPEPE KPSEPAYDID FIWKELIKRV  120
EILIEEKIDR EAYNAAIGRL SGLKRALNLY QIAFWDWLKD ENDPELQAEL RTRFTAALFE  180
LVTTIETFKY NGQELNLLTI FVQAADFHLM LLQQGIMYGV RWGFDQRTVD SLYQNDSGEG  240
LKNLLPKYSD YATYWYGQGL NRAKNLKANL SDTVRYPWAA NLEDTSVLQE LEDWNLYNDY  300
RRDMTILVLD LVAVWPTYDL HYYDNGNYGV QSELTRSIYS QAVGNVMGTV FTKEQYEVSF  360
VRPPHLVTWL EKMFVHIRDK EQGAPNDAEM AGISLDYSYS GWDNTVYDIL QGYPATGGSQ  420
IRVLAKSNVI VQDQEKNRAI YNTDLQHDKL VDRFVFYQNS GEVNYAGRDN PSSYKTFAWD  480
TDVTNYSSQM TWINGPVNEG HFGYIQAYAP EWIPASCEPF NTIVDAEDVI TQIPAVKARE  540
LKYGARVIKG LGYTGGDLVS IAPNGLCELY VSFPNVARRY QVRVHYACQD STKIKLRIGD  600
SSHDIKLQST YSGGALTYDS FGYATSEYSY LFYPDFYDEK QIVRLGNDFD ITQQDIIIDK  660
IEFIPVDIFY AEEQALKQAR KAVNALFTGA AKDVLKLNVT DYAVDQAANL VECVSDEFHA  720
QEKMILLDQV KFAK                                                   734

SEQ ID NO: 227          moltype = DNA   length = 2058
FEATURE                 Location/Qualifiers
source                  1..2058
                        mol_type = other DNA
                        organism = Bacillus thuringiensis
SEQUENCE: 227
atgaacttaa atgataataa gaatgaattt gaaatcatgg gtaatggtag catgtcctat   60
cagccaaggt atccccttgc gcaggcacca ggttctgaat tccaagggat gaattataaa  120
```

-continued

```
gattggatga atcggtgtgc aaatggggag ttaggagaat tatttgtaga ttcagatgct  180
gtgaaaatg gggtcgttgc tggtctagct attacatcct atcttctcag tataccattt  240
cctttcaat cagcagcatt aggcattatt agtgtactat taccaatact gtggccggag  300
caggcgggaa atcctggaac tacggaagca caatttacgt gggaccaatg gatgaaggct  360
gcggaaaaaa tggctgatca aaaaattgca gattcagtaa aaacaagcgc tatcaatacc  420
acaaaaaccct tacaatcacg tattgctgat tataaacaag caattttgtaa tttaaaaaca  480
gatcccaata tgaggcata taagaggaa gtaagaaggc aatttaatga tgccgacgat  540
tgggcgaaag ccactgtaat cgaatttgga aattcggcct atgcgattcc attattagct  600
gattacgcac aagcagctaa tgtacactta cttttattac aagacggcat aaaattcgga  660
gaaagctggg gattttcggc tcttaaagtg caacaattgt attctaatac cagcgtagta  720
aaccctggca tgaaagaact attagcaatc tatacggatc attgtgtacg ttattataat  780
gaggggttaa agaagagata cgaacgggc aactggtata cattcaatga ttaccgtaaa  840
aatatgaccc taatggtaat ggatatcgtg tcatttttggc caacctatga tccaatactc  900
tatccagttc ctactaaatc tcaactgaca cgaactgtgt atacagattt tctaagagac  960
accattcgc ccctgcaat ctcagatgta gaaatagtg taactgttcc cctaggccta  1020
tttagatgga tgagtggact gggatatcac ggagtaacag ttaattcaag taatgttttgg  1080
atgggtctgg aacagctcta tcattatacg ctgagggacg accggtacga ggagaggcag  1140
ggtgagttc cacatgattc aaaatttattg ggatatctca caacccaa tgatgatgtt  1200
tggtcgatta taccaaatta tatccctata gaggatggct ctgaagttgg gtatattcct  1260
aacaccgcga gtttctttca tgactttaga tttcagcttc ttaaaagtgg ggagcagaga  1320
gtacatttag cgtacgagga ggggatatcc agaaagttcg gattaccttg taaatcgaat  1380
accgggacgg attgtgatcc ttgtcaacct tgtacggcac ttcctaacgc aagcgatcct  1440
tgtgatgaca aatcactttta tagtcatcga tttttcgtata tgggtatata caatcccttat  1500
attgagttta ccttgtcccc ttgctttggc tggacacatg taagcgcaga tgcaaacaat  1560
ctgatagatg cgaaaagat tacccaaatt ccagcggtga aggcatacgc aattgctaca  1620
aatagtagag tcgtaaaggg ccctggtagt acaggggggg atgtagtcca acttttctagt  1680
ggaaccgaaa gtgggattat agccatgtgg ataacaacgc caccaggagc tcgtgcatat  1740
cgtgtaagaa tacgttatgc gagtagtatg cagacaaacg tagaaattta tatgttagga  1800
gctaacggac agtttgacgt tccagctact acaactgatc tgcaaaatct cacgtataat  1860
aaatttaaat acctagacac cgttgtttac tcttattctc aagttgaaga gaataagaaa  1920
cacataagaa taggggctac tggttcaggc tcaggttctt tcattctcga caaatcgaa  1980
ttcattccaa tcgaggttc cgtggaagaa tttgaagcga atcaggcttt agaaaaggca  2040
agaaaggaag tgaatgct                                                2058
```

```
SEQ ID NO: 228        moltype = AA   length = 686
FEATURE               Location/Qualifiers
source                1..686
                      mol_type = protein
                      organism = Bacillus thuringiensis
SEQUENCE: 228
MNLNDNKNEF EIMGNGSMSY QPRYPLAQAP GSEFQGMNYK DWMNRCANGE LGELFVDSDA   60
VKNGVVAGLA ITSYLLSIPF PFQSAALGII SVLLPILWPE QAGNPGTTEA QFTWDQWMKA  120
AEKMADQKIA DSVKTSAINT TKTLQSRIAD YKQAICNLKT DPNNEAYKEE VRRQFNDADD  180
WAKATVIEFG NSAYAIPLLA DYAQAANVHL LLLQDGIKFG ESWGFSALKV QQLYSNTSVG  240
NPGMKELLAI YTDHCVRYYN EGLKKRYETG NWYTFNDYRK NMTLMVMDIV SFWPTYDPIL  300
YPVPTKSQLT RTVYTDFLRD TISPPAISDV ENSVTVPLGL FRWMSGLGYH GVTVNSSNVW  360
MGLEQLYHYT LRDDRYEERQ GEFPHDSKLL GYLTTPNDDV WSIIPNYIPI EDGSEVGYIP  420
NTASFFHDFR FQLLKSGEQR VHLAYEEGIS RKFGLPCKSN TGTDCDPCQP CTALPNASDP  480
CDDKSLYSHR FSYMGIYNPY IEFTLSPCFG WTHVSADANN LIDAKKITQI PAVKAYAIAT  540
NSRVVKGPGS TGGDVVQLSS GTESGIIAMW ITTPPGARAY RVRIRYASSM QTNVEIYMLG  600
ANGQFDVPAT TTDLTNLTYN KFKYLDTVVY SYSQVEENRE HIRIGATGSG SGSFILDKIE  660
FIPIGGSVEE FEANQALEKA RKEVNA                                      686
```

```
SEQ ID NO: 229        moltype = DNA   length = 2748
FEATURE               Location/Qualifiers
source                1..2748
                      mol_type = other DNA
                      organism = Bacillus thuringiensis
SEQUENCE: 229
atgagtacaa tttcggtgt agatactggt gattcatcta ttgatgatgt gttgaacaat   60
gaagaattgt tacaagaaat gttggaccaa atgaatacaa tgcaaatttc aatacgagac  120
atattggagc aacaaggtat ttctgcagat atagaaaagc gatttttagc tctcacaaca  180
gaccttgcta catcgattaa tacagagctt gtgaagattg aaggaattct tactacgtat  240
ctaccagcta ttagtaacat gttaagcaat atatatgaaa aacatctgt gattgaccaa  300
aaagttgata agctcatagc tttgatgaca tttgctttaa aagaacttga ttatattaaa  360
gataatgtag tacttaattc gagtattgta gaaatcacac cacatgttca gaaattagtc  420
tatgtaaata aaaaattcct ttctctaaca agagactttt tacaaggtga gatgtaagt   480
atagatagta tgcaagaaat acaggaatgg gcaaaatcga tactagcaac tgaatgaat   540
agctttgaat tttcagttga tacattacac agtattataa tcggtgataa ccttataaa   600
agatcggcgt taaaaacatt tcagatgtt ttattagatg atgtcgatca atatggtgat   660
tttggtacac cgttagcaaa gttttataca ttttttctctt cattagcaac attcaaata   720
aatgcgtatc tatgtctaac tttcgcaagg aaagttttag gctctcaga aattgattac   780
caggtaacta tgagagacag aattgaacaa caaaatcaaa tgttttgtaaa cttaattcaa   840
gataagaact attccaatgc ccttgaaatt acaggaatct acggtatagg                900
ggagattgta aatcgacaga tttacaagca gatgctggtt gtgcgcttat tggtttagaa   960
ttttttcatgg acaatggtat atataaagca aaagcttacc aggggaaaat cggaaaaac   1020
ttttccgtat ctgctgatac agtaacagag cttattagtg atgatttaag cactttgttt   1080
catgatacga caaacgacaa tccagaacta gatgtagtat atcctttatc aggagagcta   1140
acaggccac ctaatacgat aataactcgg ataggacttg gtacaaaata cgataaaacc   1200
```

```
cgaggatcaa gtgttcaggc atttgcatat atagatactg acttttcacc ctatgattat  1260
atatctggca ctattagtaa agaagggacg caaacagttt cattagaagg gaatgaccat  1320
aaaaatagg gatatagtaa ttggcctata ggtttaattg gagacctcta catgacacct  1380
ttaaaaagtc tatcattaaa cgttgaagat actggaacca cccttaatat gagtggagaa  1440
tcttatttt ctacaatctt gtctagggaa tataatacta attttatact tttcccttac  1500
acaaataata gtagtccaat tgctgaaaat cttattcaaa atggggactt tgaaaatgat  1560
gataagtatt gggaagtagt gacaggatca gcagtaatag ctgagggtga aggaatttat  1620
ggttcaaatg caatgaaaat tagtcatgtt attaaacaag aattgaattt aaagccatac  1680
actacttatg aattaacagc atacgtacaa tcaaatgtta acgatataca aggcggaacg  1740
atttctataa catacaataa cgttgaaatc gcccggacaa aaaaaacttt ttctacaagt  1800
tataaacaaa ttgaactcaa atttaggact ggagcagaga atcaagattt ccatgttact  1860
tttgaaaaaa accttgaagg ctacctatta ttggataata taaagctcca agaaattcca  1920
caaacagata acctaattga ttgtggagat tttggaggca atgatatcct aacttctgat  1980
tataagcttt ggcgatacgc ttatctttgg gaacttgata ggggagcaaa tttaacccaa  2040
gaaggtttat tcaaaacgtt atgtttaaaa attttacaaa gtgggaggag caatcaaaaa  2100
gtacaattga aggcaaatac caactatata ttaacaactt atgtaaaagt agatgatcct  2160
actacgacag cacaaatagg gtgtggaagt aaccaggtac catgtaattc aacatctat   2220
acaccactca aactaaagtt tagaactggt gaagatcctc cgactacaga aagctctgta  2280
tattgttcaa actctaatga tagcggtaca gtttgggcag ataactttgt gttatatgaa  2340
gttccgaatt taattaaaaa cggggatttt gagcaattcg atcaatcatc ttggactttc  2400
tctccttctg agggtgggag aatttacttg caaagtggtc tagggatgtc tcgttctaat  2460
gcagttgtac tgcaaggtca aaacggacaa attagccatt ggaaaccattt  2520
actaaatatc gattgacagc atatgtaaaa gtatcaaaag atagtatatac acatattggc  2580
tatggcgata acacatgtgc atgtgctgta gatgatttca gacaagctct tgtagatttt  2640
acaactggtg ctaatcctat gcaatccgat gatgctatat acttatcctc tggtaatagc  2700
aaaatatactg ttgctgacaa cttgaactt acgaacttg accagatt              2748

SEQ ID NO: 230         moltype = AA   length = 916
FEATURE                Location/Qualifiers
source                 1..916
                       mol_type = protein
                       organism = Bacillus thuringiensis
SEQUENCE: 230
MSTIFGVDTG DSSIDDVLNN EELLQEMLDQ MNTMQISRD  ILEQQGISAD IEKQILALTT   60
DLATSINTEL VKIEGILTTY LPAISNMLSN IYEQTSVIDQ KVDKLIALMT FALKELDYIK  120
DNVVLNSSIV EITPHVQKLV YVNKKFLSLT RDFLQGEDVS IDSMQEIQEW AKSILATEMN  180
SFEFSVDTLH SIIIGDNLYK RSALKTFSDV LLDDVDQYGD FGTPLAKFYT FFSSLATLQI  240
NAYLCLTFAR KVLGLSEIDY QVTMRDRIEQ QNQMFVNLIQ DKNYSNALEI TGIYPMSLDR  300
GDCKSTDLQA DAGCALIGLE FFMDNGIYKA KAYQGKIGKN FSVSADTVTE LISDDLSTLF  360
HDTTNDNPEL DVVYPLSGEL TGPPNTIITR IGLGTKYDKT RGSSVQAFAY IDTDFSPYDY  420
ISGTISKEGT QTVSLEGNDH KNRGYSNWPI GLIGDLYMTP LKSLSLNVED TGTTLNMSGE  480
SYFSTILSRE YNTNFILFPY TNNSSPIAEN LIQNGDFENG DKYWEVVTGS AVIAEGEGIY  540
GSNAMKISHV IKQELNLKPY TTYELTAYVQ SNVNDIQGGT ISITYNNVEI ARTKKTFSTS  600
YKQIELKFRT GAENQDFHVT FEKNLEGYLL LDNIKLQEIP QTDNLIDCGD FGGNDILTSD  660
YKLWRYAYLW ELDGGANLTQ EGLFKTLCLK ILQSGGANQK VQLKANTNYI LTTYVKVDDP  720
TTTAQIGCGS NQVPCNSTSY TPLKLKFRTG EDPSTTESSV YCSNSNDSGT VWADNFVLYE  780
VPNLIKNGDF EQFDQSSWTF SPSEGGRIYL QSGLGMSRSN AVVLQGQNGQ ISQKVPLKPF  840
TKYRLTAYVK VSKDSIAHIG YGDNTCACAV DDFRQALVDF TTGANPMQSD DAIYLSSGNS  900
KYTVADNFEL YELDQI                                                  916

SEQ ID NO: 231         moltype = DNA   length = 1125
FEATURE                Location/Qualifiers
source                 1..1125
                       mol_type = other DNA
                       organism = Bacillus thuringiensis
SEQUENCE: 231
atgcgaaaac gttataaaaa gttagctact attataccgc ttacaagtat gttaagtatg   60
tcagcgattc ggttgcacc ggctacatct tttgcagcgg aaacacaaaa aaacgaagtt  120
tcactacaag aaggaacggc ccaggggttac ctaatgtaag atggtaagat gaccccctgtg  180
tacaaaaata aacttactaa gtttgataca gacggcgata tcgatcctgg ccttccacta  240
ctcccagaga atccatataa tccaattcct gatcatggaa ctgcatatgt tgaatcaacc  300
gatataggag atactgtata tttcaaacca tttgacaccc ctcaaaataa tgtattagcg  360
ttaggtgact ctgatgataa tacttctcag tgggcctag ttgtagattc aaagaaatat  420
aaaagtgtag gatactttgt tcaaaaacaa gccgatagtt gaaattagat tggatattat  480
aatccagaag atttatctct gattacagat tcaaactatg ctttcgcagg agtaccaggt  540
ttcggactgt cagcagaagc gaaagctaag atgcaacaag atttaaatcg agcatatggc  600
gatatatggg atggcacaag taactaaaa cgagaaacaa actataaact tctgccaaat  660
gcctcaggtc tacaggatga cgcatcggca tttggttata tcaaacgtt aacttcgggt  720
gtatcaacta caaatatgtt tggaatagcg acaacagttg ggtgataaaa ggggataaaa  780
gtatcggttg ttcctcttgt tgcagacgtt acgtcagaga ttagtgcaag tttaacagct  840
agttatcagc atactgtaaa cgtttcaaac caaacgagtt cgcaagtaaa atttgacata  900
tcaagagtag ataccctga ctataagtat aatgactatg cggcagctgt atacaaaata  960
caaacagact atacattaga accgggtaaa ggatttctc gtgttgtagc aaagcaagat 1020
cttaaagatc ctgtgcgtac agtcgcatta gcaaatacga attatgcata tgaaggttca 1080
aaatactact ttacagtaac acctggatca cacaagaaaa gtgtg             1125

SEQ ID NO: 232         moltype = AA   length = 375
FEATURE                Location/Qualifiers
source                 1..375
```

```
                        mol_type = protein
                        organism = Bacillus thuringiensis
SEQUENCE: 232
MRKRYKKLAT IIPLTSMLSM SAIAVAPATS FAAETQKNEV SLQEGTAQGY LMENGKMTPV    60
YKNKLTKFDT DGDIDPGLPL LPENPYNPIP DHGTAYVEST DIGDTVYFKP FDTPQNNVLA   120
LGDSDDNTSQ WAVVVDSKKY KSVGYFVQKQ ADGQIRVGYY NPEDLSLITD SNYAFAGVPG   180
FGLSAEAKAK MQQDLNRAYG DIWDGTSKLK RETNYKLLPN ASGLQDDASA FGYNQTLTSG   240
VSTTNMFGIA TTVGWKMGIK VSVVPLVADV TSEISASLTA SYQHTVNVSN QTSSQVKFDI   300
SRVDNPDYKY NDYAAAVYKI QTDYTLEPGK GLSRVVAKQD LKDPVRTAAL ANTNYAYEGS   360
KYYFTVTPGS HKKSV                                                   375

SEQ ID NO: 233          moltype = DNA  length = 2271
FEATURE                 Location/Qualifiers
source                  1..2271
                        mol_type = other DNA
                        organism = Bacillus thuringiensis
SEQUENCE: 233
atgaaaaagg taataacaaa gtcttctttt gcatgcattt taggagcatt gttcttatta    60
tcaaatcata tttcagttttt tgcagctgaa aaccaagatt ctccaccgag tgctatcaaa   120
ctggataata tttttactgt tccttcaggg tccaacagta tacttataca aaatgataag   180
ttcgatatcg ttcagttaac agacagtgtc aaggatcaga gtggagcggt tggtcaaca    240
gacgaaaata aaatggattt aacaaaagac tttgaagcag caatgtatat ctattttggt   300
gattctggtg aagatgctgc tgatggaatg gcatttgtca tgcataacga caaaaatgga   360
aacaatgctt ttagaactgg ggaaggtgct aggataggtg tatgggattc tacaaagcct   420
aaagaattcg gcttggcaat tatgaattct tttgcagtcg aatttgatac ctactttaac   480
aaagattttg atagaggggt tccaaagcag aatcatatcg catggaacta tccgggaaa    540
aaagatacat atgatgattc gggattaatc tttaaagacc gaagaatgat tcataatgat   600
cttcagtttc caggtctatt atctaatgat acttggcgct attttacggt taggtgggat   660
agcaagcaga gtatattaac gtatcaactc caaggattaa aaagcgtttc ggttcctatt   720
aatgtgaatg atgtcttttgg gacaacagaa gtgtattggg gcttaccggg ttctacaggt   780
gggagctttg aaatgaatcg aatcgtattc gataaggtac cagggcttgt tgaggctgag   840
gtaaaagaag acattctaga tattacgact aatgaaagtg tagtaggcac aaaagttgct   900
agtggtacaa agttaacgta tagcctgaaa gcgaattata ttggtggtaa gcaagcatgg   960
aaaaacatta atgtatcaag tacgattgat agcaatgtga gttacgttcc tggaagccta  1020
agattgaaag acgcatcagg taaagagact cctttggatg attcctattg gaaggatggt  1080
atgttaaacg cacccatctc agatatggat ttaaataatt caaagcaaac gattctgttt  1140
gatgtaaaaa caaataaggt tggacaggat acagtggtaa gtgagcatag taattttttat  1200
ggagacaact accatacaaa aactgcagaa ttaaattata caattagtgc aaataaggcg  1260
cctgaaataa gtttgaatca ggaaaatgaa acaatcaaag tacctatggg tcaagatgtt  1320
gaggtaagtg ggaaatggaa ggatgaagat ggtacaaaag tcacaattac atataagtta  1380
aatggtgaag taattggtca aaatcagctt caatcagaac aggaaaacac tttccaagat  1440
tggaaatata cgattccaaa ggacaaacta caattaggag taaaccactt agaagtttat  1500
gcaacagatg aaaaaggtgc taattcagaa gtgaaaagtt tagaaatatc tatatcagt   1560
cctccaacaa taactctaac tgaggaaaat aaagaggatg agatagatta tggtaaaagt  1620
tttaatttct ctggtactgt gagtgatttg gatggtgccg ataaagaatt gacgctctat  1680
tacgtaatcg acgataacga gcaggttgct ttttcgaaag ttactaatag taacccggga  1740
gaagcaatta attttgcagg agaaaatccc acttcgaatg gaatgagggg gcctcatacg  1800
atttcagttt atgctattga tgaagatggt ttacaatcta atattagcaa atttacttta  1860
catgtaataa aacgattaac ttttgccgat gacatgaagg atgtcgagtt tgtcacgaca  1920
caaattggtt ctacgccaaa gattagcgaa cgaacaacag agtatccaat tcatattatt  1980
aacagtaagg ggaaaggaag taagtggaag ctaaaagcgg aacttacaaa acctcttgtt  2040
tcaaaagaaa accatacatt agaaggctta ttctttaaaa agtctaatgg agaaacagaa  2100
gaactattat taaatacttc cgttattgtg gagactggtg aatccccaga agactattca  2160
gatattaatc taaattggaa aaatgatgaa gggctattac taaaggtaga tccatcagcg  2220
catataggtt catatgctgg tgaattaaca tggactttag aggatgcgcc t            2271

SEQ ID NO: 234          moltype = AA  length = 757
FEATURE                 Location/Qualifiers
source                  1..757
                        mol_type = protein
                        organism = Bacillus thuringiensis
SEQUENCE: 234
MKKVITKSSF ACILGALFLL SNHISVFAAE NQDSPPSAIK LDNIFTVPSG SNSILIQNDK    60
FDIVQLTDSV KDQSGAVWST DENKMDLTKD FEAAMYIYFG DSGEDAADGM AFVMHNDKNG   120
NNAFRTGEGA RIGVWDSTKP KEFGLAIMNS FAVEFDTYFN KDPDRGVPKQ NHIAWNYPGK   180
KDTYDDSGLI FKDRRMIHND LQFPGLLSND TWRYFTVRWD SKQSILTYQL QGLKSVSVPI   240
NVNDVFGTTE VYWGFTGSTG GSFEMNRIVF DKVPGLVEAE VKEDILDITT NESVVGTKVA   300
SGTKLTYSLE ANYIGGKQAW KNINVSSTID SNVSYVPGSL RLKDASGKET PLDDSYWKDG   360
MLNAPISDMD LNNSKQTILF DVKTNKVGQD TVVSEHSNFY GDNYHTKTAE LNYTISANKA   420
PEISLNQENE TIKVPMGQDV EVSGKWKDED GTKVTITYKL NGEVIGQNQL QSEQENTFQD   480
WKYTIPKDKL QLGVNHLEVY ATDEKGANSE VKSLEISISS PPTITLTEEN KEDEIDYGKS   540
FNFSGTVSDL DGADKELTLY YVIDDNEQVA FSKVTNSNPG EAINFAGEIP TSNVEGPHT    600
ISVYAIDEDG LQSNISKFTL HVIKRLTFAD DMKDVEFVTT QIGSTPKISE RTTEYPIHII   660
NSKGKGSKWK LKAELTKPLV SKENHTLEGL FFKKSNGETE ELLLNTSVIV ETGESPEDYS   720
DINLNWKNDE GLLLKVDPSA HIGSYAGELT WTLEDAP                            757

SEQ ID NO: 235          moltype = DNA  length = 1224
FEATURE                 Location/Qualifiers
source                  1..1224
```

```
                         mol_type = other DNA
                         organism = Bacillus thuringiensis
SEQUENCE: 235
atgaatgata atatggatgg aagtcaaaat ggagatacaa taactactga agattcttta  60
gcaaatgacg aaagaaatac aagtttacca gaagaaagtc gtaaatttgc atattatcaa  120
cccttaagta caaataatca agtatggcac gtatatacac atggtggtct tcctatgcca  180
attcaagcat gtgaattaag ctattttcct catgcattaa caaatcgacc atatcaagga  240
ggacaatacc aacaatttat ttggtttgaa ctcgatgatg gtcggtttgc aattgctgat  300
agacactatg ggcatgtatt acaaaggtat gagtactatg atgcgaagga aatagttatt  360
agaccatggg aaaataatta tgctcaactt tggaggaaag aaagcacttc agctactact  420
tttagattag taaatgactc gtacgcatta aatgtatgtg gaaatgagac taacaacact  480
gtcaagtata cctttgtgcc taatgattca aataatagtg cacttcaatt taagcgtaga  540
gcaattgctc aagataatgt agtaccagct ttaccatcaa aacaaccatt accacctctt  600
ccagttttat caaatctaaa tgatccagct cctcatgaaa cggtaagaaa tataactggt  660
tcttctctaa taccttgtat tatggtatcg gattatatcc ctgtatctca aagaataaaa  720
gagagtccat attatatatt ggttaaaaaa caattttgga aacgtttatg gcatgatacg  780
tttattccag gtgaaggacg tgcatttgaa gaaacaactg gtatgtcatc aactgagcaa  840
caaagtatga cacaaactac aaatatatcg ttgcaagccg attttggctt tgcatataaa  900
gccctaacac taggtatagg agtaagcgtt tctaaatcaa tagaaataag tagaagtaca  960
acggatacag taatgagtca aagtaaagat acacaaagtt ataaaaacga aaatccgttt  1020
gacctatcat gggctaaata tgctttggca actgagttta ttttaatgcg taaggatggt  1080
actaaagcag gttcatggga agctgttgat aaaaaaatct caagatctat atcctatcca  1140
cctactcaaa atctatcttg gtttgaggat acaggaaaca aaaaggataa cactgatttt  1200
ggattgacta caataacatc tgaa                                        1224

SEQ ID NO: 236           moltype = AA  length = 408
FEATURE                  Location/Qualifiers
source                   1..408
                         mol_type = protein
                         organism = Bacillus thuringiensis
SEQUENCE: 236
MNDNMDGSQN GDTITTEDSL ANDERNTSLP EESRKFAYYQ PLSTNNQVWH VYTHGGLPMP  60
IQACELSYFP HALTNRPYQG GQYQQFIWFE LDDGRFAIAD RHYGHVLQRY EYYDAKEIVI  120
RPWENNYAQL WRKESTSATT FRLVNDSYAL NVCGNETNNT VKYTFVPNDS NNSALQFKRR  180
AIAQDNVVPA LPSKQPLPPL PVLSNLNDPA PHETVRNITG SSLIPCIMVS DYIPVSQRIK  240
ESPYYILVKK QFWKRLWHDT FIPGEGRAFE ETTGMSSTEQ QSMTQTTNIS LQADFGFAYK  300
ALTLGIGVSV SKSIEISRST TDTVMSQSKD TQSYKNENPF DLSWAKYALA TEFILMRKDG  360
TKAGSWEAVD KKISRSISYP PTQNLSWFED TGNKKDNTDF GLTTITSE             408

SEQ ID NO: 237           moltype = DNA  length = 1980
FEATURE                  Location/Qualifiers
source                   1..1980
                         mol_type = other DNA
                         organism = Bacillus thuringiensis
SEQUENCE: 237
atgagtccaa ataatcaaaa tgaatatgat attatagatg caccatctcg tacgtctgta  60
tccaatgatt ctgtcagata tcctttggca gaggacccca atgccgcatt gcaaaatatg  120
aattataaag agtatttaag aatgtctgga ggaggtgaca ctggaaattt agcaaacatg  180
caagagttta ttgatactca atcagctatt aatactgcca tttctattat tggaagtata  240
gcggatgcat ttggtattcc cggtgtatct tttgtcggcg gccttattag ttcacttctc  300
gatttattgt ggccatcagg gccaagtgta tgggaattgt ttatggaaca agtagaagcg  360
ttgattaatc aaagaataga acaaaatgta agaaatgagg caattagccg attagaaggg  420
ttagctagaa tcttagaatt atatgggaca gcatttgaag agtggcggga aaattcaact  480
agggcaagaa tggaatacct tcaaaatcaa tttcaaatcg ttgataattt tttcacagca  540
tatatgccaa cttttcgatc tactaataat gaagtggcat tacttacagt atatgcgcag  600
gcggcaaatc ttcatttgct attattaaga gatgtttcta tttatggaga acagtgggga  660
tggaatcaaa atagaataaa taattattat aatcgtcaaa tgcaacttac ggctgaatat  720
actgatcatt gtgtaagatg gtataataca ggcttagaga gattacgagg gactactgct  780
caacaatggg tacgttttaa tcgttatcgt agagaaatga cgttaacagt attagatact  840
atagcaatat ttccaaacta tgacattcgt acgtacccaa ttggaacatc atttcaactt  900
acaagaaatg tgtatacaga tccaattggt tttgaaggta cgccgccaga tacttggttg  960
aatcaggcac cttcctttac gaatatagaa aatagtgttt ttcgtttccc ccactatttt  1020
gatacaataa cgaatcttac cgtttttact aggcgttcgt tatggagttc atctgtgttt  1080
atgaatctat gggcagggca tagaataaca tctcgacgta tccaggatgg tgttttatat  1140
acaagtgtgc atggagtaac tactaaccct gttagtacta gtgaattcat tttgaaggt  1200
ctggatattt acagaaccgt atcaagagca ggtatactag ctactattag tgcaagaaat  1260
tttggaatgc ctacagtgga attctttacg ttaactggtg gtggtttccc attcaatttt  1320
gagtacaatc ctggatttc aaatattgta acacagctac gagactcatt aaatgaatta  1380
cctctaatag aagatggatc tcaatcgatg caggaattgt ttagtcatag attatctcat  1440
attggaatga taccaaatgt agctgtgcct gtgtattgtt ggacacatcg aagtgctgat  1500
agaagtaatc gattgcatgg agatagaatt actcaaattc cagtagcaaa gggctacagc  1560
ggtagagctt tgtctactgg tcctggtttt actggaggaa gtataatctc aacagcattt  1620
gaaggtgatt tggttaatat agggttttcg agaagcgagt cagtaccaat atcacaacga  1680
tatcgtgtaa gagtgcgttg cggtgctgct ggtgctgacg cacgaattag ggttacgatt  1740
ttagggggtc gtactattga agctagagtt cctcgcacta tagatataag tcctaaccgt  1800
ccatatgaaa catttacttt tgtgactttt gatgatatag ttacattttc ttggctacct  1860
catgcaacaa taagttggca acctattaat ccgtctgata tttcagtaat ctttgtagat  1920
cgaatcgaat tcattccagt agatgaaaca tttgaggcgg aacaagattt agagaaagca  1980
```

-continued

```
SEQ ID NO: 238         moltype = AA  length = 660
FEATURE                Location/Qualifiers
source                 1..660
                       mol_type = protein
                       organism = Bacillus thuringiensis
SEQUENCE: 238
MSPNNQNEYD IIDAPSRTSV SNDSVRYPLA EDPNAALQNM NYKEYLRMSG GGDTGNLANM  60
QEFIDTQSAI NTAISIIGSI ADAFGIPGVS FVGGLISSLL DLLWPSGPSV WELFMEQVEA  120
LINQRIEQNV RNEAISRLEG LARILELYGT AFEEWRENST RARMEYLQNQ FQIVDNFFTA  180
YMPTFRSTNN EVALLTVYAQ AANLHLLLLR DVSIYGEQWG WNQNRINNYY NRQMQLTAEY  240
TDHCVRWYNT GLERLRGTTA QQWVRFNRYR REMTLTVLDT IAIFPNYDIR TYPIGTSFQL  300
TRNVYTDPIG FEGTPPDTWL NQAPSFTNIE NSVFRFPHYF DTITNLTVFT RRSLWSSSVF  360
MNLWAGHRIT SRRIQDGVLY TSVHGVTTNP VSTSEFIFEG LDIYRTVSRA GILATISARN  420
FGMPTVEFFT LTGGGPFNF EYNPGFSNIV TQLRDSLNEL PLIEDGSQSM QELFSHRLSH  480
IGMIPNVAVP VYCWTHRSAD RSNRLHGDRI TQIPVAKGYS GRALSTGPGF TGGSIISTAF  540
EGDLVNIGFS RSESVPISQR YRVRVRCGAA GADARIRVTI LGGRTIEARV PRTIDISPNR  600
PYETFTFVTF DDIVTFSWLP HATISWQPIN PSDISVIFVD RIEFIPVDET FEAEQDLEKA  660

SEQ ID NO: 239         moltype = DNA  length = 2073
FEATURE                Location/Qualifiers
source                 1..2073
                       mol_type = other DNA
                       organism = Bacillus thuringiensis
SEQUENCE: 239
atgaaccaat actatagaaa tgatgaaatg gaaattctcg atccaggaat gggccagccc  60
agatatccgt atgcacggcc caattccgag ttacaatcga tgcattacaa agattggcta  120
gatatgtgtg aaagaaatgg aaacggtctc acaacattac gacgaggtac attggcatct  180
gcacaagaca tcattactgt tagcttagat attcttggta ccattttggg atttatacct  240
atagtaggtg gagctttatc cgcaggcgtt tccatactta actccataat tggattactt  300
tggccagaac cagaagaacc aggaattcca acagatccaa atgcaatatg gatagaattt  360
atggaaaagg tagaacaact gattgatcaa aaaatttctc aagaagcatt taatgcagca  420
attggaaggt tgacaggctt aaaacgagct ttaaatttat atcaagtatc atttgaactt  480
tgggctgacg atcaaactga tgaagagtta aaagaggatg tacgaactcg atttacagcg  540
gccctctttg aaatggtggc tacaatagaa acgtttagat atcctggaca agaggtaaac  600
ctactcacag tgtttgcaca agccgcagat cttcacttgt tgctattaag agaagggatt  660
atgtatggat tacaatgggg ttttgatcaa agaacagttg attcttttta tacaaattct  720
caaaaagaag ggctaaaaga tttacttcct atatatactg atcattgtac ctattggtac  780
aatgaaggtt taaaaataac ctataacttg aagccggatt tatcaaatac tgaaagatat  840
ccatgggctg caaataaacc ttcatggaac attcaagttc ttgaagaatt agaaggttgg  900
aatctattta acgatttccg aagagatgtg acgattatgg cattagattt ggttgcattg  960
tggccaactt atgacctata ttattatgat aatttgaagt atggtgtaaa aactgaactt  1020
acacgtccag tgtattctca agcggctgga accagctggg gcagcatatt accaagggat  1080
cgctatgaac aaggtatagt ccgttcccca catttagtga cattgttaca atcaattgat  1140
tttaaattaa accctggtcc attcactccg agtaatagct atcaacatta tacaggtctt  1200
cagctgaaat attattattc cggccgagat tacacaatac atgcatcgcc actaataggt  1260
actacgtctt ctagtgggaa aacaattaat gtggacggta aatctgggtc tgttatttat  1320
caatcagata ttaagcataa cgatgccgta tatacaatgg agttcaagaa aactaatggg  1380
agcagtgaac aagttgggta tacgtataat cctaattatt ctacattgtc atggcctcct  1440
gagactgatg tttccaatta tggtcatcaa atgtcttgga taagtggccc agtagagcta  1500
aatactatcc cagcttttgg tgtagagtgg ctacatgaaa gttgctctcc ttttaatgtt  1560
atagcggatg acacagtaga aaatcctatc attactcaaa ttccagcagt gaaaggggca  1620
agtatatcag gaaatgcaac ggttataaaa aatcctggtc atacaggtgg tgatctcgta  1680
caattacctg cgaattctgg atcacaggct caattgttca taactgtgga aactcctcct  1740
tcgaagatag ggaaaaccta tcaaatcaga gttcgctatg cggctagttc cgctgctgcc  1800
ttacaagtga atcaatgtaa ttttagtgga ggaagttgtt ataacacagc atctattgcg  1860
gttccagcta cgtattctaa taatgcatta ttgtataatg catttcagta tgcagatgtg  1920
ttcccgataa ctatacaaaa tattgacttt tccttacagt tttcaacag aagtggtgga  1980
cctattatcc tcgataaaat cgagtttatt ccaatagaag gttccttaga agagtataca  2040
gcgaaacaag agttagagaa tgtgagaaag gca                             2073

SEQ ID NO: 240         moltype = AA  length = 691
FEATURE                Location/Qualifiers
source                 1..691
                       mol_type = protein
                       organism = Bacillus thuringiensis
SEQUENCE: 240
MNQYYRNDEM EILDPGMGQP RYPYARPNSE LQSMHYKDWL DMCERNGNGL TTLRRGTLAS  60
AQDIITVSLD ILGTILGFIP IVGGALSAGV SILNSIIGLL WPEPEEPGIP TDPNAIWIEF  120
MEKVEQLIDQ KISQEAFNAA IGRLTGLKRA LNLYQVSFEL WADDQTDEEL KEDVRTRFTA  180
ALFEMVATIE TFRYPGQEVN LLTVFAQAAD LHLLLLREGI MYGLQWGFDQ RTVDSFYTNS  240
QKEGLKDLLP IYTDHCTYWY NEGLKITYNL KPDLSNTERY PWAANKPSWN IQVLEELEGW  300
NLFNDFRRDV TIMALDLVAL WPTYDLYYYD NLKYGVKTEL TRPVYSQAAG TSWGSILPRD  360
RYEQGIVRSP HLVTLLQSID FKLNPGPFTP SNSYQHYTGL QLKYYYSGRD YTIHASPLIG  420
TTSSSGKTIN VDGKSGSVIY QSDIKHNDAV YTMEFKKTNG SSEQVGYTYN PNYSTLSWPP  480
ETDVSNYGHQ MSWISGPVEL NTIPAFGVEW LHESCSPFNV IADDTVENPI ITQIPAVKGA  540
SISGNATVIK NPGHTGGDLV QLPANSGSQA QLFITVETPP SKIGKTYQIR VRYAASSAAA  600
LQVNQCNFSG GSCYNTASIA VPATYSNNAL LYNAFQYADV FPITIQNIDF SLQFFNRSGG  660
PIILDKIEFI PIEGSLEEYT AKQELENVRK A                                 691
```

```
SEQ ID NO: 241            moltype = DNA  length = 1980
FEATURE                   Location/Qualifiers
source                    1..1980
                          mol_type = other DNA
                          organism = Bacillus thuringiensis
SEQUENCE: 241
atgaatcaaa attataataa taatgaatat gaaatcatgg ataatggtgt tcagtgctgt   60
acaccaagat atcctcttgc gcaggcacca ggttctgaac tacaaagtat gaattatcaa  120
gatgtgacgg aaacgagtat cggaagagaa taccaggcag tacaacaggt aaatgtggga  180
gaggctgtta gtgccgcact gggcattctg acaactattc ttaaggcagc caatccaata  240
ttggggacag ccgcaggggt catcagctcg attttcggat ttctctggaa acgatttgga  300
acagatcctc aatcccaatg gaaacagttc atggaggcag tagaatatct ggtgagtcaa  360
aaaattacag acgcagtacg aagtaaagcc gtttcggaat tagagggtgt acaacgagct  420
gtggaacttt atcaggaagc tgctaatgct tggaacatga atccggatga tgcagctgcc  480
aaagagagga taagaagaca atatacctct acaaatacag tgattgaatt cgcaatgcca  540
tcctttcgag tgggtggttt tgaggtaccg ttattaacgg tgtatgcgca agctgctaac  600
cttcatttac tactattgcg agatgcggtt aagtttggag cggatgggg gttttctcct  660
acagaagttg aggataatta tactagactc caagcacgta cagcagaata tacaaatcat  720
tgtacaaata cctatgataa aggttttaaa caagcatacg acttagcacc gaatccaaca  780
gattacaata agtacccta tctaaatcca tattctaaag atccgattta cggtaaaata  840
tatacagctc cagttgattg gaatctattt aatgacttcc gaagagatat gactctgatg  900
gtgctagaca ttgtggcagt ttggccaacc tataatccaa gactatataa caatccgaat  960
ggtgtgcaaa tacagctttc aagagaagtt tatagcacgg tatatggaag agcttggtct 1020
aataattcaa cagttgatgt cattgaatct accccttgtta gacctccgca tttagttacg 1080
gaactaacca agctaacatt tgatgagcgt aatttatatg aagcggaaac agtgcctgtt 1140
gcgtttagaa gggttacaaa tacgcttcat aatgtaggaa gttcaaccac atgggagcaa 1200
agttttttctg cgacttctgt tggatcaatt aaggctgttc ataatgtcgc ggctaccgat 1260
ataggtaatc ttgcactaag tctaggagct gtacctttgg gttttctctt ctataataaa 1320
aatgatcaac atctaactac agtgggctac tctggaggtt ggtggaatgg gataccctaaa 1380
gacgaagtgt gtaatcaaaa cagtcatcat ctgtcatatg ttgcagcct agaaacgcag 1440
agtacagctg gttggtggcc ttatacgtat ccggtgcct tattaggaga atgggggattt 1500
gggtggttgc ataatagttt aaccaccaacc aatactatag taagtgataa atcactcaa  1560
attccagcgt gaaggctttt caaactcaca ccatacaata gcaataccaa agttattaag  1620
ggtcctggta gtacaggagg ggatctaatc cagttagctc tggcttttt acaatatagt  1680
ttcccttcaa ccgacaatcg acaataccgt attagaattc gttatgcaag tacgaatggt  1740
agtactctaa cactcaaaaa atgggttggt aatttctata ccagctctaa tcataatctt  1800
ccatctacgt attctagtgg cccattaaca tataatacat ttgccatttt tgatactgga  1860
cacattattc gagagacaag tggattcgaa ctttggttag ataatatagg tagcggaacc  1920
ctaatcatcg acaaaatcga attcatacccg attgagggg ctttagaagc gtatcaagcg  1980

SEQ ID NO: 242            moltype = AA  length = 660
FEATURE                   Location/Qualifiers
source                    1..660
                          mol_type = protein
                          organism = Bacillus thuringiensis
SEQUENCE: 242
MNQNYNNNEY EIMDNGVQCC TPRYPLAQAP GSELQSMNYQ DVTETSIGRE YQAVQQVNVG   60
EAVSAALGIL TTILKAANPI LGTAAGVISS IFGFLWKRFG TDPQSQWKQF MEAVEYLVSQ  120
KITDAVRSKA VSELEGVQRA VELYQEAANA WNMNPDDAAA KERIRRQYTS TNTVIEFAMP  180
SFRVGGFEVP LLTVYAQAAN LHLLLLRDAV KFGAGWGFSP TEVEDNYTRL QARTAEYTNH  240
CTNTYDKGLK QAYDLAPNPT DYNKYPYLNP YSKDPIYGKY YTAPVDWNLF NDFRRDMTLM  300
VLDIVAVWPT YNPRLYNNPN GVQIQLSREV YSTVYGRAWS NNSTVDVIES TLVRPPHLVT  360
ELTKLTFDER NLYEAETVPV AFRRVTNTLH NVGSSTTWEQ SFSATSVGSI KAVHNVAATD  420
IGNLALSLGA VPLGFSFYNK NDQHLTTVGY SGGWWNGIPK DEGSNQNSHH LSYVAALETQ  480
STAGWWPYTY PVPLLGEWGF GWLHNSLTPT NTIVSDKITQ IPAVKAFKLT PYNSNTKVIK  540
GPGSTGGDLI QLASGFLQYS FPSTDNRQYR IRIRYASTNG STLTLKKWVG NFYTSSNHNL  600
PSTYSSGPLT YNTFAIFDTG HIIRETSGFE LWLDNIGSGT LIIDKIEFIP IEGSLEAYQA  660

SEQ ID NO: 243            moltype = DNA  length = 1422
FEATURE                   Location/Qualifiers
source                    1..1422
                          mol_type = other DNA
                          organism = Bacillus thuringiensis
SEQUENCE: 243
atgaattcag aacaacgtaa gcatgagcag aataatgaat ataagcatca aaatcatggt   60
gtatcttgta attgtggttg tcagcaaggt aaatatgaat acgagcaaaa acaaagtagg  120
gaagaatata caatcaata tatgtcaaat ggacaaaagc aaaatcatga aataaaaat  180
tattatagct gtagtccaac acaatttaat gcacctaatc tacctgatga agcaaaaga  240
tttcaaacga ttacaaatat taatacgaat aataacggtc atcgtgtttt agatgcaatg  300
aacacgactg tggggcaaga gcttgagagg ggctatggga attgttcaag ggtaagtgtt  360
gcaaatacag tagttaatga acaggttcga ttttttgaata aatctcaact tttttgttttt  420
tatcaagcag atgctggtga ttttttttatt gctaataaag ggaatgggcg agtcttagaa  480
gttataccta atagtacaca tggatattta gtaatctcta atttgtatga tggtgctaat  540
aataaccaaa gaattagaaa agaaaatgta actactacta attttagatt aagatcacaa  600
gatgcagtaa taaatatatg tggtcacaac atcaataggt tggtatcaat tactgctata  660
caaagtactg ccgaaacatt attccgattc agacctgaaa acatggataa tatctcgctt  720
ccaacactac caactggagg aaggttagga ttaccacctg tattaacgag tttgaatgat  780
tcaggtccaa gtccaagtcc aacaggtcca atccagcac cgagcaaaa ataggaagt  840
gcattgatac catgtctata tgtaaatgat gtacttccaa tagatagaag aatggaagta  900
```

```
agtccttatt atgtattaga atatacacag tattggcata gattatggtc agatgaggtt  960
ctttctggag atagaggagg accttacgaa gaaataacag ggatacttcc caatgcacaa  1020
gaaagcatga gaaatatgat agatatgaca ataggtgaag attggggttt aagatttgga  1080
agtaactcga ctccttttaa gagggggatt ctaagtagct taaataatct cgagtcctat  1140
gctgctaggg atttaggatc tagacattcg agttatggat ttacaaattt caatccattt  1200
ccagttagat attcaagatt tgtaaaagcg catgagtata cattgaagcg tatggatgga  1260
acagtagtaa caacaccatg ggtagcatta gaccatagaa gtcaatattt gcctagattc  1320
cctctaaacg cgacagtatc attacaagat tataaaataa taagcagtta tagcagttat  1380
gatttgccag tattagaaaa catcgatgtt aataagagat gg                     1422

SEQ ID NO: 244          moltype = AA  length = 474
FEATURE                 Location/Qualifiers
source                  1..474
                        mol_type = protein
                        organism = Bacillus thuringiensis
SEQUENCE: 244
MNSEQRKHEQ NNEYKHQNHG VSCNCGCQQG KYEYEQKQSR EEYNNQYMSN GQKQNHENKN  60
YYSCSPTQFN APNLPDESKR FQTITNINTN NNGHRVLDAM NTTVGQELER GYGNCSRVSV  120
ANTVVNEQVR FLNKSQLFVF YQADAGDFFI ANKGNGRVLE VIPNSTHGYL VISNLYDGAN  180
NNQRIRKENV TTTNFRLRSQ DAVINICGHN INRLVSITAI QSTAETLFRF RPENMDNISL  240
PTLPTGGRLG LPPVLTSLND SGPSPSPTGP NPAPRANIGS ALIPCLYVND VLPIDRRMEV  300
SPYYVLEYTQ YWHRLWSDEV LSGDRGGPYE EITGILPNAQ ESMRNMIDMT IGEDWGLRFG  360
SNSTPFKRGI LSSLNNLESY AARDLGSRHS SYGFTNFNPF PVRYSRFVKA HEYTLKRMDG  420
TVVTTPWVAL DHRSQYLPRF PLNATVSLQD YKIISSYSSY DLPVLENIDV NKRW        474

SEQ ID NO: 245          moltype = DNA  length = 1965
FEATURE                 Location/Qualifiers
source                  1..1965
                        mol_type = other DNA
                        organism = Bacillus thuringiensis
SEQUENCE: 245
atgacttcaa ataggaaaaa tgagaatgaa attataaatg ctttatcgat tccagctgta  60
tccaatgagt ctgttacaat ctctaaagaa tatgcacaaa caaatcaatt acaaaacaat  120
agcattgagg atggtttgtg tatagccgaa ggggaatata ttgatccatt tgttagcgca  180
tcaacagtcc aaacggggat tagtatcgct ggtagaatat tgggtgtatt aggtgtgccg  240
tttgccggac aattagctag tttttatagt tttattgttg gcgaattatg gcctaaaggc  300
agagaccaat gggaaatttt tatggaacat gtagaacaac ttgtaagaca acaaataaca  360
gcaaatgcta ggaatacggc ccttgctcga ttacaaggtt taggagattc ctttagagcc  420
tatcaacagt cacttgaaga ttggctagag aaccgtaatg atgcaagaac gagaagtgtt  480
ctttatactc aatatatagc cttagagctt gattttctaa atgcgatgcc gcttttcgca  540
ataagagagc aagaggttcc cttattaatg gtatacgctc aagctgcaaa cttgcaccta  600
ttattattga gagacgcctc cctttatggt cgtgaatttg ggcttacctc ccaagaaatt  660
caacgttatt atgaacgcca agtagaaaga acgagggact attctgacta ttgcgtacga  720
tggtataata cagggctaaa taacttaaga gggataaatg ccgaaagttg gatacggtat  780
aatcaattcc gtagggacct aacattagct gtattagatc tagtggcact atttccaagc  840
tatgacactc gcacttatcc cattccaact agtgcccaac ttacacgaga agtgtataca  900
gatccaaacg gtgcagtaag atcaagtaat tatagttggt ttacaaatgc tgcttcattt  960
tcggctatag aaaacgcaat tattcgacaa cctcacctat atgattttat aacgaatctt  1020
acaatttaca cgagaagaag tcaagtaggt actgctattc tgaatctgtg ggcagggcat  1080
agaattactt ctaatagaat aggctctagt agtagtagtg aatcggtgta tggggctatt  1140
actaacccag ttagtactag taacttatca tttgtcaatc aagatgtctt ccgaactata  1200
tcattactcg gcataaatgg ctctgtgagc ggcctaattt atggcttaac tcgagttgat  1260
tttgatataa gaaatcgtaa ctatactaat ataacaaata gactaactta taatcctggg  1320
catcaaaata ttggaacaca aacaagagat tcagaaactg aattaccacc agaaacaaca  1380
gaacagccaa attatagagc ctttagtcat ctactaagcc atatttcaat gggtccaagg  1440
actaaagacg cacctccagt atattcttgg acacatcgga gtgcagatcg tacaaatacg  1500
atcaattcgg ataggataac acaaatacca ttggtaaagg cacataccct tcaatcgggt  1560
tccactgtag taaaagggcc agggtttaca ggaggggata tcctccgtcg aacaagtgga  1620
ggaccattag cttttagtat tgttaatcta gattttaact tttcacaaag gtatcgtgct  1680
agaattcgtt atgcctctac tactaaccta agaatttacg taacggttgc aggtgaacga  1740
atttttgctg gtcaatttaa taaaactatg gaagctggtt ccccattaac attccaatct  1800
tttagttacg caactattaa tacagctttt acattcccta cgagatcgag cagcttgact  1860
gtaggtgctg atacgtttag ttcaggtaat gaagtttatg tagatagatt tgaattaatc  1920
ccagttactg cgatcttcga ggcagaaact gatttagaaa gggcg                  1965

SEQ ID NO: 246          moltype = AA  length = 655
FEATURE                 Location/Qualifiers
source                  1..655
                        mol_type = protein
                        organism = Bacillus thuringiensis
SEQUENCE: 246
MTSNRKNENE IINALSIPAV SNESVTISKE YAQTNQLQNN SIEDGLCIAE GEYIDPFVSA  60
STVQTGISIA GRILGVLGVP FAGQLASFYS FIVGELWPKG RDQWEIFMEH VEQLVRQQIT  120
ANARNTALAR LQGLGDSFRA YQQSLEDWLE NRNDARTRSV LYTQYIALEL DFLNAMPLFA  180
IREQEVPLLM VYAQAANLHL LLLRDASLYG REFGLTSQEI QRYYERQVER TRDYSDYCVR  240
WYNTGLNNLR GINAESWIRY NQFRRDLTLA VLDLVALFPS YDTRTYPIPT SAQLTREVYT  300
DPNGAVRSSN YSWFTNAASF SAIENAIIRQ PHLYDFITNL TIYTRRSQVG TAILNLWAGH  360
RITSNRIGSS SSSESVYGAI TNPVSTSNLS FVNQDVFRTI SLLGINGSVS GLIYGLTRVD  420
FDIRNRNYTN ITNRLTYNPG HQNIGTQTRD SETELPPETT EQPNYRAFSH LLSHISMGPR  480
```

TKDAPPVYSW THRSADRTNT INSDRITQIP LVKAHTLQSG STVVKGPGFT GGDILRRTSG 540
GPLAFSIVNL DFNFSQRYRA RIRYASTTNL RIYVTVAGER IFAGQFNKTM EAGSPLTFQS 600
FSYATINTAF TFPTRSSSLT VGADTFSSGN EVYVDRFELI PVTAIFEAET DLERA     655

SEQ ID NO: 247          moltype = DNA   length = 2244
FEATURE                 Location/Qualifiers
source                  1..2244
                        mol_type = other DNA
                        organism = Bacillus thuringiensis
SEQUENCE: 247
atgaattcat atcctaataa gaatgaatgt gaaatattgg atgattcact aaactactcg   60
aatatgacta taattatca tcggtatcca gtagctcata actcacaaac ttctatgcaa  120
aatacaaatt ataaggattg gatgaatatg tgtgattcaa atactattaa ttatagaagc  180
attgattcta gtcctgaagc ttatatttta gcacgagctg ccatttccat tgggattggt  240
attgtctcta aactattaag ttatttaggt ctaggaatat tggcagacgc aattaacata  300
acgacgtctc ttgtaaatac actttggaag gaacagaata tacatggga cgccttatta  360
atgcatgtag agaatcttat gaatcaaaaa atctccgatt tagtactatc taatgcaaat  420
gtagaattgg atgcattaaa aagagtttta agtgaatata atgctgcgtt agagaattgg  480
aaaaataaac ccaatgatcc aagtgcttta gagcttatca atcacaatt tacaattact   540
cataatttt ttgtgttacg catgtctgtg ttcgcacatc caggctatga agtattatta  600
ttatctgtat atgcacaagc tgcaaatctt catttactcc tattaagaga tgcaagtatc  660
tatgggaatc aatgggggct agctcgaagt aatggtaatt attattatga gcggcaaatg  720
tattatacga atgaatacac gaatcattgt atgatgtggt atcgcaatgg tttagatcgc  780
ttaagaggca aacagggggc acaatggttg aattttaatc gattccgtac agaaatgaca  840
ttgacagtat tagatattat tgcattattt ccaacttatg attatcgaaa ctatcccgta  900
tttacaaaaa tcgagttatc tagggtaatt tataccgatc cagtaattta tggtggattt  960
tcacaactcc ctagtaataa tcttggcaat ttcaatgatt tggaaagaga agccataggt 1020
ctccccttctt ttatcaagtg gttaaagaaa attgaaatat ctactggaga aattagattt 1080
gctacgaatc cgcatacagg tgattgggta gtaaatgtat ggaacggtaa tactaatacg 1140
tccgaattta caattcaac atcttaccca tctcaagtag ttgaaagcta tggaataatg 1200
acaaatactc gtactactct aaatatggat actttggata actttagagt agacttacgt 1260
gcacattgtt ttagtcaagg agcacctttc tacgatgtgt ttggaatcgg tcgttcacaa 1320
tttttttaata gagaaacaag cataatctat gattacggaa tcggataac agatcgttat 1380
aaccggcatc gttaccaaaa tataacaata agtttaccag gagcaaattc agaacaagca 1440
actgaaaatg attatagtca tagactagcg gatgtaagaa atctcacagg cggccttcgc 1500
caaaatactc cacagatgaa tatgggacgt tcctctttaa taggatatgg gtggacacat 1560
gtaagtatga aacgcgagaa tagagtagaa ttagataaaa tcacacaaat tccggccgtt 1620
aaagcaagta gtgcttccaa ttgcactgta attccaggtc ctggatttac gggaggccac 1680
ttagtacgtt ttgattacca aggaagattg gatatgcaaa ttgaatttcc taatacacaa 1740
aaagagtatc gcatacgtat acgatatgct tctacagcga taaatacact atatttttca 1800
tttggtggaa ttactcgagg gatagctttt agttctacag gtgcttcttc actagaaaat 1860
ttgcaccatg agaattttgc gtatggcaat gttttccagg gtattttcga tcccacctta 1920
ggtaatacat taattatttc aaattggact actgttgctc cacgtatgct aatagacaaa 1980
attgagttta ttccaattga agcttttaca aatcaaccat taggagcagc aaaagaatat 2040
aaaaacaact ataatcaaat ttttaataat tacaacaaga acataaataa tatggactac 2100
cagaataaca atgttatgtc tcatcatgac tatcacaata cttacaatca agagtctaac 2160
gattataacc aggacaacaa cgataattac aactcgaacg ctggctgcac gtgtaaccaa 2220
gggtataaca ataactatcc gaaa                                        2244

SEQ ID NO: 248          moltype = AA   length = 748
FEATURE                 Location/Qualifiers
source                  1..748
                        mol_type = protein
                        organism = Bacillus thuringiensis
SEQUENCE: 248
MNSYPNKNEC EILDDSLNYS NMTNNYHRYP VAHNSQTSMQ NTNYKDWMNM CDSNTINYRS   60
IDSSPEAYIL ARAAISIGIG IVSKLLSYLG LGILADAINI TTSLVNTLWK EQNNTWDALL  120
MHVENLMNQK ISDLVLSNAN VELDALKRVL SEYNAALENW KNKPNDPSAL ELIKSQFTIT  180
HNFFVLRMSV FAHPGYEVLL LSVYAQAANL HLLLLRDASI YGNQWGLARS NGDYYYERQM  240
YYTNEYTNHC MMWYRNGLDR LRGTTGAQWL NFNRFRTEMT LTVLDIIALF PTYDYRNYPV  300
FTKIELSRVI YTDPVIYGGF SQLPSNNLGN FNDLEREAIG LPSFIKWLKK IEISTGEIRF  360
ATNPHTGDWV VNVWNGNTNT SEFTNSTSYP SQVVESHGIM TNTRTTLNMD TLDNFRVDLR  420
AHCFSQGAPF YDVFGIGRSQ FFNRETSIIY DYGIGITDRY NRHRYQNITI SLPGANSEQA  480
TENDYSHRLA DVRNLTGGLR QNTPQMNMGR SSLIGYGWTH VSMKRENRVE LDKITQIPAV  540
KASSASNCTV IPGPGFTGGH LVRFDYQGRL DMQIEFPNTQ KEYRIRIRYA STAINTLYFS  600
FGGITRGIAF SSTGASSLEN LHHENFAYGN VFQGIFDPTL GNTLIISNWT TVAPRMVIDK  660
IEFIPIEAFT NQPLGAAKEY KNNYNQIFNN YNKNINNMDY QNNNVMSHHD YHNTYNQESN  720
DYNQDNNDNY NSNAGCTCNQ GYNNNYPK                                    748

SEQ ID NO: 249          moltype = DNA   length = 2046
FEATURE                 Location/Qualifiers
source                  1..2046
                        mol_type = other DNA
                        organism = Bacillus thuringiensis
SEQUENCE: 249
atgaatccat ataacaatga tctttataaa atctttgatc cgaatacatc atcttataat   60
ttcagccagt atacaaataa ttctagatat ccttatacct atgatcctaa acaaatacaa  120
caaatccataa attatcagca aacaatacag ccggatctaa catactcaaa atatttagaa  180
aatcctaaag catttacaac ggattggtct actatagcta gtactagtat aattatataa  240

-continued

```
ggtacctta  ttgcattaag  cggtccttta  gcgttacctg  gtgcaatcct  tatatcagtt    300
ggtactgcac  ttcctcttct  ttggcctaat  ccacaagaaa  atcaaacttg  gagagatttt    360
cttcaacaag  gaaattctct  attacctgga  aaagaattac  accaatctac  acaagacctt    420
ataataggaa  tgttaaatgg  tctacaatca  ggaatagatt  attatctaag  tgctttaaat    480
acatggaaac  aaaatccttc  aaatcatcaa  cttactgaag  aagttattaa  tagattcaac    540
attgctcgtt  acaattttgt  aaataccatg  cctgtatttg  cactagaagg  ctatgaacca    600
ttattattat  caatttatgc  caaagctgca  ttttgcatt  taacattatt  acgaaaggt    660
attcattatg  ctaatgattg  ggaactagat  ccaatactta  aaatgatct  atataaaaaa    720
gaattaacag  aattcatcgc  taaatatatt  aatcattgtg  aaaaacatta  tgatatagga    780
ttaaaaaatt  tatataataa  tcctaatgtt  ccatggatg  tatacaatca  ttatcgtaga    840
gaattaactt  taagtgtgtt  aaatataatt  gccttatttc  cacagtttga  tttaaattat    900
tttcctaata  ctattctaaa  tacaggagaa  ataaagggtg  ttaatcctca  aatcactcaa    960
aaactatatg  tatccacacc  aaacttgctc  ccaaatcaaa  acggagatcg  ctcggtagaa   1020
aaagtcgaaa  atctaattat  accccatta  actctattta  attggctaga  acaattagac   1080
atttacacag  acaacacaac  tcgaaataac  cctttttta  atggtgttca  aaatgcatat   1140
acatttacag  gcgatataaa  ttcttttcat  tggggtccaa  gatttggaat  aggaaacgag   1200
aatagagttg  gtataagttc  aaatgtagat  gaatttctta  tttctatcaa  attccaacaa   1260
atggttgaat  tacaatcaaa  taacactcca  tatttaggga  tccttatat  acaatttcat   1320
agtgataaaa  atttagcgta  cactgttggt  agttcaagtt  gttatgatca  aacaaattgt   1380
atgccgagaa  taaattatac  attcccaat  gaaacacaaa  ctgccacgaa  ctatgactat   1440
atattatctg  atgttacaat  ggtcgattct  aaaaatctac  cacttgctgg  ctggtctcct   1500
gctcctagca  tattatttt  attcgcattt  acacataaaa  gtgcaaacct  tgaaaataca   1560
atacaatcaa  tgagtaaaaa  caacgttcca  acaattacac  aaatccctgt  attcaaagct   1620
ttcaaattta  gcaatttaaa  cgataataat  aaatcagtaa  aaatcagaaa  acaatctggc   1680
catacaggag  gaaatttaat  tgaattcgat  acctttggag  atgaaatcca  aattaaattt   1740
aatattcttc  caacaaattc  aatcagaaat  tacaaattaa  gaattcgtta  tgcagcctct   1800
aattatttcg  gagaaggact  aaaaataaat  atacctactt  taaataattt  tagttcaaac   1860
gtcaatattc  aaaacactgg  tttaaatcca  aacattaata  taatacctta  tgaacaattt   1920
atatatacta  acgaaataac  aattccaaac  atacccataa  gcgaacgaaa  taataccata   1980
tttttagaaa  accgaagagt  gggagtggga  acaactatta  ttgataaaat  agaatttatt   2040
cctatg                                                                 2046

SEQ ID NO: 250           moltype = AA  length = 682
FEATURE                  Location/Qualifiers
source                   1..682
                         mol_type = protein
                         organism = Bacillus thuringiensis
SEQUENCE: 250
MNPYNNDLYK IFDPNTSSYN FSQYTNNSRY PYTYDPKQIQ QIINYQQTIQ PDLTYSKYLE    60
NPKAFTTDWS TIASTSIIII GTLIALSGPL ALPGAILISV GTALPLLWPN PQENQTWRDF   120
LQQGNSLLPG KELHQSTQDL IIGMLNGLQS GIDYYLSALN TWKQNPSNHQ LTEEVINRFN   180
IARYNFVNTM PVFALEGYEP LLLSIYAKAA FLHLTLLREG IHYANDWELD PILINDLYKK   240
ELTEFIAKYI NHCEKHYDIG LKNLYNNPNV PWDVYNHYRR ELTLSVLNII ALFPQFDLNY   300
FPNTILNTGE IKGVNPQITQ KLYVSTPNLL PNQNGDRSVE KVENLIIPPL TLFNWLEQLD   360
IYTDNTTRNN PFFNGVQNAY TFTGDINSPH WGPRFGIGNE NRVGISSNVD EFLISIKFQQ   420
MVELQSNNTP YLGIPYIQFH SDKNLAYTVG SSSCYDQTNC MPRINYTLPN ETQTATNYDY   480
ILSDVTMVDS KNLPAGWSP APSILYLFAF THKSANLENT IQSMSKNNVP TITQIPVFKA   540
FKFSNLNDNN KSVKIRKQSG HTGGNLIEFD TFGDEIQIKF NILPTNSIRN YKLRIRYAAS   600
NYFGEGLKIN IPTLNNFSSN VNIQNTGLNP NINIIPYEQF IYTNEITIPN IPISERNNTI   660
FLENRRVGVG TTIIDKIEFI PM                                            682

SEQ ID NO: 251           moltype = DNA  length = 2013
FEATURE                  Location/Qualifiers
source                   1..2013
                         mol_type = other DNA
                         organism = Bacillus thuringiensis
SEQUENCE: 251
atgaaccaaa attataacaa caatgagtat gaaatttttag atcatggtaa taggagctat     60
cagactaagt atcccttttgc acaagcacca ggttctgaaa gccaaaagcc gaatgccaaa   120
gatgggatat acacacctgt aggtagggtg gatacagtcc tccaaactaa tagatatagga   180
ttatctgttc gtacagcgat ttctatctta caaatgcttc tgtctgtaag ttttccagca    240
ctaggaaag ctgctggact aataaatatt atttttggat ttctgtgggg aacacttggt    300
ggtcaatctg tttgggaaag ttttatgaaa gcggtagagt ctcttgtaaa tcaaaaaatt    360
acagatgctg tcagagcaaa agccattca gaattagaag gtgtacaaaa cgcttttagag    420
ttatatcaag aagcagcaga tgattggaat gcaaatccag atgatgcatc taataaaaag    480
cgtgttagaa gacagtttac atctacgaat acaataatcg agtatgctat gcatcatttt    540
cgagttccaa cttttgaagt accgttgtta actgtgtatg cgcaagcggc taatttacat    600
ttacaattat tacgagatgc cgttaagttt ggaaacgaat ggggtatgcc atctgaggaa    660
gtagaggatc tatatactag attaacaagg cgtacggcag agtatacaga tcattgtgtg    720
actgccatatg ataaaggttt aagggtgct tacgacttag caccgaatcc aacagattac    780
aacaaatacc cttattaaaa tccatattcg aaagatccaa tttacggtaa atactatact    840
gcacccgttg attggaatct attttaatgac tttcggagag acatgacaat tatggtacta    900
gacattgtag cagtatggcc aacctataat ccgagaatct atacccaatcc aaatggcgta    960
caagtagaat tatcaagaga atatatagc acggtgtata gaagaggcgg tagtggtaat   1020
tcatctgtgg aggcaattga atctcaaatt gtcagaccac tcatttagt gacagaacta   1080
accacccctta aaatcgagca aggtggtact ttagatatgg aacagataca atatcctaag   1140
tatatgaagg ttacgaatac gcttcattat attggaagtt ctagcacatg ggagcaaagc   1200
tcttccgcta ttcctattag accaattaca aagattcata ctatcccagc caataatatc   1260
gggaaccttt cattatctca attagaagta ccttaccgat ttctctttcta taacaaagat   1320
```

-continued

```
gatgctttaa tttctgaaat tggagctgaa ttccctccaa acaatgtaac ctggaacgga    1380
atacctagag ctgaagatag tgatcaaaat agtcatcatt tatcttatgt tggtgcgtta    1440
agtacacaat cttcagctgg gtttccttgg acatatccga cggagctttt gggagaatgg    1500
ggatttggct gggtgtctaa cagtttaaca cccgaaaata aaatagtaaa tgataaaatt    1560
acccaaattc cagcggtgaa gggatatttg ttagaactag tgggggatagt tataaaagga    1620
cctggaagta caggaggaga tttagtacaa ctatcttcta atcagtcaca ggtaaaacta    1680
aacatgattt caccactatt taccccgag ctcaccggac attatataag aattcgttat    1740
gcaagcagtg cggacactcg attatatata agctggggga caggacagg atattatgat    1800
gcgaaagcta cctattcaga ggggccattg acatataaaa cctttggata tatgaatgcg    1860
ggatggctgt atatgacggg ggcaggtgga aataacttca ctgcagtaat taaaaatcag    1920
ggagatactc ccattattat tgacaaaatc gagttcattc catttacagg cttatacctta   1980
gaggatcaag cttagaaaaa ggcaagaacg gca                                 2013
```

SEQ ID NO: 252          moltype = AA   length = 671
FEATURE                 Location/Qualifiers
source                  1..671
                        mol_type = protein
                        organism = Bacillus thuringiensis
SEQUENCE: 252
MNQNYNNNEY EILDHGNRSY QTKYPFAQAP GSECQKPNAK DGIYTPVGRV DTVLQTIDIG    60
LSVRTAISIL QMLLSVSFPA LGRAAGLINI IFGFLWGTLG GQSVWESFMK AVESLVNQKI   120
TDAVRAKAIS ELEGVQNALE LYQEAADDWN ANPDDASNKE RVRRQFTSTN TIIEYAMPSF   180
RVPTFEVPLL TVYAQAANLH LQLLRDAVKF GNEWGMPSEE VEDLYTRLTR RTAEYTDHCV   240
TAYDKGLKGA YDLAPNPTDY NKYPYLNPYS KDPIYGKYYT APVDWNLFND FRRDMTIMVL   300
DIVAVWPTYN PRIYTNPNGV QVELSREVYS TVYGRGGSGN SSVEAIESQI VRPPHLVTEL   360
TTLKIEQGGT LDMEQIQYPK YMKVTNTLHY IGSSSTWEQS SSAIPIRPIT KIHTIPANNI   420
GNLSLSQLEV PYRFSFYNKD DALISEIGAE FPPNNVTWNG IPRAEDSDQN SHHLSYVGAL   480
STQSSAGFPW TYPTELLGEW GFGWVSNSLT PENKIVNDKI TQIPAVKGYL LELGGIVIKG   540
PGSTGGDLVQ LSSNQSQVKL NMISPLFTPE LTGHYIRIRY ASSADTRLYI SWGSRTGYYD   600
AKATYSEGPL TYKTFGYMNA GWLYMTGAGG NNFTAVIKNQ GDTPIIIDKI EFIPFTGLYL   660
EDQALEKART A                                                        671

SEQ ID NO: 253          moltype = DNA   length = 1983
FEATURE                 Location/Qualifiers
source                  1..1983
                        mol_type = other DNA
                        organism = Bacillus thuringiensis
SEQUENCE: 253
atgaattcaa ataatcttaa tgaatatgaa attattgatt caaataattc tgcttatcta    60
tctaacagaa ataatacgta cgatagatat ccttatgcga ataattcaaa ccaacaatta   120
caaaatatga attataaaga ttgggtaaag gattgtcaaa gtaatcaaca atatagcgaa   180
aatccggaaa atttcgctga ccctaataca attgcagcaa tcagcgcagg tactattgtt   240
gtaggtacaa tgctatctat ttttgctgtt gttcctcctt tacttccagc ttggtattata   300
gcttttggaa ctttattacc actttttgttt cttcttcagga gatgaaacaaa agtttggaaa  360
ggttttttac aaattggaac aagagcctat aataaagata tagatgaagc agtatttact   420
acaataagta gattagcact tgctgcaaaa gaccatattg ataattttga aaaacagttt   480
aatcaatgaa aggctaatcg tacacaagcc actgcaaaag aagtacagct atatttgct    540
acaacaaatt cagccttaat aggttattta ggcgaattaa gagagcaaac ttatgaaata   600
tccgcactcc ctatttatgc aaatttatct ttactacaca taaatttatt aaaacatgct   660
gctctgtact atgatgattg gcttaaagat caagggatct ccaaaaatcc tagttcttca   720
tctgatatgt atgtatcaac tttaaatact gcaatacaaa attataccaa ccattgtaaa   780
aatatatata ataaaggctct aaatatgctt aaaaatattc cacacataaa ttggagtatt   840
tttaacacat atcgtagaga catgactata actgtacttg atattattgc acttttttcct  900
acttataatc cgaaaaattt taagatgggg ggagttcact ctgaacttac tagaaaaata   960
tatcatcat catggcaact agaagaagaa aatttagata atgatattca tacattagaa   1020
aatcaactta cccgtcccc tacactattt acttggttaa aaatttaga cctttataca   1080
atgaacgcat cagactggca aacttatta acactaggtg gtattcagaa caaatattct   1140
tataccaatg atgaaactaa atttagtact aacctacaag gatttatgt tccaccagtt   1200
aaaccaattg aaacggaaaa ttcacttatt tataaattac aaatgcaaca ctattataat   1260
cctggttcaa cttcaaaccc agtaagtgga atttctaaaa ttatttttta tagaaagaag   1320
ttaaacggtg aggataaacc tgaagaaatt tatgattcag gcaataaaaa tgaaaatgta   1380
aaggaattca ttatgagtgg tcccaaagat agtataacta ataattcaga ctctgcacat   1440
atattatctt ctattaaatt aacaaataat aaaacaggaa tactacgtaa ttttggatat   1500
tcatttgaat ggacacatat tagtgttgat tatcataata caattttcca agataagta   1560
actcaaattc cagctgtcaa agcttatttt attactgcag attcaaaagt cgttctggc    1620
cctggtcata caggtggaga cctaattact ttaaaaaggt ttatagattt tggaattca   1680
tcacttacta aaggttctta tgatatacgg attcgatatg cagctaacaa ggaaagttca   1740
ttagttatat cattccaagg aagcgatgca tttgtaatta tagataagac gacagatgtt   1800
cgaaatagta gtgatctaca gtatcaacat tttcaatatg ttacatttaa gaaggcattt   1860
ctgataagca caataggagt accattatta ttaagattac agggtatacc taatgatcca   1920
gataacgtct ggatagataa aattgaattt attccaataa ctccacaata cttagaaata   1980
agt                                                                 1983

SEQ ID NO: 254          moltype = AA   length = 661
FEATURE                 Location/Qualifiers
source                  1..661
                        mol_type = protein
                        organism = Bacillus thuringiensis
SEQUENCE: 254

```
MNSNNLNEYE IIDSNNSAYL SNRNNTYDRY PYANNSNQQL QNMNYKDWVK DCQSNQQYSE  60
NPENFADPNT IAAISAGTIV VGTMLSIFAV VPPLLPAGII AFGTLLPLLF LSGDETKVWK  120
GFLQIGTRAY NKDIDEAVFT TISRLALAAK DHIDNFEKQF NQWKANRTQA TAKEVQLYFA  180
TTNSALIGYL GELREQTYEI SALPIYANLS LLHINLLKHA ALYYDDWLKD QGISQNPSSS  240
SDMYVSTLNT AIQNYTNHCT NIYNKGLNML KNIPHINWSI FNTYRRDMTI TVLDIIALFP  300
TYNPKNFKMG GVHSELTRKI YTSSWQLEEE NLDNDIHTLE NQLTRPPTLF TWLKNLDLYT  360
MNASDWQTYL TLGGIQNKYS YTNDETKFST NLQGFYVPPV KPIETENSLI YKLQMQHYYN  420
PGSTSNPVSG ISKIIFYRKK LNGEDKPEEI YDSGNKNENV KEFIMSGPKD SITNNSDSAH  480
ILSSIKLTNN KTGILRNFGY SFEWTHISVD YHNTIFQDKI TQIPAVKAYF ITADSKVVSG  540
PGHTGGDLIT LKRFIDFGIS SLTKGSYDIR IRYAANKESS LVISFQGSDA FVIIDKTTDV  600
RNSSDLQYQH FQYVTFKKAF LISTIGVPLL LRLQGIPNDP DNVWIDKIEF IPITPQYLEI  660
S                                                                 661

SEQ ID NO: 255         moltype = DNA  length = 1389
FEATURE                Location/Qualifiers
source                 1..1389
                       mol_type = other DNA
                       organism = Bacillus thuringiensis
SEQUENCE: 255
atggatagaa gtggatttaa tgttaatcga actgttgatt atacaaatac aaattggatg  60
ggtcgtattc ctgattctcg taggatcagt gaattatcaa ttccaggaac acatggatcc  120
atggcacttc atggtggagt tgctggaact ataggagata tagctatcaa tcaaacaatg  180
aatctagaaa ctcaattaaa ctcaggtatt cgatatattg atattcgctg taggcatcat  240
cataataatt tggctatcca tcatggccag atattccaac acgcattttt tggttctcat  300
gttttagaac ccgtgataag ctttttaagg cgaaatcccc gtgaaacaat tttaatgcgt  360
gtaaaagaag aatacaatcc aacaggtaat acaagaactt ttagtgaaac ttttgaatct  420
ttctggagtc caaatcaacg ttatttttgg actcctacta gtagtaatcc aacattggga  480
gaagtccgcg gagaattatt tgtactacaa gactttccta gttggcatag aatttttggt  540
attcattggg gacagttaaa catacaagat cggtggcatg tagcgggtaa tttagacata  600
tacaataaat ggatagctgt taaaaaccat ttttctaatg caatgaataa tagaaatcga  660
atatctgtta atcatttaag tggcactggt ggtgccggtg caccaaggcc ctggtttta  720
gcaagtggct atagcgtacg aagtaactat tcttttttat tttcgcctat accttggttt  780
cctttgaatc agtttcctga tttcccacgt cctagtgcca catcaggccc tgtattttt  840
ggaggaatga acgtccttgc aactagaaga attagagacc gtaggtttac tcatacagga  900
atagttgctg ctgatttccc tggaagagga ttaattgaca gcacaattgc attaaacttc  960
cctgaagatt ttaggggtaa ttttaaaatt ataacaatgc tcaacaacac aagtcttgta  1020
gatatgcgtt taggatctag caatatagta catgtatggg acgatgtgaa tcagagaaat  1080
gcacaatggg attttgtatt tgatcaacaa agaaatgcat atctaataag aaatttattt  1140
gatagcagat tagttttatc tatggatgct cctcgtatga atcatgtatt tgcttatcca  1200
gttaatggag atgattctca gttttggatt ttagaaccta atcagggtgg atatatattt  1260
agaagtctta gagatagaaa tttagtttta actgttgaag gtaacaatcc caatccacgt  1320
cctgaaacaa gaatattagt ttctcctttt aataatggaa ccaatcaaag atttagatta  1380
gcaagagta                                                         1389

SEQ ID NO: 256         moltype = AA  length = 463
FEATURE                Location/Qualifiers
source                 1..463
                       mol_type = protein
                       organism = Bacillus thuringiensis
SEQUENCE: 256
MDRSGFNVNR TVDYTNTNWM GRIPDSRRIS ELSIPGTHGS MALHGGVAGT IGDIAINQTM  60
NLETQLNSGI RYIDIRCRHH HNNLAIHHGQ IFQHAFFGSH VLEPVISFLR RNPRETILMR  120
VKEEYNPTGN TRTFSETFES FWSPNQRYFW TPTSSNPTLG EVRGRIIVLQ DFPSWHRIFG  180
IHWGQLNIQD RWHVAGNLDI YNKWIAVKNH FSNAMNNRNR ISVNHLSGTG GAGAPRPWFL  240
ASGYSVRSNY SFLFSPIPWF PLNQFPDFPR PSATSGPVFF GGMNVLATRR IRDRRFTHTG  300
IVAADFPGRG LIDSTIALNF PEDFRGNFKI ITMLNNTSLV DMRLGSSNIV HVWDDVNQRN  360
AQWDFVFDQQ RNAYLIRNLF DSRLVLSMDA PRMNHVFAYP VNGDDSQFWI LEPNQGGYIF  420
RSLRDRNLVL TVEGNNPNPR PETRILVSPF NNGTNQRFRL ARV                   463

SEQ ID NO: 257         moltype = DNA  length = 2187
FEATURE                Location/Qualifiers
source                 1..2187
                       mol_type = other DNA
                       organism = Bacillus thuringiensis
SEQUENCE: 257
atgaatcgaa actatccgaa taatgaatat gagattatga ataataatga gatccatcaa  60
ccaaggtatc ctcttgcaga ggcaccaggt tctgaattac aacggatgaa ttacacagat  120
tggatgaaga ggtgtgcagg aggagaacca gaagacttat tttcaaattc aaatgctatt  180
aggaatggga ttattatcgg tacaagtatt gtaacagcaa ttcttagtgt atcatcccca  240
ttggcggcgg caacaacggg cataatcgcc gtactccttc catacttatg gccagaaaca  300
cctgcaacta tccaagcgca atttacatgg gaccagctga tgagtgctgc tggagaactt  360
attgataata gaatttcaga tctagtaaga accaatgcga ttaatacttt acgaatatta  420
caatcacgta taagagacta tcaacaagca atctgtaatt tgaaagcgga tccaaataat  480
gaagcataca aagcggacgt aagaagagaa tttaatgatg ctgaagacca ggcgaaatcc  540
gttattatcg aattacaatc taacggctat gaaatttcgt tattagctag ttatgcgcaa  600
gctgccaatt tacacttact tttattacga gatgtcgtaa aatacggaga aagctggggg  660
ttttcattca ctgaagtcca acaatattat tcgaatacta gtgcagtagg aaacccaggc  720
atgctacagt tattagcaac ctatacggat tattgtgtga attggtacaa cacaggtgta  780
aataatttaa aacaacaagc tggcctcact attgctgatt ggaataaggt caatgatttc  840
```

```
cgtagggaca tgaccattat ggtactagat attgtgtcat tatggccaac ttataatcca    900
agaatctatg cacaacctac aaaatcacaa cttacacgta gtgtgtatac acccatgtcg    960
gggcaagttt ttcgttctat tgaggcgatt gataatgaga taatgcccc tccgtctcta   1020
tttcatggc tacgtgaagt aactttattt agaagagcat ttcctgtgtc tactaatgag   1080
tatgcgctat ttacgcagta tgctggttat aaaatgtcat tccagaatac tttaaatcct   1140
acgttacagg aaaacaccaat atccggcgaa agagggatg aggttaatag tgtaaggatt   1200
ggtgaggagc taatttgga agtttataaa atgcaaaata ttttattggg atcaggagct   1260
agcagagatt ttgaatcgcc acaaacattt gatttcatt ttacgccatc aggaacagtt   1320
gaacgagtgg gaatcaatta tgcaaatata cagggagagc caacaagtgc tacaaatcaa   1380
ggacttgctt gtaacaataa cagtagtgaa ccttgtgatc cttgtacttc tgtcactcct   1440
tgttcagttg gtcctatcaa tactactatt ccttgtgata gccttactta ttatagtcat   1500
cgattgtcaa ggataggtgg cgttatgggt gcaaatcccc aaagtataat aggcttacc   1560
tacggctgga cacatgtaag tgcagataga accaatacaa tagaaactga aaagattacc   1620
caaattccag cggtgaaggg ccgtaaattg gagggagatg taataaaggg acctggttct   1680
acaggaggtg atttggtgaa actatatcct gtgtatggtc gtaatcaatt gcagatatac   1740
ttgaatattc cggcaagaac gaacaatata tcaggctata agataagaat tcgttatgca   1800
agtaagcagt ctacagatat cggcgtagag ttggaaagga cgataaatcc acaatggcga   1860
agatctacta ttctagctac ctattctggt gataatctaa catacaattc ttttagttat   1920
catgatgttt tagaaataga ctctcaagaa agtgcacacc ttgctaattt acgaatccgc   1980
aaggtcactg actatagtgc aggtacagaa atcacccttg acaaaatcga attcattcca   2040
atagaaggat ccgtggaaga atataaagcg atcaggatt tagaaaaggc aagaaatgca   2100
gtgaacgcct tgtttacagg tgctgcgaaa aatgctctga agttgaatgt gacggattat   2160
gctgtggacc aagctgctaa ccttgta                                      2187

SEQ ID NO: 258        moltype = AA  length = 729
FEATURE               Location/Qualifiers
source                1..729
                      mol_type = protein
                      organism = Bacillus thuringiensis
SEQUENCE: 258
MNRNYPNNEY EIMNNNEIHQ PRYPLAEAPG SELQRMNYTD WMKRCAGGEP EDLFSNSNAI    60
RNGIIIGTSI VTAILSVSSP LAAATTGIIA VLLPYLWPET PATIQAQFTW DQLMSAAGEL   120
IDNRISDLVR TNAINTLRIL QSRIRDYQQA ICNLKADPNN EAYKADVRRE FNDAEDQAKS   180
VIIELQSNGY EISLLASYAQ AANLHLLLLR DVVKYGESWG FSPTEVQQYY SNTSAVGNPG   240
MLQLLATYTD YCVNWYNTGV NNLKQQAGLT IADWNKVNDF RRDMTIMVLD IVSLWPTYNP   300
RIYAQPTKSQ LTRSVYTPMS GQVFRSIEAI DNEIMPPPSL FSWLREVTLF RRAFPVSTNE   360
YALFTQYAGY KMSFQNTLNP TLQETPISGE RGDEVNSVRI GEEPNLEVYK MQNILLGSGA   420
SRDFESPQTF DFHFTPSGTV ERVGINYANI QGEPTSATNQ GLACNNNSSE PCDPCTSVTP   480
CSVGPINTTI PCDSLTYYSH RLSRIGGVMG ANPQSIIGLT YGWTHVSADR TNTIETEKIT   540
QIPAVKGRKL EGDVIKGPGS TGGDLVKLYP VYGRNQLQIY LNIPARTNNI SGYKIRIRYA   600
SKQSTDIGVE LERTINPQWR RSTILATYSG DNLTYNSFSY HDVLEIDSQE SAHLANLRIR   660
KVTDYSAGTE ITLDKIEFIP IEGSVEEYKA DQDLEKARNA VNALFTGAAK NALKLNVTDY   720
AVDQAANLV                                                          729

SEQ ID NO: 259        moltype = DNA  length = 1137
FEATURE               Location/Qualifiers
source                1..1137
                      mol_type = other DNA
                      organism = Bacillus thuringiensis
SEQUENCE: 259
atgttacgga aaatgctaat tgcgtgtatg gcatgtttgt tcggtctgca aacaggagtc    60
atacaggcag aggaaaagaa tgaatccaga caagaaacga cttctacaac tgaagaggaa   120
acgactaaag atagatctga agcatccaga gcaaagaatg actctactga aaataggtct   180
gaagattcag aacaaaataa agaagaat attgaagaac aaaaacaaaa cgatgttgaa   240
aaaaatcaaa atagcccaat aaaggatatt gcaggtcatg cggctgaaaa agagattata   300
tctctattcg ataacaagat catatcttct acagatgggc tttttcgtcc agatgaaagg   360
attaccatgg ctgaatttat cgtcctgcta ttgaagagta aacaaattga accttctact   420
gatgaaaaa gtagcttcag tgatgtaccc ttgcaaaact gggtggctcc ctatgcagaa   480
acagcatttc gtctaggtat cattcaagga actgtagaga atggcaaacg aacacttaat   540
ccgaatggct tggtagaaag gcaggagttg attgccattc taaatagagc aagtggtaaa   600
agtggagaag taataatgt gaaatggtca acaacctatc atacattaaa aaactatccc   660
gacagtcaag atgttcctac gtggagccaa gggaatatg cgtatgcctt gcaaaatgaa   720
gaaactcaga aagctttaaa tggaaagctg agcctgaaa aaaggtaac tcgggcagag   780
acggctagtc aggtttacta ctcattattt ttgcctgata aacaagaggc ttcatctaaa   840
aatacgactc ctgtggagtt tccgtataaa cgcgttctac aggtaaaaac aacggcctat   900
gacttcacga atggacccac gaagggatac cttggttggg acttacgaga ggggattgta   960
gctgttgatc cttctgtaat accgcttgga acccatttat atatcgaggg ctacgggtat  1020
gctgtagccg ctgacatagg ctcgaaagta aaaaagaatc atattgattt gttcatgatc  1080
tccccaaaac aggcgaggga tcacggtatt aagcaagcaa aggtgtatat cttgaat     1137

SEQ ID NO: 260        moltype = AA  length = 379
FEATURE               Location/Qualifiers
source                1..379
                      mol_type = protein
                      organism = Bacillus thuringiensis
SEQUENCE: 260
MLRKMLIACM ACLFGLQTGV IQAEEKNESR QETTSTTEEE TTKDRSEASE AKNDSTENRS    60
EDSEQNKEKN IEEQKQNDVE KQNSPIKDI AGHAAEKEII SLFDNKIISS TDGLFRPDEE   120
ITMAEFIVLL LKSKQIEPST DGKSSFSDVP LQNWVAPYAE TAFRLGIIQG TVENGKRTLN   180
```

```
PNGLVERQEL IAILNRASGK SGEVNNVKWS TTYHTLKNYP DSQDVPTWSQ REYAYALQNE  240
ETQKALNGKL EPEKKVTRAE TASQVYYSLF LPDKQEASSK NTTPVEFPYK RVLQVKTTAY  300
DFTNGPTKGY LGWDLREGIV AVDPSVIPLG THLYIEGYGY AVAADIGSKV KKNHIDLFMI  360
SPKQARDHGI KQAKVYILN                                             379

SEQ ID NO: 261         moltype = DNA  length = 1197
FEATURE                Location/Qualifiers
source                 1..1197
                       mol_type = other DNA
                       organism = Bacillus thuringiensis
SEQUENCE: 261
atgaaatcat tatcaaaaaa agtcgtggca ggattacttg taggagcaac gagtctatct  60
atctgggctc ctgcaagcga agcagcaact ctaaaaaata ataaatatta cactattaat  120
tcgaaagttg atacaaaatt agcttgggct ccatatagct catcttttga ttcagtcatg  180
gaggtgctac cagtaaacaa tcaggacgaa caaaaatatc tatttttcca acttgatgga  240
ggttcgtatg cgattgtaaa taaaagtagt ggaaaagttt catcatatga tcccaatatc  300
gctataacta cattatcatc tacgagttgg aagggttccc ctagtcaaca atggcattta  360
cgagatcagg gaaatggtta ttatgaaatt atgaatcaag gaaatgggaa agtcgcaaca  420
actagattga agtcctcatg ggatcacca aatttgaata ttgatctcga taattcaaat  480
ccttctgatc cagagaaatt atttttaatt gaagacattg atgttaatgc agtttttggg  540
agtataactg gtattccact accggggggc gttcacctag ttgatccaaa cgctttttca  600
gtacaaaatt taccgaatat aggaactagg ccaaatgccc cagattatga ttataatgga  660
ggtgttgatc aacaattacc tcaaacttca aattctgttg ttgttggcgc atctttaata  720
ccttgtatta tggtacagga taattcagcg gatgattata caaaaataca caattcacca  780
tattatactt tggtaaaaga agaatattgg gataaaacat tttcagcggt tgttccagct  840
ggtttaactc gtaattatag ttttaaaaca ggtatgactt ctgtagatca acaaaagatg  900
actgatacgc tttctatgaa gattggagca gattttggat tgaaatttgg agacttaact  960
gcaggactta aaaccgaaat ttcaagaaca atacaaacag aaattagtac aactaacacg  1020
gaattatcgg aagaacaaat tacaagtaac attgtaagtg aagctggtaa aacaacagga  1080
tttacagaat atcaactggc aacaaaatat acgttaaaga gagcagatgg ttcaattgtt  1140
tcagatcctt gggttgtaaa aaacaataag ataacaatag ctagaaaaaa tgcaaaa     1197

SEQ ID NO: 262         moltype = AA  length = 399
FEATURE                Location/Qualifiers
source                 1..399
                       mol_type = protein
                       organism = Bacillus thuringiensis
SEQUENCE: 262
MKSLSKKVVA GLLVGATSLS IWAPASEAAT LKNNKYYTIN SKVDTKLAWA PYSSSFDSVM  60
EVLPVNNQDE QKYLFFQLDG GSYAIVNKSS GKVSSYDPNI AITTLSSTSW KGSPSQQWHL  120
RDQGNGYYEI MNQGNGKVAT TRLKSSWGSP NLNIDLDNSN PSDPEKLFLI EDIDVNAVFG  180
SITGIPLPGG VHLVDPNAFS VQNLPNIGTR PNAPDYDYNG GVDQQLPQTS NSVVVGASLI  240
PCIMVQDNSA DDYTKIHNSP YYTLVKEEYW DKTFSAVVPA GLTRNYSFKT GMTSVDQQKM  300
TDTLSMKIGA DFGLKFGDLT AGLKTEISRT IQTEISTTNT ELSEEQITSN IVSEAGKTTG  360
FTEYQLATKY TLKRADGSIV SDPWVVKNNK ITIARKNAK                       399

SEQ ID NO: 263         moltype = DNA  length = 1887
FEATURE                Location/Qualifiers
source                 1..1887
                       mol_type = other DNA
                       organism = Bacillus thuringiensis
SEQUENCE: 263
atggatcaaa tttatcaacc ttgttctttt ccatataatg tattagcaca acctattaat  60
ttaacagact ctgctgcatt ttattctcct actattttag gtacagatga tgctactatt  120
ttggataaaa ttttagagga tattaaaaaa tattatacaa aaggaacatt tgcttctgat  180
tttgctaaaa caattcttcc tcttattaca caacataaaa ttaattggag ctctatctta  240
agtattgctt tttcttttac aagttccatt cctttttttag gtacagcagt atccattcta  300
tctccttttt tacaaatgtt attcccatca gatcctgctg ctcaaagtag aaaaataatg  360
gaagatattt tggctcaaac acaaattatg attaatcaac aaattggatc tgccgaatta  420
gatcgtatta cacaaaatat tgttggatta ggtaatgtac tatctcatca taatcaaaca  480
attggtcaaa ttgcaaatct tgatccggcc aaagtattta atgcaattga aactattgca  540
gacattttta taactactgt tccacagtta gtttctcttg gttatattcc tcaaacttta  600
ccactgtatg tacaaggtat taatttatat tttatgtttt taaaaacaac aatcgatagt  660
gctaatctaa ttaaattaac agatggtgaa accaattttt ttaaaatagt tttaaaggaa  720
gcaatacctc attatacaaa tgaagtcata caatatttta atagaattcc tgatgcatct  780
aaaacaactg aaattcgcaa tgcaatgcag attaactgtt ttgattttgt tgcattatgg  840
cctcttttag atcctgataa ttatcctact caaacagata ttgaacaaac acgtttatta  900
tttgaaaaaa gtggatatgg tgaatttgat ggaggacgtg ttccaactcc gtatgatgat  960
tcagtaggtt atcgttctga tttagaatta acgaatattg taacaagagg tgcagatcgg  1020
gttgatttcg tacaagaaca atttgcaaat ggaacaacta tcactggggg aagtggacca  1080
ggatatcaat tccctgattt tccttcttct cgaaataatc ccgttacaga tatttatgaa  1140
tctagcacaa atggtgagca ataccaagct attcactata aagctgcaga tggaacactt  1200
ggaccttatc gacaaacaac atatgatctt actccaccac ctggtcaaaa aatccattac  1260
actgcattag gtacacataa ttttatgggt gttgggcaag ttggaccaat cttatccatg  1320
tttattccta tcaatttatt tccagaaaat atcattggtg taacagattc agaaacaggt  1380
aacattccca ttaaaggtat tccttttgaa aaaggacata cagaaggact tcgccataca  1440
agagaagaag tgaatgctgc ttccgctgtt gtattagaac ctggacaatc cattatactt  1500
cctattacct gtgttacagc aagtatatat caattacgaa tcagatatgc atatactgaa  1560
aattcaggaa gagctatacc tataacaata tctacaagca atggcagttt aaatagaaca  1620
```

```
aaacttctag aaaatacagc aggtaatcca tatggagtta ttggaaaataa tggaacatat  1680
gtaattgaat atgatccttc aagtatatat attcctatag gtaactttac agttaaaatt  1740
tttaataatg gaagaaatga attattttta gatcgtttag agtttatccc tataaaatca  1800
tcgtcctctc catcttctat gtttaatcaa gattttcaag atttatcccc aggtacttca  1860
aaaatttat ggtctggttc tatagca                                        1887

SEQ ID NO: 264          moltype = AA   length = 629
FEATURE                 Location/Qualifiers
source                  1..629
                        mol_type = protein
                        organism = Bacillus thuringiensis
SEQUENCE: 264
MDQIYQPCSF PYNVLAQPIN LTDSAAFYSP TILGTDDATI LDKILEDIKK YYTKGTFASD   60
FAKTILPLIT QHKINWSSIL SIAFSFTSSI PFLGTAVSIL SPFLQMLFPS DPAAQSRKIM  120
EDILAQTQIM INQQIGSAEL DRITQNIVGL GNVLSHHNQT IGQIANLDPA KVFNAIETIA  180
DIFITTVPQL VSLGYIPQTL PLYVQGINLY FMFLKTTIDS ANLIKLTDGE TNFFKIVLKE  240
AIPHYTNEVI QYFNRIPDAS KTTEIRNAMQ INCFDFVALW PLLDPDNYPT QTDIEQTRLL  300
FEKSGYGEFD GGRVPTPYDD SVGYRSDLEL TNIVTRGADR VDFVQEQFAN GTTITGGSGP  360
GYQFPDFPSS RNNPVTDIYE SSTNGEQYQA IHYKAADGTL GPYRQTTYDL TPPPGQKIHY  420
TALGTHNFMG VGQVGPILSM FIPINLFPEN IIGVTDSETG NIPIKGIPFE KGHTEGLRHT  480
REEVNAASAV VLEPGQSIIL PITCVTASIY QLRIRYAYTE NSGRAIPITI STSNGSLNRT  540
KLLENTAGNP YGVIGNNGTY VIEYDPSSIY IPIGNFTVKI FNNGRNELFL DRLEFIPIKS  600
SSSPSSMFNQ DFQDLSPGTS KILWSGSIA                                    629

SEQ ID NO: 265          moltype = DNA   length = 906
FEATURE                 Location/Qualifiers
source                  1..906
                        mol_type = other DNA
                        organism = Bacillus thuringiensis
SEQUENCE: 265
atggctattt ttgattacaa cgccaaagta gtagagttta gtcagtggta cgcttcaagg   60
tatggttata caaatctaag aaatttcaaa tattattata atattacaga tatcaatgct  120
gttccagaat caagtaatcc cagtgtcact gtgactcctg ttttagcaag aacatctatt  180
caagaattga caaataatac aagtgtacca cagacacaaa cagtcagttt ttcggaaact  240
acaacagaaa gtcagtcttc tactacaaca aatggggcga agtttttctac aacagttact  300
tctaccacta aatttacagc tagcgtcaat ttcaaagcga ttggctcttc cgttgatcaa  360
accattgctg tcgccatgac aggcgagtat aattatagct cttcacaaac aaaaacgaca  420
acaagtagta gaacgtggac cattacacag ccagtaagtg taccaccacg ttcacgtgta  480
acttgtactt tattgattta tgatgctcca tttgcaatac ctgtaaactt aaattgtaat  540
atagtgggta ctcaaccttt tatcacctct acacagttag tgggatctac ccatgatttc  600
tctactccaa caggtaccgc gggcacgcct ccgggaataa tgtatcttaa taattggcca  660
ggtagaccgt ctgaatatat tggttctggt cgttcatcgg gttcttcaag tgaaaatata  720
cttaaatttc gaggaaaagg ttcgcaaaca gctgtacagg gattatactc aacagttaga  780
tttgacgaaa ccccattgcc aggaaatcaa ggggaaacga gaacctatta ctctccaata  840
caacttgcaa atcaggataa tatcattcct acaaattcta cttctattcc aattatcaat  900
ccagtt                                                              906

SEQ ID NO: 266          moltype = AA   length = 302
FEATURE                 Location/Qualifiers
source                  1..302
                        mol_type = protein
                        organism = Bacillus thuringiensis
SEQUENCE: 266
MAIFDYNAKV VEFSQWYASR YGYTNLRNFK YYYNITDINA VPESSNPSVT VTPVLARTSI   60
QELTNNTSVP QTQTVSFSET TTESQSSTTT NGAKFSTTVT STTKFTASVN FKAIGSSVDQ  120
TIAVAMTGEY NYSSSQTKTT TSSRWTITQ PVSVPPRSRV TCTLLIYDAP FAIPVNLNCN  180
IVGTQPFITS TQLVGSTHDF STPTGTAGTP PGIMYLNNWP GRPSEYIGSG RSSGSSSENI  240
LKFRGKGSQT AVQGLYSTVR FDETPLPGNQ GETRTYYSPI QLANQDNIIP TNSTSIPIIN  300
PV                                                                  302

SEQ ID NO: 267          moltype = DNA   length = 912
FEATURE                 Location/Qualifiers
source                  1..912
                        mol_type = other DNA
                        organism = Bacillus thuringiensis
SEQUENCE: 267
atgtataata ctactcaagt agcaagggga tttcaagctg atctggataa tcaagcaata   60
gaaacatttc agccaacaac aaatgttatc caagaatatc ttacgtttgc tgacttacaa  120
gcattaggtt caagtgtaca aagtgtacgt tctagatttt cagccatttta tggtactact  180
cccgatggca ttgcattaaa taatgaaaca tattttaatg ctgttcaacc acctattact  240
gttcaatatg gatattattg ttacaaaaat gttggcactg ttcaatatgt aaataagcct  300
actgatatga atccaaacgt tattcttgct caagatacat tgacaaattc taccgatgaa  360
cctttttacta cgactataac tttaactgga tcttggacca aaacatctac tgttacatct  420
agtacaacag cgggtcttaa aattactact aaactctcaa ttaaaaaagt tttgaaatt   480
ggtgagaag tttcatttc tactaccgtt ggatcatctg aagccaactc agaaacatt   540
actgtctcta aagctgttac ggtcacagtt ccagctcaaa gtagaaggaa tattcaatta  600
acagcgagag tagcaagaga atctgcagat ttcagtgctc ctattactgt cgatggttat  660
tttggtgcta acttccctcg tcgagtagga ccaggcggac attattttg gtttaaccca  720
gctagagacg ttttaaatgc tacctctggc gtactcagag gtacagttaa taatgtatct  780
```

-continued

```
agttacgatt ttcaaactgt agtgcaacca gcatttagct tattagctga acagcatgag  840
gctttagaag ctgctatacc cggcgatcct tctgaagaac aattaacaca aatagaacaa  900
atgactagaa tg                                                      912

SEQ ID NO: 268         moltype = AA  length = 304
FEATURE                Location/Qualifiers
source                 1..304
                       mol_type = protein
                       organism = Bacillus thuringiensis
SEQUENCE: 268
MYNTTQVARG FQADLDNQAI ETFQPTTNVI QEYLTFADLQ ALGSSVQSVR SRFSAIYGTT  60
PDGIALNNET YFNAVQPPIT VQYGYYCYKN VGTVQYVNKP TDMNPNVILA QDTLTNSTDE  120
PFTTTITLTG SWTKTSTVTS STTAGLKITT KLSIKKVFEI GGEVSFSTTV GSSEANSETF  180
TVSKAVTVTV PAQSRRNIQL TARVARESAD FSAPITVDGY FGANFPRRVG PGGHYFWFNP  240
ARDVLNATSG VLRGTVNNVS SYDFQTVVQP AFSLLAEQHE ALEAAIPGDP SEEQLTQIEQ  300
MTRM                                                               304

SEQ ID NO: 269         moltype = DNA  length = 783
FEATURE                Location/Qualifiers
source                 1..783
                       mol_type = other DNA
                       organism = Bacillus thuringiensis
SEQUENCE: 269
atgcaaactc agctaatacg agagaaattt ttattttcag atttacctgc aatgaattca  60
agttatgaca aagtgagaga agcattcaaa gaaaaattca aagtaaatcc agatggtatt  120
gcagtaaata gcgaaactta ttttaaagga gttacgcctg caatcactga gcaatatggc  180
cacccttgct acaaaacact tggtgacttt acgtatacta aaggagacgg ggcacccccct  240
aaatctgtca tagtcggtag taatattgct gtaaatcatg gggatgaagc agccactatg  300
actttagaag ttcaaggcag ttggcaaagt caacaaacat ggtctacaga aagtacaaca  360
ggcttaactt tcgcttctaa atttacaata gagggctttt ttgaatcagg gatggaattc  420
tctgttagta ctactatagg ggaatcaaaa actgaaacag aatcaaaaac ggcaactgcc  480
aagatagagg taacagtacc accaagaagt aagaagaagg ttgtaatagt tgggacatta  540
aaaaaagaaa cgatgcattt tcgtgcaccg atttttgtca atggcatgtt tggtgcaaac  600
ttccctaaga gagtacaaga tcattatttt tggttcctta atgcgacaag tgtactcaaa  660
aatacttctg gagaaatatc tggaacgatt aaaaactctg ccgtctttga tgttcatacg  720
gagattggta aaacagagcc tttaacagct gaagaattaa gtgaatttat ggcattaact  780
aaa                                                                783

SEQ ID NO: 270         moltype = AA  length = 261
FEATURE                Location/Qualifiers
source                 1..261
                       mol_type = protein
                       organism = Bacillus thuringiensis
SEQUENCE: 270
MQTQLIREKF LFSDLPAMNS SYDKVREAFK EKFKVNPDGI AVNSETYFKG VTPAITEQYG  60
HPCYKTLGDF TYTKGDGAPP KSVIVGSNIA VNHGDEAATM TLEVQGSWQS QQTWSTESTT  120
GLTFASKFTI EGFFESGMEF SVSTTIGESK TETESKTATA KIEVTVPPRS KKKVVIVGTL  180
KKETMHFRAP IFVNGMFGAN FPKRVQDHYF WFLNATSVLK NTSGEISGTI KNSAVFDVHT  240
EIGKTEPLTA EELSEFMALT K                                            261
```